(12) United States Patent
Kamath et al.

(10) Patent No.: US 9,717,449 B2
(45) Date of Patent: Aug. 1, 2017

(54) SYSTEMS AND METHODS FOR PROCESSING SENSOR DATA

(71) Applicant: DexCom, Inc., San Diego, CA (US)

(72) Inventors: Apurv Ullas Kamath, San Diego, CA (US); John Michael Dobbles, San Clemente, CA (US); Aarthi Mahalingam, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 894 days.

(21) Appl. No.: 13/742,178

(22) Filed: Jan. 15, 2013

(65) Prior Publication Data

US 2013/0150692 A1    Jun. 13, 2013

Related U.S. Application Data

(63) Continuation of application No. 12/258,235, filed on Oct. 24, 2008, now Pat. No. 8,417,312.
(Continued)

(51) Int. Cl.
*A61B 5/00* (2006.01)
*A61B 5/1477* (2006.01)
(Continued)

(52) U.S. Cl.
CPC .......... *A61B 5/1477* (2013.01); *A61B 5/0004* (2013.01); *A61B 5/1495* (2013.01);
(Continued)

(58) Field of Classification Search
CPC . A61B 5/145; A61B 5/14503; A61B 5/14532; A61B 5/1468; A61B 5/1473;
(Continued)

(56) References Cited

U.S. PATENT DOCUMENTS 1,564,641 A    12/1925  St. James
2,402,306 A     6/1946  Turkel
(Continued)

FOREIGN PATENT DOCUMENTS

EP    0 098 592    1/1984
EP    0 107 634    5/1984
(Continued)

OTHER PUBLICATIONS

US 7,530,950, 05/2009, Brister et al. (withdrawn)
(Continued)

*Primary Examiner* — Navin Natnithithadha
*Assistant Examiner* — Eric Messersmith
(74) *Attorney, Agent, or Firm* — Knobbe Martens Olson & Bear, LLP

(57) ABSTRACT

Systems and methods for processing sensor data are provided. In some embodiments, systems and methods are provided for calibration of a continuous analyte sensor. In some embodiments, systems and methods are provided for classification of a level of noise on a sensor signal. In some embodiments, systems and methods are provided for determining a rate of change for analyte concentration based on a continuous sensor signal. In some embodiments, systems and methods for alerting or alarming a patient based on prediction of glucose concentration are provided.

17 Claims, 23 Drawing Sheets

Related U.S. Application Data

(60) Provisional application No. 60/982,647, filed on Oct. 25, 2007.

(51) Int. Cl.
*A61B 5/145* (2006.01)
*A61B 5/1486* (2006.01)
*A61B 5/1495* (2006.01)

(52) U.S. Cl.
CPC ...... *A61B 5/14532* (2013.01); *A61B 5/14865* (2013.01); *A61B 5/7203* (2013.01); *A61B 5/7264* (2013.01); *A61B 5/7275* (2013.01); *A61B 5/7278* (2013.01); *A61B 5/742* (2013.01); *A61B 5/743* (2013.01)

(58) Field of Classification Search
CPC ..... A61B 5/00; A61B 5/14865; A61B 5/1495; A61B 5/7203; A61B 5/7264; A61B 5/743; A61B 5/1477; A61B 5/7275; A61B 5/7278; A61B 5/742; A61B 5/00
See application file for complete search history.

(56) References Cited

U.S. PATENT DOCUMENTS

| | | |
|---|---|---|
| 3,210,578 A | 10/1965 | Sherer |
| 3,219,533 A | 11/1965 | Mullins |
| 3,381,371 A | 5/1968 | Russell |
| 3,775,182 A | 11/1973 | Patton et al. |
| 3,780,727 A | 12/1973 | King |
| 3,791,871 A | 2/1974 | Rowley |
| 3,826,244 A | 7/1974 | Salcman et al. |
| 3,838,033 A | 9/1974 | Mindt et al. |
| 3,874,850 A | 4/1975 | Sorensen et al. |
| 3,898,984 A | 8/1975 | Mandel et al. |
| 3,929,971 A | 12/1975 | Roy |
| 3,933,593 A | 1/1976 | Sternberg |
| 3,943,918 A | 3/1976 | Lewis |
| 3,957,613 A | 5/1976 | Macur |
| 3,964,974 A | 6/1976 | Banauch et al. |
| 3,979,274 A | 9/1976 | Newman |
| 3,982,530 A | 9/1976 | Storch |
| 4,008,717 A | 2/1977 | Kowarski |
| 4,024,312 A | 5/1977 | Korpman |
| 4,036,749 A | 7/1977 | Anderson et al. |
| 4,052,754 A | 10/1977 | Homsy |
| 4,067,322 A | 1/1978 | Johnson |
| 4,073,713 A | 2/1978 | Newman |
| 4,076,656 A | 2/1978 | White et al. |
| 4,197,840 A | 4/1980 | Beck et al. |
| 4,206,755 A | 6/1980 | Klein |
| 4,215,703 A | 8/1980 | Willson |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,265,249 A | 5/1981 | Schindler et al. |
| 4,369,785 A | 1/1983 | Rehkopf et al. |
| 4,374,013 A | 2/1983 | Enfors |
| 4,378,016 A | 3/1983 | Loeb |
| 4,388,166 A | 6/1983 | Suzuki et al. |
| 4,402,694 A | 9/1983 | Ash et al. |
| 4,403,984 A | 9/1983 | Ash et al. |
| 4,415,666 A | 11/1983 | D'Orazio et al. |
| 4,418,148 A | 11/1983 | Oberhardt |
| 4,431,004 A | 2/1984 | Bessman et al. |
| 4,436,094 A | 3/1984 | Cerami |
| 4,442,841 A | 4/1984 | Uehara et al. |
| 4,454,295 A | 6/1984 | Wittmann et al. |
| 4,477,314 A | 10/1984 | Richter et al. |
| 4,492,575 A | 1/1985 | Mabille |
| 4,494,950 A | 1/1985 | Fischell |
| 4,506,680 A | 3/1985 | Stokes |
| RE31,916 E | 6/1985 | Oswin et al. |
| 4,526,569 A | 7/1985 | Bernardi |
| 4,554,927 A | 11/1985 | Fussell |
| 4,571,292 A | 2/1986 | Liu et al. |
| 4,577,642 A | 3/1986 | Stokes |
| 4,578,215 A | 3/1986 | Bradley |
| 4,602,922 A | 7/1986 | Cabasso et al. |
| 4,625,730 A | 12/1986 | Fountain et al. |
| RE32,361 E | 2/1987 | Duggan |
| 4,650,547 A | 3/1987 | Gough |
| 4,655,880 A | 4/1987 | Liu |
| 4,663,824 A | 5/1987 | Kenmochi |
| 4,671,288 A | 6/1987 | Gough |
| 4,672,970 A | 6/1987 | Uchida et al. |
| 4,680,268 A | 7/1987 | Clark, Jr. |
| 4,686,044 A | 8/1987 | Behnke et al. |
| 4,689,309 A | 8/1987 | Jones |
| 4,703,756 A | 11/1987 | Gough et al. |
| 4,711,245 A | 12/1987 | Higgins |
| 4,711,251 A | 12/1987 | Stokes |
| 4,721,677 A | 1/1988 | Clark, Jr. |
| 4,726,381 A | 2/1988 | Jones |
| 4,731,726 A | 3/1988 | Allen |
| 4,747,822 A | 5/1988 | Peabody |
| 4,750,496 A | 6/1988 | Reinhart et al. |
| 4,757,022 A | 7/1988 | Shults et al. |
| 4,759,828 A | 7/1988 | Young et al. |
| 4,763,658 A | 8/1988 | Jones |
| 4,777,953 A | 10/1988 | Ash et al. |
| 4,781,798 A | 11/1988 | Gough |
| 4,787,398 A | 11/1988 | Garcia et al. |
| 4,789,467 A | 12/1988 | Lindsay et al. |
| 4,805,625 A | 2/1989 | Wyler |
| 4,810,470 A | 3/1989 | Burkhardt et al. |
| 4,813,424 A | 3/1989 | Wilkins |
| 4,820,281 A | 4/1989 | Lawler |
| 4,823,808 A | 4/1989 | Clegg et al. |
| 4,832,034 A | 5/1989 | Pizziconi |
| 4,849,458 A | 7/1989 | Reed et al. |
| 4,852,573 A | 8/1989 | Kennedy |
| 4,854,322 A | 8/1989 | Ash et al. |
| 4,858,615 A | 8/1989 | Meinema |
| 4,867,741 A | 9/1989 | Portnoy |
| 4,871,440 A | 10/1989 | Nagata et al. |
| 4,874,363 A | 10/1989 | Abell |
| 4,883,057 A | 11/1989 | Broderick |
| 4,886,740 A | 12/1989 | Vadgama |
| 4,890,620 A | 1/1990 | Gough |
| 4,890,621 A | 1/1990 | Hakky |
| 4,907,857 A | 3/1990 | Giuliani et al. |
| 4,919,141 A | 4/1990 | Zier et al. |
| 4,921,477 A | 5/1990 | Davis |
| 4,925,444 A | 5/1990 | Orkin et al. |
| 4,927,407 A | 5/1990 | Dorman |
| 4,927,516 A | 5/1990 | Yamaguchi et al. |
| 4,944,299 A | 7/1990 | Silvian |
| 4,946,439 A | 8/1990 | Eggers |
| 4,953,552 A | 9/1990 | DeMarzo |
| 4,955,861 A | 9/1990 | Enegren et al. |
| 4,966,579 A | 10/1990 | Polaschegg |
| 4,967,940 A | 11/1990 | Blette |
| 4,974,929 A | 12/1990 | Curry |
| 4,975,175 A | 12/1990 | Karube et al. |
| 4,975,636 A | 12/1990 | Desautels |
| 4,979,509 A | 12/1990 | Hakky |
| 4,986,671 A | 1/1991 | Sun et al. |
| 4,988,341 A | 1/1991 | Columbus et al. |
| 4,989,607 A | 2/1991 | Keusch et al. |
| 4,992,794 A | 2/1991 | Brouwers |
| 4,994,026 A | 2/1991 | Fecondini |
| 4,994,167 A | 2/1991 | Shults et al. |
| 5,002,055 A | 3/1991 | Merki et al. |
| 5,002,572 A | 3/1991 | Picha |
| 5,009,251 A | 4/1991 | Pike et al. |
| 5,030,333 A | 7/1991 | Clark, Jr. |
| 5,034,112 A | 7/1991 | Murase et al. |
| 5,035,711 A | 7/1991 | Aoki et al. |
| 5,050,612 A | 9/1991 | Matsumura |
| 5,055,171 A | 10/1991 | Peck |
| 5,055,198 A | 10/1991 | Shettigar |

(56) References Cited

U.S. PATENT DOCUMENTS

| | | |
|---|---|---|
| 5,059,654 A | 10/1991 | Hou et al. |
| 5,063,081 A | 11/1991 | Cozzette et al. |
| 5,067,491 A | 11/1991 | Taylor, II et al. |
| 5,068,536 A | 11/1991 | Rosenthal |
| 5,071,452 A | 12/1991 | Avrillon et al. |
| 5,077,476 A | 12/1991 | Rosenthal |
| 5,082,550 A | 1/1992 | Rishpon et al. |
| 5,089,112 A | 2/1992 | Skotheim et al. |
| 5,097,834 A | 3/1992 | Skrabal |
| 5,098,377 A | 3/1992 | Borsanyi et al. |
| 5,101,814 A | 4/1992 | Palti |
| 5,108,819 A | 4/1992 | Heller et al. |
| 5,128,408 A | 7/1992 | Tanaka et al. |
| 5,130,231 A | 7/1992 | Kennedy et al. |
| 5,137,028 A | 8/1992 | Nishimura |
| 5,140,985 A | 8/1992 | Schroeder et al. |
| 5,145,565 A | 9/1992 | Kater et al. |
| 5,160,418 A | 11/1992 | Mullen |
| 5,165,406 A | 11/1992 | Wong et al. |
| 5,165,407 A | 11/1992 | Wilson et al. |
| 5,171,689 A | 12/1992 | Kawaguri et al. |
| 5,178,142 A | 1/1993 | Harjunmaa et al. |
| 5,190,041 A | 3/1993 | Palti |
| 5,198,771 A | 3/1993 | Fidler et al. |
| 5,200,051 A | 4/1993 | Cozzette et al. |
| 5,202,261 A | 4/1993 | Musho et al. |
| 5,208,147 A | 5/1993 | Kagenow et al. |
| 5,212,050 A | 5/1993 | Mier et al. |
| 5,242,835 A | 9/1993 | Jensen |
| 5,243,982 A | 9/1993 | Mostl et al. |
| 5,243,983 A | 9/1993 | Tarr et al. |
| 5,249,576 A | 10/1993 | Goldberger et al. |
| 5,250,439 A | 10/1993 | Musho et al. |
| 5,264,104 A | 11/1993 | Gregg et al. |
| 5,265,594 A | 11/1993 | Olsson et al. |
| 5,266,179 A | 11/1993 | Nankai et al. |
| 5,269,891 A | 12/1993 | Colin |
| 5,279,294 A | 1/1994 | Anderson et al. |
| 5,281,319 A | 1/1994 | Kaneko et al. |
| 5,282,848 A | 2/1994 | Schmitt |
| 5,284,140 A | 2/1994 | Allen et al. |
| 5,285,513 A | 2/1994 | Kaufman et al. |
| 5,286,364 A | 2/1994 | Yacynych et al. |
| 5,287,753 A | 2/1994 | Routh et al. |
| 5,298,022 A | 3/1994 | Bernardi |
| 5,298,144 A | 3/1994 | Spokane |
| 5,299,571 A | 4/1994 | Mastrototaro |
| 5,302,093 A | 4/1994 | Owens et al. |
| 5,304,468 A | 4/1994 | Phillips et al. |
| 5,307,263 A | 4/1994 | Brown |
| 5,310,469 A | 5/1994 | Cunningham et al. |
| 5,311,908 A | 5/1994 | Barone et al. |
| 5,312,361 A | 5/1994 | Zadini et al. |
| 5,316,008 A | 5/1994 | Suga et al. |
| 5,321,414 A | 6/1994 | Alden et al. |
| 5,322,063 A | 6/1994 | Allen et al. |
| 5,324,322 A | 6/1994 | Grill, Jr. et al. |
| 5,330,521 A | 7/1994 | Cohen |
| 5,330,634 A | 7/1994 | Wong et al. |
| 5,331,555 A | 7/1994 | Hashimoto et al. |
| 5,337,747 A | 8/1994 | Neftel |
| 5,342,409 A | 8/1994 | Mullett |
| 5,343,869 A | 9/1994 | Pross et al. |
| 5,352,351 A | 10/1994 | White |
| 5,354,449 A | 10/1994 | Band et al. |
| 5,356,375 A | 10/1994 | Higley |
| 5,356,378 A | 10/1994 | Doan |
| 5,368,028 A | 11/1994 | Palti |
| 5,368,224 A | 11/1994 | Richardson et al. |
| 5,368,562 A | 11/1994 | Blomquist et al. |
| 5,372,133 A | 12/1994 | Hogen Esch |
| 5,372,135 A | 12/1994 | Mendelson et al. |
| 5,372,709 A | 12/1994 | Hood |
| 5,372,719 A | 12/1994 | Afeyan et al. |
| 5,376,070 A | 12/1994 | Purvis et al. |
| 5,384,028 A | 1/1995 | Ito |
| 5,390,671 A | 2/1995 | Lord et al. |
| 5,391,250 A | 2/1995 | Cheney, II et al. |
| 5,411,647 A | 5/1995 | Johnson et al. |
| 5,411,866 A | 5/1995 | Luong |
| 5,423,738 A | 6/1995 | Robinson et al. |
| 5,425,717 A | 6/1995 | Mohiuddin |
| 5,428,123 A | 6/1995 | Ward et al. |
| 5,429,735 A | 7/1995 | Johnson et al. |
| 5,431,160 A | 7/1995 | Wilkins |
| 5,431,174 A | 7/1995 | Knute |
| 5,434,412 A | 7/1995 | Sodickson et al. |
| 5,438,984 A | 8/1995 | Schoendorfer |
| 5,448,992 A | 9/1995 | Kupershmidt |
| 5,453,199 A | 9/1995 | Afeyan et al. |
| 5,462,051 A | 10/1995 | Oka et al. |
| 5,462,064 A | 10/1995 | DAngelo et al. |
| 5,462,645 A | 10/1995 | Albery et al. |
| 5,466,575 A | 11/1995 | Cozzette et al. |
| 5,469,846 A | 11/1995 | Khan |
| 5,474,552 A | 12/1995 | Palti |
| 5,476,094 A | 12/1995 | Allen et al. |
| 5,476,776 A | 12/1995 | Wilkins |
| 5,482,008 A | 1/1996 | Stafford et al. |
| 5,482,446 A | 1/1996 | Williamson et al. |
| 5,482,473 A | 1/1996 | Lord et al. |
| 5,484,404 A | 1/1996 | Schulman et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,505,828 A | 4/1996 | Wong et al. |
| 5,507,288 A | 4/1996 | Bocker et al. |
| 5,513,636 A | 5/1996 | Palti |
| 5,518,601 A | 5/1996 | Foos et al. |
| 5,531,679 A | 7/1996 | Schulman et al. |
| 5,531,878 A | 7/1996 | Vadgama et al. |
| 5,540,828 A | 7/1996 | Yacynych |
| 5,541,305 A | 7/1996 | Yokota et al. |
| 5,551,850 A | 9/1996 | Williamson et al. |
| 5,553,616 A | 9/1996 | Ham et al. |
| 5,562,614 A | 10/1996 | O'Donnell |
| 5,562,615 A | 10/1996 | Nassif |
| 5,564,439 A | 10/1996 | Picha |
| 5,568,806 A | 10/1996 | Cheney, II et al. |
| 5,569,186 A | 10/1996 | Lord et al. |
| 5,571,395 A | 11/1996 | Park et al. |
| 5,575,930 A | 11/1996 | Tietje-Girault et al. |
| 5,578,463 A | 11/1996 | Berka et al. |
| 5,582,184 A | 12/1996 | Erickson et al. |
| 5,582,593 A | 12/1996 | Hultman |
| 5,582,697 A | 12/1996 | Ikeda et al. |
| 5,584,813 A | 12/1996 | Livingston et al. |
| 5,584,876 A | 12/1996 | Bruchman et al. |
| 5,586,553 A | 12/1996 | Halili et al. |
| 5,589,563 A | 12/1996 | Ward et al. |
| 5,590,651 A | 1/1997 | Shaffer et al. |
| 5,593,852 A | 1/1997 | Heller et al. |
| 5,609,572 A | 3/1997 | Lang |
| 5,611,900 A | 3/1997 | Worden |
| 5,624,409 A | 4/1997 | Seale |
| 5,624,537 A | 4/1997 | Turner et al. |
| 5,628,619 A | 5/1997 | Wilson |
| 5,628,890 A | 5/1997 | Carter et al. |
| 5,640,470 A | 6/1997 | Iyer et al. |
| 5,641,539 A | 6/1997 | Afeyan et al. |
| 5,653,863 A | 8/1997 | Genshaw et al. |
| 5,658,250 A | 8/1997 | Blomquist et al. |
| 5,660,163 A | 8/1997 | Schulman et al. |
| 5,665,061 A | 9/1997 | Antwiler |
| 5,673,694 A | 10/1997 | Rivers |
| 5,676,651 A | 10/1997 | Larson et al. |
| 5,676,820 A | 10/1997 | Wang et al. |
| 5,682,884 A | 11/1997 | Hill |
| 5,683,562 A | 11/1997 | Schaffar et al. |
| 5,686,829 A | 11/1997 | Girault |
| 5,688,239 A | 11/1997 | Walker |
| 5,695,623 A | 12/1997 | Michel et al. |

(56) References Cited

U.S. PATENT DOCUMENTS

| | | |
|---|---|---|
| 5,707,502 A | 1/1998 | McCaffrey et al. |
| 5,711,861 A | 1/1998 | Ward et al. |
| 5,730,654 A | 3/1998 | Brown |
| 5,735,273 A | 4/1998 | Kurnik et al. |
| 5,741,330 A | 4/1998 | Brauker et al. |
| 5,741,634 A | 4/1998 | Nozoe et al. |
| 5,743,262 A | 4/1998 | Lepper, Jr. et al. |
| 5,749,832 A | 5/1998 | Vadgama et al. |
| 5,749,907 A | 5/1998 | Mann |
| 5,756,632 A | 5/1998 | Ward et al. |
| 5,758,643 A | 6/1998 | Wong et al. |
| 5,773,270 A | 6/1998 | D'Orazio et al. |
| 5,776,324 A | 7/1998 | Usala |
| 5,777,060 A | 7/1998 | Van Antwerp |
| 5,779,665 A | 7/1998 | Mastrototaro et al. |
| 5,782,912 A | 7/1998 | Brauker et al. |
| 5,787,900 A | 8/1998 | Butler et al. |
| 5,791,344 A | 8/1998 | Schulman et al. |
| 5,791,880 A | 8/1998 | Wilson |
| 5,795,774 A | 8/1998 | Matsumoto et al. |
| 5,800,383 A | 9/1998 | Chandler et al. |
| 5,800,420 A | 9/1998 | Gross |
| 5,800,529 A | 9/1998 | Brauker et al. |
| 5,804,048 A | 9/1998 | Wong et al. |
| 5,807,375 A | 9/1998 | Gross et al. |
| 5,810,770 A | 9/1998 | Chin et al. |
| 5,814,599 A | 9/1998 | Mitragotri et al. |
| 5,820,622 A | 10/1998 | Gross et al. |
| 5,822,715 A | 10/1998 | Worthington et al. |
| 5,833,603 A | 11/1998 | Kovacs et al. |
| 5,836,887 A | 11/1998 | Oka et al. |
| 5,836,989 A | 11/1998 | Shelton |
| 5,837,454 A | 11/1998 | Cozzette et al. |
| 5,837,728 A | 11/1998 | Purcell |
| 5,840,020 A | 11/1998 | Heinonen et al. |
| 5,840,026 A | 11/1998 | Uber et al. |
| 5,840,148 A | 11/1998 | Campbell et al. |
| 5,851,197 A | 12/1998 | Marano et al. |
| 5,858,365 A | 1/1999 | Faller |
| 5,858,747 A | 1/1999 | Schinstine et al. |
| 5,861,019 A | 1/1999 | Sun et al. |
| 5,863,400 A | 1/1999 | Drummond et al. |
| 5,871,514 A | 2/1999 | Wiklund et al. |
| 5,872,198 A | 2/1999 | Mosbach et al. |
| 5,879,373 A | 3/1999 | Roper et al. |
| 5,882,354 A | 3/1999 | Brauker et al. |
| 5,882,494 A | 3/1999 | Van Antwerp |
| 5,895,235 A | 4/1999 | Droz |
| 5,897,525 A | 4/1999 | Dey et al. |
| 5,897,578 A | 4/1999 | Wiklund et al. |
| 5,899,855 A | 5/1999 | Brown |
| 5,904,708 A | 5/1999 | Goedeke |
| 5,910,554 A | 6/1999 | Kempe et al. |
| 5,911,219 A | 6/1999 | Aylsworth et al. |
| 5,913,998 A | 6/1999 | Butler et al. |
| 5,914,026 A | 6/1999 | Blubaugh, Jr. et al. |
| 5,917,346 A | 6/1999 | Gord |
| 5,919,215 A | 7/1999 | Wiklund et al. |
| 5,928,130 A | 7/1999 | Schmidt |
| 5,928,155 A | 7/1999 | Eggers et al. |
| 5,931,814 A | 8/1999 | Alex et al. |
| 5,933,136 A | 8/1999 | Brown |
| 5,944,661 A | 8/1999 | Swette et al. |
| 5,954,643 A | 9/1999 | Van Antwerp et al. |
| 5,954,954 A | 9/1999 | Houck et al. |
| 5,957,854 A | 9/1999 | Besson et al. |
| 5,957,903 A | 9/1999 | Mirzaee et al. |
| 5,959,050 A | 9/1999 | Mosbach et al. |
| 5,961,451 A | 10/1999 | Reber et al. |
| 5,963,132 A | 10/1999 | Yoakum |
| 5,964,261 A | 10/1999 | Neuenfeldt et al. |
| 5,964,745 A | 10/1999 | Lyles et al. |
| 5,964,804 A | 10/1999 | Brauker et al. |
| 5,964,993 A | 10/1999 | Blubaugh et al. |
| 5,965,380 A | 10/1999 | Heller et al. |
| 5,971,922 A | 10/1999 | Arita et al. |
| 5,972,199 A | 10/1999 | Heller |
| 5,976,085 A | 11/1999 | Kimball et al. |
| 5,987,352 A | 11/1999 | Klein et al. |
| 5,995,860 A | 11/1999 | Sun et al. |
| 5,999,848 A | 12/1999 | Gord et al. |
| 6,001,067 A | 12/1999 | Shults et al. |
| 6,001,471 A | 12/1999 | Bries et al. |
| 6,002,954 A | 12/1999 | Van Antwerp et al. |
| 6,011,984 A | 1/2000 | Van Antwerp et al. |
| 6,013,113 A | 1/2000 | Mika |
| 6,015,572 A | 1/2000 | Lin et al. |
| 6,016,448 A | 1/2000 | Busacker et al. |
| 6,017,435 A | 1/2000 | Hassard et al. |
| 6,024,720 A | 2/2000 | Chandler et al. |
| 6,027,445 A | 2/2000 | Von Bahr |
| 6,036,924 A | 3/2000 | Simons et al. |
| 6,043,328 A | 3/2000 | Domschke et al. |
| 6,049,727 A | 4/2000 | Crothall |
| 6,051,389 A | 4/2000 | Ahl et al. |
| 6,059,946 A | 5/2000 | Yukawa et al. |
| 6,063,637 A | 5/2000 | Arnold et al. |
| 6,066,448 A | 5/2000 | Wohlstadter et al. |
| 6,071,391 A | 6/2000 | Gotoh et al. |
| 6,074,775 A | 6/2000 | Gartstein et al. |
| 6,081,735 A | 6/2000 | Diab et al. |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,091,975 A | 7/2000 | Daddona et al. |
| 6,093,156 A | 7/2000 | Cunningham et al. |
| 6,093,172 A | 7/2000 | Funderburk et al. |
| 6,103,033 A | 8/2000 | Say et al. |
| 6,107,083 A | 8/2000 | Collins et al. |
| 6,115,634 A | 9/2000 | Donders et al. |
| 6,117,290 A | 9/2000 | Say |
| 6,119,028 A | 9/2000 | Schulman et al. |
| 6,120,676 A | 9/2000 | Heller et al. |
| 6,121,009 A | 9/2000 | Heller et al. |
| 6,122,536 A | 9/2000 | Sun et al. |
| 6,123,827 A | 9/2000 | Wong et al. |
| 6,134,461 A | 10/2000 | Say et al. |
| 6,135,978 A | 10/2000 | Houben et al. |
| 6,144,869 A | 11/2000 | Berner et al. |
| 6,144,871 A | 11/2000 | Saito et al. |
| RE36,991 E | 12/2000 | Yamamoto et al. |
| 6,159,186 A | 12/2000 | Wickham et al. |
| 6,162,611 A | 12/2000 | Heller et al. |
| 6,164,921 A | 12/2000 | Moubayed et al. |
| 6,167,614 B1 | 1/2001 | Tuttle et al. |
| 6,168,568 B1 | 1/2001 | Gavriely |
| 6,171,276 B1 | 1/2001 | Lippe et al. |
| 6,175,752 B1 | 1/2001 | Say et al. |
| 6,175,767 B1 | 1/2001 | Doyle et al. |
| 6,180,416 B1 | 1/2001 | Kurnik et al. |
| 6,183,437 B1 | 2/2001 | Walker |
| 6,187,062 B1 | 2/2001 | Oweis et al. |
| 6,189,536 B1 | 2/2001 | Martinez et al. |
| 6,191,860 B1 | 2/2001 | Klinger et al. |
| 6,201,980 B1 | 3/2001 | Darrow et al. |
| 6,201,993 B1 | 3/2001 | Kruse et al. |
| 6,206,856 B1 | 3/2001 | Mahurkar |
| 6,208,894 B1 | 3/2001 | Schulman et al. |
| 6,212,416 B1 | 4/2001 | Ward et al. |
| 6,212,424 B1 | 4/2001 | Robinson |
| 6,214,185 B1 | 4/2001 | Offenbacher et al. |
| 6,223,080 B1 | 4/2001 | Thompson |
| 6,223,083 B1 | 4/2001 | Rosar |
| 6,230,059 B1 | 5/2001 | Duffin |
| 6,232,783 B1 | 5/2001 | Merrill |
| 6,233,471 B1 | 5/2001 | Berner et al. |
| 6,241,863 B1 | 6/2001 | Monbouquette |
| 6,248,067 B1 | 6/2001 | Causey, III et al. |
| 6,251,280 B1 | 6/2001 | Dai et al. |
| 6,254,586 B1 | 7/2001 | Mann et al. |
| 6,256,522 B1 | 7/2001 | Schultz |
| 6,259,937 B1 | 7/2001 | Schulman et al. |
| 6,263,222 B1 | 7/2001 | Diab et al. |

(56) References Cited

U.S. PATENT DOCUMENTS

| | | |
|---|---|---|
| 6,264,825 B1 | 7/2001 | Blackburn et al. |
| 6,268,161 B1 | 7/2001 | Han et al. |
| 6,270,478 B1 | 8/2001 | Mern et al. |
| 6,272,364 B1 | 8/2001 | Kurnik |
| 6,272,480 B1 | 8/2001 | Tresp et al. |
| 6,275,717 B1 | 8/2001 | Gross et al. |
| 6,280,408 B1 | 8/2001 | Sipin |
| 6,284,478 B1 | 9/2001 | Heller et al. |
| 6,293,925 B1 | 9/2001 | Safabash et al. |
| 6,294,281 B1 | 9/2001 | Heller |
| 6,299,578 B1 | 10/2001 | Kurnik et al. |
| 6,299,583 B1 | 10/2001 | Eggers et al. |
| 6,300,002 B1 | 10/2001 | Webb et al. |
| 6,302,855 B1 | 10/2001 | Lav et al. |
| 6,309,351 B1 | 10/2001 | Kurnik et al. |
| 6,309,884 B1 | 10/2001 | Cooper et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,358,225 B1 | 3/2002 | Butterfield |
| 6,360,888 B1 | 3/2002 | McIvor et al. |
| 6,366,794 B1 | 4/2002 | Moussy et al. |
| 6,368,141 B1 | 4/2002 | VanAntwerp et al. |
| 6,368,274 B1 | 4/2002 | Van Antwerp et al. |
| 6,370,941 B2 | 4/2002 | Nakamura et al. |
| 6,379,301 B1 | 4/2002 | Worthington et al. |
| 6,383,478 B1 | 5/2002 | Prokop et al. |
| 6,400,974 B1 | 6/2002 | Lesho |
| 6,402,703 B1 | 6/2002 | Kensey et al. |
| 6,405,066 B1 | 6/2002 | Essenpreis et al. |
| 6,406,066 B1 | 6/2002 | Uegane |
| 6,406,426 B1 | 6/2002 | Reuss et al. |
| 6,409,674 B1 | 6/2002 | Brockway et al. |
| 6,413,393 B1 | 7/2002 | Van Antwerp et al. |
| 6,416,651 B1 | 7/2002 | Millar |
| 6,418,332 B1 | 7/2002 | Mastrototaro et al. |
| 6,424,847 B1 | 7/2002 | Mastrototaro et al. |
| 6,430,437 B1 | 8/2002 | Marro |
| 6,447,448 B1 | 9/2002 | Ishikawa et al. |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,464,849 B1 | 10/2002 | Say et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,045 B1 | 11/2002 | Holker et al. |
| 6,484,046 B1 | 11/2002 | Say et al. |
| 6,494,830 B1 | 12/2002 | Wessel |
| 6,498,043 B1 | 12/2002 | Schulman et al. |
| 6,498,941 B1 | 12/2002 | Jackson |
| 6,510,329 B2 | 1/2003 | Heckel |
| 6,512,939 B1 | 1/2003 | Colvin et al. |
| 6,520,326 B2 | 2/2003 | McIvor et al. |
| 6,526,298 B1 | 2/2003 | Khalil et al. |
| 6,527,729 B1 | 3/2003 | Turcott |
| 6,534,711 B1 | 3/2003 | Pollack |
| 6,542,765 B1 | 4/2003 | Guy et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,554,805 B2 | 4/2003 | Hiejima |
| 6,554,822 B1 | 4/2003 | Holschneider et al. |
| 6,558,320 B1 | 5/2003 | Causey |
| 6,558,321 B1 | 5/2003 | Burd et al. |
| 6,558,347 B1 | 5/2003 | Jhuboo et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,565,807 B1 | 5/2003 | Patterson et al. |
| 6,569,309 B2 | 5/2003 | Otsuka et al. |
| 6,569,521 B1 | 5/2003 | Sheridan et al. |
| 6,572,545 B2 | 6/2003 | Knobbe et al. |
| 6,572,579 B1 | 6/2003 | Raghavan et al. |
| 6,574,490 B2 | 6/2003 | Abbink et al. |
| 6,575,905 B2 | 6/2003 | Knobbe et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,072 B2 | 8/2003 | Struys et al. |
| 6,607,509 B2 | 8/2003 | Bobroff et al. |
| 6,612,984 B1 | 9/2003 | Kerr |
| 6,613,379 B2 | 9/2003 | Ward et al. |
| 6,618,603 B2 | 9/2003 | Varalli et al. |
| 6,618,934 B1 | 9/2003 | Feldman et al. |
| 6,633,772 B2 | 10/2003 | Ford et al. |
| 6,641,533 B2 * | 11/2003 | Causey et al. .......... 600/300 |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,656,157 B1 | 12/2003 | Duchon et al. |
| 6,673,022 B1 | 1/2004 | Bobo et al. |
| 6,673,596 B1 | 1/2004 | Sayler et al. |
| 6,679,872 B2 | 1/2004 | Turovskiy et al. |
| 6,683,535 B1 | 1/2004 | Utke |
| 6,689,265 B2 | 2/2004 | Heller et al. |
| 6,694,191 B2 | 2/2004 | Starkweather et al. |
| 6,695,860 B1 | 2/2004 | Ward et al. |
| 6,699,188 B2 | 3/2004 | Wessel |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,702,972 B1 | 3/2004 | Markle |
| 6,721,587 B2 | 4/2004 | Gough |
| 6,730,200 B1 | 5/2004 | Stewart et al. |
| 6,731,976 B2 | 5/2004 | Penn et al. |
| 6,737,158 B1 | 5/2004 | Thompson |
| 6,740,075 B2 | 5/2004 | Lebel et al. |
| 6,741,877 B1 | 5/2004 | Shults et al. |
| 6,743,635 B2 | 6/2004 | Neel et al. |
| 6,749,587 B2 | 6/2004 | Flaherty |
| 6,770,030 B1 | 8/2004 | Schaupp et al. |
| 6,770,067 B2 | 8/2004 | Lorenzen et al. |
| 6,773,565 B2 | 8/2004 | Kunimoto et al. |
| 6,784,274 B2 | 8/2004 | van Antwerp et al. |
| 6,801,041 B2 | 10/2004 | Karinka et al. |
| 6,802,957 B2 | 10/2004 | Jung et al. |
| 6,805,693 B2 | 10/2004 | Gray et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,813,519 B2 | 11/2004 | Lebel et al. |
| 6,814,845 B2 | 11/2004 | Wilson et al. |
| 6,850,790 B2 | 2/2005 | Berner et al. |
| 6,862,465 B2 | 3/2005 | Shults et al. |
| 6,869,413 B2 | 3/2005 | Langley et al. |
| 6,887,228 B2 | 5/2005 | Mckay |
| 6,892,085 B2 | 5/2005 | McIvor et al. |
| 6,893,552 B1 | 5/2005 | Wang et al. |
| 6,895,263 B2 | 5/2005 | Shin et al. |
| 6,925,393 B1 | 8/2005 | Kalatz et al. |
| 6,931,327 B2 | 8/2005 | Goode et al. |
| 6,948,492 B2 | 9/2005 | Wermeling et al. |
| 6,952,604 B2 | 10/2005 | DeNuzzio et al. |

(56) References Cited

U.S. PATENT DOCUMENTS

| | | |
|---|---|---|
| 6,954,662 B2 | 10/2005 | Freger et al. |
| 6,960,192 B1 | 11/2005 | Flaherty et al. |
| 6,965,791 B1 | 11/2005 | Hitchcock et al. |
| 6,966,325 B2 | 11/2005 | Erickson |
| 6,972,080 B1 | 12/2005 | Tomioka et al. |
| 6,989,891 B2 | 1/2006 | Braig et al. |
| 6,997,921 B2 | 2/2006 | Gray et al. |
| 6,998,247 B2 | 2/2006 | Monfre et al. |
| 7,003,336 B2 | 2/2006 | Holker et al. |
| 7,003,341 B2 | 2/2006 | Say et al. |
| 7,008,979 B2 | 3/2006 | Schottman et al. |
| 7,011,630 B2 | 3/2006 | Desai et al. |
| 7,025,727 B2 | 4/2006 | Brockway et al. |
| 7,025,743 B2 | 4/2006 | Mann et al. |
| 7,029,444 B2 | 4/2006 | Shin et al. |
| 7,060,059 B2 | 6/2006 | Keith et al. |
| 7,061,593 B2 | 6/2006 | Braig et al. |
| 7,063,086 B2 | 6/2006 | Shahbazpour et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,115,884 B1 | 10/2006 | Walt et al. |
| 7,131,967 B2 | 11/2006 | Gray et al. |
| 7,134,999 B2 | 11/2006 | Brauker et al. |
| 7,150,741 B2 | 12/2006 | Erickson et al. |
| 7,153,265 B2 | 12/2006 | Vachon |
| 7,169,289 B2 | 1/2007 | Schulein et al. |
| 7,190,988 B2 | 3/2007 | Say et al. |
| 7,192,450 B2 | 3/2007 | Brauker et al. |
| 7,207,974 B2 | 4/2007 | Safabash et al. |
| 7,223,253 B2 | 5/2007 | Hogendijk |
| 7,229,288 B2 | 6/2007 | Stuart et al. |
| 7,238,165 B2 | 7/2007 | Vincent et al. |
| 7,248,906 B2 | 7/2007 | Dirac et al. |
| 7,255,690 B2 | 8/2007 | Gray et al. |
| 7,261,690 B2 | 8/2007 | Teller et al. |
| 7,266,400 B2 | 9/2007 | Fine et al. |
| 7,267,665 B2 | 9/2007 | Steil et al. |
| 7,276,029 B2 | 10/2007 | Goode et al. |
| 7,278,983 B2 | 10/2007 | Ireland et al. |
| 7,295,867 B2 | 11/2007 | Berner et al. |
| 7,310,544 B2 | 12/2007 | Brister et al. |
| 7,311,690 B2 | 12/2007 | Burnett |
| 7,313,425 B2 | 12/2007 | Finarov et al. |
| 7,316,662 B2 | 1/2008 | Delnevo et al. |
| 7,327,273 B2 | 2/2008 | Hung et al. |
| 7,338,464 B2 | 3/2008 | Blischak et al. |
| 7,354,420 B2 | 4/2008 | Steil et al. |
| 7,359,723 B2 | 4/2008 | Jones |
| 7,364,562 B2 | 4/2008 | Braig et al. |
| 7,366,556 B2 | 4/2008 | Brister et al. |
| 7,381,184 B2 | 6/2008 | Funderburk et al. |
| 7,396,353 B2 | 7/2008 | Lorenzen et al. |
| 7,399,277 B2 | 7/2008 | Saidara et al. |
| 7,402,153 B2 | 7/2008 | Steil et al. |
| 7,417,164 B2 | 8/2008 | Suri |
| 7,424,318 B2 | 9/2008 | Brister et al. |
| 7,426,408 B2 | 9/2008 | DeNuzzio et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,583,990 B2 | 9/2009 | Goode, Jr. et al. |
| 7,587,287 B2 | 9/2009 | Connolly et al. |
| 7,591,801 B2 | 9/2009 | Brauker et al. |
| 7,599,726 B2 | 10/2009 | Goode, Jr. et al. |
| 7,618,368 B2 | 11/2009 | Brown |
| 7,624,028 B1 | 11/2009 | Brown |
| 7,636,602 B2 | 12/2009 | Baru Fassio et al. |
| 7,640,048 B2 | 12/2009 | Dobbles et al. |
| 7,647,237 B2 | 1/2010 | Malave et al. |
| 7,711,402 B2 | 5/2010 | Shults et al. |
| 7,771,352 B2 | 8/2010 | Shults et al. |
| 7,774,145 B2 | 8/2010 | Brauker et al. |
| 7,792,562 B2 | 9/2010 | Shults et al. |
| 8,206,297 B2 | 6/2012 | Kamath et al. |
| 8,229,535 B2 | 7/2012 | Mensinger et al. |
| 8,527,025 B1 | 9/2013 | Shults et al. |
| 2001/0016682 A1 | 8/2001 | Berner et al. |
| 2001/0041830 A1 | 11/2001 | Varalli et al. |
| 2001/0051768 A1 | 12/2001 | Schulman et al. |
| 2002/0009810 A1 | 1/2002 | O'Connor et al. |
| 2002/0018843 A1 | 2/2002 | Van Antwerp et al. |
| 2002/0019022 A1 | 2/2002 | Dunn et al. |
| 2002/0019330 A1 | 2/2002 | Murray et al. |
| 2002/0023852 A1 | 2/2002 | McIvor et al. |
| 2002/0026111 A1 | 2/2002 | Ackerman |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0065453 A1 | 5/2002 | Lesho et al. |
| 2002/0068860 A1 | 6/2002 | Clark, Jr. |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0106709 A1 | 8/2002 | Potts et al. |
| 2002/0111547 A1 | 8/2002 | Knobbe et al. |
| 2002/0119711 A1 | 8/2002 | Van Antwerp et al. |
| 2002/0155615 A1 | 10/2002 | Novikov et al. |
| 2002/0161288 A1* | 10/2002 | Shin et al. ............... 600/316 |
| 2002/0177763 A1 | 11/2002 | Burns et al. |
| 2002/0188185 A1 | 12/2002 | Sohrab |
| 2002/0198513 A1 | 12/2002 | Lebel et al. |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0028089 A1 | 2/2003 | Galley et al. |
| 2003/0032874 A1 | 2/2003 | Rhodes et al. |
| 2003/0036773 A1 | 2/2003 | Whitehurst et al. |
| 2003/0050537 A1 | 3/2003 | Wessel |
| 2003/0050546 A1 | 3/2003 | Desai et al. |
| 2003/0059631 A1 | 3/2003 | Al/Lamee |
| 2003/0060765 A1 | 3/2003 | Campbell et al. |
| 2003/0065254 A1 | 4/2003 | Schulman et al. |
| 2003/0069383 A1 | 4/2003 | Van Antwerp et al. |
| 2003/0070548 A1 | 4/2003 | Clausen |
| 2003/0072741 A1 | 4/2003 | Berglund et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0099682 A1 | 5/2003 | Moussy et al. |
| 2003/0100040 A1 | 5/2003 | Bonnecaze et al. |
| 2003/0100821 A1 | 5/2003 | Heller et al. |
| 2003/0104119 A1 | 6/2003 | Wilson et al. |
| 2003/0117296 A1 | 6/2003 | Seely |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0132227 A1 | 7/2003 | Geisler |
| 2003/0134347 A1 | 7/2003 | Heller et al. |
| 2003/0138674 A1 | 7/2003 | Zeikus et al. |
| 2003/0176183 A1 | 9/2003 | Drucker et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199878 A1 | 10/2003 | Pohjonen |
| 2003/0200040 A1 | 10/2003 | Trygg et al. |
| 2003/0203498 A1 | 10/2003 | Neel et al. |
| 2003/0208113 A1 | 11/2003 | Mault et al. |
| 2003/0211625 A1 | 11/2003 | Cohan |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0217966 A1 | 11/2003 | Tapsak et al. |
| 2003/0225437 A1 | 12/2003 | Ferguson |
| 2003/0228681 A1 | 12/2003 | Ritts et al. |

(56) References Cited

U.S. PATENT DOCUMENTS

| | | |
|---|---|---|
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0023253 A1 | 2/2004 | Kunwar et al. |
| 2004/0024327 A1 | 2/2004 | Brodnick |
| 2004/0030285 A1 | 2/2004 | Lavi et al. |
| 2004/0030294 A1 | 2/2004 | Mahurkar |
| 2004/0039298 A1 | 2/2004 | Abreu |
| 2004/0039406 A1 | 2/2004 | Jessen |
| 2004/0045879 A1 | 3/2004 | Shults et al. |
| 2004/0054352 A1 | 3/2004 | Adams et al. |
| 2004/0068230 A1 | 4/2004 | Estes et al. |
| 2004/0074785 A1 | 4/2004 | Holker |
| 2004/0078219 A1 | 4/2004 | Kaylor |
| 2004/0106857 A1 | 6/2004 | Gough |
| 2004/0106859 A1 | 6/2004 | Say et al. |
| 2004/0133164 A1 | 7/2004 | Funderburk et al. |
| 2004/0143173 A1 | 7/2004 | Reghabi et al. |
| 2004/0146909 A1 | 7/2004 | Duong et al. |
| 2004/0152187 A1 | 8/2004 | Haight et al. |
| 2004/0152622 A1 | 8/2004 | Keith et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0199059 A1 | 10/2004 | Brauker et al. |
| 2004/0204687 A1 | 10/2004 | Mogensen |
| 2004/0219664 A1 | 11/2004 | Heller et al. |
| 2004/0236200 A1 | 11/2004 | Say et al. |
| 2004/0236251 A1 | 11/2004 | Roe et al. |
| 2004/0242982 A1 | 12/2004 | Sakata et al. |
| 2004/0253365 A1 | 12/2004 | Warren et al. |
| 2004/0254433 A1 | 12/2004 | Bandis |
| 2005/0003399 A1 | 1/2005 | Blackburn et al. |
| 2005/0006122 A1 | 1/2005 | Burnette |
| 2005/0010265 A1 | 1/2005 | Baru Fassio |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode, Jr. et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056551 A1 | 3/2005 | White et al. |
| 2005/0056552 A1 | 3/2005 | Simpson et al. |
| 2005/0065464 A1 | 3/2005 | Talbot et al. |
| 2005/0070770 A1 | 3/2005 | Dirac et al. |
| 2005/0090607 A1 | 4/2005 | Tapsak et al. |
| 2005/0096519 A1 | 5/2005 | DeNuzzio et al. |
| 2005/0101847 A1 | 5/2005 | Routt et al. |
| 2005/0112169 A1 | 5/2005 | Brauker et al. |
| 2005/0113653 A1 | 5/2005 | Fox et al. |
| 2005/0115832 A1 | 6/2005 | Simpson et al. |
| 2005/0121322 A1 | 6/2005 | Say |
| 2005/0124873 A1 | 6/2005 | Shults et al. |
| 2005/0133368 A1 | 6/2005 | Davies et al. |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182451 A1 | 8/2005 | Griffin et al. |
| 2005/0183954 A1 | 8/2005 | Hitchcock et al. |
| 2005/0187720 A1 | 8/2005 | Goode et al. |
| 2005/0192557 A1 | 9/2005 | Brauker et al. |
| 2005/0195930 A1 | 9/2005 | Spital et al. |
| 2005/0203360 A1 | 9/2005 | Brauker et al. |
| 2005/0211571 A1 | 9/2005 | Schulein et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0251083 A1 | 11/2005 | Carr/Brendel et al. |
| 2005/0258037 A1 | 11/2005 | Hajizadeh et al. |
| 2005/0261563 A1 | 11/2005 | Zhou et al. |
| 2005/0272989 A1 | 12/2005 | Shah et al. |
| 2006/0001550 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1* | 2/2006 | Talbot .............. A61B 5/0002 600/365 |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0067908 A1 | 3/2006 | Ding |
| 2006/0079740 A1 | 4/2006 | Silver et al. |
| 2006/0079809 A1 | 4/2006 | Goldberger et al. |
| 2006/0094946 A1 | 5/2006 | Kellogg et al. |
| 2006/0100588 A1 | 5/2006 | Brunnberg et al. |
| 2006/0155180 A1 | 7/2006 | Brister et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0200020 A1 | 9/2006 | Brister et al. |
| 2006/0222566 A1 | 10/2006 | Brauker et al. |
| 2006/0224141 A1 | 10/2006 | Rush et al. |
| 2006/0229512 A1 | 10/2006 | Petisce et al. |
| 2006/0235285 A1 | 10/2006 | Brister et al. |
| 2006/0258761 A1 | 11/2006 | Boock et al. |
| 2006/0258929 A1 | 11/2006 | Goode et al. |
| 2006/0270922 A1 | 11/2006 | Brauker et al. |
| 2006/0270923 A1 | 11/2006 | Brauker et al. |
| 2006/0272958 A1 | 12/2006 | Lee |
| 2006/0281985 A1 | 12/2006 | Ward et al. |
| 2006/0293487 A1 | 12/2006 | Gaymans et al. |
| 2007/0016381 A1 | 1/2007 | Kamath et al. |
| 2007/0017805 A1 | 1/2007 | Hodges et al. |
| 2007/0032706 A1 | 2/2007 | Kamath et al. |
| 2007/0038044 A1 | 2/2007 | Dobbles et al. |
| 2007/0045902 A1 | 3/2007 | Brauker et al. |
| 2007/0049873 A1 | 3/2007 | Hansen et al. |
| 2007/0066873 A1 | 3/2007 | Kamath et al. |
| 2007/0085995 A1 | 4/2007 | Pesach et al. |
| 2007/0129524 A1 | 6/2007 | Sunkara |
| 2007/0129621 A1 | 6/2007 | Kellogg et al. |
| 2007/0135698 A1 | 6/2007 | Shah et al. |
| 2007/0173710 A1 | 7/2007 | Petisce et al. |
| 2007/0173711 A1 | 7/2007 | Shah et al. |
| 2007/0197889 A1 | 8/2007 | Brister et al. |
| 2007/0200254 A1 | 8/2007 | Curry |
| 2007/0202672 A1 | 8/2007 | Curry |
| 2007/0203407 A1 | 8/2007 | Hoss et al. |
| 2007/0203410 A1 | 8/2007 | Say et al. |

(56) References Cited

U.S. PATENT DOCUMENTS

| | | |
|---|---|---|
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0213611 A1 | 9/2007 | Simpson et al. |
| 2007/0232876 A1 | 10/2007 | Otto et al. |
| 2007/0232879 A1 | 10/2007 | Brister et al. |
| 2007/0235331 A1 | 10/2007 | Simpson et al. |
| 2007/0244382 A1 | 10/2007 | Robinson et al. |
| 2007/0259217 A1 | 11/2007 | Logan |
| 2007/0275193 A1 | 11/2007 | DeSimone et al. |
| 2007/0299409 A1 | 12/2007 | Whitbourne et al. |
| 2008/0021666 A1 | 1/2008 | Goode et al. |
| 2008/0027245 A1 | 1/2008 | Suri |
| 2008/0033254 A1 | 2/2008 | Kamath et al. |
| 2008/0045824 A1 | 2/2008 | Tapsak et al. |
| 2008/0071157 A1 | 3/2008 | Mcgarraugh et al. |
| 2008/0071158 A1 | 3/2008 | Mcgarraugh et al. |
| 2008/0072663 A1 | 3/2008 | Keenan et al. |
| 2008/0086040 A1 | 4/2008 | Heller et al. |
| 2008/0086041 A1 | 4/2008 | Heller et al. |
| 2008/0086043 A1 | 4/2008 | Heller et al. |
| 2008/0091094 A1 | 4/2008 | Heller et al. |
| 2008/0091095 A1 | 4/2008 | Heller et al. |
| 2008/0154101 A1 | 6/2008 | Jain et al. |
| 2008/0183061 A1 | 7/2008 | Goode et al. |
| 2008/0183399 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195967 A1 | 8/2008 | Goode et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005666 A1 | 1/2009 | Shin et al. |
| 2009/0012379 A1 | 1/2009 | Goode et al. |
| 2009/0018418 A1 | 1/2009 | Markle et al. |
| 2009/0018426 A1 | 1/2009 | Markle et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054748 A1* | 2/2009 | Feldman .............. A61B 5/0031 600/316 |
| 2009/0061528 A1 | 3/2009 | Suri |
| 2009/0062633 A1 | 3/2009 | Brauker et al. |
| 2009/0062635 A1 | 3/2009 | Brauker et al. |
| 2009/0076356 A1 | 3/2009 | Simpson |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0099436 A1 | 4/2009 | Brister et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0143660 A1 | 6/2009 | Brister et al. |
| 2009/0156924 A1 | 6/2009 | Shariati et al. |
| 2009/0177143 A1 | 7/2009 | Markle et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247857 A1 | 10/2009 | Harper et al. |
| 2009/0264719 A1 | 10/2009 | Markle et al. |
| 2009/0264856 A1 | 10/2009 | Lebel et al. |
| 2009/0287074 A1 | 11/2009 | Shults et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0045465 A1 | 2/2010 | Brauker et al. |
| 2010/0081908 A1 | 4/2010 | Dobbles et al. |
| 2010/0161269 A1 | 6/2010 | Kamath et al. |
| 2010/0174158 A1 | 7/2010 | Kamath et al. |
| 2010/0174167 A1 | 7/2010 | Kamath et al. |
| 2010/0174168 A1 | 7/2010 | Goode, Jr. et al. |
| 2010/0179399 A1 | 7/2010 | Goode, Jr. et al. |
| 2010/0179405 A1 | 7/2010 | Goode, Jr. et al. |
| 2010/0179406 A1 | 7/2010 | Goode, Jr. et al. |
| 2010/0185065 A1 | 7/2010 | Goode, Jr. et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0204555 A1 | 8/2010 | Shults et al. |
| 2010/0214104 A1 | 8/2010 | Goode, Jr. et al. |
| 2010/0217106 A1 | 8/2010 | Goode, Jr. et al. |
| 2010/0217555 A1 | 8/2010 | Kamath et al. |
| 2010/0217557 A1 | 8/2010 | Kamath et al. |
| 2010/0234796 A1 | 9/2010 | Kamath et al. |
| 2011/0231141 A1 | 9/2011 | Goode et al. |
| 2012/0215462 A1 | 8/2012 | Goode et al. |

FOREIGN PATENT DOCUMENTS

| | | |
|---|---|---|
| EP | 0 127 958 | 12/1984 |
| EP | 0 284 518 | 9/1988 |
| EP | 0 320 109 | 6/1989 |
| EP | 0 353 328 | 2/1990 |
| EP | 0 390 390 | 10/1990 |
| EP | 0 396 788 | 11/1990 |
| EP | 0 476 980 | 3/1992 |
| EP | 0 535 898 | 4/1993 |
| EP | 0 561 966 | 10/1994 |
| EP | 0 776 628 | 6/1997 |
| EP | 0 838 230 | 4/1998 |
| EP | 0 880 936 | 12/1998 |
| EP | 0 967 788 | 12/1999 |
| EP | 1 078 258 | 2/2001 |
| EP | 1 153 571 | 11/2001 |

(56) References Cited

FOREIGN PATENT DOCUMENTS

| | | |
|---|---|---|
| FR | 2656423 | 6/1991 |
| FR | 2760962 | 9/1998 |
| GB | 2149918 | 6/1985 |
| JP | 62083649 | 4/1987 |
| JP | 02002913 | 1/1990 |
| JP | 3/293556 | 12/1991 |
| JP | 2002/189015 | 7/2002 |
| WO | WO 89/02720 | 4/1989 |
| WO | WO 90/10861 | 9/1990 |
| WO | WO 90/13021 | 11/1990 |
| WO | WO 91/09302 | 6/1991 |
| WO | WO 92/07525 | 5/1992 |
| WO | WO 92/10584 | 6/1992 |
| WO | WO 93/14693 | 8/1993 |
| WO | WO 93/23744 | 11/1993 |
| WO | WO 96/03117 | 2/1996 |
| WO | WO 96/14026 | 5/1996 |
| WO | WO 96/25089 | 8/1996 |
| WO | WO 97/01986 | 1/1997 |
| WO | WO 97/06727 | 2/1997 |
| WO | WO 97/19188 | 5/1997 |
| WO | WO 97/28737 | 8/1997 |
| WO | WO 97/38625 | 10/1997 |
| WO | WO 98/24358 | 6/1998 |
| WO | WO 98/38906 | 9/1998 |
| WO | WO 99/56613 | 4/1999 |
| WO | WO 99/48419 | 9/1999 |
| WO | WO 99/58051 | 11/1999 |
| WO | WO 99/58973 | 11/1999 |
| WO | WO 00/13003 | 3/2000 |
| WO | WO 00/19887 | 4/2000 |
| WO | WO 00/32098 | 6/2000 |
| WO | WO 00/33065 | 6/2000 |
| WO | WO 00/49941 | 8/2000 |
| WO | WO 00/59373 | 10/2000 |
| WO | WO 00/74753 | 12/2000 |
| WO | WO 01/12158 | 2/2001 |
| WO | WO 01/16579 | 3/2001 |
| WO | WO 01/20334 | 3/2001 |
| WO | WO 01/52727 | 7/2001 |
| WO | WO 01/58348 | 8/2001 |
| WO | WO 01/88534 | 11/2001 |
| WO | WO 02/24065 | 3/2002 |
| WO | WO 02/082989 | 10/2002 |
| WO | WO 02/100266 | 12/2002 |
| WO | WO 03/016882 | 2/2003 |
| WO | WO 2005/026689 | 10/2005 |
| WO | WO 2006/105146 | 10/2006 |
| WO | WO 2008/001091 | 1/2008 |

OTHER PUBLICATIONS

Aalders et al. 1991. Development of a wearable glucose sensor; studies in healthy volunteers and in diabetic patients. The International Journal of Artificial Organs 14(2):102/108.
Abe et al. 1992. Characterization of glucose microsensors for intracellular measurements. Alan. Chem. 64(18):2160/2163.
Abel et al. 2002. Biosensors for in vivo glucose measurement: can we cross the experimental stage. Biosens Bioelectron 17:1059/1070.
Amin et al. 2003. Hypoglycemia prevalence in prepubertal children with type 1 diabetes on standard insulin regimen: Use of continuous glucose monitoring system. Diabetes Care 26(3):662/667.
Answers.com. "xenogenic." The American Heritage Stedman's Medical Dictionary. Houghton Mifflin Company, 2002. Answers.com Nov. 7, 2006 http://www.Answers.com/topic/xenogenic.
Armour et al. Dec. 1990. Application of Chronic Intravascular Blood Glucose Sensor in Dogs. Diabetes 39:1519/1526.
Atanasov et al. 1994. Biosensor for continuous glucose monitoring. Biotechnology and Bioengineering and Bioengineering 43:262/266.
Atanasov et al. 1997. Implantation of a refillable glucose monitoring/telemetry device. Biosens Bioelectron 12:669/680.

Aussedat et al. 1997. A user/friendly method for calibrating a subcutaneous glucose sensor/based hypoglycaemic alarm. Biosensors & Bioelectronics 12(11):1061/1071.
Bailey et al. 2007. Reduction in hemoglobin A1c with real/time continuous glucose monitoring: results from a 12/week observational study. Diabetes Technology & Therapeutics 9(3):203/210.
Baker et al. 1993. Dynamic concentration challenges for biosensor characterization. Biosensors & Bioelectronics 8:433/441.
Baker et al. 1996. Dynamic delay and maximal dynamic error in continuous biosensors. Anal Chem 68(8):1292/1297.
Bani Amer, M. M. 2002. An accurate amperometric glucose sensor based glucometer with eliminated cross/sensitivity. J Med Eng Technol 26(5):208/213.
Bard et al. 1980. Electrochemical Methods. John Wiley & Sons, pp. 173/175.
Beach et al. 1999. Subminiature implantable potentiostat and modified commercial telemetry device for remote glucose monitoring. IEEE Transactions on Instrumentation and Measurement 48(6):1239/1245.
Bellucci et al. Jan. 1986. Electrochemical behaviour of graphite/epoxy composite materials (GECM) in aqueous salt solutions, Journal of Applied Electrochemistry, 16(1):15/22.
Biermann et al. 2008. How would patients behave if they were continually informed of their blood glucose levels? A simulation study using a "virtual" patient. Diab. Thechnol. & Therapeut., 10:178/187.
Bindra et al. 1991. Design and in Vitro Studies of a Needle/Type Glucose Senso for Subcutaneous Monitoring. Anal. Chem 63:1692/96.
Bisenberger et al. 1995. A triple/step potential waveform at enzyme multisensors with thick/film gold electrodes for detection of glucose and sucrose. Sensors and Actuators, B 28:181/189.
Bland et al. 1986. Statistical methods for assessing agreement between two methods of clinical measurement. Lancet 1:307/310.
Bland et al. 1990. A note on the use of the intraclass correlation coefficient in the evaluation of agreement between two methods of measurement. Comput. Biol. Med. 20(5):337/340.
Bobbioni/Harsch et al. 1993. Lifespan of subcutaneous glucose sensors and their performances during dynamic glycaemia changes in rats, J. Biomed. Eng. 15:457/463.
Bode et al. 1999. Continuous glucose monitoring used to adjust diabetes therapy improves glycisylated hemoglobin: A pilot study. Diabetes Research and Clinical Practice 46:183/190.
Bode et al. 2000. Using the continuous glucose monitoring system to improve the management of type 1 diabetes. Diabetes Technology & Therapeutics, 2(Suppl 1):S43/48.
Bode, B. W. 2000. Clinical utility of the continuous glucose monitoring system. Diabetes Technol Ther, 2(Suppl 1):S35/41.
Boland et al. 2001. Limitations of conventional methods of self/monitoring of blood glucose. Diabetes Care 24(11):1858/1862.
Bolinder et al. 1992. Microdialysis measurement of the absolute glucose concentration in subcutaneous adipose tissue allowing glucose monitoring in diabetic patients. Diabetologia 35:1177/1180.
Bolinder et al. 1997. Self/monitoring of blood glucose in type 1 diabetic patients: Comparison with continuous microdialysis measurements of glucose in subcutaneous adipose tissue during ordinary life conditions. Diabetes Care 20(1):64/70.
Bott, A. 1998. Electrochemical methods for the determination of glucose. Current Separations 17(1):25/31.
Bowman, L.; Meindl, J. D. 1986. The packaging of implantable integrated sensors. IEEE Trans Biomed Eng BME33(2):248/255.
Brauker et al. Jun. 27, 1996. Local Inflammatory Response Around Diffusion Chambers Containing Xenografts Transplantation 61(12):1671/1677.
Bremer et al. 1999. Is blood glucose predictable from previous values? A solicitation for data. Diabetes 48:445/451.
Bremer et al. 2001. Benchmark data from the literature for evaluation of new glucose sensing technologies. Diabetes Technology & Therapeutics 3(3):409/418.
Brooks et al. "Development of an on/line glucose sensor for fermentation monitoring," Biosensors, 3:45/56 (1987/88).

(56) References Cited

OTHER PUBLICATIONS

Bruckel et al. 1989. In vivo measurement of subcutaneous glucose concentrations with an enzymatic glucose sensor and a wick method. Klin Wochenschr 67:491/495.
Brunstein et al. 1989. Preparation and validation of implantable electrodes for the measurement of oxygen and glucose. Biomed Biochim. Acta 48(11/12):911/917.
Cai et al. 2004. A wireless, remote query glucose biosensor based on a pH/sensitive polymer. Anal Chem 76(4):4038/4043.
Cameron et al. 1997. Micromodular Implants to provide electrical stimulation of paralyzed muscles and limbs. IEEE Transactions on Biomedical Engineering 44(9):781/790.
Campanella et al. 1993. Biosensor for direct determination of glucose and lactate in undiluted biological fluids. Biosensors & Bioelectronics 8:307/314.
Candas et al (1994). "An adaptive plasma glucose controller basedon on a nonlinear insulin/glucose model." IEEE Transactions on Biomedical Engineering, 41(2): 116/124.
Cass et al. "Ferrocene/mediated enzyme electrodes for amperometric determination of glucose," Anal. Chem., 36:667/71 (1984).
Chase et al. 2001. Continuous subcutaneous glucose monitoring in children with type 1 diabetes. Pediatrics 107:222/226.
Chen et al. 2002. Defining the period of recovery of the glucose concentration after its local perturbation by the implantation of a miniature sensor. Clin. Chem. Lab. Med. 40:786/789.
Chia et al. 2004. Glucose sensors: toward closed loop insulin delivery. Endocrinol Metab Clin North Am 33:175/95.
Choleau et al. 2002. Calibration of a subcutaneous amperometric glucose sensor implanted for 7 days in diabetic patients. Part 1. Effect of measurement uncertainties on the determination of sensor sensitivity and background current . Biosensors and Bioelectronics 14:641/646.
Choleau et al. 2002. Calibration of a subcutaneous amperometric glucose sensor implanted for 7 days in diabetic patients. Part 2. Superiority of the one/point calibration method. Biosensors and Bioelectronics 17:647/654.
Ciba® Irgacure 2959 Photoinitiator Product Description, Ciba Specialty Chemicals Inc., Basel, Switzerland.
Claremont et al. 1986. Subcutaneous implantation of a ferrocene/ mediated glucose sensor in pigs. Diabetologia 29:817/821.
Claremont et al. Jul. 1986. Potentially/impintable, ferrocene/mediated glucose sensor. J. Biomed. Eng. 8:272/274.
Clark et al. 1987. Configurational cyclic voltammetry: increasing the specificity and reliablity of implanted electrodes, IEEE/Ninth Annual Conference of the Engineering in Medicine and Biollogy Society, pp. 0782/0783.
Clark et al. 1988. Long/term stability of electroenzymatic glucose sensors implanted in mice. Trans Am Soc Artif Intern Organs 34:259/265.
Clarke et al. Sep./Oct. 1987. Evaluating Clinical Accuracy of Systems for Self/Monitoring of Blood Glucose. Diabetes Care 10(5):622/628.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529/536.
Csöregi et al. 1994. Amperometric microbiosensors for detection of hydrogen peroxide and glucose based on peroxidase/modified carbon fibers. Electroanalysis 6:925/933.
Csoregi et al., 1994. Design, characterization, and one/point in vivo calibration of a subcutaneously implanted glucose electrode. Anal Chem. 66(19):3131/3138.
Davies, et al. 1992. Polymer membranes in clinical sensor applications. I. An overview of membrane function, Biomaterials, 13(14):971/978.
Direct 30/30® meter (Markwell Medical) (Catalog). 1998.
Dixon et al. 2002. Characterization in vitro and in vivo of the oxygen dependence of an enzyme/polymer biosensor for monitoring brain glucose. Journal of Neuroscience Methods 119:135/142.
DuPont[1] Dimension AR® (Catalog), 1998.
Edwards Lifesciences. Accuracy for your and your patients. Marketing materials, 4 pp. 2002.
El Deheigy et al. 1986. Optimization of an implantable coated wire glucose sensor. J. Biomed Eng. 8: 121/129.
El/Khatib et al. 2007. Adaptive closed/loop control provides blood/ glucose regulation using dual subcutaneous insulin and glucagon infusion in diabetic swine, Journal of Diabetes Science and Technology, 1(2):181/192.
El/Sa'ad et al. 1990. Moisture Absorption by Epoxy Resins: the Reverse Thermal Effect. Journal of Materials Science 25:3577/ 3582.
Ernst et al. 2002. Reliable glucose monitoring through the use of microsystem technology. Anal. Bioanal. Chem. 373:758/761.
Fabietti et al. 2007. Clinical validation of a new control/oriented model of insulin and glucose dynamcs in subjects with type 1 diabetes, Diabetes Technology & Therapeutics, 9(4):327/338.
Fare et al. 1998. Functional characterization of a conducting polymer/based immunoassay system. Biosensors & Bioelectronics 13(3/ 4):459/470.
Feldman et al. 2003. A continuous glucose sensor based on wired enzyme technology // results from a 3/day trial in patients with type 1 diabetes. Diabetes Technol Ther 5(5):769/779.
Fischer et al. 1989. Oxygen Tension at the Subcutaneous Implantation Site of Glucose Sensors. Biomed. Biochem 11/12:965/972.
Fischer et al. 1995. Hypoglycaemia/warning by means of subcutaneous electrochemical glucose sensors: an animal study, Horm. Metab. Rese. 27:53.
Frohnauer et al. 2001. Graphical human insulin time/activity profiles using standardized definitions. Diabetes Technology & Therapeutics 3(3):419/429.
Frost et al. 2002. Implantable chemical sensors for real/time clinical monitoring: Progress and challenges. Current Opinion in Chemical Biology 6:633/641.
Garg et al. 1999. Correlation of fingerstick blood glucose measurements with GlucoWatch biographer glucose results in young subjects with type 1 diabetes. Diabetes Care 22(10):1708/1714.
Garg et al. 2004. Improved Glucose Excursions Using an Implantable Real/Time continuous Glucose Sensor in Adults with Type I Diabetes. Diabetes Care 27:734/738.
Gerritsen et al. 1999. Performance of subcutaneously implanted glucose sensors for continuous monitoring. The Netherlands Journal of Medicine 54:167/179.
Gerritsen, M. 2000. Problems associated with subcutaneously implanted glucose sensors. Diabetes Care 23(2):143/145.
Gilligan et al. 1994. Evaluation of a subcutaneous glucose sensor out to 3 months in a dog model. Diabetes Care 17(8):882/887.
Gilligan et al. 2004, Feasibility of continuous long/term glucose monitoring from a subcutaneous glucose sensor in humans. Diabetes Technol Ther 6:378/386.
Godsland et al. 2001. Maximizing the Success Rate of Minimal Model Insulin Sensitivity Measurement in Humans: The Importance of Basal Glucose Levels. The Biochemical Society and the Medical Research Society, 1/9.
Gough et al. 2000. Immobilized glucose oxidase in implantable glucose sensor technology. Diabetes Technology & Therapeutics 2(3):377/380.
Gough et al. 2003. Frequency characterization of blood glucose dynamics. Annals of Biomedical Engineering 31:91/97.
Gross et al. 2000. Efficacy and reliability of the continuous glucose monitoring system. Diabetes Technology & Therapeutics, 2(Suppl 1):S19/26.
Gross et al. 2000. Performance evaluation of the MiniMed® continuous glucose monitoring system during patient home use. Diabetes Technology & Therapeutics 2(1):49/56.
Guerci et al., Clinical performance of CGMS in type 1 diabetic patents treated by continuous subcutaneous insulin infusion using insulin analogs, Diabetes Care, 26:582/589, 2003.
Hall et al. 1998. Electrochemical oxidation of hydrogen peroxide at platinum electrodes. Part II: Effect of potential. Electrochimica Acta 43(14/15):2015/2024.

(56) References Cited

OTHER PUBLICATIONS

Hall et al. 1998. Electrochemical oxidation of hydrogen peroxide at platinum electrodes. Part I: An adsorption/controlled mechanism. Electrochimica Acta, 43(5/6):579/588.

Hall et al. 1999. Electrochemical oxidation of hydrogen peroxide at platinum electrodes. Part III: Effect of temperature. Electrochimica Acta, 44:2455/2462.

Hall et al. 1999. Electrochemical oxidation of hydrogen peroxide at platinum electrodes. Part IV: Phosphate buffer dependence. Electrochimica Acta, 44:4573/4582.

Hall et al. 2000. Electrochemical oxidation of hydrogen peroxide at platinum electrodes. Part V: Inhibition by chloride. Electrochimica Acta, 45:3573/3579.

Hashiguchi et al. (1994). "Development of a miniaturized glucose monitoring system by combining a needle/type glucose sensor with microdialysis sampling method: Long/term subcutaneous tissue glucose monitoring in ambulatory diabetic patients," Diabetes Care, 17(5): 387/396.

Heise et al. 2003. Hypoglycemia warning signal and glucose sensors: Requirements and concepts. Diabetes Technology & Therapeutics 5:563/571.

Heller, "Electrical wiring of redox enzymes," Acc. Chem. Res., 23:128/134 (1990).

Heller, A. 1992. Electrical Connection of Enzyme Redox Centers to Electrodes. J. Phys. Chem. 96:3579/3587.

Heller, A. 1999. Implanted electrochemical glucose sensors for the management of diabetes. Annu Annu Rev Biomed Eng 1:153/175.

Heller, A. 2003. Plugging metal connectors into enzymes. Nat Biotechnol 21:631/2.

Hicks, 1985. In Situ Monitoring, Clinical Chemistry, 31(12):1931/1935.

Hitchman, M. L. 1978. Measurement of Dissolved Oxygen. In Elving et al. (Eds.). Chemical Analysis, vol. 49, Chap. 3, pp. 34/49, 59/123. New York: John Wiley & Sons.

Hrapovic et al. 2003. Picoamperometric detection of glucose at ultrasmall platinum/based biosensors: preparation and characterization. Anal Chem 75:3308/3315.

Hu, et al. 1993. A needle/type enzyme/based lactate sensor for in vivo monitoring, Analytica Chimica Acta, 281:503/511.

Huang et al. A 0.5mV passive telemetry IC for biomedical applications. Swiss Federal Institute of Technology. 4 pp.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1/116.

Hunter, I., Jones, L., Kanigan, T., Brenan, C., Sanbol, L. Sosnowski, L. 2000. Minimally Invasive Glucose Sensor and Insulin Delivery System. MIT Home Automation and Healthcare Consortium. Progress Report No. 25.

Ishikawa et al. 1998. Initial evaluation of a 290/mm diameter subcutaneous glucose sensor: Glucose monitoring with a biocompatible, flexible/wire, enzyme/based amperometric microsensor in diabetic and nondiabetic humans. Journal of Diabetes and Its Complications, 12:295/301.

Jablecki et al. 2000. Simulations of the frequency response of implantable glucose sensors. Analytical Chemistry 72:1853/1859.

Jaremko et al. 1998. Advances toward the implantable artificial pancreas for treatment of diabetes. Diabetes Care 21(3):444/450.

Jensen et al. 1997. Fast wave forms for pulsed electrochemical detection of glucose by incorporation of reductive desorption of oxidation products. Analytical Chemistry 69(9):1776/1781.

Jeong et al. 2003. In vivo calibration of the subcutaneous amperometric glucose sensors using a non/enzyme electrode. Biosensors and Bioelectronics 19:313/319.

Jeutter et al. 1993. Design of a radio/linked implantable cochlear prosthesis using surface acoustic wave devices. IEEE Transactions on ultrasonics, ferroelectrics and frequency control 40(5):469/477.

Jeutter, D. C. 1982. A transcutaneous implanted battery recharging and biotelemeter power switching system. IEEE Trans Biomed Eng 29:314/321.

Johnson (1991). "Reproducible electrodeposition of biomolecules for the fabrication of miniature electroenzymatic biosensors," Sensors and Actuators B, 5:85/89.

Johnson et al. 1992. In vivo evaluation of an electroenzymatic glucose sensor implanted in subcutaneous tissue. Biosensors & Bioelectronics, 7:709/714.

Joung et al. 1998. An energy transmission system for an artificial heart using leakage inductance compensation of transcutaneous transformer. IEEE Transactions on Power Electronics 13(6):1013/1022.

Jovanovic, L. 2000. The role of continuous glucose monitoring in gestational diabetes mellitus. Diabetes Technology & Therapeutics, 2 Suppl 1, S67/71.

Kamath et al. Calibration of a continuous glucose monitor: effect of glucose rate of change, Eighth Annual Diabetes Technology Meeting, Nov. 13/15, 2008, p. A88.

Kang et al. 2003. In vitro and short/term in vivo characteristics of a Kel/F thin film modified glucose sensor. Anal Sci 19:1481/1486.

Kaufman et al. 2001. A pilot study of the continuous glucose monitoring system. Diabetes Care 24(12):2030/2034.

Kaufman. 2000. Role of the continuous glucose monitoring system in pediatric patients. Diabetes Technology & Therapeutics 2(1):S/49 / S/52.

Kawagoe et al. 1991. Enzyme/modified organic conducting salt microelectrode, Anal. Chem. 63:2961/2965.

Kerner et al. "The function of a hydrogen peroxide/detecting electroenzymatic glucose electrode is markedly impaired in human sub/cutaneous tissue and plasma," Biosensors & Bioelectronics, 8:473/482 (1993).

Kerner et al. 1988. A potentially implantable enzyme electrode for amperometric measurement of glucose, Norm Metab Res Suppl. 20:8/13.

Kerner, W. 2001. Implantable glucose sensors: Present status and future developments. Exp. Clin. Endocrinol. Diabetes 109(Suppl 2):S341/346.

Klueh et al. 2003. Use of Vascular Endothelia Cell Growth Factor Gene Transfer to Enhance Implantable Sensor Function in Vivo, Biosensor Function and Vegf/Gene Transfer, pp. 1072/1086.

Kondo et al. 1982. A miniature glucose sensor, implantable in the blood stream. Diabetes Care. 5(3):218/221.

Koschinsky et al. 1988. New approach to technical and clinical evaluation of devices for self/monitoring of blood glucose. Diabetes Care 11(8): 619/619.

Koschinsky et al. 2001. Sensors for glucose monitoring: Technical and clinical aspects. Diabetes Metab. Res. Rev. 17:113/123.

Koudelka et al. 1989. In vivo response of microfabricated glucose sensors to glycemia changes in normal rats. Biomed Biochim Acta 48(11/12):953/956.

Koudelka et al. 1991. In/vivo behaviour of hypodermically implanted microfabricated glucose sensors. Biosensors & Bioelectronics 6:31/36.

Kovatchev et al. Aug. 2004. Evaluating the accuracy of continuous glucose/monitoring sensors: continuous glucose/error grid analysis illustrated by TheraSense Freestyle Navigator data. Diabetes Care 27(8):1922/1928.

Kraver et al. 2001. A mixed/signal sensor interface microinstrument. Sensors and Actuators A 91:266/277.

Krouwer, J. S. 2002. Setting performance goals and evaluating total analytical error for diagnostic assays. Clinical Chemistry 48(6):919/927.

Kruger et al. 2000. Psychological motivation and patient education: A role for continuous glucose monitoring. Diabetes Technology & Therapeutics, 2(Suppl 1):S93/97.

Kurnik et al. 1999. Application of the mixtures of experts algorithm for signal processing in a noninvasive glucose monitoring system. Sensors and Actuators B, 60:19/26.

Kurtz et al. 2005. Recommendations for blood pressure measurement in humans and experimental animals, Part 2: Blood pressure measurement in experimental animals, A statement for professionals from the subcommittee of professional and public education of the

(56) References Cited

OTHER PUBLICATIONS

American Heart Association Council on High Blood Pressure Research. Hypertension 45:299/310.
LaCourse et al. 1993. Optimization of waveforms for pulsed amperometric detection of carbohydrates based on pulsed voltammetry. Analytical Chemistry 65:50/52.
Lerner et al. 1984. An implantable electrochemical glucose sensor. Ann. N. Y. Acad. Sci. 428:263/278.
Lewandowski et al. 1988. Evaluation of a miniature blood glucose sensor. Trans Am Soc Artif Intern Organs 34:255/258.
Leypoldt et al. 1984. Model of a two/substrate enzyme electrode for glucose. Anal. Chem. 56:2896/2904.
Linke et al. 1994. Amperometric biosensor for in vivo glucose sensing based on glucose oxidase immobilized in a redox hydrogel. Biosensors & Bioelectronics 9:151/158.
Lohn et al., A knowledge/based system for real/time validation of calibrations and measurements, Chemometrics and Intelligent Laboratory Systems, 1999 46, 57/66.
Luong et al. 2004. Solubilization of Multiwall Carbon Nanotubes by 3/Aminopropyltriethoxysilane Towards the Fabrication of Electrochemical Biosensors with Promoted Electron Transfer. Electroanalysis 16(1/2):132/139.
Lynch et al. 2001. Estimation/based model predictive control of blood glucose in type I diabetics: A simulation study. Proceedings of the IEEE 27th Annual Northeast Bioengineering Conference, pp. 79/80.
Lynn, P. A. 1971. Recursive digital filters for biological signals. Med. & Biol. Engng. 9:37/43.
Maidan et al. 1992. Elimination of Electrooxidizable Interferent/Produced Currents in Amperometric Biosensors, Analytical Chemistry, 64:2889/2896.
Makale et al. 2003. Tissue window chamber system for validation of implanted oxygen sensors. Am. J. Physiol. Heart Circ. Physiol. 284:H2288/2294.
Malin et al. 1999. Noninvasive Prediction of Glucose by Near/Infrared Diffuse Reflectance Spectroscopy. Clinical Chemistry 45:9, 1651/1658.
Mancy et al. 1962. A galvanic cell oxygen analyzer. Journal of Electroanalytical Chemistry 4:65/92.
Maran et al. 2002. Continuous subcutaneous glucose monitoring in diabetic patients: A multicenter analysis. Diabetes Care 25(2):347/352.
March, W. F. 2002. Dealing with the delay. Diabetes Technol Ther 4(1):49/50.
Martin, R. F. 2000. General Deming regression for estimating systematic bias and its confidence interval in method/comparison studies. Clinical Chemistry, 46(1):100/104.
Mastrototaro et al. "An electroenzymatic glucose sensor fabricated on a flexible substrate," Sensors and Actuators B, 5:139/44 (1991).
Mastrototaro et al. 2003. Reproducibility of the continuous glucose monitoring system matches previous reports and the intended use of the product. Diabetes Care 26:256; author reply p. 257.
Mastrototaro, J. J. 2000. The MiniMed continuous glucose monitoring system. Diabetes Technol Ther 2(Suppl 1):S13/8.
Matsuki. 1994. Energy transfer system utilizing amorphous wires for implantable medical devices. IEEE Transactions on Magnetics 31(2):1276/1282.
Matsumoto et al. 1998. A micro/planar amperometeric glucose sensor unsusceptible to interference species. Sensors and Actuators B 49:68/72.
Matthews et al. 1988. An amperometric needle/type glucose sensor testing in rats and man. Diabetic Medicine 5:248/252.
Mazze et al. 2008. Characterizing glucose exposure for individuals with normal glucose tolerance using continuous glucose monitoring and ambulatory glucose profile analysis. Diab. Thechnol. & Therapeut., 10:149/159.
McCartney et al. 2001. Near/infrared fluorescence lifetime assay for serum glucose based on allophycocyanin/labeled concanavalin A. Anal Biochem 292:216/221.
McGrath et al. 1995. The use of differential measurements with a glucose biosensor for interference compensation during glucose determinations by flow injection analysis. Biosens Bioelectron 10:937/943.
McKean, et al. Jul. 7, 1988. A Telemetry Instrumentation System for Chronically Implanted Glucose and Oxygen Sensors. Transactions on Biomedical Engineering 35:526/532.
Memoli et al. 2002. A comparison between different immobilised glucoseoxidase/based electrodes. J Pharm Biomed Anal 29:1045/1052.
Metzger et al. Jul. 2002. Reproducibility of glucose measurements using the glucose sensor. Diabetes Care 25(6):1185/1191.
Meyerhoff et al. 1992. On line continuous monitoring of subcutaneous tissue glucose in men by combining portable glucosensor with microdialysis. Diabetologia 35:1087/1092.
Miller et al. 1993. Development of an autotuned transcutaneous energy transfer system ASAIO Journal 39:M706/M710.
Moatti/Sirat et al. 1992. Towards continuous glucose monitoring: in vivo evaluation of a miniaturized glucose sensor implanted for several days in rat subcutaneous tissue. Diabetologia 35:224/230.
Moatti/Sirat et al., Reduction of acetaminophen interference in glucose sensors by a composite Nafion membrane: demonstration in rats and man, Diabetologia 37(6):610/616, Jun. 1994.
Moatti/Sirat, D et al. 1992. Evaluating in vitro and in vivo the interference of ascorbate and acetaminophen on glucose detection by a needle/type glucose sensor. Biosensors and Bioelectronics 7:345/352.
Monsod et al. 2002. Do sensor glucose levels accurately predict plasma glucose concentrations during hypoglycemia and hyperinsulinemia? Diabetes Care 25(5):889/893.
Morff et al. 1990. Microfabrication of reproducible, economical, electroenzymatic glucose sensors, Annual International Conference of the IEEE Engineering in Medicine and Biology Society, 12(2):0483/0484.
Moussy et al. 1994. A miniaturized Nafion/based glucose sensor: In vitro and in vivo evaluation in dogs. Int. J. Artif. Organs 17(2):88/94.
Murphy, et al. 1992. Polymer membranes in clinical sensor applications. II. The design and fabrication of permselective hydrogels for electrochemical devices, Biomaterials, 13(14):979/990.
Muslu. 1991. Trickling filter performance. Apllied Biochemistry and Biotechnology 37:211/224.
Neuburger et al. 1987. Pulsed amperometric detection of carbohydrates at gold electrodes with a two/step potential waveform. Anal. Chem. 59:150/154.
Ohara et al. 1994. "Wired" enzyme electrodes for amperometric determination of glucose or lactate in the presence of interfering substances. Anal Chem 66:2451/2457.
Ohara, et al. Dec. 1993. Glucose electrodes based on cross/linked bis(2,2'/bipyridine)chloroosmium(+/2+) complexed poly(1/vinylimidazole) films, Analytical Chemistry, 65:3512/3517.
Okuda et al. 1971. Mutarotase effect on micro determinations of D/glucose and its anomers with β/D/glucose oxidase. Anal Biochem 43:312/315.
Palmisano et al. 2000. Simultaneous monitoring of glucose and lactate by an interference and cross/talk free dual electrode amperometric biosensor based on electropolymerized thin films. Biosensors & Bioelectronics 15:531/539.
Panteleon et al. 2003. The role of the independent variable to glucose sensor calibration. Diabetes Technology & Therapeutics 5(3):401/410.
Parker et al. 1999. A model/based algorithm for blood glucose control in type I diabetic patients. IEEE Trans. Biomed. Eng. 46(2):148/157.
Patel et al. 2003. Amperometric glucose sensors based on ferrocene containing polymeric electron transfer systems/a preliminary report. Biosens Bioelectron 18:1073/6.
Pfeiffer et al. 1992. On line continuous monitoring of subcutaneous tissue glucose is feasible by combining portable glucosensor with microdialysis. Horm. Metab. Res. 25:121/124.
Pfeiffer, E.F. 1990. The glucose sensor: the missing link in diabetes therapy, Horm Metab Res Suppl. 24:154/164.

(56) References Cited

OTHER PUBLICATIONS

Philips. 1995. A high capacity transcutaneous energy transmission system. ASAIO Journal 41:M259/M262.
Pichert et al. 2000. Issues for the coming age of continuous glucose monitoring Diabetes Educ 26(6):969/980.
Pickup et al. "Implantable glucose sensors: choosing the appropriate sensing strategy," Biosensors, 3:335/346 (1987/88).
Pickup et al. "Implantable glucose sensors: choosing the appropriate sensor strategy," Biosensors, 3:335/346 (1987/88).
Pickup et al. "In vivo molecular sensing in diabetes mellitus: an implantable glucose sensor with direct electron transfer," Diabetologia, 32:213/217 (1989).
Pickup et al. 1989. Potentially/implantable, amperometric glucose sensors with mediated electron transfer: improving the operating stability. Biosensors 4:109/119.
Pickup et al. 1993. Responses and Calibration of Amperometric Glucose Sensors Implanted in the Subcutaneous Tissue of Man. ACTA Diabetol, pp. 143/148.
Pishko et al. "Amperometric glucose microelectrodes prepared through immobilization of glucose oxidase in redox hydrogels," Anal. Chem., 63:2268/72 (1991).
Pitzer et al. 2001. Detection of hypoglycemia with the GlucoWatch biographer. Diabetes Care 24(5):881/885.
Poirier et al. 1998. Clinical and statistical evaluation of self/monitoring blood glucose meters. Diabetes Care 21(11):1919/1924.
Poitout et al. 1993. A glucose monitoring system for on line estimation in man of blood glucose concentration using a miniaturized glucose sensor implanted in the subcutaneous tissue and a wearable control unit. Diabetologia 36:658/663.
Poitout et al. 1994. Development of a glucose sensor for glucose monitoring in man: the disposable implant concept. Clinical Materials 15:241/246.
Poitout, et al. 1991. In Vitro and In Vivo Evaluation in Dogs of a Miniaturized Glucose Sensor, ASAIO Transactions, 37:M298/M300.
Postlethwaite et al. 1996. Interdigitated array electrode as an alternative to the rotated ring/disk electrode for determination of the reaction products of dioxygen reduction. Analytical Chemistry 68:2951/2958.
Prabhu et al. 1981. Electrochemical studies of hydrogen peroxide at a platinum disc electrode, Electrochimica Acta 26(6):725/729.
Quinn et al. 1995. Kinetics of glucose delivery to subcutaneous tissue in rats measured with 0.3/mm amperometric microsensors. The American Physiological Society E155/E161.
Quinn et al. 1997. Biocompatible, glucose/permeable hydrogel for in situ coating of implantable biosensors. Biomaterials 18:1665/1670.
Reach et al. 1986. A Method for Evaluating in vivo the Functional Characteristics of Glucose Sensors. Biosensors 2:211/220.
Reach et al. 1992. Can continuous glucose monitoring be used for the treatment of diabetes? Analytical Chemistry 64(5):381/386.
Reach, G. 2001. Which threshold to detect hypoglycemia? Value of receiver/operator curve analysis to find a compromise between sensitivity and specificity. Diabetes Care 24(5):803/804.
Reach, Gerard. 2001. Letters to the Editor Re: Diabetes Technology & Therapeutics, 2000;2:49/56. Diabetes Technology & Therapeutics 3(1):129/130.
Rebrin et al. "Automated feedback control of subcutaneous glucose concentration in diabetic dogs," Diabetologia, 32:573/76 (1989).
Rebrin et al. 1992. Subcutaenous glucose monitoring by means of electrochemical sensors: fiction or reality? J. Biomed. Eng. 14:33/40.
Rebrin et al. 1999. Subcutaneous glucose predicts plasma glucose independent of insulin: Implications for continuous monitoring. Am. J. Physiol. 277:E561/71.
Rhodes et al. 1994. Prediction of pocket/portable and implantable glucose enzyme electrode performance from combined species permeability and digital simulation analysis. Analytical Chemistry 66(9):1520/1529.
Rigla et al. 2008. Real/time continuous glucose monitoring together with telemedical assitance improves glycemic control and glucose stability in pump/treated patients. Diab. Thechnol. & Therapeut., 10:194/199.
Rinken et al. 1998. Calibration of glucose biosensors by using pre/steady state kinetic data. Biosensors & Bioelectronics, 13:801/807.
Sakakida et al. 1992. Development of Ferrocene/Mediated Needle/Type Glucose Sensor as a Measure of True Subcutaneous Tissue Glucose Concentrations. Artif. Organs Today 2(2):145/158.
Sakakida et al. 1993. Ferrocene/Mediated Needle Type Glucose Sensor Covered with Newly Designed Biocompatible Membran, Sensors and Actuators B 13/14:319/322.
Salardi et al. 2002. The glucose area under the profiles obtained with continuous glucose monitoring system relationships with HbA1c in pediatric type 1 diabetic patients. Diabetes Care 25(10):1840/1844.
Sansen et al. 1985. "Glucose sensor with telemetry system." In Ko, W. H. (Ed.). Implantable Sensors for Closed Loop Prosthetic Systems. Chap. 12, pp. 167/175, Mount Kisco, NY: Futura Publishing Co.
Sansen et al. 1990. A smart sensor for the voltammetric measurement of oxygen or glucose concentrations. Sensors and Actuators B 1:298/302.
Schmidt et al. 1992. Calibration of a wearable glucose sensor. The International Journal of Artificial Organs 15(1):55/61.
Schmidt et al. 1993. Glucose concentration in subcutaneous extracellular space. Diabetes Care 16(5):695/700.
Schmidtke et al. 1998. Accuracy of the one/point in vivo calibration of "wired" glucose oxidase electrodes implanted in jugular veins of rats in periods of rapid rise and decline of the glucose concentration. Anal Chem 70:2149/2155.
Schoemaker et al. 2003. The SCGM1 system: Subcutaneous continuous glucose monitoring based on microdialysis technique. Diabetes Technology & Therapeutics 5(4):599/608.
Schoonen et al. 1990 Development of a potentially wearable glucose sensor for patients with diabetes mellitus: design and in/vitro evaluation. Biosensors & Bioelectronics 5:37/46.
Service et al. 1970. Mean amplitude of glycemic excursions, a measure of diabetic instability. Diabetes, 19: 644/655.
Service, R. F. 2002. Can sensors make a home in the body? Science 297:962/3.
Shaw et al. "In vitro testing of a simply constructed, highly stable glucose sensor suitable for implantation in diabetic patients," Biosensors & Bioelectronics, 6:401/406 (1991).
Shichiri et al. 1982. Wearable artificial endocrine pancrease with needle/type glucose sensor. Lancet 2:1129/1131.
Shichiri et al. 1986. Telemetry Glucose Monitoring Device with Needle/Type Glucose Sensor: A Useful Tool for Blood Glucose Monitoring in Diabetic Individuals. Diabetes Care, Inc. 9(3):298/301.
Shichiri et al. 1983. Glycaemic Control in Pancreatectomized Dogs with a Wearable Artificial Endocrine Pancreas. Diabetologia 24:179/184.
Shichiri et al. 1985. Needle/type Glucose Sensor for Wearable Artificial Endocrine Pancreas in Implantable Sensors 197/210.
Shichiri et al. 1989. Membrane Design for Extending the Long/Life of an Implantable Glucose Sensor. Diab. Nutr. Metab. 2:309/313.
Shults et al. 1994. A telemetry/instrumentation system for monitoring multiple subcutaneously implanted glucose sensors. IEEE Transactions on Biomedical Engineering 41(10):937/942.
Skyler, J. S. 2000. The economic burden of diabetes and the benefits of improved glycemic control: The potential role of a continuous glucose monitoring system. Diabetes Technology & Therapeutics 2 Suppl 1:S7/12.
Smith et al. 1998. An externally powered, multichannel, implantable stimulator/telemeter for control of paralyzed muscle. IEEE Transactions on Biomedical Engineering 45(4):463/475.
Sokol et al. 1980, Immobilized/enzyme rate/determination method for glucose analysis, Clin. Chem. 26(1):89/92.
Sokolov et al. 1995. Metrological opportunities of the dynamic mode of operating an enzyme amperometric biosensor. Med. Eng. Phys. 17(6):471/476.

(56) References Cited

OTHER PUBLICATIONS

Sproule et al. 2002. Fuzzy pharmacology: Theory and applications. Trends in Pharmacological Sciences, 23(9):412/417.
Sriyudthsak et al. 1996. Enzyme/epoxy membrane based glucose analyzing system and medical applications. Biosens Bioelectron 11:735/742.
Steil et al. 2003. Determination of plasma glucose during rapid glucose excursions with a subcutaneous glucose sensor. Diabetes Technology & Therapeutics 5(1):27/31.
Sternberg et al. 1996. Does fall in tissue glucose precede fall in blood glucose? Diabetologia 39:609/612.
Sternberg et al. 1988. Study and Development of Multilayer Needle/type Enzyme/based Glucose Microsensors. Biosensors 4:27/40.
Street et al. 1988. A note on computing robust regression estimates via iteratively reweighted least squares. The American Statistician 42(2):152/154.
Sumino T. et al. 1998. Preliminary study of continuous glucose monitoring with a microdialysis technique. Proceedings of the IEEE, 20(4):1775/1778.
Tamura, T. et al. 2000. Preliminary study of continuous glucose monitoring with a microdialysis technique and a null method—a numerical analysis. Frontiers Med. Biol. Engng. 10(2):147/156.
Tanenberg et al. 2000. Continuous glucose monitoring system: A new approach to the diagnosis of diabetic gastroparesis. Diabetes Technology & Therapeutics, 2 Suppl 1:S73/80.
Thome et al. 1995. Can the decrease in subcutaneous glucose concentration precede the decrease in blood glucose level? Proposition for a push/pull kinetics hypothesis, Norm. Metab. Res. 27:53.
Thomé/Duret et al. 1996. Modification of the sensitivity of glucose sensor implanted into subcutaneous tissue. Diabetes Metabolism, 22:174/178.
Thomé/Duret et al. 1998. Continuous glucose monitoring in the free/moving rat. Metabolism, 47:799/803.
Thompson et al., In Vivo Probes: Problems and Perspectives, Department of Chemistry, University of Toronto, Canada, pp. 255/261, 1986.
Tierney et al. 2000. Effect of acetaminophen on the accuracy of glucose measurements obtained with the GlucoWatch biographer. Diabetes Technol Ther 2:199/207.
Tierney et al. 2000. The GlucoWatch® biographer: A frequent, automatic and noninvasive glucose monitor. Ann. Med. 32:632/641.
Tilbury et al. 2000. Receiver operating characteristic analysis for intelligent medical systems//A new approach for finding confidence intervals. IEEE Transactions on Biomedical Engineering 47(7):952/963.
Trajanoski et al. 1998. Neural predictive controller for insulin delivery using the subcutaneous route. IEEE Transactions on Biomedical Engineering 45(9):1122/1134.
Trecroci, D. 2002. A Glimpse into the Future/ Continuous Monitoring of Glucose with a Microfiber. Diabetes Interview 42/43.
Tse and Gough. 1987. Time/Dependent Inactivation of Immobilized Glucose Oxidase and Catalase. Biotechnol. Bioeng. 29:705/713.
Turner and Pickup, "Diabetes mellitus: biosensors for research and management," Biosensors, 1:85/115 (1985).
Unger et al. 2004. Glucose control in the hospitalized patient. Emerg Med 36(9):12/18.
Updike et al. 1967. The enzyme electrode. Nature, 214:986/988.
Updike et al. 1979. Continuous glucose monitor based on an immobilized enzyme electrode detector. J Lab Clin Med, 93(4):518/527.
Updike et al. 1982. Implanting the glucose enzyme electrode: Problems, progress, and alternative solutions. Diabetes Care, 5(3):207/212.
Updike et al. 1988. Laboratory Evaluation of New Reusable Blood Glucose Sensor. Diabetes Care, 11:801/807.
Updike et al. 1994. Enzymatic glucose sensor: Improved long/term performance in vitro and in vivo. ASAIO Journal, 40(2):157/163.
Updike et al. 1997. Principles of long/term fully impleated sensors with emphasis on radiotelemetric monitoring of blood glucose form inside a subcutaneous foreign body capsule (FBC). In Fraser, ed., Biosensors in the Body. New York. John Wiley & Sons, pp. 117/137.
Updike et al. 2000. A subcutaneous glucose sensor with improved longevity, dynamic range, and stability of calibration. Diabetes Care 23(2):208/214.
Utah Medical Products Inc., Blood Pressure Tranducers product specifications. 6 pp. 2003/2006, 2003.
Vadgama, P. Nov. 1981. Enzyme electrodes as practical biosensors. Journal of Medical Engineering & Technology 5(6):293/298.
Valdes et al. 2000. In vitro and in vivo degradation of glucose oxidase enzyme used for an implantable glucose biosensor. Diabetes Technol. Ther. 2:367/376.
Van den Berghe 2004. Tight blood glucose control with insulin in "real/life" intensive care. Mayo Clin Proc 79(8):977/978.
Velho et al. 1989. In vitro and in vivo stability of electrode potentials in needle/type glucose sensors. Influence of needle material. Diabetes 38:164/171.
Velho et al. 1989. Strategies for calibrating a subcutaneous glucose sensor. Biomed Biochim Acta 48(11/12):957/964.
von Woedtke et al. 1989. In situ calibration of implanted electrochemical glucose sensors. Biomed Biochim. Acta 48(11/12):943/952.
Wagner et al. 1998. Continuous amperometric monitoring of glucose in a brittle diabetic chimpanzee with a miniature subcutaneous electrode. Proc. Natl. Acad. Sci. A, 95:6379/6382.
Wang et al. 1994. Highly Selective Membrane/Free, Mediator/Free Glucose Biosensor. Anal. Chem. 66:3600/3603.
Wang et al. 1997. Improved ruggedness for membrane/based amperometric sensors using a pulsed amperometric method. Anal Chem 69:4482/4489.
Ward et al. 1999. Assessment of chronically implanted subcutaneous glucose sensors in dogs: The effect of surrounding fluid masses. ASAIO Journal, 45:555/561.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540/546.
Ward et al. 2000. Rise in background current over time in a subcutaneous glucose sensor in the rabbit: Relevance to calibration and accuracy. Biosensors & Bioelectronics, 15:53/61.
Ward et al. 2002. A new amperometric glucose microsensor: In vitro and short/term in vivo evaluation. Biosensors & Bioelectronics, 17:181/189.
Wientjes, K. J. C. 2000. Development of a glucose sensor for diabetic patients (Ph.D. Thesis).
Wilkins et al. 1988. The coated wire electrode glucose sensor, Horm Metab Res Suppl., 20:50/55.
Wilkins et al. 1995. Glucose monitoring: state of the art and future possibilities. Med Eng Phys 18:273/288.
Wilkins et al. 1995. Integrated implantable device for long/term glucose monitoring. Biosens. Bioelectron 10:485/494.
Wilson et al. 1992. Progress toward the development of an implantable sensor for glucose. Clin. Chem. 38(9):1613/1617.
Wilson et al. 2000. Enzyme/based biosensors for in vivo measurements. Chem. Rev., 100:2693/2704.
Wood, W. et al. Mar. 1990. Hermetic Sealing with Epoxy. Mechanical Engineering 1/3.
Woodward. 1982. How Fibroblasts and Giant Cells Encapsulate Implants: Considerations in Design of Glucose Sensor. Diabetes Care 5:278/281.
Wu et al. 1999. In situ electrochemical oxygen generation with an immunoisolation device. Annals New York Academy of Sciences, pp. 105/125.
Yamasaki et al. 1989. Direct measurement of whole blood glucose by a needle/type sensor. Clinica Chimica Acta. 93:93/98.
Yamasaki, Yoshimitsu. Sep. 1984. The development of a needle/type glucose sensor for wearable artificial endocrine pancreas. Medical Journal of Osaka University 35(1/2):25/34.
Yang et al (1996). "A glucose biosensor based on an oxygen electrode: In/vitro performances in a model buffer solution and in blood plasma," Biomedical Instrumentation & Technology, 30:55/61.

(56) References Cited

OTHER PUBLICATIONS

Yang et al. 1998. Development of needle/type glucose sensor with high selectivity. Science and Actuators B 46:249/256.
Yang, et al. 2004. A Comparison of Physical Properties and Fuel Cell Performance of Nafion and Zirconium Phosphate/Nafion Composite Membranes. Journal of Membrane Science 237:145/161.
Zamzow et al. Development and evaluation of a wearable blood glucose monitor. pp. M588/M591, 1990.
Zavalkoff et al. 2002. Evaluation of conventional blood glucose monitoring as an indicator of integrated glucose values using a continuous subcutaneous sensor. Diabetes Care 25(9):1603/1606.
Zhang et al (1993). Electrochemical oxidation of H2O2 on Pt and Pt + Ir electrodes in physiological buffer and its applicability to H2O2/based biosensors. J. Electroanal. Chem., 345:253/271.
Zhang et al. 1994. Elimination of the acetaminophen interference in an implantable glucose sensor. Analytical Chemistry 66(7):1183/1188.
Zhu et al. (1994). "Fabrication and characterization of glucose sensors based on a microarray H2O2 electrode." Biosensors & Bioelectronics, 9: 295/300.
Zhu et al. 2002. Planar amperometric glucose sensor based on glucose oxidase immobilized by chitosan film on prussian blue layer. Sensors, 2:127/136.
Ziaie et al. 1997. A single/channel implantable microstimulator for functional neuromuscular stimulation. IEEE Transactions on Biomedical Engineering 44(10):909/920.
Abel et al. 1984. Biomed. Biochim. Acta 43(5):577-584. Experience with an implantable glucose sensor as a prerequisite of an artificial beta cell.
Adilman 1983. Creative Computing 9:244(5), Dialog file 148, Acc# 01891055. Videoganes: Knowing the Score.
Alcock and Turner 1994. IEEE Engineering in Med. and Biology 13:319-325. Continuous Analyte Monitoring to Aid Clinical Practice.
American Heritage Dictionary, 4th Edition. 2000. Company, Houghton Mifflin Company, p. 82.
Bessman et al. 1973. Progress toward a glucose sensor for the artificial pancreas, Proceedings of a Workshop on Ion-Selective Microelectrodes, Jun. 4-5, 1973, Boston, MA, pp.
Bindra et al. 1989. Analytical Chemistry 61:2566-2570. Pulsed amperometric detection of glucose in biological fluids at a surface-modified gold electrode.
Boedeker Plastics, Inc. 2009. Polyethylene Specidications Data Sheet, http://www.boedeker.com/poly.sub.--p.htm [Aug. 19, 2009 3:36:33 PM].
Bott, A. W. 1997. Current Separations 16(1):23-26. A comparison cyclic voltammetry and cyclic staircase voltammetry.
Braunwald 2008. NEJM 358:2148-2159. Biomarkers in heart failure.
Cassidy et al. 1993. Analyst 118:415-418. Novel electrochemical device for the detection of cholesterol or glucose.
Claremont et al. 1986. J. Biomed Eng. 8:272-274. Potentially-implntable, ferrocene-mediated glucode sensor.
CLSI 2008. Clinical and Laboratory Standards Institute 28(33)—72 pages. Performance metrics for continuous interstitial glucose monitoring; approved guideline, CLSI docume.
Colangelo et al. 1967. J. Biomedical Matls Research 1:405-414. Corrosion rate measurements in vivo.
Currie et al. 2004. RTO HFM Symposium, Aug. 16-18, 2004, St. Pete Beach, RTO-MP-HFH-109:24-1 to 24-18. Novel non-intrusive trans-dermal remote wireless micro-fluidic moni.
Danielsson et al. 1988. Methods in Enzymology 137:181-197. Enzyme thermistors.
Dessau et al. 2009. Diabetes Technology and Therapeutics 11(3):1-8. In silico evaluation platform for artifical pancreatic .beta.-cell development—a dynamic simulator for c.
Davis et al. 1983. Enzyme Microb. Technolgoy 5:383-388. Bioelectrochemical fuel cell and sensor based on a quinoprotein, alcohol dehydrogenase.

Deutsch et al. 1994. Computer Method and Programs in Biomedicine 41:167-182. Time series analysis and control of blood glucose levels in diabetic patients.
Diabetes Educations Video Game Recognized by Software Publishers Association, Press Release, Novo Nordisk, Mar. 14, 1994.
Durliat et al. 1976. Clinical Chemistry 22(1):1802-1805. Spectrophotometric and electrochemical determinations of L(+)-lactate in blood by use of lactate dehydrogenase fro.
Fahy et al. 2008. J. Diabetes Science and Technology 2(2):201-204. An analysis: hyperglycemic intensive case patients need continuous glucose monitoring—easier said than do.
Fisher et al. 1987. Assessment for subcutaneous glucose concentration: validation of the wick technique as a reference for implanted electrochemical sensors in normal and diab.
Freedman et al. 1991. Statistics, Second Edition, W.W. Norton & Company, p. 74.
Freiberger, Paul, 1992. San Francisco Examiner, Jun. 26, 1992, Fourth Edition, Busainess Section B1. Video Game Takes on Diabetes Superhero Captain Novolin Offers Treatment.
Gabbay et al. 2008. Diabetes Technology and Therapeutics 10:188-193. Optical tomography-based continuous noninvasive glucose monitoring in patients with diabetes.
Ganesan et al. 2005. Analytical Biochemistry 343:181-191. Gold layer-based dual crosslinking procedure of glucose oxidase with ferrocene monocarboxylic acid provides a stabl.
Ganesh et al. 2008, J. Diabetes Science and Technlogy 2(2):182-193. Evaluation of the VIA.RTM blood chemistry monitor for glucose in healthy and diabetic volunteers.
Gouda et al. 2003. J. Biological Chemistry 278(27);24324-24333, Thermal inactiviation of glucose oxidase.
Gross 2001. Diabetes Technology and Therapeutics 3(1):130-131, "Letters to the Editor Re: Diabetes Technology & Therapeutics, 2000;2:49-56".
Hamilton Syringe Selection Guide. 2006. Syringe Selection. www.hamiltoncompany.com.
Hoel, Paul G. 1976. Elementary Statistics, Fourth Edition. John Wiley & Sons, Inc.. pp. 113-114.
http://www.merriam-webster.com/dictionary, definition for "aberrant," Aug. 19, 2008, p. 1.
Jaffari et al. 1995. Physiol. Meas. 16:1-15. Recent advances in amperometric glucose biosensors for in vivo monitoring.
Jeutter 1982. IEEE Transactions in Biomedical Engineering 29:314-321. A transcutaneous implanted battery recharging and biotelemeter power switching system.
Jobst et al. 1996. Analytical Chemistry 8(18):3173-3179. Thin-Film Microbiosensors for Glucose-Lactate Monitoring.
Kacaniklic 1994. Electroanalysis 6(5-6):381-390.
Keedy et al. 1991. Biosensors and Bioelectronics 6:491-499. Determination of urate in undiluted whole blood by enzyme electrode.
Kost et al. 1985. J. Biomedical Materials Research 19:1117-1133. Glucose-sensitive membranes containing glucose oxidase: activitiy, swelling, and permeability studies.
Kulys et al. 1994. Biosensors and Bioelectronics 9;491-500. Carbon-paste biosensors array for long-term glucose measurement.
Kunjan et al. 2008. J. Diabetes Science and Technology 2(3):194-200. Automated blood sampling and glocuse sensing in critical care settings.
Ladd et al. 1996. Structure Determination by X-ray Crystallography, 3rd ed. Plenum, Ch. 1, pp. xxi-xxiv and 1-58.
Lehmann et al. 1994. Med. Eng. Phys. 16:193-202. Retrospective valication of a physiological model of glucose-iunsulin interaaction in tyhpe 1 diabetes mellitus.
Lowe 1984. Trends in Biotechnology, 2(3):59-65. Biosensors.
Lyandres et al. 2008. Diabetes Technology and Therapeutics 10(4):257-265. Progress toward an in vivo surface-enhanced raman spectroscopy glucose sensor.
Mar. 2002. Diabetes Technology and Therapeutics 4(1):49-50. Dealing with the delay.
Marena et al. 1993. Panminerva Meidca 35(2):67-74. The artifical endocrine pancreas in clinical practice and research.
Mascini et al. 1989. J. Pharm. Biomed. Anal. 7(12):1507-1512. Glucose electrochemical probe with extended linearity for whole blood.

(56) References Cited

OTHER PUBLICATIONS

Mazzola et al. 1983. (Video) Diabetes: A Teaching Tool or Children with Insulin-Dependent Diabetes. Proceedings—7th Annual Symposium on Computer Applications in Medical Car.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Mosbach et al. 1975. Biochim. Biophys. Acta (Enzymology) 403:256-265. Determination of heat changes in the proximity of immobilized enzymoes with an enzyme termistor and its.
Motonaka et al. 1993. Analytical Chemistry 65:3258-3261. Determination of cholesterol and cholesterol ester with novel enzyme microsensors.
Moussy 2002. Sensors 1:270-273. Implantable Glucose Sensor: Progress and Problems.
Moussy et al. 1993. Analyticak Chemistry 85:2072-2077. Performance of subcutaneously implanted needle-type glucose sensors employing a novel trilayer coating.
Nintendo Healthcare, Wired, Dec. 1993.
Oxford English Dictionary Online. Definition of "impending". http://www.askoxford.com/results/?view=dev dict&filed-12668446Impending&branch= Jan. 11, 2010.
Peacock et al. 2008. NEJM 358:2117-2126. Cardiac troponin and outcome in acute heart failure.
Pickup et al. 1993. TIBTECH 11:285-291. Developing glucose sensors for in vivo use.
Pinner et al. 1959. Nature 184:1303-1304. Cross-linking of cellulose acetate by ionizing radiation.
Rabah et al. 1991. Carbon 29(2):165-171. Electrochemical wear of graphite anodes during electrolysis of brine.
Raya Systems Pioneers Healthy Video Games, PlayRight, Nov. 1993 (pp. 14-15).
Reach 2001. Diabetes Technology and Therapeutics 3(1):129-130. Letters to the Editor Re: Diabetes Technology and Therapeutics 2000 (2):49-56.
Reusch. 2004. Chemical Reactivity. Organometallic Compounds. Virtual Textbook of Organic Chem. pp. 1-16, http://www.cem.msu.edu/.about.reusch/VirtualText/orgmetal.htm.
Rivers et al. 2001. Current Opinion in Critical Care 7:204-211. Central venous oxygen saturation monitoring in the critically ill patient.
Samuels, M.P. 2004. Arch. Dis. Child 89:448-455. The effects of flight and altitude.
San Diego Plastics, Inc. 2009. Polyethylene Data Sheet, http://www.sdplastics.com/polyeth.html.
Schmidtke et al. 1998. PNAS USA 95:294-299. Measurement and modeling of the transient difference between blood and subcutaneous glucose concentrations in the rat after injec.
Service et al. 1987. Diabetes Care 10:225-237. Measurements of glucose control.
Sharkawy et al. 1996. J. Biomedical Materials Research 37:401-412. Engineering the tissue which encapsulates subcutaneous implants. I. Diffusion properties.
Shichiri 1985. Chapter 15 in Ko, Wen H., Ed. 1985. Implantable Sensors for Closed-Loop Prosthetic Systems, Futura Pub. Co., Inc., Mt. Kisco, NY, pp. 197-210. Needle-Type Glu.
Slater-Maclean et al. 2008. Diab. Technology and Therapeutics 10:169-177. Accuracy of glycemic measurements in the critically ill.
Smith, Steven W. The Scientist and Engineers Guide to Digital Signal Processing. California Technical Publishing 1997-2007 [retrieved Jan. 1, 2009] http://www.dspguide.com/ch.
Sparacino et al. 2008. Current Diabetes Reviews 4:181-192. Continuous glucose monitoring time series and hypo-hyperglycemia prevention: requirements, methods, open problems.
Sriyudthsak et al. 1996. Biosensors and Bioelectronics 11:735-742. Enzyme-epoxy membrane based glucose analyzing system and medical applications.
Stern et al. 1957. J. Electrochemical Society 104(1):56-63. Electrocheical polarization: 1. A theoretical analysis of the shape of polarization curves.
Takegami et al. 1992. J. Membrane Science 75:93-105. Pervaporation of ethanol water mixture using novel hydrophobic membranes containing polydimethylsiloxane.
Tatsuma et al. 1991. Analytical Chemica Acta 242:85-89. Oxidase/peroxidase bilayer-modified electrodes as sensors for lactate, pyruvate, cholesteral and uric acid.
Thijssen 1984. Analytical Chimica Acta 162:253-262. A Kalman Filder for Calibration, Evaluation of Unknown Samples and Quality Control in Drifting Systems, Part 2. Optimal D.
Thijssen et al. 1984. Analytica Chimica Acta 156:87-101. A Kalman Filter for Calibration, Evaluation of Unknown Samples and Quality Control in Drifting Systems, Part 1. Theo.
Thijssen et al. 1985. Analytica Chimica Acta 173:265-272. A Kalman Filter for Calibration, Evaluation of Unknown Samples and Quality Control in Drifting Systems, Part 3. Var.
Thijssen et al. 1985. Analytical Chimica Acta 174:27-40. A Kalman Filter for Calibration, Evaluation of Unknown Samples and Quality Control in Drifting Systems, Part 4. Flow.
Thome-Duret et al. 1996. Analytical Chemistr4y 68:3822-3826. Use of a subcutaneous glucose sensor to detect decreases in glucose concentration prior to observation in blood.
Torjman et al. 2008. J. Diabetes Science and Technology 2(2):178-181, Glucose monitoring in acute care: technologies on the horizon.
Turner et al. 1984. Analytical Chimica Acta 163:161-174. Carbon Monoxide: Acceptor Oxidoreductase from Pseudomonas Thermocarboxydovorans Strain C2 and its use in a Carbon Mo.
Updike et al. 1967. Nature 214:986-988. The enzyme electrode.
Updike et al. 1979. J. Laboratory Clinical Medicine 93(4):518-527. Continuous glucose monitor based on an immobilized enzyme electrode detector.
Updike et al. 1982. Diabetes Care 5(3):207-212. Implanting the glucose enzyme electrode: Problems, progress, and alternative solutions.
Vadgama 1988. NATO ASI Series: C, Math and Phys. Sci. 226:359-377. Diffusion limited enzyme electodes.
Vig et al. 2000. IEEE/EIA International Frequency Control Symposium and Exhibition, pp. 30-33. A Review of Sensor Sensitivity and Stability.
Ward et al. 2004. Diabetes Technology and Therapeutics 6(3):389-401. A wire-based dual-analyte sensor for Glucose and Lactate: in Vitro and in Vivo Evaluation.
Wientjes, K. J. C. 2000. Development of a glucose sensor for diabetic patients. Ph.D. Thesis.
Wikipedia 2006. "Intravenous therapy," http://en.wikipedia.org/wiki/Intravenous.sub.--therapy, Aug. 15, 2006, 6 pp.
Wiley Electrical and Electronics Engineenng Dictionary. 2004. John Wiley & Sons, Inc. pp. 141, 142, 548, 549.
Worsley et al. 2008. J. Diabetes Science and Technology 2(2):213-220. Measurement of glucose in blood with a phenylboronic acid optical sensor.
Wright et al. 1999. Electrochemistry Communications 1:603-611. Bioelectrochemical dehalogenations via direct electrochemistry of poly(ethylene oxide)-modified myoglobin.
Ye et al. 1993. Analytical Chemistry 65:238-241. High Current Density Wired Quinoprotein Glucose Dehydrogenase Electrode.
Zethelius et al. 2008. NEJM 358:2107-2116. Use of multiple biomarkers to improve the prediction of death from cardiovascular causes.
Zhang et al. 1993, Analytical Chimica Acta 281:513-520. In vitro and in vivo evaluation of oxygen effects on a glucose oxidase based implantable glucose sensor.

\* cited by examiner

SYSTEMS AND METHODS FOR PROCESSING SENSOR DATA

CROSS-REFERENCE TO RELATED APPLICATIONS

This application is a continuation of U.S. application Ser. No. 12/258,235 filed Oct. 24, 2008, which claims the benefit of U.S. Provisional Application No. 60/982,647 filed Oct. 25, 2007, the disclosure of each of which is hereby incorporated by reference herein in its entirety, and is hereby expressly made a part of this specification.

FIELD OF THE INVENTION

The present invention relates generally to systems and methods for processing data received from an analyte sensor, such as a glucose sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose levels two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of glucose sensors are being developed for continuously detecting and/or quantifying blood glucose values. Many implantable glucose sensors suffer from complications within the body and provide only short-term and less-than-accurate sensing of blood glucose. Similarly, transdermal sensors have run into problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have occurred.

SUMMARY OF THE INVENTION

In a first aspect, a method for calibrating an analyte sensor is provided, the method comprising: receiving sensor data from an analyte sensor, the sensor data comprising at least one sensor data point; receiving reference data from a reference analyte monitor, the reference data comprising at least one reference analyte value; matching at least one sensor data point with at least one reference analyte value to form a matched data pair; converting sensor data into at least one estimated analyte value, utilizing the matched data pair; and displaying the estimated analyte value within about 10 minutes of receiving the reference analyte value.

In an embodiment of the first aspect, the step of displaying the estimated analyte value is performed within about 5 minutes of receiving the reference analyte value.

In an embodiment of the first aspect, the step of displaying the estimated analyte value is performed within about 1 minute of receiving the reference analyte value.

In a second aspect, a method for calibrating glucose sensor data from a continuous glucose sensor is provided, the method comprising: obtaining a reference glucose value; and matching the reference glucose value with a sensor glucose value without compensating for a time lag between the reference glucose value and the sensor glucose value such that a time stamp for the reference glucose value is as close as possible to a time stamp of the sensor glucose value.

In an embodiment of the second aspect, the time stamp of the reference glucose value is within about 5 minutes of the time stamp of the sensor glucose value.

In an embodiment of the second aspect, the time lag between the reference glucose value and the sensor glucose value is determined, at least in part, by a filter applied to raw glucose sensor data measured by the continuous glucose sensor.

In a third aspect, a method for calibrating glucose sensor data from a continuous glucose sensor is provided, the method comprising: immediately calibrating a continuous glucose sensor by matching a reference glucose value with a first sensor glucose value; and subsequently calibrating the continuous glucose sensor by matching the reference glucose value with a second sensor glucose value.

In an embodiment of the third aspect, the first sensor glucose value and the second sensor glucose value are different.

In an embodiment of the third aspect, the step of immediately calibrating comprises matching the reference glucose value with the first sensor glucose value without compensating for a time lag.

In an embodiment of the third aspect, the step of subsequently calibrating comprises matching the reference glucose value with the second sensor glucose value, whereby a time lag is compensated for.

In an embodiment of the third aspect, the step of immediately calibrating further comprises determining a calibration state comprising one of an out-of-calibration state and an in-calibration state.

In an embodiment of the third aspect, the step of determining a calibration state further comprises displaying information indicative of the calibration state on a user interface.

In an embodiment of the third aspect, the method further comprises displaying immediately calibrated sensor data after the step of immediately calibrating.

In an embodiment of the third aspect, the method further comprises displaying subsequently calibrated sensor data after the step of subsequently calibrating.

In a fourth aspect, a system for calibrating an analyte sensor is provided, the system comprising: a sensor data module configured to receive sensor data from an analyte sensor, the sensor data comprising at least one sensor data point; a reference input module, configured to receive reference data from a reference analyte monitor, the reference data comprising at least one reference analyte value; a processor module configured to match at least one sensor data point with at least one reference analyte value to form a matched data pair, wherein the processor module is further configured to convert sensor data into at least one estimated analyte value utilizing the matched data pair; and an output module configured to display the estimated analyte value within about 10 minutes of receiving the reference analyte value.

In a fifth aspect, a system is provided for calibrating glucose sensor data from a continuous glucose sensor, the system comprising: a processor module configured to obtain a reference glucose value and match the reference glucose value with a sensor glucose value without compensating for a time lag such that a time stamp of the reference glucose value is as close as possible to a time stamp of the sensor glucose value.

In a sixth aspect, a system is provided for calibrating glucose sensor data from a continuous glucose sensor, the system comprising: a processor module configured to immediately calibrate a continuous glucose sensor by matching a reference glucose value with a first sensor glucose value and subsequently calibrating the continuous glucose sensor by matching the reference glucose value with a second sensor glucose value.

In a seventh aspect, a system is provided for processing data from a continuous analyte sensor, comprising: a continuous analyte sensor configured to continuously measure a concentration of analyte in a host and provide continuous analyte sensor data associated therewith; and a processor module configured to set a mode selected from a plurality of predetermined modes, wherein the processor module is configured to process the continuous analyte sensor data based at least in part on the mode.

In an embodiment of the seventh aspect, the processor module is configured to set the mode at least in part responsive to receipt of a user input.

In an embodiment of the seventh aspect, the system comprises one or more buttons, and wherein the processor module is configured to receive the user input by selection of one or more buttons.

In an embodiment of the seventh aspect, the system comprises a screen, wherein the processor module is configured to display one or more menus on the screen, and wherein the processor module is configured to receive the user input by selection of one or more items from the one or more menus.

In an embodiment of the seventh aspect, the system is configured to operably connect with an external system such that data can be transmitted from the external system to the system, and wherein the processor module is configured to receive the user input by a data transmission received from the external system.

In an embodiment of the seventh aspect, the operable connection is a wired connection.

In an embodiment of the seventh aspect, the operable connection is a wireless connection.

In an embodiment of the seventh aspect, the external system comprises a programming configured to schedule events on a calendar.

In an embodiment of the seventh aspect, the processor module is configured to automatically set the mode based at least in part on a comparison of data with one or more criteria.

In an embodiment of the seventh aspect, the system further comprises an accelerometer, wherein the data comprises data received from the accelerometer.

In an embodiment of the seventh aspect, the system further comprises a temperature sensor, wherein the data comprises data received from the temperature sensor.

In an embodiment of the seventh aspect, the continuous analyte sensor comprises a continuous glucose sensor, wherein the data comprises glucose sensor data, and wherein the one or more criteria comprise one or more thresholds associated with hyperglycemia and/or hypoglycemia.

In an embodiment of the seventh aspect, the processor module comprises programming configured to automatically set the mode at least in part responsive to an adaptive mode learning module, wherein the adaptive mode learning module is configured to process sensor data and time-corresponding mode over time and subsequently modify the automatic mode-setting programming at least in part responsive thereto.

In an embodiment of the seventh aspect, the system is further configured to provide an alarm responsive to the sensor data meeting one or more criteria.

In an embodiment of the seventh aspect, the one or more criteria are based at least in part on the mode.

In an embodiment of the seventh aspect, the system is configured to provide the alarm via an audible sound, visual display, vibration, alphanumeric message, and/or wireless transmission based on the mode.

In an embodiment of the seventh aspect, the system is further configured to determine a therapy instruction based at least in part on the mode.

In an embodiment of the seventh aspect, the system is further configured to determine the therapy instruction based at least on the continuous analyte sensor data.

In an embodiment of the seventh aspect, the system is operably connected with a medicament delivery module, and wherein the medicament delivery module comprises programming configured to require a validation of the therapy instruction prior to delivery of the therapy via the medicament delivery module, and wherein validation requirement is dependent upon the mode.

In an embodiment of the seventh aspect, the processor module is further configured to classify a level of noise in the continuous analyte sensor data In an embodiment of the seventh aspect, the processor module is configured to set the mode responsive at least in part to the level of noise.

In an embodiment of the seventh aspect, the plurality of predetermined modes include two or more modes selected from the group consisting of resting mode, do not disturb mode, exercise mode, illness mode, menstruation mode, mealtime mode, day mode, night mode, hypoglycemic mode, hyperglycemic mode, noise mode.

In an embodiment of the seventh aspect, the processor module further comprises a timer associated with one or more modes, wherein the timer is configured to set the mode for a predetermined amount of time.

In an embodiment of the seventh aspect, the timer is user settable.

In an embodiment of the seventh aspect, the processor module is further configured to set the mode at least in part responsive to a mode profile.

In an embodiment of the seventh aspect, the mode profile is user settable.

In an eighth aspect, a method for processing data from a continuous analyte sensor is provided, comprising: receiving continuous analyte sensor data from a continuous analyte sensor; setting a mode selected from a plurality of predetermined modes; and processing the continuous analyte sensor data based at least in part on the mode.

In an embodiment of the eighth aspect, the step of setting the mode comprises receiving a user input.

In an embodiment of the eighth aspect, the step of receiving user input comprises receiving a selection of one or more buttons.

In an embodiment of the eighth aspect, the step of receiving user input comprises receiving a selection of one or more items from the one or more menus displayed on a screen.

In an embodiment of the eighth aspect, the step of receiving user input comprises receiving a data transmission from an external system.

In an embodiment of the eighth aspect, the step of receiving a data transmission comprises receiving a wired data transmission.

In an embodiment of the eighth aspect, the step of receiving a data transmission comprises receiving a wireless data transmission.

In an embodiment of the eighth aspect, the step of receiving a data transmission comprises receiving a data transmission from an event scheduling software.

In an embodiment of the eighth aspect, the step of processing comprises comparing the continuous analyte sensor data with one or more criteria.

In an embodiment of the eighth aspect, the method further comprises receiving data from an accelerometer, wherein the step of setting the mode is responsive at least in part to the data received from an accelerometer.

In an embodiment of the eighth aspect, the method further comprises receiving data from a temperature sensor, wherein the step of setting the mode is responsive at least in part to the received data.

In an embodiment of the eighth aspect, the step of receiving continuous analyte sensor data comprises receiving data from a continuous glucose sensor and wherein the one or more criteria comprise one or more thresholds associated with hypoglycemia and/or hyperglycemia.

In an embodiment of the eighth aspect, the step of setting the mode comprises automatically setting the mode.

In an embodiment of the eighth aspect, the method further comprises processing sensor data and time-corresponding mode settings over time and wherein the step of automatically setting the mode is based at least in part on one or more modes.

In an embodiment of the eighth aspect, the step of processing comprises initiating an alarm responsive to the sensor data meeting one or more criteria.

In an embodiment of the eighth aspect, the one or more criteria are based at least in part on the mode.

In an embodiment of the eighth aspect, the alarm comprises an audible alarm, visual alarm, vibration alarm, alphanumeric message alarm, and/or wireless transmission alarm based at least in part on the mode.

In an embodiment of the eighth aspect, the step of processing comprises determining a therapy instruction based at least in part on the mode.

In an embodiment of the eighth aspect, the step of determining the therapy instruction is based at least in part on the continuous analyte sensor data.

In an embodiment of the eighth aspect, the step of determining a therapy instruction further comprises requiring a validation of the therapy instruction prior to delivery of the therapy via the medicament delivery device, and wherein validation is based at least in part on the mode.

In an embodiment of the eighth aspect, the step of processing comprises classifying a level of noise in the continuous analyte sensor data.

In an embodiment of the eighth aspect, the step of classifying a level of noise comprises setting the mode based at least in part on the level of noise.

In an embodiment of the eighth aspect, the step of setting a mode from a plurality of predetermined modes comprise two or more modes selected from the group consisting of resting mode, do not disturb mode, exercise mode, illness mode, menstruation mode, mealtime mode, day mode, night mode, hypoglycemic mode, hyperglycemic mode, noise mode.

In an embodiment of the eighth aspect, the step of setting the mode comprises setting a mode for a predetermined amount of time based at least in part upon a timer.

In an embodiment of the eighth aspect, the timer is user settable.

In an embodiment of the eighth aspect, the step of setting the mode comprises setting the mode based at least in part on a mode profile.

In an embodiment of the eighth aspect, setting the mode profile is user settable.

In a ninth aspect, a method is provided for processing of a continuous glucose sensor signal, the method comprising: receiving sensor data from a continuous analyte sensor, including one or more sensor data points; comparing sensor data against one or more criteria for at least one of hypoglycemia, hyperglycemia, predicted hypoglycemia, and predicted hyperglycemia; and triggering an alarm when the sensor data meets one or more predetermined criteria.

In an embodiment of the ninth aspect, the alarm comprises first and second user selectable alarms.

In an embodiment of the ninth aspect, the first alarm is configured to alarm during a first time of day and wherein the second alarm is configured to alarm during a second time of day.

In an embodiment of the ninth aspect, the alarm is configured to turn on a light.

In an embodiment of the ninth aspect, the alarm is configured to alarm a remote device.

In an embodiment of the ninth aspect, the alarm comprises sending a text message to a remote device.

In a tenth aspect, a system is provided for processing continuous glucose sensor data, the system comprising: a continuous glucose sensor configured to generate sensor data associated with a glucose concentration in a host; and a computer system that compares sensor data against predetermined criteria for at least one of hypoglycemia, hyperglycemia, predicted hypoglycemia and predicted hyperglycemia, and triggers an alarm when the sensor data meets predetermined criteria.

In an embodiment of the tenth aspect, the alarm comprises first and second user selectable alarms.

In an embodiment of the tenth aspect, the first alarm is configured to alarm during a first time of day and wherein the second alarm is configured to alarm during a second time of day.

In an embodiment of the tenth aspect, the alarm is configured to turn a light on.

In an embodiment of the tenth aspect, the alarm is configured to alarm a remote device located more than about 10 feet away from the continuous glucose sensor.

In an embodiment of the tenth aspect, the alarm comprises a text message, and wherein the computer system is configured to send the text message a remote device.

In an eleventh aspect, a method for processing continuous glucose sensor data is provided, the method comprising: receiving sensor data from a continuous glucose sensor, wherein the sensor data comprises one or more sensor data points; obtaining an estimated sensor glucose value from the one or more sensor data points; calculating at least two rate of change values; and filtering the at least two rate of change values to obtain a filtered rate of change value.

In an embodiment of the eleventh aspect, the at least two rate of change values are point-to-point rate of change values.

In an embodiment of the eleventh aspect, the method further comprises determining a predicted value for a future time period based on the estimated sensor glucose value, the filtered rate of change value, and a time to the future time period.

In an embodiment of the eleventh aspect, the time to the future time period is user selectable.

In an embodiment of the eleventh aspect, the method further comprises comparing the predicted value against a threshold.

In an embodiment of the eleventh aspect, the method further comprises triggering an alarm when the predicted value passes the threshold.

In an embodiment of the eleventh aspect, the threshold is user selectable.

In an embodiment of the eleventh aspect, the method further comprises determining a predicted time to a threshold, wherein the predicted time is based at least in part on the estimated sensor glucose value, the filtered rate of change value, and the threshold.

In an embodiment of the eleventh aspect, the threshold is user selectable.

In an embodiment of the eleventh aspect, the method further comprises displaying the predicted time to the threshold on a user interface.

In an embodiment of the eleventh aspect, the step of displaying the predicted time to the threshold is performed only when the predicted time is below a predetermined value In an embodiment of the eleventh aspect, the method further comprises determining an insulin therapy based at least in part on the filtered rate of change value.

In an embodiment of the eleventh aspect, the step of filtering to obtain a filtered rate of change value is performed continuously.

In an embodiment of the eleventh aspect, the step of filtering to obtain a filtered rate of change value is not performed when a level of noise is above a threshold.

In an embodiment of the eleventh aspect, the method further comprises displaying a trend arrow representative of the filtered rate of change values.

In a twelfth aspect, a system is provided for processing continuous glucose sensor data, the system comprising: a continuous glucose sensor configured to generate sensor data associated with glucose concentration in a host; and a computer system that obtains an estimated sensor glucose value, calculates at least two rate of change values, and filters the at least two rate of change values to obtain a filtered rate of change value.

In an embodiment of the twelfth aspect, the at least two rate of change values are point-to-point rate of change values.

In an embodiment of the twelfth aspect, the computer system determines a predicted value for a future time period based on the estimated sensor glucose value, the filtered rate of change value and a time to the future time period.

In an embodiment of the twelfth aspect, the time to the future time period is user selectable.

In an embodiment of the twelfth aspect, the computer system compares the predicted value against a threshold.

In an embodiment of the twelfth aspect, the computer system triggers an alarm when the predicted value passes the threshold.

In an embodiment of the twelfth aspect, the threshold is user selectable.

In an embodiment of the twelfth aspect, the computer system determines a predicted time to a threshold, wherein the predicted time is based at least in part on the estimated sensor glucose value, the filtered rate of change value, and a threshold In an embodiment of the twelfth aspect, the threshold is user selectable.

In an embodiment of the twelfth aspect, the computer system is configured to display the predicted time to threshold on a user interface.

In an embodiment of the twelfth aspect, the computer system is configured to display the predicted time to threshold only when the predicted time is below a predetermined value.

In an embodiment of the twelfth aspect, the computer system determines an insulin therapy based at least in part on the filtered rate of change value.

In an embodiment of the twelfth aspect, the computer system continuously filters the at least two rate of change values to obtain a filtered rate of change value.

In an embodiment of the twelfth aspect, the computer system displays a trend arrow representative of the filtered rate of change values.

In an embodiment of the twelfth aspect, the computer system filters the at least two rate of change values to obtain a filtered rate of change value only when a level of noise is below a threshold.

In a thirteenth aspect, a method for determining a rate of change of a continuous glucose sensor signal is provided, comprising: receiving sensor data from a continuous analyte sensor, the sensor data comprising one or more sensor data points; and calculating a rate of change for a window of sensor data, wherein the window of sensor data comprises two or more sensor data points.

In an embodiment of the thirteenth aspect, the window of sensor data comprises a user selectable time period.

In an embodiment of the thirteenth aspect, the window of sensor data comprises a programmable time period.

In an embodiment of the thirteenth aspect, the window of sensor data adaptively adjusts based at least in part on a level of noise in the sensor data.

In a fourteenth aspect, a system is provided for determining a rate of change of a continuous glucose sensor signal, comprising: a continuous glucose sensor configured to generate sensor data associated with a glucose concentration in a host; and a computer system configured to calculate a rate of change for a window of sensor data, the sensor data comprising two or more sensor data points.

In an embodiment of the fourteenth aspect, the window of sensor data is a user selectable time period.

In an embodiment of the fourteenth aspect, the window of sensor data is a programmable time period.

In an embodiment of the fourteenth aspect, the computer system is configured to adaptively adjust the window of sensor data based at least in part on a level of noise in the sensor data.

In a fifteenth aspect, a method is provided for determining a rate of change of a continuous glucose sensor signal, comprising: receiving sensor data from a continuous analyte sensor; determining a level of noise in the sensor data; and calculating a rate of change for a window of the sensor data, wherein the window of sensor data comprises two or more sensor data points.

In an embodiment of the fifteenth aspect, the step of calculating a rate of change uses either raw sensor data or filtered sensor data, depending at least in part upon the level of noise determined.

In an embodiment of the fifteenth aspect, the step of calculating a rate of change comprises at least two rate of change calculations, and wherein the step of calculating a rate of change further comprises adaptively selecting a filter to apply to the at least two rate of change calculations based at least in part on the level of noise determined.

In a sixteenth aspect, a system is provided for determining a rate of change of a continuous glucose sensor signal, comprising: a continuous glucose sensor configured to generate sensor data associated with a glucose concentration in a host; and a computer system configured to determine a level of noise in the sensor data and calculate a rate of change for a window of the sensor data, wherein the window of sensor data comprises two or more sensor data points.

In an embodiment of the sixteenth aspect, the computer system is configured to use either raw sensor data or filtered sensor data in the rate of change calculation depending at least in part upon the level of noise determined.

In an embodiment of the sixteenth aspect, the rate of change calculation comprises calculating at least two rate of change calculations, and wherein the rate of change calculation further comprises adaptively selecting a filter to apply to the rate of change calculation based at least in part on the level of noise determined.

In a seventeenth aspect, a method is provided for classifying a level of noise in a signal obtained from a continuous glucose sensor, the method comprising: receiving a signal from a continuous glucose sensor; and classifying a level of noise on the signal.

In an embodiment of the seventeenth aspect, the step of classifying comprises applying a low pass filter to the signal to determine a signal strength.

In an embodiment of the seventeenth aspect, the step of classifying comprises defining one or more noise thresholds for classification of the level of noise on the signal, wherein the one or more noise thresholds are based at least in part on a percentage of the signal strength.

In an embodiment of the seventeenth aspect, the step of classifying comprises applying one or more low pass filters to the noise signal to obtain one or more noise indicators and comparing the noise indicators with the one or more noise thresholds.

In an embodiment of the seventeenth aspect, the method further comprises determining a noise signal from the sensor signal, and wherein the step of classifying comprises applying one or more filters to the noise signal to obtain one or more noise indicators and comparing the noise indicators with one or more noise thresholds.

In an embodiment of the seventeenth aspect, the step of classifying comprises performing spectral analysis to determine at least one of a signal strength and a noise indicator.

In an embodiment of the seventeenth aspect, the step of classifying a level of noise comprises using hysteresis.

In an embodiment of the seventeenth aspect, the method further comprises controlling an output based at least in part on the level of noise.

In an embodiment of the seventeenth aspect, the method further comprises controlling a display based at least in part on the level of noise.

In an embodiment of the seventeenth aspect, the step of controlling a display comprises controlling the display of raw and/or filtered data based at least in part on the level of noise.

In an embodiment of the seventeenth aspect, the step of controlling a display comprises displaying rate of change information based at least in part on the level of noise.

In an embodiment of the seventeenth aspect, the method further comprises a step of controlling at least one alarm indicative of at least one of hypoglycemia, hyperglycemia, predicted hypoglycemia, and predicted hyperglycemia based at least in part on the level of noise.

In an embodiment of the seventeenth aspect, the method further comprises a step of controlling medicament delivery and/or medicament therapy instructions based at least in part on the level of noise.

In an embodiment of the seventeenth aspect, the method further comprises a step of diagnosing a sensor condition based at least in part on the level of noise.

In an embodiment of the seventeenth aspect, the method further comprises a step of suspending display of sensor data based at least in part on the level of noise.

In an embodiment of the seventeenth aspect, the method further comprises a step of shutting down a sensor session based at least in part on the level of noise.

In an embodiment of the seventeenth aspect, the method further comprises a step of displaying the level of noise on the user interface.

In an embodiment of the seventeenth aspect, the method further comprises a step of displaying information indicative of the level of noise on the sensor signal.

In an embodiment of the seventeenth aspect, the method further comprises a step of displaying information indicative of an amount of time that the signal has been classified as having a level of noise.

In an eighteenth aspect, a system is provided for classifying a level of noise in a signal obtained from a continuous glucose sensor, the system comprising: a continuous glucose sensor that provides a signal indicative of a glucose concentration in a host; and a computer system that classifies a level of noise on the signal.

In an embodiment of the eighteenth aspect, the method further comprises the computer system filters the signal by applying a low pass filter to the signal to determine a signal strength.

In an embodiment of the eighteenth aspect, the computer system defines one or more noise thresholds for classification of the level of noise on the signal, and wherein the one or more noise thresholds are based at least in part on a percentage of the signal strength.

In an embodiment of the eighteenth aspect, the computer system classifies the level of noise by applying one or more low pass filters to the noise signal to obtain one or more noise indicators and comparing the noise indicators to the one or more noise thresholds.

In an embodiment of the eighteenth aspect, the computer system classifies a level of noise by applying one or more filters to the noise signal to obtain one or more noise indicators and comparing the noise indicators with one or more noise thresholds.

In an embodiment of the eighteenth aspect, the computer system classifies a level of noise by performing spectral analysis to determine at least one of a signal strength and a noise indicator.

In an embodiment of the eighteenth aspect, the computer system uses hysteresis to classify the level of noise.

In an embodiment of the eighteenth aspect, the computer system provides an output based at least in part on the level of noise.

In an embodiment of the eighteenth aspect, the system further comprises a user interface configured to display the glucose concentration to the host, wherein the computer system is configured to control the display based at least in part on the level of noise.

In an embodiment of the eighteenth aspect, the computer system controls the display of raw and/or filtered data based at least in part on the level of noise.

In an embodiment of the eighteenth aspect, the computer system controls the display of rate of change information based at least in part on the level of noise.

In an embodiment of the eighteenth aspect, the computer system is configured to control alarms indicative of at least one of hypoglycemia, hyperglycemia, predicted hypoglycemia, and predicted hyperglycemia based at least in part on the level of noise.

In an embodiment of the eighteenth aspect, the computer system is configured to control medicament delivery and/or medicament therapy instructions based at least in part on the level of noise.

In an embodiment of the eighteenth aspect, the computer system is configured to diagnose a sensor condition based at least in part on the level of noise.

In an embodiment of the eighteenth aspect, the computer system is configured to suspend display of a glucose concentration based at least in part on the level of noise.

In an embodiment of the eighteenth aspect, the computer system is configured to shut down a sensor session based at least in part on the level of noise.

In an embodiment of the eighteenth aspect, the computer system is configured to display the level of noise on the user interface.

In an embodiment of the eighteenth aspect, the computer system is configured to display information indicative of the level of noise on the sensor signal.

In an embodiment of the eighteenth aspect, the computer system is configured to display information indicative of an amount of time the signal has been classified as having a level of noise.

In a nineteenth embodiment, a method is provided for calibration of a continuous glucose sensor, the method comprising: receiving sensor data from a continuous analyte sensor, the sensor data comprising one or more sensor data points; receiving and processing calibration information; evaluating a predictive accuracy of calibration information; and determining when to request reference data based at least in part on the predictive accuracy of calibration information.

In an embodiment of the nineteenth aspect, the step of determining when to request reference data comprises determining a time period.

In an embodiment of the nineteenth aspect, the time period is between about 0 minutes and 7 days.

In an embodiment of the nineteenth aspect, the step of receiving and processing calibration information comprises receiving one or more matched data pairs, wherein the step of evaluating a predictive accuracy comprises evaluating a correlation of at least one matched data pair with at least some of the calibration information.

In an embodiment of the nineteenth aspect, the step of determining is based at least in part on the correlation of the at least one matched data pair and the calibration information.

In an embodiment of the nineteenth aspect, the step of receiving and processing calibration information comprises receiving reference data from a reference analyte monitor, forming at least one matched data pair, forming a calibration set including said at least one matched data pair, and forming a calibration line from said calibration set, wherein the step of evaluating a predictive accuracy comprises evaluating a correlation of the matched data pairs in the calibration set with the calibration line.

In an embodiment of the nineteenth aspect, the step of determining is based at least in part on the correlation of the matched pairs in the calibration set and the calibration line.

In an embodiment of the nineteenth aspect, the step of receiving and processing calibration information comprises receiving a matched data pair and forming a calibration set including said matched data pair, wherein the step of evaluating a predictive accuracy comprises evaluating a discordance of the matched data pair and/or the matched data pairs in the calibration set.

In an embodiment of the nineteenth aspect, the step of determining is based at least in part on the discordance of the matched data pair and/or the matched data pairs in the calibration set.

In an embodiment of the nineteenth aspect, the step of receiving and processing calibration information comprises forming one or more matched data pairs by matching time corresponding sensor and reference data and forming a calibration set including one or more matched data pairs wherein the step of evaluating a predictive accuracy comprises iteratively evaluating a plurality of combinations of matched data pairs in the calibration set to obtain a plurality of calibration lines.

In an embodiment of the nineteenth aspect, the method further comprises removing matched data pairs from the calibration set in response to the iterative evaluation.

In an embodiment of the nineteenth aspect, the step of determining is based at least in part on the iterative evaluation.

In an embodiment of the nineteenth aspect, the step of receiving and processing calibration information comprises receiving reference data, forming one or more matched data pairs, and forming a calibration set including one or more matched data pairs, wherein the step of evaluating a predictive accuracy comprises evaluating an goodness of fit of the calibration set with a calibration line drawn from the calibration set.

In an embodiment of the nineteenth aspect, the step of determining is based at least in part on the goodness of fit.

In an embodiment of the nineteenth aspect, the step of receiving and processing calibration information comprises receiving reference data, and wherein the step of evaluating a predictive accuracy comprises evaluating a leverage of the reference data based at least in part on a glucose concentration associated with the reference data.

In an embodiment of the nineteenth aspect, the step of determining is based at least in part on the leverage of the reference data.

In an embodiment of the nineteenth aspect, the method further comprises requesting reference data responsive to the step of determining.

In an embodiment of the nineteenth aspect, the method further comprises displaying an amount of time before reference data will be requested.

In a twentieth aspect, a system is provided for calibration of a continuous analyte sensor, comprising: a continuous analyte sensor configured to continuously measure a concentration of analyte in a host; and a computer system that receives sensor data from the continuous analyte sensor, wherein the computer system is configured to receive and process calibration information, and wherein the computer system evaluates a predictive accuracy of calibration information to determine when to request additional reference data.

In an embodiment of the twentieth aspect, the computer system determines a time period to request additional reference data.

In an embodiment of the twentieth aspect, the time period is between about 0 minutes and 7 days.

In an embodiment of the twentieth aspect, the computer system is configured to receive reference data from a reference analyte monitor, wherein the computer system is configured to match reference data to substantially time corresponding sensor data to form at least one matched data pair, and wherein the computer system is configured to evaluate a predictive accuracy by evaluating a correlation of at least one matched data pair with at least some of the calibration information.

In an embodiment of the twentieth aspect, the computer system determines when to request reference data based at least in part on the correlation of the at least one matched data pair and the calibration information.

In an embodiment of the twentieth aspect, the computer system is configured to receive reference data from a reference analyte monitor, match reference data to substantially time corresponding sensor data to form at least one matched data pair, form a calibration set from at least one matched data pair, and form a calibration line from the calibration set, wherein the computer system is configured to evaluate a predictive accuracy by evaluating a correlation of matched data pairs in the calibration set with a calibration line based on a calibration set including a newly received matched data pair.

In an embodiment of the twentieth aspect, the computer system determines when to request reference data based at least in part on the correlation of the matched pairs in the calibration set and the calibration line.

In an embodiment of the twentieth aspect, the computer system is configured to receive reference data from a reference analyte monitor, match reference data to substantially time corresponding sensor data to form at least one matched data pair, and form a calibration set from at least one matched data pair, wherein the computer system is configured to evaluate a predictive accuracy by evaluating a discordance of a matched data pair and/or a plurality of matched data pairs in a calibration set.

In an embodiment of the twentieth aspect, the computer system determines when to request reference data based at least in part on the discordance of the matched data pair and/or the matched data pairs in the calibration set.

In an embodiment of the twentieth aspect, the computer system is configured to receive reference data from a reference analyte monitor, match reference data to substantially time corresponding sensor data to form at least one matched data pair, and form a calibration set from at least one matched data pair, wherein the computer system iteratively evaluates a plurality of combinations of matched data pairs in the calibration set to obtain a plurality of calibration lines.

In an embodiment of the twentieth aspect, the computer system is configured to remove matched data pairs from the calibration set in response to the iterative evaluation.

In an embodiment of the twentieth aspect, the computer system determines when to request reference data based at least in part on the iterative evaluation.

In an embodiment of the twentieth aspect, the computer system is configured to receive reference data from a reference analyte monitor, match reference data to substantially time corresponding sensor data to form at least one matched data pair, and form a calibration set from at least one matched data pair, wherein the computer system is configured to evaluate a predictive accuracy by evaluating a goodness of fit of the calibration set with a calibration line drawn from the calibration set.

In an embodiment of the twentieth aspect, the computer system determines when to request reference data based at least in part on the goodness of fit.

In an embodiment of the twentieth aspect, the computer system is configured to receive reference data from a reference analyte monitor, and wherein the computer system is configured to evaluate a predictive accuracy by evaluating a leverage of the reference data based at least in part on a glucose concentration associated with reference data.

In an embodiment of the twentieth aspect, the computer system determines when to request reference data based at least in part on leverage of the reference data.

In an embodiment of the twentieth aspect, the computer system is configured to request reference data at a time determined by the predictive evaluation.

In an embodiment of the twentieth aspect, the computer system is configured to display an amount of time before reference data will be requested.

In a twenty-first aspect, a method is provided for calibration of a continuous glucose sensor, the method comprising: receiving a signal from a continuous glucose sensor, evaluating a sensor performance during a sensor session; and determining when to request reference data responsive to the sensor performance determined.

In an embodiment of the twenty-first aspect, the step of evaluating a sensor performance comprises determining an amount of drift on the sensor signal over a time period, and wherein the step of determining when to request reference data comprises requesting reference data when the amount of drift is greater than a threshold.

In an embodiment of the twenty-first aspect, the step of determining an amount of drift comprises monitoring a change in signal strength.

In an embodiment of the twenty-first aspect, the step of determining an amount of drift comprises analyzing a fluctuation in a second working electrode of a dual electrode system.

In an embodiment of the twenty-first aspect, the step of monitoring a change in signal strength comprises applying a low pass filter.

In an embodiment of the twenty-first aspect, the step of determining an amount of drift comprises monitoring a change in calibration information.

In an embodiment of the twenty-first aspect, the method further comprises controlling an output in response to the sensor performance.

In a twenty-second aspect, a method is provided for calibration of a continuous glucose sensor, the method comprising: receiving a signal from a continuous glucose sensor; determining a predictive accuracy of sensor calibration; and controlling an output based at least in part on the predictive accuracy determined.

In an embodiment of the twenty-second aspect, the step of controlling an output comprises controlling a display of data based at least in part on the level of noise.

In an embodiment of the twenty-second aspect, the step of controlling an output comprises controlling alarms indicative of at least one of hypoglycemia, hyperglycemia, predicted hypoglycemia, and predicted hyperglycemia based at least in part on the predictive accuracy.

In an embodiment of the twenty-second aspect, the method further comprises controlling insulin delivery and/or insulin therapy instructions based at least in part on the predictive accuracy.

In an embodiment of the twenty-second aspect, the method further comprises diagnosing a sensor condition based at least in part on the predictive accuracy.

DETAILED DESCRIPTION OF THE PREFERRED EMBODIMENTS

Figure 1A:
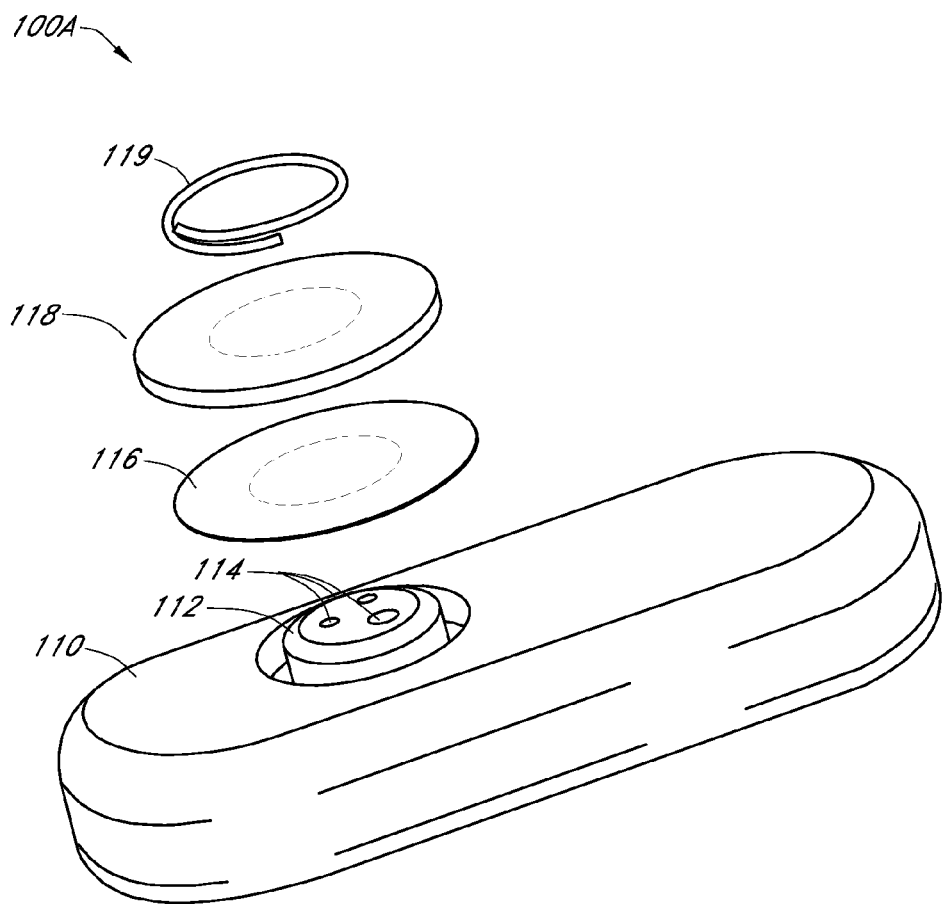
FIG. 1A is an exploded perspective view of a glucose sensor in one embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, rickettsia (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "ROM" as used herein is a broad term and is to be given its ordinary and customary meaning to a person of ordinary skill in the art (and is not to be limited to a special or customized meaning), and furthermore refers without limitation to read-only memory, which is a type of data storage device manufactured with fixed contents. ROM is broad enough to include EEPROM, for example, which is electrically erasable programmable read-only memory (ROM).

The term "RAM" as used herein is a broad term and is to be given its ordinary and customary meaning to a person of ordinary skill in the art (and is not to be limited to a special or customized meaning), and furthermore refers without limitation to a data storage device for which the order of access to different locations does not affect the speed of access. RAM is broad enough to include RAM, for example, which is static random access memory that retains data bits in its memory as long as power is being supplied.

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The term "RF transceiver" as used herein is a broad term and is to be given its ordinary and customary meaning to a person of ordinary skill in the art (and is not to be limited to a special or customized meaning), and furthermore refers without limitation to a radio frequency transmitter and/or receiver for transmitting and/or receiving signals.

The term "jitter" as used herein is a broad term and is to be given its ordinary and customary meaning to a person of ordinary skill in the art (and is not to be limited to a special or customized meaning), and furthermore refers without limitation to noise above and below the mean caused by ubiquitous noise caused by a circuit and/or environmental effects; jitter can be seen in amplitude, phase timing, or the width of the signal pulse.

The terms "raw data stream" and "data stream" as used herein are broad terms and are to be given their ordinary and customary meaning to a person of ordinary skill in the art (and are not to be limited to a special or customized meaning), and furthermore refer without limitation to an analog or digital signal directly related to the measured glucose from the glucose sensor. In one example, the raw data stream is digital data in "counts" converted by an A/D converter from an analog signal (e.g., voltage or amps) and includes one or more data points representative of a glucose concentration. The terms broadly encompass a plurality of time spaced data points from a substantially continuous glucose sensor, which comprises individual measurements taken at time intervals ranging from fractions of a second up to, e.g., 1, 2, or 5 minutes or longer. In another example, the raw data stream includes an integrated digital value, wherein the data includes one or more data points representative of the glucose sensor signal averaged over a time period.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data. In some embodiments, namely, in continuous analyte sensors, calibration can be updated or recalibrated over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates components of a signal that are undesired, such as reducing noise errors in a signal. In some embodiments, smoothing refers to modification of a set of data to make it smoother and more continuous or to remove or diminish outlying points, for example, by performing a moving average of the raw data stream.

The term "noise signal" as used herein is a broad term and is to be given its ordinary and customary meaning to a person of ordinary skill in the art (and is not to be limited to a special or customized meaning), and furthermore refers without limitation to a signal associated with noise on the data stream (e.g., non-analyte related signal). The noise signal can be determined by filtering and/or averaging, for example. In some embodiments, the noise signal is a signal residual, delta residual (difference of residual), absolute delta residual, and/or the like, which are described in more detail elsewhere herein.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified and/or the device itself.

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

$$Glucose+O_2 \rightarrow Gluconate+H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "electronic circuitry" as used herein is a broad term and is to be given its ordinary and customary meaning to a person of ordinary skill in the art (and is not to be limited to a special or customized meaning), and furthermore refers without limitation to the components of a device configured to process biological information obtained from a host. In the case of a glucose-measuring device, the biological information is obtained by a sensor regarding a particular glucose in a biological fluid, thereby providing data regarding the amount of that glucose in the fluid. U.S. Pat. Nos. 4,757,022, 5,497,772 and 4,787,398, which are hereby incorporated by reference, describe suitable electronic circuits that can be utilized with devices including the biointerface membrane of a preferred embodiment.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte (or glucose) sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for the continuous analyte sensor, for example a self-monitoring blood glucose meter (SMBG) can be used as a reference for a continuous glucose sensor for comparison, calibration, and the like.

The term "Clarke Error Grid", as used herein, is a broad term and is to be given its ordinary and customary meaning to a person of ordinary skill in the art (and is not to be limited to a special or customized meaning), and refers without limitation to an error grid analysis, which evaluates the clinical significance of the difference between a reference glucose value and a sensor generated glucose value, taking into account 1) the value of the reference glucose measurement, 2) the value of the sensor glucose measurement, 3) the relative difference between the two values, and 4) the clinical significance of this difference. See Clarke et al., "Evaluating Clinical Accuracy of Systems for Self-Monitoring of Blood Glucose", Diabetes Care, Volume 10, Number 5, September-October 1987, which is incorporated by reference herein in its entirety.

The term "Consensus Error Grid", as used herein, is a broad term and is to be given its ordinary and customary meaning to a person of ordinary skill in the art (and is not to be limited to a special or customized meaning), and refers without limitation to an error grid analysis that assigns a specific level of clinical risk to any possible error between two time corresponding glucose measurements. The Consensus Error Grid is divided into zones signifying the degree of risk posed by the deviation. See Parkes et al., "A New Consensus Error Grid to Evaluate the Clinical Significance of Inaccuracies in the Measurement of Blood Glucose", Diabetes Care, Volume 23, Number 8, August 2000, which is incorporated by reference herein in its entirety.

The term "clinical acceptability", as used herein, is a broad term and is to be given its ordinary and customary meaning to a person of ordinary skill in the art (and is not to be limited to a special or customized meaning), and refers without limitation to determination of the risk of inaccuracies to a patient. Clinical acceptability considers a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "R-value," as used herein is a broad term and is to be given its ordinary and customary meaning to a person of ordinary skill in the art (and is not to be limited to a special or customized meaning), and refers without limitation to one conventional way of summarizing the correlation of data; that is, a statement of what residuals (e.g., root mean square deviations) are to be expected if the data are fitted to a straight line by the a regression.

The terms "data association" and "data association function," as used herein, are broad terms and are to be given their ordinary and customary meaning to a person of ordinary skill in the art (and are not to be limited to a special or customized meaning), and refer without limitation to a statistical analysis of data and particularly its correlation to, or deviation from, from a particular curve. A data association function is used to show data association. For example, data that form as calibration set as described herein may be analyzed mathematically to determine its correlation to, or deviation from, a curve (e.g., line or set of lines) that defines the conversion function; this correlation or deviation is the data association. A data association function is used to determine data association. Examples of data association functions include, but are not limited to, linear regression, non-linear mapping/regression, rank (e.g., non-parametric) correlation, least mean square fit, mean absolute deviation (MAD), mean absolute relative difference. In one such example, the correlation coefficient of linear regression is indicative of the amount of data association of the calibration set that forms the conversion function, and thus the quality of the calibration.

The term "quality of calibration" as used herein, is a broad term and is to be given its ordinary and customary meaning to a person of ordinary skill in the art (and is not to be limited to a special or customized meaning), and refers without limitation to the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The terms "congruence" and "correlation" as used herein, are broad terms and are to be given their ordinary and customary meaning to a person of ordinary skill in the art (and are not to be limited to a special or customized meaning), and refer without limitation to the quality or state of agreeing, coinciding, or being concordant. In one example, correlation may be determined using a data association function.

The term "discordance" as used herein, is a broad term and is to be given its ordinary and customary meaning to a person of ordinary skill in the art (and is not to be limited to a special or customized meaning), and refers without limitation to the disassociation of comparative data. In one example, discordance may be determined using a data association function.

The phrase "goodness of fit" as used herein, is a broad term and is to be given its ordinary and customary meaning to a person of ordinary skill in the art (and is not to be limited to a special or customized meaning), and refers without limitation to a degree to which a model fits the observed data. For example, in a regression analysis, the goodness-of-fit can be quantified in terms of R-squared, R-value and/or error distribution.

The term "sensor session" as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of the transmitter from the sensor housing).

The terms "sensor head" and "sensing region" as used herein are broad terms and are to be given their ordinary and customary meaning to a person of ordinary skill in the art (and are not to be limited to a special or customized meaning), and furthermore refer without limitation to the region of a monitoring device responsible for the detection of a particular analyte. The sensing region generally comprises a non-conductive body, a working electrode (anode), a reference electrode (optional), and/or a counter electrode (cathode) passing through and secured within the body forming electrochemically reactive surfaces on the body and an electronic connective means at another location on the body, and a multi-domain membrane affixed to the body and covering the electrochemically reactive surface.

The term "physiologically feasible" as used herein is a broad term and is to be given its ordinary and customary meaning to a person of ordinary skill in the art (and is not to be limited to a special or customized meaning), and furthermore refers without limitation to the physiological parameters obtained from continuous studies of glucose data in humans and/or animals. For example, a maximal sustained rate of change of glucose in humans of about 4 to 5 mg/dL/min and a maximum acceleration of the rate of change of about 0.1 to 0.2 mg/dL/min/min are deemed physiologically feasible limits. Values outside of these limits would be considered non-physiological and likely a result of signal error, for example. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (e.g., about 20 to 30 minutes) is a straight line, which can be used to set physiological limits.

The term "system noise" as used herein is a broad term and is to be given its ordinary and customary meaning to a person of ordinary skill in the art (and is not to be limited to a special or customized meaning), and furthermore refers without limitation to unwanted electronic or diffusion-related noise which can include Gaussian, motion-related, flicker, kinetic, or other white noise, for example.

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is caused by substantially non-glucose related, such as interfering species, macro- or micro-motion, ischemia, pH changes, temperature changes, pressure, stress, or even unknown sources of mechanical, electrical and/or biochemical noise for example. In some embodiments, signal artifacts are transient and characterized by a higher amplitude than system noise, and described as "transient non-glucose related signal artifact(s) that have a higher amplitude than system noise." In some embodiments, noise is caused by rate-limiting (or rate-increasing) phenomena. In some circumstances, the source of the noise is unknown.

The terms "constant noise" and "constant background" as used herein are broad terms, and are to be given their ordinary and customary meaning to a person of ordinary skill in the art (and are not to be limited to a special or customized meaning), and refer without limitation to the component of the noise signal that remains relatively constant over time. In some embodiments, constant noise may be referred to as "background" or "baseline." For example, certain electroactive compounds found in the human body are relatively constant factors (e.g., baseline of the host's physiology). In some circumstances, constant background noise can slowly drift over time (e.g., increase or decrease), however this drift need not adversely affect the accuracy of a sensor, for example, because a sensor can be calibrated and re-calibrated and/or the drift measured and compensated for.

The terms "non-constant noise," "non-constant background," "noise event(s)," "noise episode(s)," "signal artifact(s)," "signal artifact event(s)," and "signal artifact episode(s)" as used herein are broad terms, and are to be given their ordinary and customary meaning to a person of ordinary skill in the art (and are not to be limited to a special or customized meaning), and refer without limitation to a component of the background signal (e.g., non-analyte related signal) that is relatively non-constant, for example, transient and/or intermittent. For example, certain electroactive compounds, are relatively non-constant due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The term "linear regression" as used herein is a broad term and is to be given its ordinary and customary meaning to a person of ordinary skill in the art (and is not to be limited to a special or customized meaning), and furthermore refers without limitation to finding a line in which a set of data has a minimal measurement from that line. Byproducts of this algorithm include a slope, a y-intercept, and an R-Squared value that determine how well the measurement data fits the line.

The term "non-linear regression" as used herein is a broad term and is to be given its ordinary and customary meaning to a person of ordinary skill in the art (and is not to be limited to a special or customized meaning), and furthermore refers without limitation to fitting a set of data to describe the relationship between a response variable and one or more explanatory variables in a non-linear fashion.

The term "mean" as used herein is a broad term and is to be given its ordinary and customary meaning to a person of ordinary skill in the art (and is not to be limited to a special or customized meaning), and furthermore refers without limitation to the sum of the observations divided by the number of observations.

The term "trimmed mean" as used herein is a broad term and is to be given its ordinary and customary meaning to a person of ordinary skill in the art (and is not to be limited to a special or customized meaning), and furthermore refers without limitation to a mean taken after extreme values in the tails of a variable (e.g., highs and lows) are eliminated or reduced (e.g., "trimmed"). The trimmed mean compensates for sensitivities to extreme values by dropping a certain percentage of values on the tails. For example, the 50% trimmed mean is the mean of the values between the upper and lower quartiles. The 90% trimmed mean is the mean of the values after truncating the lowest and highest 5% of the values. In one example, two highest and two lowest measurements are removed from a data set and then the remaining measurements are averaged.

The term "non-recursive filter" as used herein is a broad term and is to be given its ordinary and customary meaning to a person of ordinary skill in the art (and is not to be limited to a special or customized meaning), and furthermore refers without limitation to an equation that uses moving averages as inputs and outputs.

The terms "recursive filter" and "auto-regressive algorithm" as used herein are broad terms and are to be given their ordinary and customary meaning to a person of ordinary skill in the art (and are not to be limited to a special or customized meaning), and furthermore refer without limitation to an equation in which includes previous averages are part of the next filtered output. More particularly, the generation of a series of observations whereby the value of each observation is partly dependent on the values of those that have immediately preceded it. One example is a regression structure in which lagged response values assume the role of the independent variables.

The term "signal estimation algorithm factors" as used herein is a broad term and is to be given its ordinary and customary meaning to a person of ordinary skill in the art (and is not to be limited to a special or customized meaning), and furthermore refers without limitation to one or more algorithms that use historical and/or present signal data stream values to estimate unknown signal data stream values. For example, signal estimation algorithm factors can include one or more algorithms, such as linear or non-linear regression. As another example, signal estimation algorithm factors can include one or more sets of coefficients that can be applied to one algorithm.

The terms "physiological parameters" and "physiological boundaries" as used herein are broad terms and are to be given their ordinary and customary meaning to a person of ordinary skill in the art (and are not to be limited to a special or customized meaning), and furthermore refer without limitation to the parameters obtained from continuous studies of physiological data in humans and/or animals. For example, a maximal sustained rate of change of glucose in humans of about 4 to 5 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (for example, about 20 to 30 minutes) is a straight line, which can be used to set physiological limits. These terms are broad enough to include physiological parameters for any analyte.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values. In some embodiments, estimated analyte values are estimated for a time period during which no data exists. However, estimated analyte values can also be estimated during a time period for which measured data exists, but is to be replaced by algorithmically extrapolated (e.g. processed or filtered) data due to noise or a time lag in the measured data, for example.

The term "calibration information" as used herein is a broad term and is to be given its ordinary and customary meaning to a person of ordinary skill in the art (and is not to be limited to a special or customized meaning), and furthermore refers without limitation to any information useful in calibration of a sensor. Calibration information includes reference data received from a reference analyte monitor, including one or more reference data points, one or more matched data pairs formed by matching reference data (e.g., one or more reference glucose data points) with substantially time corresponding sensor data (e.g., one or more continuous sensor data points), a calibration set formed from a set of one or more matched data pairs, and/or a calibration line drawn from the calibration set, for example.

The term "mode" as used herein is a broad term and is to be given its ordinary and customary meaning to a person of ordinary skill in the art (and is not to be limited to a special or customized meaning), and furthermore refers without limitation to an automatic and/or user configurable setting within a system associated with an activity, event, physiological condition, sensor condition, and/or preference of a user.

The term "mode profile" as used herein is a broad term and is to be given its ordinary and customary meaning to a person of ordinary skill in the art (and is not to be limited to a special or customized meaning), and furthermore refers without limitation to a programmable, predetermined, and/or user selectable sequence of modes based on time. In one embodiment, the mode profile enables an automated setting of modes based upon a mode profile, which can be associated with, for example, a schedule of events or blocks of events corresponding to various times throughout their day.

As employed herein, the following abbreviations apply: Eq and Eqs (equivalents); mEq (milliequivalents); M (molar); mM (millimolar) μM (micromolar); N (Normal); mol (moles); nmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

The preferred embodiments relate to the use of an analyte sensor that measures a concentration of glucose or a substance indicative of the concentration or presence of the analyte. In some embodiments, the analyte sensor is a continuous device, for example a subcutaneous, transdermal, or intravascular device. In some embodiments, the device can analyze a plurality of intermittent blood samples. The analyte sensor can use any method of glucose-measurement, including enzymatic, chemical, physical, electrochemical, spectrophotometric, polarimetric, calorimetric, iontophoretic, radiometric, and the like.

The analyte sensor can use any known method, including invasive, minimally invasive, and non-invasive sensing techniques, to provide a data stream indicative of the concentration of the analyte in a host. The data stream is typically a raw data signal that is used to provide a useful value of the analyte to a user, such as a patient or doctor, who may be using the sensor.

Sensor

Although much of the description and examples are drawn to a glucose sensor, the systems and methods of the preferred embodiments can be applied to any measurable analyte. In some preferred embodiments, the analyte sensor is a glucose sensor capable of measuring the concentration of glucose in a host. One exemplary embodiment is described below, which utilizes an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In yet another preferred embodiment, the analyte sensor is a dual electrode analyte sensor, such as described with reference to U.S. patent application Ser. No. 12/055,149. In still other embodiments, the sensor is configured to be implanted in a host vessel or extracorporeally, such as is described in U.S. Patent Publication No. US-2007-0027385-A1, co-pending U.S. patent application Ser. No. 11/543,396 filed Oct. 4, 2006, co-pending U.S. patent application Ser. No. 11/691,426 filed on Mar. 26, 2007, and co-pending U.S. patent application Ser. No. 11/675,063 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

FIG. 1A is an exploded perspective view of one exemplary embodiment comprising an implantable glucose sensor 100A that utilizes amperometric electrochemical sensor technology to measure glucose concentration. In this exemplary embodiment, a body 110 and head 112 house the electrodes 114 and sensor electronics, which are described in more detail below with reference to FIG. 2. Three electrodes 114 are operably connected to the sensor electronics (FIG. 2) and are covered by a sensing membrane 116 and a biointerface membrane 118, which are attached by a clip 119.

In one embodiment, the three electrodes 114, which protrude through the head 112, include a platinum working electrode, a platinum counter electrode, and a silver/silver chloride reference electrode. The top ends of the electrodes are in contact with an electrolyte phase (not shown), which is a free-flowing fluid phase disposed between the sensing membrane 116 and the electrodes 114. The sensing membrane 116 includes an enzyme, e.g., glucose oxidase, which covers the electrolyte phase. The biointerface membrane 118 covers the sensing membrane 116 and serves, at least in part, to protect the sensor 100A from external forces that can result in environmental stress cracking of the sensing membrane 116.

In the illustrated embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

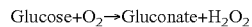

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2 e^-$), and one oxygen molecule ($O_2$).

Figure 1B:
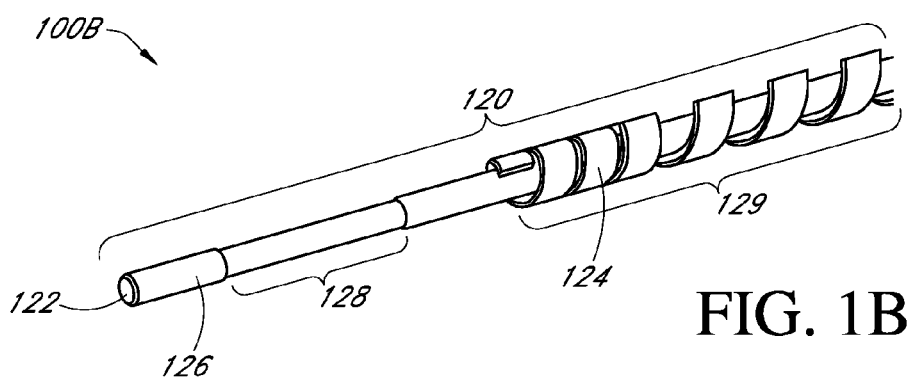
FIG. 1B is side view of a distal portion of a transcutaneously inserted sensor in one embodiment.

FIG. 1B is side view of a distal portion 120 of a transcutaneously- or intravascularly-inserted sensor 100B in one embodiment, showing working and reference electrodes. In preferred embodiments, the sensor 100B is formed from a working electrode 122 and a reference electrode 124 helically wound around the working electrode 122. An insulator 126 is disposed between the working and reference electrodes to provide necessary electrical insulation there between. Certain portions of the electrodes are exposed to enable electrochemical reaction thereon, for example, a window 128 can be formed in the insulator to expose a portion of the working electrode 122 for electrochemical reaction.

In preferred embodiments, each electrode is formed from a fine wire with a diameter of from about 0.001 or less to about 0.010 inches or more, for example, and is formed from, e.g., a plated insulator, a plated wire, or bulk electrically conductive material. Although the illustrated electrode configuration and associated text describe one preferred method of forming a sensor, a variety of known sensor configurations can be employed with the analyte sensor system of the preferred embodiments, such as are described in U.S. Pat. No. 6,695,860 to Ward et al., U.S. Pat. No. 6,565,509 to Say et al., U.S. Pat. No. 6,248,067 to Causey III, et al., and U.S. Pat. No. 6,514,718 to Heller et al.

In preferred embodiments, the working electrode comprises a wire formed from a conductive material, such as platinum, platinum-iridium, palladium, graphite, gold, carbon, conductive polymer, alloys, and the like. Although the electrodes can by formed by a variety of manufacturing techniques (bulk metal processing, deposition of metal onto a substrate, and the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

The working electrode 122 is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current. For example, in the detection of glucose wherein glucose oxidase produces hydrogen peroxide as a byproduct, hydrogen peroxide reacts with the surface of the working electrode producing two protons ($2H^+$), two electrons ($2\ e^-$) and one molecule of oxygen ($O_2$), which produces the electronic current being detected.

In preferred embodiments, the working electrode 122 is covered with an insulating material 126, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, and the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

The reference electrode 124, which can function as a reference electrode alone, or as a dual reference and counter electrode, is formed from silver, silver/silver chloride, and the like. Preferably, the reference electrode 124 is juxtapositioned and/or twisted with or around a wire 122 that forms the working electrode 128; however other configurations are also possible. In the illustrated embodiments, the reference electrode 124 is helically wound around the wire 122. The assembly of wires is then optionally coated or adhered together with an insulating material, similar to that described above, so as to provide an insulating attachment.

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), and the like, to expose the electroactive surfaces. Alternatively, a portion of the electrode can be masked prior to depositing the insulator in order to maintain an exposed electroactive surface area.

In the embodiment illustrated in FIG. 1B, a radial window is formed through the insulating material 126 to expose a circumferential electroactive surface of the working electrode 128. Additionally, sections 129 of electroactive surface of the reference electrode are exposed. For example, the 129 sections of electroactive surface can be masked during deposition of an outer insulating layer or etched after deposition of an outer insulating layer.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes) as described in more detail elsewhere herein. U.S. Patent Publication No. US-2005-0161346-A1 and U.S. Patent Publication No. US-2005-0143635-A1 describe some systems and methods for implementing and using additional working, counter, and/or reference electrodes.

Preferably, a membrane system is deposited over the electroactive surfaces of the sensor 100B and includes a plurality of domains or layers. The membrane system may be deposited on the exposed electroactive surfaces using known thin film techniques (for example, spraying, electro-depositing, dipping, and the like). In one exemplary embodiment, each domain is deposited by dipping the sensor into a solution and drawing out the sensor at a speed that provides the appropriate domain thickness. In general, the membrane system may be disposed over (e.g., deposited on) the electroactive surfaces using methods appreciated by one skilled in the art.

In some embodiments, the sensing membranes and/or membrane systems include a plurality of domains or layers, for example, an interference domain, an enzyme domain, and a resistance domain, and may include additional domains, such as an electrode domain, a cell impermeable domain (also referred to as a bioprotective layer), and/or an oxygen domain, as described in more detail in co-pending U.S. patent application Ser. No. 11/750,907 filed on May 18, 2007 and entitled "ANALYTE SENSORS HAVING A SIGNAL-TO-NOISE RATIO SUBSTANTIALLY UNAFFECTED BY NON-CONSTANT NOISE," which is incorporated herein by reference in its entirety. However, it is understood that a sensing membrane modified for other sensors, for example, by including fewer or additional domains is within the scope of some embodiments. In some embodiments, one or more domains of the sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers. U.S. Patent Publication No. US-2005-024579912-A1, which is incorporated herein by reference in its entirety, describes biointerface and sensing membrane configurations and materials that may be applied to some embodiments.

In one exemplary embodiment, the sensor is an enzyme-based electrochemical sensor, wherein the glucose-measuring working electrode measures the hydrogen peroxide produced by the enzyme catalyzed reaction of glucose being detected and creates a measurable electronic current (for example, detection of glucose utilizing glucose oxidase produces $H_2O_2$ peroxide as a byproduct, $H_2O_2$ reacts with the surface of the working electrode producing two protons ($2H^+$), two electrons ($2 e^-$) and one molecule of oxygen ($O_2$) which produces the electronic current being detected), such as described in more detail above and as is appreciated by one skilled in the art. Typically, the working and reference electrodes operatively connect with sensor electronics, such as described in more detail elsewhere herein. Additional aspects of the above-described transcutaneously inserted sensor can be found in co-pending U.S. Patent Publication No. US-2006-0020187-A1.

Figure 1C:
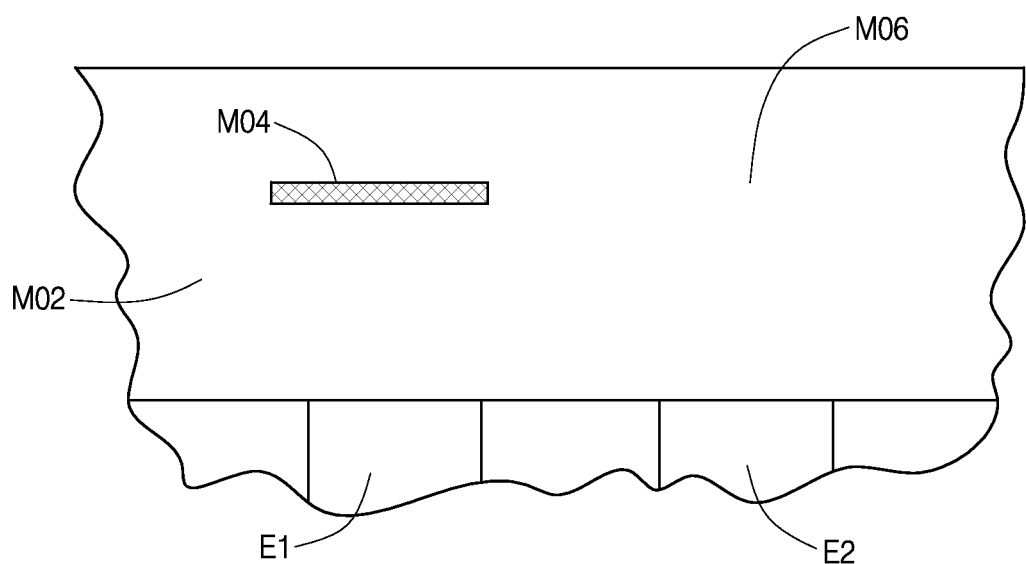
FIG. 1C is a cross-sectional schematic view of a sensing region of a dual-electrode continuous analyte sensor in one embodiment wherein an active enzyme of an enzyme domain is positioned over the first working electrode but not over the second working electrode.

FIG. 1C is a cross-sectional schematic view of a sensing region of a dual-electrode analyte sensor in one embodiment wherein an active enzyme of an enzyme domain is positioned over the first working electrode but not over the second working electrode, such as described with reference to U.S. patent application Ser. No. 12/055,149, which is incorporated herein by reference in its entirety. In general, electrochemical analyte sensors provide at least one working electrode and at least one reference electrode, which are configured to generate a signal associated with a concentration of the analyte in the host, such as described herein, and as appreciated by one skilled in the art. The output signal is typically a raw data stream that is used to provide a useful value of the measured analyte concentration in a host to the patient or doctor, for example. However, the analyte sensors of the preferred embodiments may further measure at least one additional signal. For example, in some embodiments, the additional signal is associated with the baseline and/or sensitivity of the analyte sensor, thereby enabling monitoring of baseline and/or sensitivity changes that may occur in a continuous analyte sensor over time.

In preferred embodiments, the analyte sensor comprises a first working electrode E1 and a second working electrode E2, in addition to a reference electrode, which is referred to as a dual-electrode system herein. The first and second working electrodes may be in any useful conformation, as described in US Patent Publications Nos. US-2007-0027385-A1, US-2007-0213611-A1, US-2007-0027284-A1, US-2007-0032717-A1, US-2007-0093704, and U.S. patent application Ser. No. 11/865,572 filed on Oct. 1, 2007 and entitled "DUAL-ELECTRODE SYSTEM FOR A CONTINUOUS ANALYTE SENSOR," each of which is incorporated herein by reference in its entirety. In some preferred embodiments, the first and second working electrodes are twisted and/or bundled. For example, two wire working electrodes can be twisted together, such as in a helix conformation. The reference electrode can then be wrapped around the twisted pair of working electrodes. In some preferred embodiments, the first and second working electrodes include a coaxial configuration. A variety of dual-electrode system configurations are described with reference to FIG. 7A$_1$, FIG. 7A$_2$, FIG. 7B, FIG. 7C, FIG. 7D, FIG. 7E, FIG. 7F, FIG. 7G, FIG. 7H, FIG. 7I, FIG. 7J, FIG. 7K, FIG. 7L, FIG. 7M, FIG. 7N, FIG. 8A, FIG. 8B, FIG. 9A, FIG. 9B, FIG. 10, and FIG. 11, as described in each of US Patent Publication Nos. US-2007-0027385-A1, US-2007-0213611-A1, US-2007-0027284-A1, US-2007-0032717-A1, US-2007-0093704, and U.S. patent application Ser. No. 11/865,572 filed on Oct. 1, 2007 and entitled "DUAL-ELECTRODE SYSTEM FOR A CONTINUOUS ANA-LYTE SENSOR", for example. In some embodiments, the sensor is configured as a dual electrode sensor, such as described in US Patent Publication Nos. US-2005-0143635-A1; US-2007-0027385-A1; and US-2007-0213611-A1, and co-pending U.S. patent application Ser. No. 11/865,572, each of which is incorporated herein by reference in its entirety. However, a dual-electrode system can be provided in any planar or non-planar configuration, such as can be appreciated by one skilled in the art, and can be found in U.S. Pat. No. 6,175,752 to Say et al.; U.S. Pat. No. 6,579,690 to Bonnecaze et al.; U.S. Pat. No. 6,484,046 to Say et al.; U.S. Pat. No. 6,512,939 to Colvin et al.; U.S. Pat. No. 6,477,395 to Schulman et al.; U.S. Pat. No. 6,424,847 to Mastrototaro et al; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. 5,985,129 to Gough et al.; WO Patent Application Publication No. 04/021877 to Caduff; U.S. Pat. No. 5,494,562 to Maley et al.; U.S. Pat. No. 6,120,676 to Heller et al.; and U.S. Pat. No. 6,542,765 to Guy et al., each of which are incorporated in their entirety herein by reference in their entirety. In general, it is understood that the disclosed embodiments are applicable to a variety of continuous analyte measuring device configurations The dual-electrode sensor system includes a first working electrode E1 and the second working electrode E2, both of which are disposed beneath a sensor membrane M02. The first working electrode E1 is disposed beneath an active enzymatic portion M04 of the sensor membrane M02, which includes an enzyme configured to detect the analyte or an analyte-related compound. Accordingly, the first working electrode E1 is configured to generate a first signal composed of both signal related to the analyte and signal related to non-analyte electroactive compounds (e.g., physiological baseline, interferents, and non-constant noise) that have an oxidation/reduction potential that overlaps with the oxidation/reduction potential of the analyte. This oxidation/reduction potential may be referred to as a "first oxidation/reduction potential" herein. The second working electrode E2 is disposed beneath an inactive-enzymatic or non-enzymatic portion M06 of the sensor membrane M02. The non-enzymatic portion M06 of the membrane includes either an inactivated form of the enzyme contained in the enzymatic portion M04 of the membrane or no enzyme. In some embodiments, the non-enzymatic portion M06 can include a non-specific protein, such as BSA, ovalbumin, milk protein, certain polypeptides, and the like. The non-enzymatic portion M06 generates a second signal associated with noise of the analyte sensor. The noise of the sensor comprises signal contribution due to non-analyte electroactive species (e.g., interferents) that have an oxidation/reduction potential that substantially overlaps the first oxidation/reduction potential (e.g., that overlap with the oxidation/reduction potential of the analyte). In some embodiments of a dual-electrode analyte sensor configured for fluid communication with a host's circulatory system, the non-analyte related electroactive species comprises at least one species selected from the group consisting of interfering species, non-reaction-related hydrogen peroxide, and other electroactive species.

In one exemplary embodiment, the dual-electrode analyte sensor is a glucose sensor having a first working electrode E1 configured to generate a first signal associated with both glucose and non-glucose related electroactive compounds that have a first oxidation/reduction potential. Non-glucose related electroactive compounds can be any compound, in the sensor's local environment that has an oxidation/reduction potential substantially overlapping with the oxidation/reduction potential of $H_2O_2$, for example. While not wishing to be bound by theory, it is believed that the glucose-measuring electrode can measure both the signal directly related to the reaction of glucose with GOx (produces $H_2O_2$ that is oxidized at the working electrode) and signals from unknown compounds that are in the tissue or blood surrounding the sensor. These unknown compounds can be constant or non-constant (e.g., intermittent or transient) in concentration and/or effect. In some circumstances, it is believed that some of these unknown compounds are related to the host's disease state. For example, it is known that tissue/blood chemistry changes dramatically during/after a heart attack (e.g., pH changes, changes in the concentration of various blood components/protein, and the like). Additionally, a variety of medicaments or infusion fluid components (e.g., acetaminophen, ascorbic acid, dopamine, ibuprofen, salicylic acid, tolbutamide, tetracycline, creatinine, uric acid, ephedrine, L-dopa, methyl dopa and tolazamide) that may be given to the host may have oxidation/reduction potentials that overlap with that of $H_2O_2$.

In this exemplary embodiment, the dual-electrode analyte sensor includes a second working electrode E2 that is configured to generate a second signal associated with the non-glucose related electroactive compounds that have the same oxidation/reduction potential as the above-described first working electrode (e.g., para supra). In some embodiments, the non-glucose related electroactive species includes at least one of interfering species, non-reaction-related $H_2O_2$, and other electroactive species. For example, interfering species includes any compound that is not directly related to the electrochemical signal generated by the glucose-GOx reaction, such as but not limited to electroactive species in the local environment produces by other bodily processes (e.g., cellular metabolism, a disease process, and the like). Other electroactive species includes any compound that has an oxidation/reduction potential similar to or overlapping that of $H_2O_2$.

The non-analyte (e.g., non-glucose) signal produced by compounds other than the analyte (e.g., glucose) obscures the signal related to the analyte, contributes to sensor inaccuracy, and is considered background noise. Background noise includes both constant and non-constant components and must be removed to accurately calculate the analyte concentration. While not wishing to be bound by theory, it is believed that preferred dual electrode sensors are designed such that the first and second electrodes are influenced by substantially the same external/environmental factors, which enables substantially equivalent measurement of both the constant and non-constant species/noise. This advantageously allows the substantial elimination of noise on the sensor signal (using electronics described elsewhere herein) to substantially reduce or eliminate signal effects due to noise, including non-constant noise (e.g., unpredictable biological, biochemical species, medicaments, pH fluctuations, $O_2$ fluctuations, or the like) known to effect the accuracy of conventional continuous sensor signals. Preferably, the sensor includes electronics operably connected to the first and second working electrodes. The electronics are configured to provide the first and second signals that are used to generate glucose concentration data substantially without signal contribution due to non-glucose-related noise. Preferably, the electronics include at least a potentiostat that provides a bias to the electrodes. In some embodiments, sensor electronics are configured to measure the current (or voltage) to provide the first and second signals. The first and second signals are used to determine the glucose concentration substantially without signal contribution due to non-glucose-related noise such as by but not limited to subtraction of the second signal from the first signal or alternative data analysis techniques. In some embodiments, the sensor electronics include a transmitter that transmits the first and second signals to a receiver, where additional data analysis and/or calibration of glucose concentration can be processed. U.S. Patent Publication No. US-2005-0027463-A1, US-2005-0203360-A1 and U.S. Patent Publication No. US-2006-0036142-A1 describes systems and methods for processing sensor analyte data and is incorporated herein by reference in their entirety.

In preferred embodiments, the dual-electrode sensor includes electronics (e.g., a processor module, processing memory) that are operably connected to the first and second working electrodes and are configured to provide the first and second signals to generate analyte concentration data substantially without signal contribution due to non-analyte-related noise. For example, the sensor electronics process and/or analyze the signals from the first and second working electrodes and calculate the portion of the first electrode signal that is due to analyte concentration only. The portion of the first electrode signal that is not due to the analyte concentration can be considered to be background, such as but not limited to noise. Accordingly, in one embodiment of a dual-electrode sensor system configured for fluid communication with a host's circulatory system (e.g., via a vascular access device) the system comprising electronics operably connected to the first and second working electrodes; the electronics are configured to process the first and second signals to generate analyte concentration data substantially without signal contribution due to noise.

In various embodiments, the electrodes can be stacked or grouped similar to that of a leaf spring configuration, wherein layers of electrode and insulator (or individual insulated electrodes) are stacked in offset layers. The offset layers can be held together with bindings of non-conductive material, foil, or wire. As is appreciated by one skilled in the art, the strength, flexibility, and/or other material property of the leaf spring-configured or stacked sensor can be either modified (e.g., increased or decreased), by varying the amount of offset, the amount of binding, thickness of the layers, and/or materials selected and their thicknesses, for example.

In preferred embodiments, the analyte sensor substantially continuously measures the host's analyte concentration. In some embodiments, for example, the sensor can measure the analyte concentration every fraction of a second, about every fraction of a minute or every minute. In other exemplary embodiments, the sensor measures the analyte concentration about every 2, 3, 4, 5, 6, 7, 8, 9, or 10 minutes. In still other embodiments, the sensor measures the analyte concentration every fraction of an hour, such as but not limited to every 15, 30 or 45 minutes. Yet in other embodiments, the sensor measures the analyte concentration about every hour or longer. In some exemplary embodiments, the sensor measures the analyte concentration intermittently or periodically. In one preferred embodiment, the analyte sensor is a glucose sensor and measures the host's glucose concentration about every 4-6 minutes. In a further embodiment, the sensor measures the host's glucose concentration every 5 minutes.

In some embodiments (e.g., sensors such as illustrated in FIGS. 1A, 1B, and 1C), a potentiostat is employed to monitor the electrochemical reaction at the electrochemical cell. The potentiostat applies a constant potential to the working and reference electrodes to determine a current value. The current that is produced at the working electrode (and flows through the circuitry to the counter electrode) is proportional to the amount of $H_2O_2$ that diffuses to the working electrode. Accordingly, a raw signal can be produced that is representative of the concentration of glucose in the user's body, and therefore can be utilized to estimate a meaningful glucose value, such as described herein.

One problem with raw data stream output of some enzymatic glucose sensors such as described above is caused by transient non-glucose reaction rate-limiting phenomena. For example, if oxygen is deficient, relative to the amount of glucose, then the enzymatic reaction will be limited by oxygen rather than glucose. Consequently, the output signal will be indicative of the oxygen concentration rather than the glucose concentration, producing erroneous signals. Other non-glucose reaction rate-limiting phenomena could include interfering species, temperature and/or pH changes, or even unknown sources of mechanical, electrical and/or biochemical noise, for example.

Figure 2:
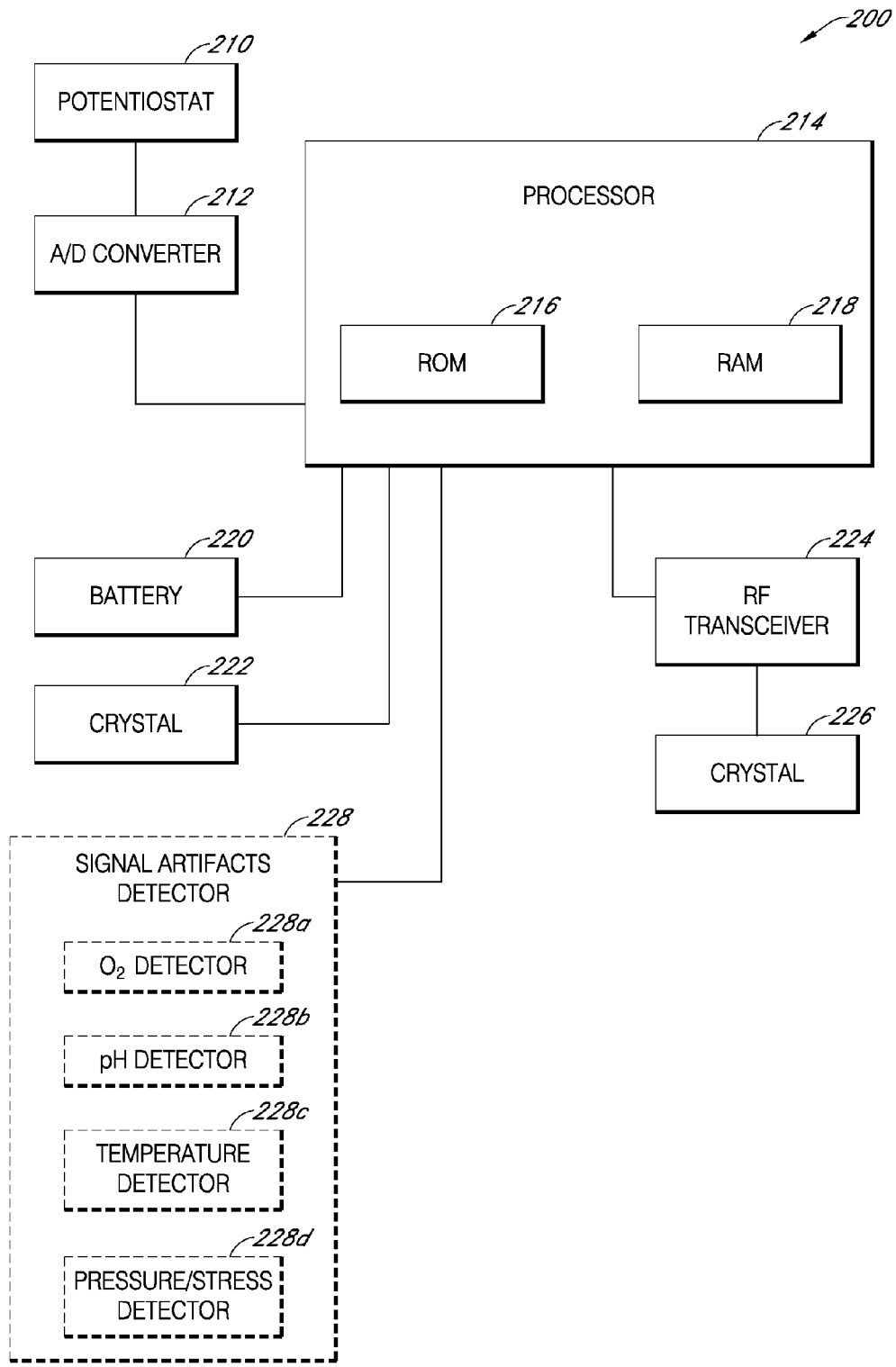
FIG. 2 is a block diagram that illustrates sensor electronics in one embodiment.

FIG. 2 is a block diagram that illustrates one possible configuration of the sensor electronics 200 in one embodiment. In this embodiment, a potentiostat 210 is shown, which is operatively connected to an electrode system (FIG. 1A or 1B) and provides a voltage to the electrodes, which biases the sensor to enable measurement of a current value indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device. In the illustrated embodiment, an A/D converter 212 digitizes the analog signal into "counts" for processing. Accordingly, the resulting raw data stream in counts is directly related to the current measured by the potentiostat 210.

A processor module 214 is the central control unit that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in more detail elsewhere herein). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, ROM 216 provides semi-permanent storage of data, for example, storing data such as sensor identifier (ID) and programming to process data streams (e.g., programming for signal artifacts detection and/or replacement such as described elsewhere herein). In one exemplary embodiment, RAM 218 can be used for the system's cache memory, for example for temporarily storing recent sensor data.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition of time from about 2 seconds to about 512 seconds is preferred; however any acquisition time can be programmed into the processor module. A programmable acquisition time is advantageous in optimizing noise filtration, time lag, and processing/battery power.

In some embodiments, the processor module is configured to build the data packet for transmission to an outside source, for example, an RF transmission to a receiver as described in more detail below. Generally, the data packet comprises a plurality of bits that can include a sensor/transmitter ID code, raw data, filtered data, and/or error detection or correction. The processor module can be configured to transmit any combination of raw and/or filtered data.

A battery 220 is operatively connected to the processor 214 and provides the necessary power for the sensor (e.g., 100A or 100B). In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. In yet other embodiments, the receiver can be transcutaneously powered via an inductive coupling, for example. A Quartz Crystal 222 is operatively connected to the processor 214 and maintains system time for the computer system as a whole.

An optional RF module (e.g., an RF Transceiver) 224 is operably connected to the processor 214 and transmits the sensor data from the sensor (e.g., 100A or 100B) to a receiver (see FIGS. 3 and 4). Although an RF transceiver is shown here, some other embodiments can include a wired rather than wireless connection to the receiver. A second quartz crystal 226 provides the system time for synchronizing the data transmissions from the RF transceiver. It is noted that the transceiver 224 can be substituted with a transmitter in other embodiments. In some alternative embodiments, however, other mechanisms, such as optical, infrared radiation (IR), ultrasonic, and the like, can be used to transmit and/or receive data.

In some embodiments, a Signal Artifacts Detector 228 is provided that includes one or more of the following: an oxygen detector 228a, a pH detector 228b, a temperature detector 228c, and a pressure/stress detector 228d, which is described in more detail with reference to signal artifacts detection. It is noted that in some embodiments the signal artifacts detector 228 is a separate entity (e.g., temperature detector) operatively connected to the processor, while in other embodiments, the signal artifacts detector is a part of the processor and utilizes readings from the electrodes, for example, to detect ischemia and other signal artifacts. Although the above description is focused on an embodiment of the Signal Artifacts Detector within the sensor, some embodiments provide for systems and methods for detecting signal artifacts in the sensor and/or receiver electronics (e.g., processor module) as described in more detail elsewhere herein.

Receiver

FIGS. 3A to 3D are schematic views of a receiver 300 including representations of estimated glucose values on its user interface in first, second, third, and fourth embodiments, respectively. The receiver 300 comprises systems to receive, process, and display sensor data from the glucose sensor (e.g., 100A or 100B), such as described herein. Particularly, the receiver 300 can be a pager-sized device, for example, and comprise a user interface that has a plurality of buttons 302 and a liquid crystal display (LCD) screen 304, and which can optionally include a backlight. In some embodiments, the user interface can also include a keyboard, a speaker, and a vibrator, as described below with reference to FIG. 4A.

Figure 3A:
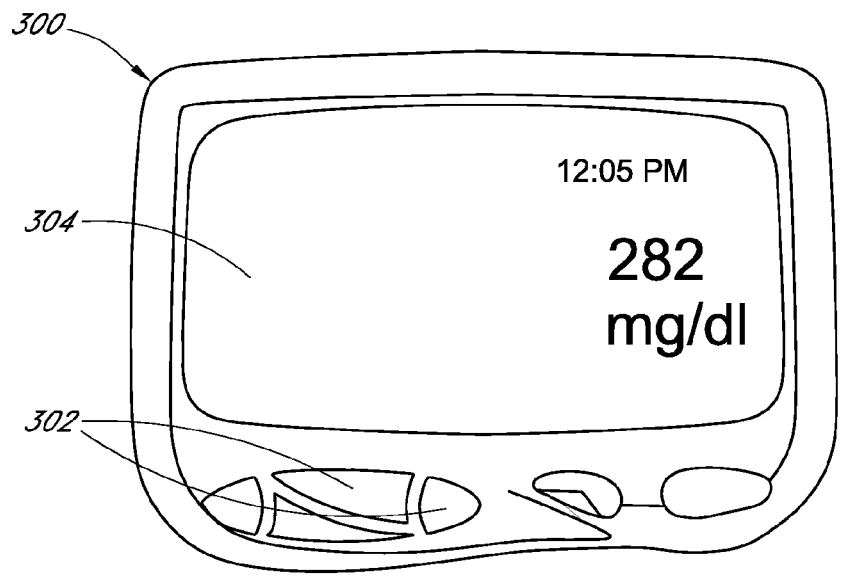
FIGS. 3A to 3D are schematic views of a receiver in first, second, third, and fourth embodiments, respectively.

FIG. 3A illustrates a first embodiment wherein the receiver 300 shows a numeric representation of the estimated glucose value on its user interface, which is described in more detail elsewhere herein.

Figure 3B:
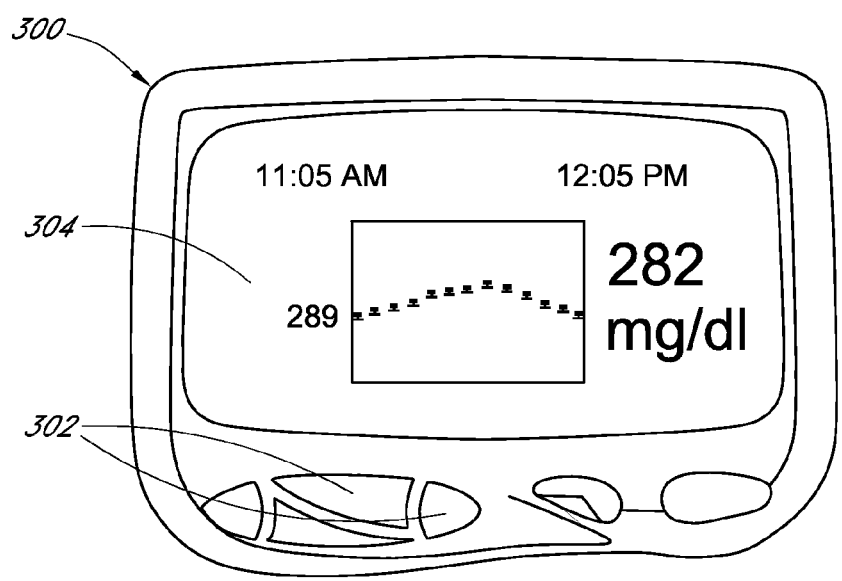

FIG. 3B illustrates a second embodiment wherein the receiver 300 shows an estimated glucose value and approximately one hour of historical trend data on its user interface, which is described in more detail elsewhere herein.

Figure 3C:
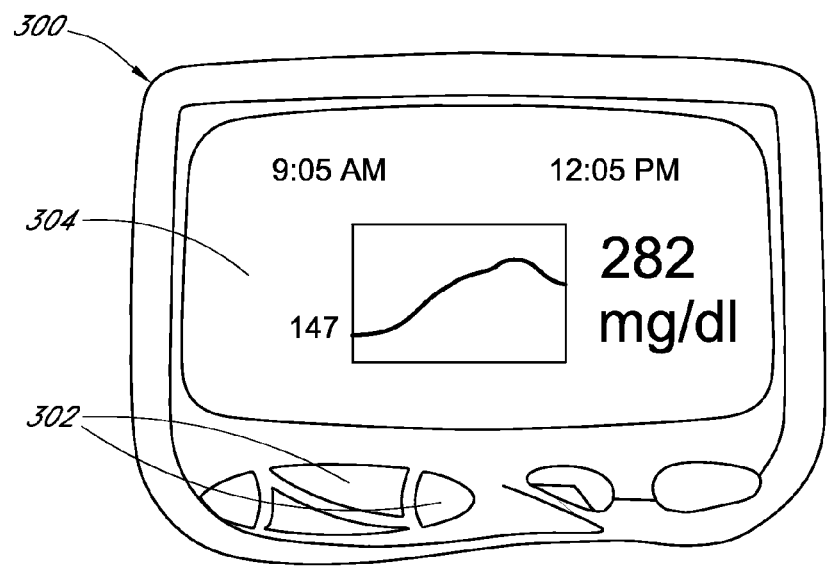

FIG. 3C illustrates a third embodiment wherein the receiver 300 shows an estimated glucose value and approximately three hours of historical trend data on its user interface, which is described in more detail elsewhere herein.

Figure 3D:
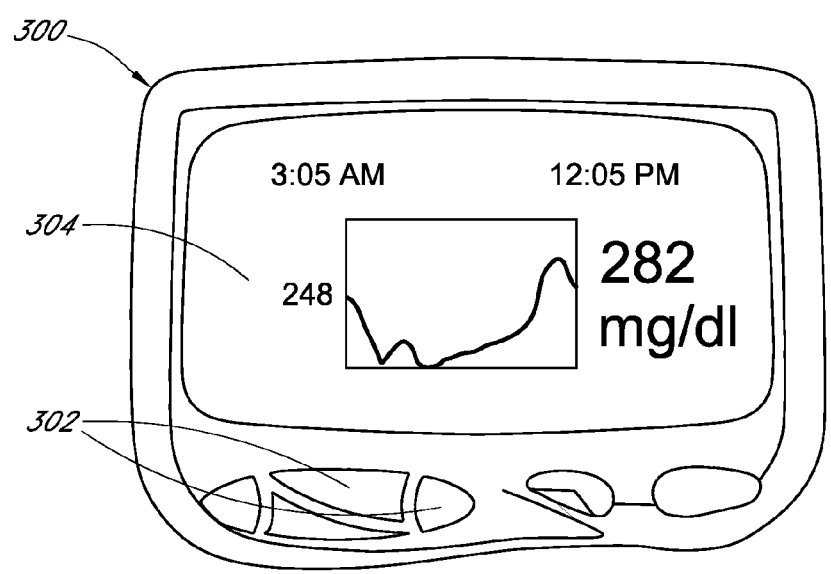

FIG. 3D illustrates a fourth embodiment wherein the receiver 300 shows an estimated glucose value and approximately nine hours of historical trend data on its user interface, which is described in more detail elsewhere herein.

In some embodiments, a user can toggle through some or all of the screens shown in FIGS. 3A to 3D using a toggle button on the receiver. In some embodiments, the user will be able to interactively select the type of output displayed on their user interface. In other embodiments, the sensor output can have alternative configurations.

Figure 4A:
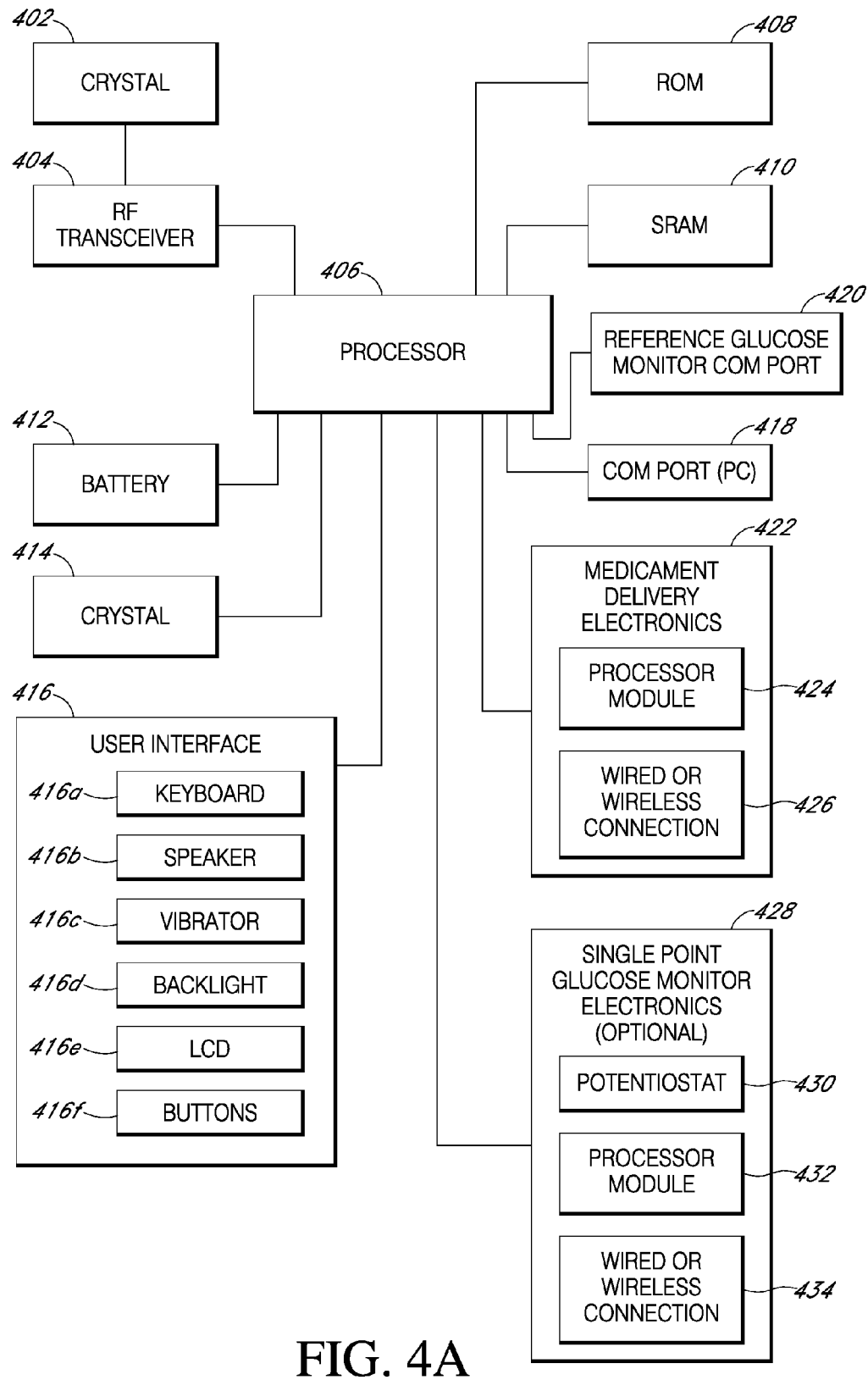
FIG. 4A is a block diagram of receiver electronics in one embodiment.

FIG. 4A is a block diagram that illustrates one possible configuration of the receiver's electronics. It is noted that the receiver 300 can comprise a configuration such as described with reference to FIGS. 3A to 3D, above. Alternatively, the receiver 300 can comprise other configurations, including a phone, insulin pump, desktop computer, laptop computer, a personal digital assistant (PDA), a server (local or remote to the receiver), and the like. In some embodiments, the receiver 300 can be adapted to connect (via wired or wireless connection) to a phone, insulin pump, desktop computer, laptop computer, PDA, server (local or remote to the receiver), and the like, in order to download data from the receiver 300. In some alternative embodiments, the receiver 300 and/or receiver electronics can be housed within or directly connected to the sensor (e.g., 100A or 100B) in a manner that allows sensor and receiver electronics to work directly together and/or share data processing resources. Accordingly, the receiver's electronics can be generally referred to as a "computer system."

A quartz crystal 402 is operatively connected to an optional RF transceiver 404 that together function to receive and synchronize data streams (e.g., raw data streams transmitted from the RF transceiver). Once received, whether via wired or wireless transmission, a processor 406 processes the signals, such as described below.

The processor 406, also referred to as the processor module, is the central control unit that performs the processing, such as storing data, analyzing data streams, calibrating analyte sensor data, detecting signal artifacts, classifying a level of noise, calculating a rate of change, predicting analyte values, setting of modes, estimating analyte values, comparing estimated analyte values with time corresponding measured analyte values, analyzing a variation of estimated analyte values, downloading data, and controlling the user interface by providing analyte values, prompts, messages, warnings, alarms, and the like. The processor includes hardware and software that performs the processing described herein, for example flash memory provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing.

In one exemplary embodiment, the processor is a microprocessor that provides the processing, such as calibration algorithms stored within a ROM 408. The ROM 408 is operatively connected to the processor 406 and provides semi-permanent storage of data, storing data such as receiver ID and programming to process data streams (e.g., programming for performing calibration and other algorithms described elsewhere herein). In this exemplary embodiment, an RAM 410 is used for the system's cache memory and is helpful in data processing. The term "processor module" can include some portions or all of ROM 408 and RAM 410 in addition to the processor 406.

A battery 412 is operatively connected to the processor 406 and provides power for the receiver. In one embodiment, the battery is a standard AAA alkaline battery, however any appropriately sized and powered battery can be used. In some embodiments, a plurality of batteries can be used to power the system. A quartz crystal 414 is operatively connected to the processor 406 and maintains system time for the computer system as a whole.

A user interface 416 comprises a keyboard 416a, speaker 416b, vibrator 416c, backlight 416d, liquid crystal display (LCD 416e), and one or more buttons 416f. The components that comprise the user interface 416 provide controls to interact with the user. The keyboard 416a can allow, for example, input of user information about himself/herself, such as mealtime, exercise, insulin administration, and reference glucose values. The speaker 416b can provide, for example, audible signals or alerts for conditions such as present and/or predicted hyper- and hypoglycemic conditions. The vibrator 416c can provide, for example, tactile signals or alerts for reasons such as described with reference to the speaker, above. The backlight 416d can be provided, for example, to aid the user in reading the LCD in low light conditions. The LCD 416e can be provided, for example, to provide the user with visual data output such as is illustrated in FIGS. 3A to 3D. The buttons 416f can provide for toggle, menu selection, option selection, mode selection, and reset, for example.

In some embodiments, prompts or messages can be displayed on the user interface to convey information to the user, such as reference outlier values, requests for reference analyte values, therapy recommendations, deviation of the measured analyte values from the estimated analyte values, and the like. Additionally, prompts can be displayed to guide the user through calibration or trouble-shooting of the calibration.

Output can be provided via a user interface 416, including but not limited to, visually on a screen 416e, audibly through a speaker 416b, or tactilely through a vibrator 416c. Additionally, output can be provided via wired or wireless connection to an external device, including but not limited to, phone, computer, laptop, server, personal digital assistant, modem connection, insulin delivery mechanism, medical device, or other device that can be useful in interfacing with the receiver.

Output can be continuously provided, or certain output can be selectively provided based on modes, events, analyte concentrations and the like. For example, an estimated analyte path can be continuously provided to a patient on an LCD screen 416e, while audible alerts can be provided only during a time of existing or approaching clinical risk to a patient. As another example, estimation can be provided based on event triggers (for example, when an analyte concentration is nearing or entering a clinically risky zone). As yet another example, analyzed deviation of estimated analyte values can be provided when a predetermined level of variation (for example, due to known error or clinical risk) is known.

In some embodiments, alarms prompt or alert a patient when a measured or projected analyte value or rate of change simply passes a predetermined threshold. In some embodiments, the clinical risk alarms combine intelligent and dynamic estimative algorithms to provide greater accuracy, more timeliness in pending danger, avoidance of false alarms, and less annoyance for the patient. For example, clinical risk alarms of these embodiments include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms.

In some embodiments, at least one of a hypoglycemia, hyperglycemia, predicted hypoglycemia, and predicted hyperglycemia alarm includes first and second user selectable alarms. In some embodiments, the first alarm is configured to alarm during a first time of day and wherein the second alarm is configured to alarm during a second time of day (for example, so that a host can set different alarm settings for day vs. night, avoiding unnecessary night-time alarming). In some embodiments, the alarm is configured to turn on a light. In some embodiments, the alarm is configured to alarm a remote receiver located more than about 10 feet away from the continuous glucose sensor (for example, in a parent's bedroom or to a health care provider). In some embodiments, the alarm comprises a text message, and wherein the computer system is configured to send the text message to a remote device. Accordingly, alarms and other system processing can be set by modes of the system, such as described in more detail elsewhere herein.

In some embodiments, clinical risk alarms can be activated for a predetermined time period to allow for the user to attend to his/her condition. Additionally, the clinical risk alarms can be de-activated when leaving a clinical risk zone so as not to annoy the patient by repeated clinical risk alarms, when the patient's condition is improving.

In some embodiments, the system determines a possibility of the patient avoiding clinical risk, based on the analyte concentration, the rate of change, and other aspects of the sensor algorithms. If there is minimal or no possibility of avoiding the clinical risk, a clinical risk alarm will be triggered. However, if there is a possibility of avoiding the clinical risk, the system can wait a predetermined amount of time and re-analyze the possibility of avoiding the clinical risk. In some embodiments, when there is a possibility of avoiding the clinical risk, the system will further provide targets, therapy recommendations, or other information that can aid the patient in proactively avoiding the clinical risk.

In some embodiments, a variety of different display methods are used, such as described in the preferred embodiments, which can be toggled through or selectively displayed to the user based on conditions or by selecting a button, for example. As one example, a simple screen can be normally shown that provides an overview of analyte data, for example present analyte value and directional trend. More complex screens can then be selected when a user desires more detailed information, for example, historical analyte data, alarms, clinical risk zones, and the like.

In some embodiments, electronics 422 associated with a medicament delivery device 502 are operably connected to the processor 406 and include a processor 424 for processing data associated with the delivery device 502 and include at least a wired or wireless connection (for example, RF transceiver) 426 for transmission of data between the processor 406 of the receiver 300 and the processor 424 of the delivery device 502. Other electronics associated with any of the delivery devices cited herein, or other known delivery devices, may be implemented with the delivery device electronics 422 described herein, as is appreciated by one skilled in the art. In some embodiments, type, amount, validation and other processing related to medicament delivery is based at least in part on a mode of the system, which is described in more detail elsewhere herein.

In some embodiments, the processor 424 comprises programming for processing the delivery information in combination with the continuous sensor information. In some alternative embodiments, the processor 406 comprises programming for processing the delivery information in combination with the continuous sensor information. In some embodiments, both processors 406 and 422 mutually process information related to each component.

In some embodiments, the medicament delivery device 502 further includes a user interface (not shown), which may include a display and/or buttons, for example. U.S. Pat. Nos. 6,192,891, 5,536,249, and 6,471,689 describe some examples of incorporation of a user interface into a medicament delivery device, as is appreciated by one skilled in the art.

In some embodiments, electronics 428 associated with the single point glucose monitor 428 are operably connected to a processor 432 and include a potentiostat 430 in one embodiment that measures a current flow produced at the working electrode when a biological sample is placed on a sensing membrane, such as described above. The single point glucose monitor 428 can include at least one of a wired and a wireless connection 434.

Figure 4B:
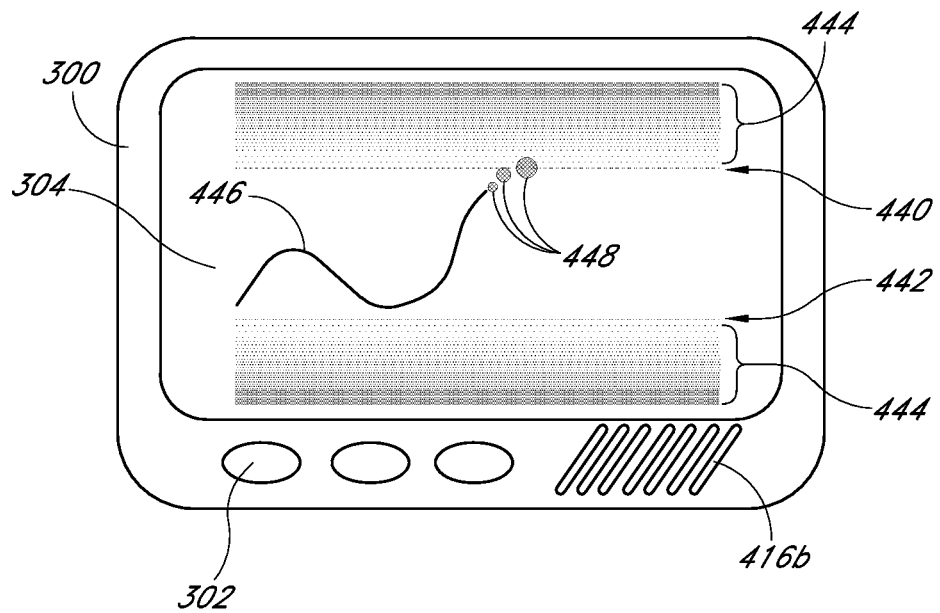
FIG. 4B is an illustration of the receiver in one embodiment showing an analyte trend graph, including measured analyte values, estimated analyte values, and a clinical risk zone.

FIG. 4B is an illustration of the receiver in one embodiment showing an analyte trend graph, including measured analyte values, estimated analyte values, and a clinical risk zone. The receiver 300 includes an LCD screen 304, buttons 302, and a speaker 416d and/or microphone. The screen 304 displays a trend graph in the form of a line representing the historical trend of a patient's analyte concentration.

Although axes may or may not be shown on the screen 304, it is understood that a theoretical x-axis represents time and a theoretical y-axis represents analyte concentration.

In some embodiments such as shown in FIG. 4B, the screen shows thresholds, including a high threshold 440 and a low threshold 442, which represent boundaries between clinically safe and clinically risky conditions for the patients. In one exemplary embodiment, a normal glucose threshold for a glucose sensor is set between about 100 and 160 mg/dL, and the clinical risk zones 444 are illustrated outside of these thresholds. In alternative embodiments, the normal glucose threshold is between about 80 and about 200 mg/dL, between about 55 and about 220 mg/dL, or other threshold that can be set by the manufacturer, physician, patient, computer program, and the like. Although a few examples of glucose thresholds are given for a glucose sensor, the setting of any analyte threshold is not limited by the preferred embodiments, including rate of change and/or acceleration information. In some embodiments, one or more criteria that define clinical risk and/or alarms are based at least in part on a mode of the system, which is described in more detail elsewhere herein.

In some embodiments, the screen 304 shows clinical risk zones 444, also referred to as danger zones, through shading, gradients, or other graphical illustrations that indicate areas of increasing clinical risk. Clinical risk zones 444 can be set by a manufacturer, customized by a doctor, and/or set by a user via buttons 302, for example. In some embodiments, the danger zone 444 can be continuously shown on the screen 304, or the danger zone can appear when the measured and/or estimated analyte values fall into the danger zone 444. Additional information can be displayed on the screen, such as an estimated time to clinical risk. In some embodiments, the danger zone can be divided into levels of danger (for example, low, medium, and high) and/or can be color-coded (for example, yellow, orange, and red) or otherwise illustrated to indicate the level of danger to the patient. Additionally, the screen or portion of the screen can dynamically change colors or illustrations that represent a nearness to the clinical risk and/or a severity of clinical risk.

In some embodiments, such as shown in FIG. 4B, the screen 304 displays a trend graph of measured analyte data 446. Measured analyte data can be smoothed and calibrated such as described in more detail elsewhere herein. Measured analyte data can be displayed for a certain time period (for example, previous 1 hour, 3 hours, 9 hours, etc.) In some embodiments, the user can toggle through screens using buttons 302 to view the measured analyte data for different time periods, using different formats, or to view certain analyte values (for example, highs and lows).

In some embodiments such as shown in FIG. 4B, the screen 304 displays estimated analyte data 448 using dots. In this illustration, the size of the dots can represent the confidence of the estimation, a variation of estimated values, and the like. For example, as the time gets farther away from the present (t=0) the confidence level in the accuracy of the estimation can decline as is appreciated by one skilled in the art. In some alternative embodiments, dashed lines, symbols, icons, and the like can be used to represent the estimated analyte values. In some alternative embodiments, shaded regions, colors, patterns, and the like can also be used to represent the estimated analyte values, a confidence in those values, and/or a variation of those values, such as described in more detail in preferred embodiments.

Axes, including time and analyte concentration values, can be provided on the screen, however are not required. While not wishing to be bound by theory, it is believed that trend information, thresholds, and danger zones provide sufficient information to represent analyte concentration and clinically educate the user. In some embodiments, time can be represented by symbols, such as a sun and moon to represent day and night. In some embodiments, the present or most recent measured analyte concentration, from the continuous sensor and/or from the reference analyte monitor can be continually, intermittently, or selectively displayed on the screen.

The estimated analyte values 448 of FIG. 4B include a portion, which extends into the danger zone 444. By providing data in a format that emphasizes the possibility of clinical risk to the patient, appropriate action can be taken by the user (for example, patient, or caretaker) and clinical risk can be preempted.

Figure 4C:
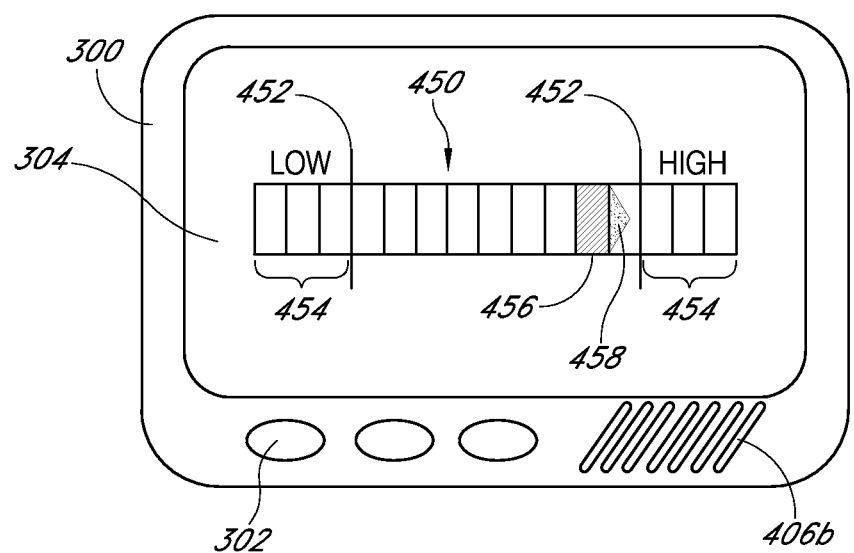
FIG. 4C is an illustration of the receiver in another embodiment showing a representation of analyte concentration and directional trend using a gradient bar.

FIG. 4C is an illustration of the receiver in another embodiment showing a representation of analyte concentration and directional trend using a gradient bar. In this embodiment, the screen illustrates the measured analyte values and estimated analyte values in a simple but effective manner that communicates valuable analyte information to the user.

In this embodiment, a gradient bar 450 is provided that includes thresholds 452 set at high and lows such as described in more detail with reference to FIG. 4B, above. Additionally, colors, shading, or other graphical illustration can be present to represent danger zones 454 on the gradient bar 450 such as described in more detail with reference to FIG. 4B, above.

The measured analyte value is represented on the gradient bar 450 by a marker 456, such as a darkened or colored bar. By representing the measured analyte value with a bar 456, a low-resolution analyte value is presented to the user (for example, within a range of values). For example, each segment on the gradient bar 450 can represent about 10 mg/dL of glucose concentration. As another example, each segment can dynamically represent the range of values that fall within the "A" and "B" regions of the Clarke Error Grid. While not wishing to be bound by theory, it is believed that inaccuracies known both in reference analyte monitors and/or continuous analyte sensors are likely due to known variables such as described in more detail elsewhere herein, and can be de-emphasized such that a user focuses on proactive care of the condition, rather than inconsequential discrepancies within and between reference analyte monitors and continuous analyte sensors.

Additionally, the representative gradient bar communicates the directional trend of the analyte concentration to the user in a simple and effective manner, namely by a directional arrow 458. For example, in conventional diabetic blood glucose monitoring, a person with diabetes obtains a blood sample and measures the glucose concentration using a test strip, and the like. Unfortunately, this information does not tell the person with diabetes whether the blood glucose concentration is rising or falling. Rising or falling directional trend information can be particularly important in a situation such as illustrated in FIG. 4C, wherein if the user does not know that the glucose concentration is rising, he/she may assume that the glucose concentration is falling and not attend to his/her condition. However, because rising directional trend information 458 is provided, the person with diabetes can preempt the clinical risk by attending to his/her condition (for example, administer insulin). Estimated analyte data can be incorporated into the directional trend information by characteristics of the arrow, for example, size, color, flash speed, and the like.

In some embodiments, the gradient bar can be a vertical instead of horizontal bar. In some embodiments, a gradient fill can be used to represent analyte concentration, variation, or clinical risk, for example. In some embodiments, the bar graph includes color, for example the center can be green in the safe zone that graduates to red in the danger zones; this can be in addition to or in place of the divided segments. In some embodiments, the segments of the bar graph are clearly divided by lines; however color, gradation, and the like can be used to represent areas of the bar graph. In some embodiments, the directional arrow can be represented by a cascading level of arrows to a represent slow or rapid rate of change. In some embodiments, the directional arrow can be flashing to represent movement or pending danger.

The screen 304 of FIG. 4C can further comprise a numerical representation of analyte concentration, date, time, or other information to be communicated to the patient. However, a user can advantageously extrapolate information helpful for his/her condition using the simple and effective representation of this embodiment shown in FIG. 4C, without reading a numeric representation of his/her analyte concentration.

In some alternative embodiments, a trend graph or gradient bar, a dial, pie chart, or other visual representation can provide analyte data using shading, colors, patterns, icons, animation, and the like.

Figure 4D:
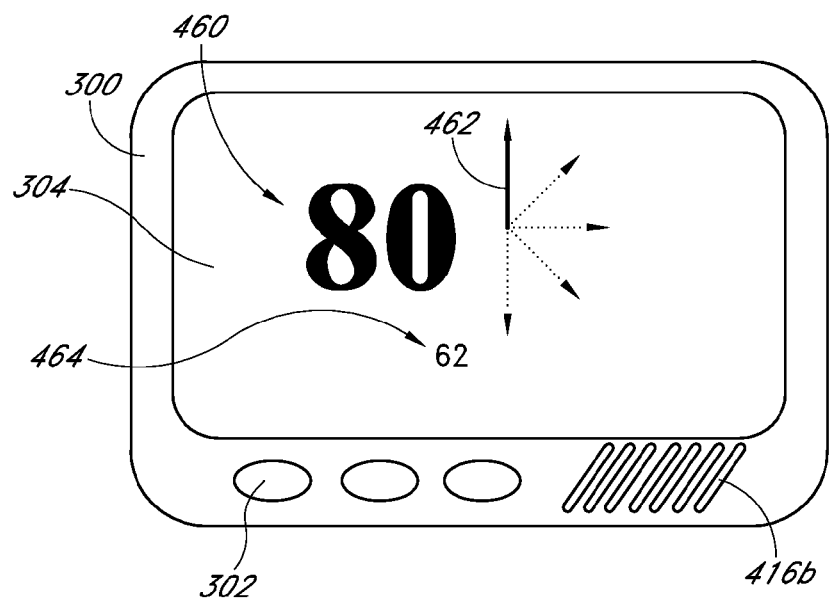
FIG. 4D is an illustration of the receiver in yet another embodiment, including a screen that shows a numerical representation of the most recent measured analyte value.

FIG. 4D is an illustration of a receiver 300 in another embodiment, including a screen 304 that shows a numerical representation of the most recent measured analyte value 460. This numerical value 460 is preferably a calibrated analyte value, such as described in more detail with reference to FIGS. 5 and 6. Additionally, this embodiment preferably provides an arrow 462 on the screen 304, which represents the rate of change of the host's analyte concentration. A bold "up" arrow is shown on the drawing, which preferably represents a relatively quickly increasing rate of change. The arrows shown with dotted lines illustrate examples of other directional arrows (for example, rotated by 45 degrees), which can be useful on the screen to represent various other positive and negative rates of change. Although the directional arrows shown have a relative low resolution (45 degrees of accuracy), other arrows can be rotated with a high resolution of accuracy (for example one degree of accuracy) to more accurately represent the rate of change of the host's analyte concentration (e.g., the amplitude and/or direction of the rate of change). In some alternative embodiments, the screen provides an indication of the acceleration of the host's analyte concentration.

A second numerical value 464 is shown, which is representative of a variation of the measured analyte value 460. The second numerical value is preferably determined from a variation analysis based on statistical, clinical, or physiological parameters, such as described in more detail elsewhere herein. In one embodiment, the second numerical value 464 is determined based on clinical risk (for example, weighted for the greatest possible clinical risk to a patient). In another embodiment, the second numerical representation 464 is an estimated analyte value extrapolated to compensate for a time lag, such as described in more detail elsewhere herein. In some alternative embodiments, the receiver displays a range of numerical analyte values that best represents the host's estimated analyte value (for example, +/-10%). In some embodiments, the range is weighted based on clinical risk to the patient. In some embodiments, the range is representative of a confidence in the estimated analyte value and/or a variation of those values. In some embodiments, the range is adjustable.

Referring again to FIG. 4A, communication ports, including a PC communication (com) port 418 and a reference glucose monitor com port 420 can be provided to enable communication with systems that are separate from, or integral with, the receiver 300. The PC com port 418, for example, a serial communications port, allows for communicating with another computer system (e.g., PC, PDA, server, and the like). In one exemplary embodiment, the receiver 300 is able to download historical data to a physician's PC for retrospective analysis by the physician. The reference glucose monitor com port 420 allows for communicating with a reference glucose monitor (not shown) so that reference glucose values can be downloaded into the receiver 300, for example, automatically. In one embodiment, the reference glucose monitor is integral with the receiver 300, and the reference glucose com port 420 allows internal communication between the two integral systems. In another embodiment, the reference glucose monitor com port 420 allows a wireless or wired connection to reference glucose monitor such as a self-monitoring blood glucose monitor (e.g., for measuring finger stick blood samples).

Integrated System

Figure 5:
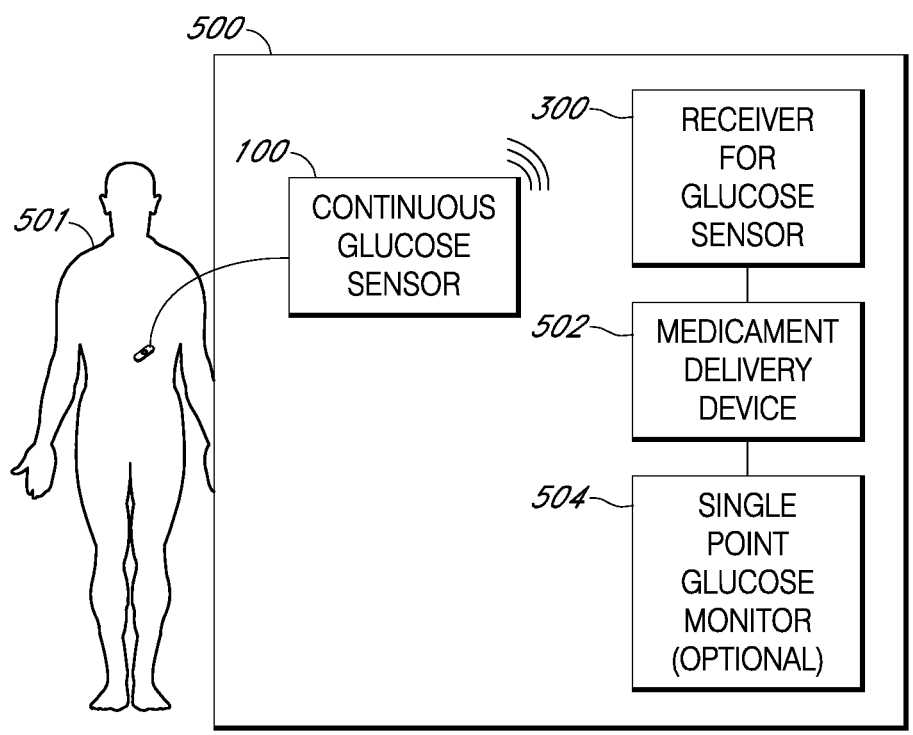
FIG. 5 is a block diagram of an integrated system of the preferred embodiments, including a continuous glucose sensor, a receiver for processing and displaying sensor data, a medicament delivery device, and an optional single point glucose-monitoring device.

Referring now to FIG. 5, in some embodiments, the receiver 300 is integrally formed with at least one of a medicament delivery device 502, and a single point glucose monitor 504. In some embodiments, the receiver 300, medicament delivery device 502 and/or single point glucose monitor 504 are detachably connected, so that one or more of the components can be individually detached and attached at the user's convenience. In some embodiments, the receiver 300, medicament delivery device 502, and/or single point glucose monitor 504 are separate from, detachably connectable to, or integral with each other; and one or more of the components are operably connected through a wired or wireless connection, allowing data transfer and thus integration between the components. In some embodiments, one or more of the components are operably linked as described above, while another one or more components (for example, the syringe or patch) are provided as a physical part of the system for convenience to the user and as a reminder to enter data for manual integration of the component with the system. Each of the components of the integrated system 500 may be manually, semi-automatically, or automatically integrated with each other, and each component may be in physical and/or data communication with another component, which may include wireless connection, wired connection (for example, via cables or electrical contacts), or the like. Additional description of integrated systems can be found in U.S. Patent Publication 2005/0192557, entitled "INTEGRATED DELIVERY DEVICE FOR CONTINUOUS GLUCOSE SENSOR," which is incorporated herein by reference in its entirety.

The preferred embodiments provide an integrated system 500, which includes a medicament delivery device 502 for administering a medicament to the patient 501. The integrated medicament delivery device can be designed for bolus injection, continuous injection, inhalation, transdermal absorption, other method for administering medicament, or any combinations thereof. The term medicament includes any substance used in therapy for a patient using the system 500, for example, insulin, glucagon, or derivatives thereof. Published International Application WO 02/43566 describes glucose, glucagon, and vitamins A, C, or D that may be used with the preferred embodiments. U.S. Pat. Nos. 6,051,551 and 6,024,090 describe types of insulin suitable for inhalation that may be used with the preferred embodiments. U.S. Pat. No. 5,234,906, U.S. Pat. No. 6,319,893, and EP 760677 describe various derivatives of glucagon that may be used with the preferred embodiments. U.S. Pat. No. 6,653,332 describes a combination therapy that may be used with the preferred embodiments. U.S. Pat. No. 6,471,689 and WO 81/01794 describe insulin useful for delivery pumps that may be used with the preferred embodiments. U.S. Pat. No. 5,226,895 describes a method of providing more than one type of insulin that may be used with the preferred embodiments. All of the above references are incorporated herein by reference in their entirety and may be useful as the medicament(s) in the preferred embodiments.

A single point glucose monitor 504 includes a meter for measuring glucose within a biological sample including a sensing region that has a sensing membrane impregnated with an enzyme, similar to the sensing membrane described with reference to U.S. Pat. Nos. 4,994,167 and 4,757,022, which are incorporated herein in their entirety by reference. However, in alternative embodiments, the single point glucose monitor 504 can use other measurement techniques such as optical, for example. It is noted that the meter is optional in that a separate meter can be used and the glucose data downloaded or input by a user into the receiver.

Calibration

Figure 6A:
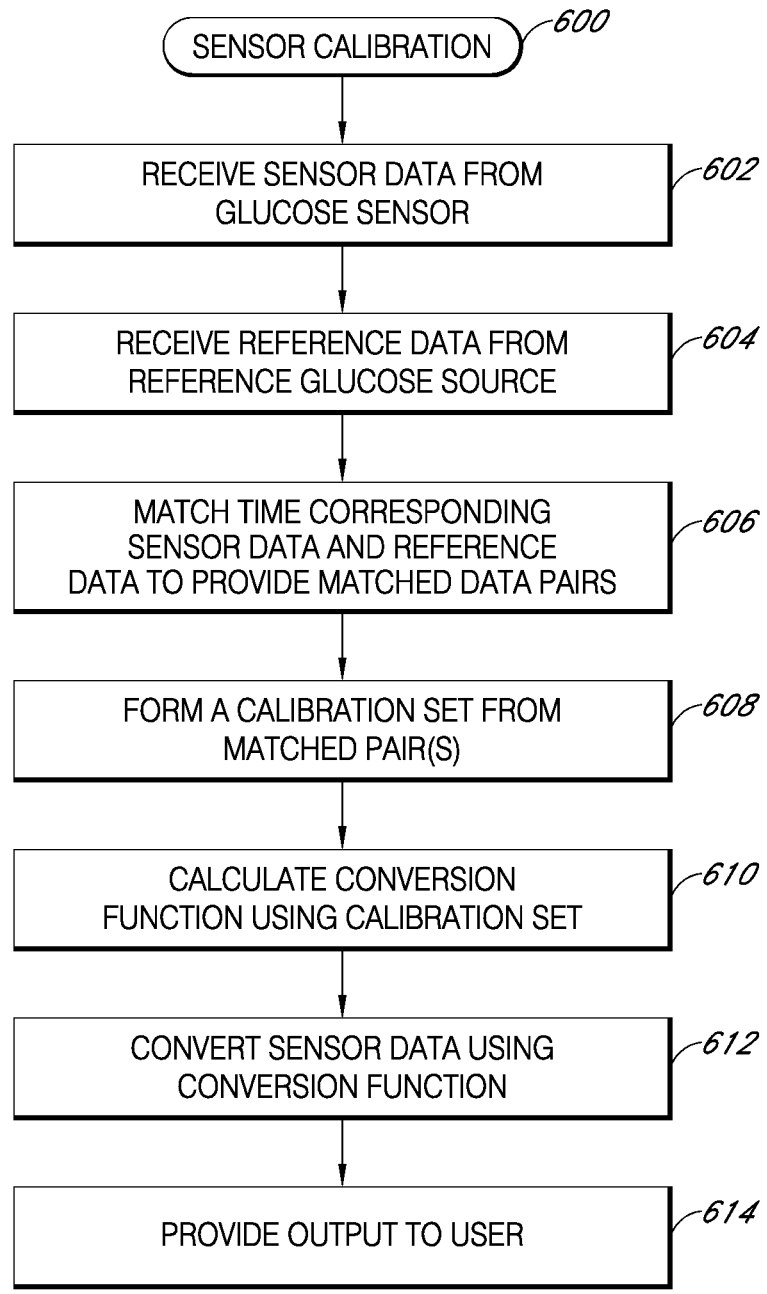
FIG. 6A is a flow chart that illustrates the process of calibrating the sensor data in one embodiment.

Reference is now made to FIG. 6A, which is a flow chart 600 that illustrates the process of calibration and data output of the glucose sensor (e.g., 100A or 100B) in one embodiment.

Calibration of the glucose sensor comprises data processing that converts a sensor data stream into an estimated glucose measurement that is meaningful to a user. In some embodiments, a reference glucose value can be used to calibrate the data stream from the glucose sensor. In one embodiment, the analyte sensor is a continuous glucose sensor and one or more reference glucose values are used to calibrate the data stream from the sensor. At initialization of a sensor, "initial calibration" is performed wherein the sensor is initially calibrated. In some embodiments, during sensor use, "update calibration" is performed to update the calibration of the sensor. In some embodiments, "recalibration" is performed to either reinitialize the calibration or perform an update calibration, for example, when the sensor has determined that the previous calibration is no longer valid. The calibration can be performed on a real-time basis and/or retrospectively recalibrated. However in alternative embodiments, other calibration techniques can be utilized, for example using another constant analyte (for example, folic acid, ascorbate, urate, and the like) as a baseline, factory calibration, periodic clinical calibration, oxygen calibration (for example, using a plurality of sensor heads), and the like can be used.

At block 602, a sensor data receiving module, also referred to as the sensor data module, or processor module, receives sensor data (e.g., a data stream), including one or more time-spaced sensor data points hereinafter referred to as "data stream," "sensor data," "sensor analyte data", or "glucose signal," from a sensor via the receiver, which can be in wired or wireless communication with the sensor. The sensor data can be raw or smoothed (filtered), or include both raw and smoothed data. In some embodiments, raw sensor data may include an integrated digital data value, e.g., a value averaged over a time period such as by a charge capacitor. Smoothed sensor data point(s) can be filtered in certain embodiments using a filter, for example, a finite impulse response (FIR) or infinite impulse response (IIR) filter. Some or all of the sensor data point(s) can be replaced by estimated signal values to address signal noise such as described in more detail elsewhere herein. It is noted that during the initialization of the sensor, prior to initial calibration, the receiver 300 (e.g., computer system) receives and stores the sensor data, however it may not display any data to the user until initial calibration and eventually stabilization of the sensor has been determined. In some embodiments, the data stream can be evaluated to determine sensor break-in (equilibrium of the sensor in vitro or in vivo).

At block 604, a reference data receiving module, also referred to as the reference input module, or the processor module, receives reference data from a reference glucose monitor, including one or more reference data points. In one embodiment, the reference glucose points can comprise results from a self-monitored blood glucose test (e.g., from a finger stick test). In one such embodiment, the user can administer a self-monitored blood glucose test to obtain a glucose value (e.g., point) using any known glucose sensor, and enter the numeric glucose value into the computer system. In another such embodiment, a self-monitored blood glucose test comprises a wired or wireless connection to the receiver 300 (e.g. computer system) so that the user simply initiates a connection between the two devices, and the reference glucose data is passed or downloaded between the self-monitored blood glucose test and the receiver 300. In yet another such embodiment, the self-monitored glucose test is integral with the receiver 300 so that the user simply provides a blood sample to the receiver 300, and the receiver 300 runs the glucose test to determine a reference glucose value. Co-pending U.S. patent application Ser. No. 10/991,966 filed on Nov. 17, 2004 and entitled "INTEGRATED RECEIVER FOR CONTINUOUS ANALYTE SENSOR" describes some systems and methods for integrating a reference analyte monitor into a receiver for a continuous analyte sensor.

In some alternative embodiments, the reference data is based on sensor data from another substantially continuous analyte sensor, e.g., a transcutaneous analyte sensor or another type of suitable continuous analyte sensor. In an embodiment employing a series of two or more transcutaneous (or other continuous) sensors, the sensors can be employed so that they provide sensor data in discrete or overlapping periods. In such embodiments, the sensor data from one continuous sensor can be used to calibrate another continuous sensor, or be used to confirm the validity of a subsequently employed continuous sensor.

In some embodiments, the calibration process 600 monitors the continuous analyte sensor data stream to determine a preferred time for capturing reference analyte concentration values for calibration of the continuous sensor data stream. In an example wherein the analyte sensor is a continuous glucose sensor, when data (for example, observed from the data stream) changes too rapidly, the reference glucose value may not be sufficiently reliable for calibration due to unstable glucose changes in the host. In contrast, when sensor glucose data are relatively stable (for example, relatively low rate of change), a reference glucose value can be taken for a reliable calibration. In one embodiment, the calibration process 600 can prompt the user via the user interface to "calibrate now" when the analyte sensor is considered stable.

In some embodiments, the calibration process 600 can prompt the user via the user interface 416 to obtain a reference analyte value for calibration at intervals, for example when analyte concentrations are at high and/or low values. In some additional embodiments, the user interface 416 can prompt the user to obtain a reference analyte value for calibration based upon certain events, such as meals, exercise, large excursions in analyte levels, faulty or interrupted data readings, and the like. In some embodiments, the estimative algorithms can provide information useful in determining when to request a reference analyte value. For example, when estimated analyte values indicate approaching clinical risk, the user interface 416 can prompt the user to obtain a reference analyte value.

Certain acceptability parameters can be set for reference values received from the user. For example, in one embodiment, the receiver may only accept reference glucose values between about 40 and about 400 mg/dL.

In some embodiments, the calibration process 600 performs outlier detection on the reference data and time corresponding sensor data. Outlier detection compares a reference analyte value with a time corresponding measured analyte value to ensure a predetermined statistically, physiologically, or clinically acceptable correlation between the corresponding data exists. In an example wherein the analyte sensor is a glucose sensor, the reference glucose data is matched with substantially time corresponding calibrated sensor data and the matched data are plotted on a Clarke Error Grid to determine whether the reference analyte value is an outlier based on clinical acceptability, such as described in more detail with reference U.S. Patent Publication No. US-2005-0027463-A1. In some embodiments, outlier detection compares a reference analyte value with a corresponding estimated analyte value, such as described in more detail elsewhere herein and with reference to the above-described patent application, and the matched data is evaluated using statistical, clinical, and/or physiological parameters to determine the acceptability of the matched data pair. In alternative embodiments, outlier detection can be determined by other clinical, statistical, and/or physiological boundaries.

In some embodiments, outlier detection utilizes signal artifacts detection, described in more detail elsewhere herein, to determine the reliability of the reference data and/or sensor data responsive to the results of the signal artifacts detection. For example, if a certain level of signal artifacts is not detected in the data signal, then the sensor data is determined to be reliable. As another example, if a certain level of signal artifacts is detected in the data signal, then the reference glucose data is determined to be reliable.

The reference data can be pre-screened according to environmental and physiological issues, such as time of day, oxygen concentration, postural effects, and patient-entered environmental data. In one exemplary embodiment, wherein the sensor comprises an implantable glucose sensor, an oxygen sensor within the glucose sensor is used to determine if sufficient oxygen is being provided to successfully complete the necessary enzyme and electrochemical reactions for accurate glucose sensing. In another exemplary embodiment, the patient is prompted to enter data into the user interface, such as meal times and/or amount of exercise, which can be used to determine likelihood of acceptable reference data. In yet another exemplary embodiment, the reference data is matched with time-corresponding sensor data, which is then evaluated on a modified clinical error grid to determine its clinical acceptability.

Some evaluation data, such as described in the paragraph above, can be used to evaluate an optimum time for reference analyte measurement, such as described in more detail with reference to FIG. 7. Correspondingly, the user interface can then prompt the user to provide a reference data point for calibration within a given time period. Consequently, because the receiver proactively prompts the user during optimum calibration times, the likelihood of error due to environmental and physiological limitations can decrease and consistency and acceptability of the calibration can increase.

At block 606, a data matching module, also referred to as the processor module, matches reference data (e.g., one or more reference glucose data points) with substantially time corresponding sensor data (e.g., one or more sensor data points) to provide one or more matched data pairs. In one embodiment, one reference data point is matched to one time corresponding sensor data point to form a matched data pair. In another embodiment, a plurality of reference data points are averaged (e.g., equally or non-equally weighted average, mean-value, median, and the like) and matched to one time corresponding sensor data point to form a matched data pair. In another embodiment, one reference data point is matched to a plurality of time corresponding sensor data points averaged to form a matched data pair. In yet another embodiment, a plurality of reference data points are averaged and matched to a plurality of time corresponding sensor data points averaged to form a matched data pair.

In one embodiment, a time corresponding sensor data comprises one or more sensor data points that occur, for example, 15±5 min after the reference glucose data timestamp (e.g., the time that the reference glucose data is obtained). In this embodiment, the minute time delay has been chosen to account for an approximately 10 minute delay introduced by the filter used in data smoothing and an approximately 5 minute diffusional time-lag (e.g., the time necessary for the glucose to diffusion through a membrane(s) of a glucose sensor). In alternative embodiments, the time corresponding sensor value can be more or less than in the above-described embodiment, for example ±60 minutes. Variability in time correspondence of sensor and reference data can be attributed to, for example, a longer or shorter time delay introduced during signal estimation, or if the configuration of the glucose sensor incurs a greater or lesser physiological time lag.

In another embodiment, time corresponding sensor data comprises one or more sensor data points that occur from about 0 minutes to about 20 minutes after the reference analyte data time stamp (e.g., the time that the reference analyte data is obtained). In one embodiment, a 5-minute time delay is chosen to compensate for a system time-lag (e.g., the time necessary for the analyte to diffusion through a membrane(s) of an analyte sensor). In alternative embodiments, the time corresponding sensor value can be earlier than or later than that of the above-described embodiment, for example ±60 minutes. Variability in time correspondence of sensor and reference data can be attributed to, for example, a longer or shorter time delay introduced by the data smoothing filter, or if the configuration of the analyte sensor incurs a greater or lesser physiological time lag.

In some practical implementations of the sensor, the reference glucose data can be obtained at a time that is different from the time that the data is input into the receiver 300. Accordingly, it should be noted that the "time stamp" of the reference glucose (e.g., the time at which the reference glucose value was obtained) may not be the same as the time at which the receiver 300 obtained the reference glucose data. Therefore, some embodiments include a time stamp requirement that ensures that the receiver 300 stores the accurate time stamp for each reference glucose value, that is, the time at which the reference value was actually obtained from the user.

In some embodiments, tests are used to evaluate the best-matched pair using a reference data point against individual sensor values over a predetermined time period (e.g., about 30 minutes). In one such embodiment, the reference data point is matched with sensor data points at 5-minute intervals and each matched pair is evaluated. The matched pair with the best correlation can be selected as the matched pair for data processing. In some alternative embodiments, matching a reference data point with an average of a plurality of sensor data points over a predetermined time period can be used to form a matched pair.

In some embodiments wherein the data signal is evaluated for signal artifacts, as described in more detail elsewhere herein, the processor module is configured to form a matched data pair only if a signal artifact is not detected. In some embodiments wherein the data signal is evaluated for signal artifacts, the processor module is configured to prompt a user for a reference glucose value during a time when one or more signal artifact(s) is not detected.

At block 608, a calibration set module, also referred to as the processor module, forms an initial calibration set from a set of one or more matched data pairs, which are used to determine the relationship between the reference glucose data and the sensor glucose data, such as described in more detail with reference to block 610, below.

The matched data pairs, which make up the initial calibration set, can be selected according to predetermined criteria. In some embodiments, the number (n) of data pair(s) selected for the initial calibration set is one. In other embodiments, n data pairs are selected for the initial calibration set wherein n is a function of the frequency of the received reference data points. In one exemplary embodiment, six data pairs make up the initial calibration set. In another embodiment, the calibration set includes only one data pair. In an embodiment wherein a substantially continuous analyte sensor provides reference data, numerous data points are used to provide reference data from more than 6 data pairs (e.g., dozens or even hundreds of data pairs). In one exemplary embodiment, a substantially continuous analyte sensor provides 288 reference data points per day (every five minutes for twenty-four hours), thereby providing an opportunity for a matched data pair 288 times per day, for example. While specific numbers of matched data pairs are referred to in the preferred embodiments, any suitable number of matched data pairs per a given time period can be employed.

In some embodiments, the data pairs are selected only within a certain glucose value threshold, for example wherein the reference glucose value is between about 40 and about 400 mg/dL. In some embodiments, the data pairs that form the initial calibration set are selected according to their time stamp. In certain embodiments, the data pairs that form the initial calibration set are selected according to their time stamp, for example, by waiting a predetermined "break-in" time period after implantation, the stability of the sensor data can be increased. In certain embodiments, the data pairs that form the initial calibration set are spread out over a predetermined time period, for example, a period of two hours or more. In certain embodiments, the data pairs that form the initial calibration set are spread out over a predetermined glucose range, for example, spread out over a range of at least 90 mg/dL or more.

In some embodiments, wherein the data signal is evaluated for signal artifacts, as described in more detail elsewhere herein, the processor module is configured to utilize the reference data for calibration of the glucose sensor only if a signal artifact is not detected.

At block 610, the conversion function module, also referred to as the processor module, uses the calibration set to create a conversion function. The conversion function substantially defines the relationship between the reference glucose data and the glucose sensor data. A variety of known methods can be used with the preferred embodiments to create the conversion function from the calibration set. In one embodiment, wherein a plurality of matched data points form the initial calibration set, a linear least squares regression is performed on the initial calibration set such as described in more detail with reference to FIG. 6B.

At block 612, a sensor data transformation module, also referred to as the processor module, uses the conversion function to transform sensor data into substantially real-time glucose value estimates, also referred to as calibrated data, or converted sensor data, as sensor data is continuously (or intermittently) received from the sensor. For example, the sensor data, which can be provided to the receiver in "counts," is translated in to estimate analyte value(s) in mg/dL. In other words, the offset value at any given point in time can be subtracted from the raw value (e.g., in counts) and divided by the slope to obtain the estimated glucose value:

$$mg/dL = \frac{(rawvalue - \text{offset})}{slope}$$

In some alternative embodiments, the sensor and/or reference glucose values are stored in a database for retrospective analysis.

At block 614, an output module, also referred to as the processor module, provides output to the user via the user interface. The output is representative of the estimated glucose value, which is determined by converting the sensor data into a meaningful glucose value such as described in more detail with reference to block 612, above. User output can be in the form of a numeric estimated glucose value, an indication of directional trend of glucose concentration, and/or a graphical representation of the estimated glucose data over a period of time, for example. Other representations of the estimated glucose values are also possible, for example audio and tactile.

In one embodiment, such as shown in FIG. 3A, the estimated glucose value is represented by a numeric value. In other exemplary embodiments, such as shown in FIGS. 3B to 3D, the user interface graphically represents the estimated glucose data trend over predetermined a time period (e.g., one, three, and nine hours, respectively). In alternative embodiments, other time periods can be represented. In alternative embodiments, pictures, animation, charts, graphs, ranges of values, and numeric data can be selectively displayed.

Accordingly, after initial calibration of the sensor, real-time continuous glucose information can be displayed on the user interface so that the user can regularly and proactively care for his/her diabetic condition within the bounds set by his/her physician.

In alternative embodiments, the conversion function is used to predict glucose values at future points in time. These predicted values can be used to alert the user of upcoming hypoglycemic or hyperglycemic events. Additionally, predicted values can be used to compensate for a time lag (e.g., 15 minute time lag such as described elsewhere herein), if any, so that an estimated glucose value displayed to the user represents the instant time, rather than a time delayed estimated value.

In some embodiments, the substantially real-time estimated glucose value, a predicted future estimated glucose value, a rate of change, and/or a directional trend of the glucose concentration is used to control the administration of a constituent to the user, including an appropriate amount and time, in order to control an aspect of the user's biological system. One such example is a closed loop glucose sensor and insulin pump, wherein the glucose data (e.g., estimated glucose value, rate of change, and/or directional trend) from the glucose sensor is used to determine the amount of insulin, and time of administration, that can be given to a diabetic user to evade hyper- and hypoglycemic conditions.

Figure 6B:
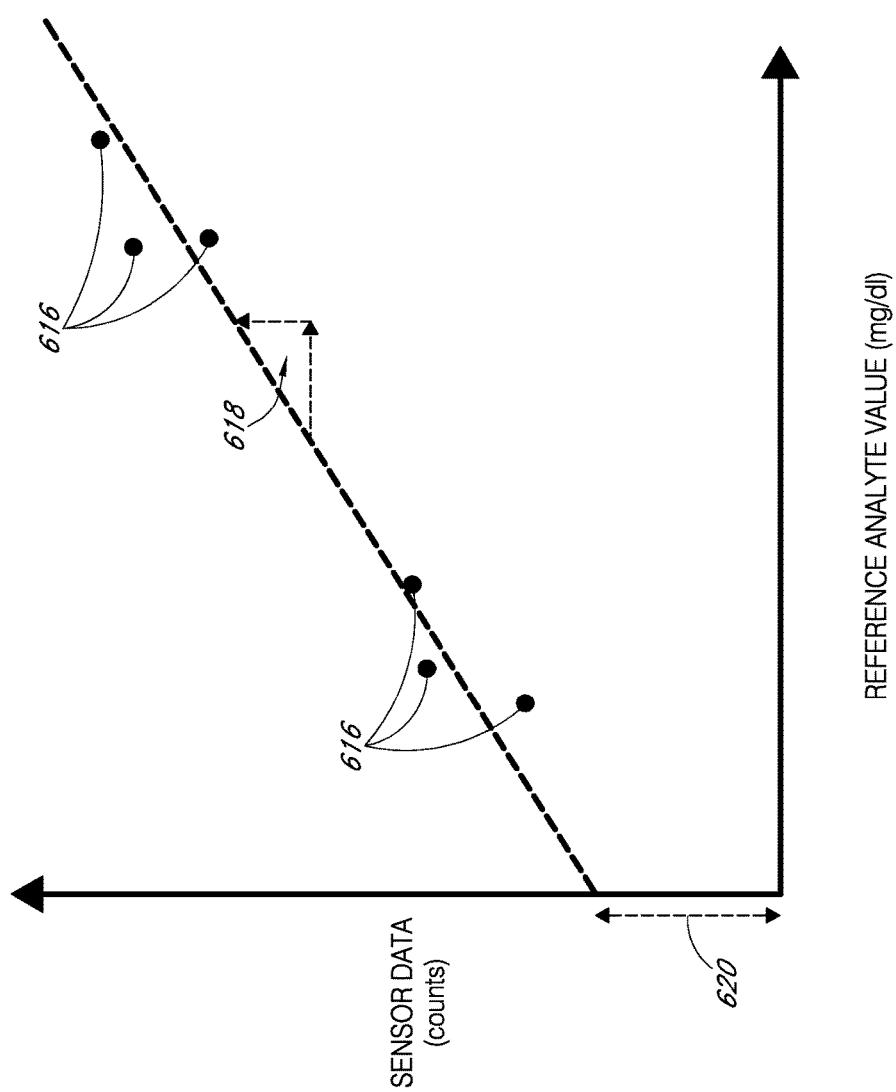
FIG. 6B is a graph that illustrates a linear regression used to calibrate the sensor data in one embodiment.

FIG. 6B is a graph that illustrates one embodiment of a regression performed on a calibration set to create a conversion function such as described with reference to FIG. 6A, block 610, above. In this embodiment, a linear least squares regression is performed on the initial calibration set. The x-axis represents reference glucose data; the y-axis represents sensor data. The graph pictorially illustrates regression of matched pairs 616 in the calibration set. The regression calculates a slope 618 and an offset 620, for example, using the well-known slope-intercept equation (y=mx+b), which defines the conversion function.

In alternative embodiments, other algorithms could be used to determine the conversion function, for example forms of linear and non-linear regression, for example fuzzy logic, neural networks, piece-wise linear regression, polynomial fit, genetic algorithms, and other pattern recognition and signal estimation techniques.

In yet other alternative embodiments, the conversion function can comprise two or more different optimal conversions because an optimal conversion at any time is dependent on one or more parameters, such as time of day, calories consumed, exercise, or glucose concentration above or below a set threshold, for example. In one such exemplary embodiment, the conversion function is adapted for the estimated glucose concentration (e.g., high vs. low). For example in an implantable glucose sensor it has been observed that the cells surrounding the implant will consume at least a small amount of glucose as it diffuses toward the glucose sensor. Assuming the cells consume substantially the same amount of glucose whether the glucose concentration is low or high, this phenomenon will have a greater effect on the concentration of glucose during low blood sugar episodes than the effect on the concentration of glucose during relatively higher blood sugar episodes. Accordingly, the conversion function can be adapted to compensate for the sensitivity differences in blood sugar level. In one implementation, the conversion function comprises two different regression lines, wherein a first regression line is applied when the estimated blood glucose concentration is at or below a certain threshold (e.g., 150 mg/dL) and a second regression line is applied when the estimated blood glucose concentration is at or above a certain threshold (e.g., 150 mg/dL). In one alternative implementation, a predetermined pivot of the regression line that forms the conversion function can be applied when the estimated blood is above or below a set threshold (e.g., 150 mg/dL), wherein the pivot and threshold are determined from a retrospective analysis of the performance of a conversion function and its performance at a range of glucose concentrations. In another implementation, the regression line that forms the conversion function is pivoted about a point in order to comply with clinical acceptability standards (e.g., Clarke Error Grid, Consensus Grid, mean absolute relative difference, or other clinical cost function). Although only a few example implementations are described, other embodiments include numerous implementations wherein the conversion function is adaptively applied based on one or more parameters that can affect the sensitivity of the sensor data over time.

In some other alternative embodiments, the sensor is calibrated with a single-point through the use of a dual-electrode system to simplify sensor calibration. In one such dual-electrode system, a first electrode functions as a hydrogen peroxide sensor including a membrane system containing glucose-oxidase disposed thereon, which operates as described herein. A second electrode is a hydrogen peroxide sensor that is configured similar to the first electrode, but with a modified membrane system (with the enzyme domain removed, for example). This second electrode provides a signal composed mostly of the baseline signal, b.

In some dual-electrode systems, the baseline signal is (electronically or digitally) subtracted from the glucose signal to obtain a glucose signal substantially without baseline. Accordingly, calibration of the resultant difference signal can be performed by solving the equation y=mx with a single paired measurement. Calibration of the implanted sensor in this alternative embodiment can be made less dependent on the values/range of the paired measurements, less sensitive to error in manual blood glucose measurements, and can facilitate the sensor's use as a primary source of glucose information for the user. Co-pending U.S. patent application Ser. No. 11/004,561 filed Dec. 3, 2004 and entitled, "CALIBRATION TECHNIQUES FOR A CONTINUOUS ANALYTE SENSOR" describes systems and methods for subtracting the baseline from a sensor signal.

In some alternative dual-electrode system embodiments, the analyte sensor is configured to transmit signals obtained from each electrode separately (e.g., without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (e.g., without the use of a reference analyte value). In one such example, by monitoring the corresponding first and second signals over time, an amount of signal contributed by baseline can be measured. In another such example, by comparing fluctuations in the correlating signals over time, changes in sensitivity can be detected and/or measured.

In some alternative embodiments, a regression equation y=mx+b is used to calculate the conversion function; however, prior information can be provided for m and/or b, thereby enabling calibration to occur with fewer paired measurements. In one calibration technique, prior information (e.g., obtained from in vivo or in vitro tests) determines a sensitivity of the sensor and/or the baseline signal of the sensor by analyzing sensor data from measurements taken by the sensor (e.g., prior to inserting the sensor). For example, if there exists a predictive relationship between in vitro sensor parameters and in vivo parameters, then this information can be used by the calibration procedure. For example, if a predictive relationship exists between in vitro sensitivity and in vivo sensitivity, $m \approx f(m_{in\ vitro})$, then the predicted m can be used, along with a single matched pair, to solve for b (b=y−mx). If, in addition, b can be assumed=0, for example with a dual-electrode configuration that enables subtraction of the baseline from the signal such as described above, then both m and b are known a priori, matched pairs are not needed for calibration, and the sensor can be completely calibrated e.g. without the need for reference analyte values (e.g. values obtained after implantation in vivo.)

In another alternative embodiment, prior information can be provided to guide or validate the baseline (b) and/or sensitivity (m) determined from the regression analysis. In this embodiment, boundaries can be set for the regression line that defines the conversion function such that working sensors are calibrated accurately and easily (with two points), and non-working sensors are prevented from being calibrated. If the boundaries are drawn too tightly, a working sensor may not enter into calibration. Likewise, if the boundaries are drawn too loosely, the scheme can result in inaccurate calibration or can permit non-working sensors to enter into calibration. For example, subsequent to performing regression, the resulting slope and/or baseline are tested to determine whether they fall within a predetermined acceptable threshold (boundaries). These predetermined acceptable boundaries can be obtained from in vivo or in vitro tests (e.g., by a retrospective analysis of sensor sensitivities and/or baselines collected from a set of sensors/patients, assuming that the set is representative of future data).

If the slope and/or baseline fall within the predetermined acceptable boundaries, then the regression is considered acceptable and processing continues to the next step. Alternatively, if the slope and/or baseline fall outside the predetermined acceptable boundaries, steps can be taken to either correct the regression or fail-safe such that a system will not process or display errant data. This can be useful in situations wherein regression results in errant slope or baseline values. For example, when points (matched pairs) used for regression are too close in value, the resulting regression is statistically less accurate than when the values are spread farther apart. As another example, a sensor that is not properly deployed or is damaged during deployment can yield a skewed or errant baseline signal.

Figure 6C:
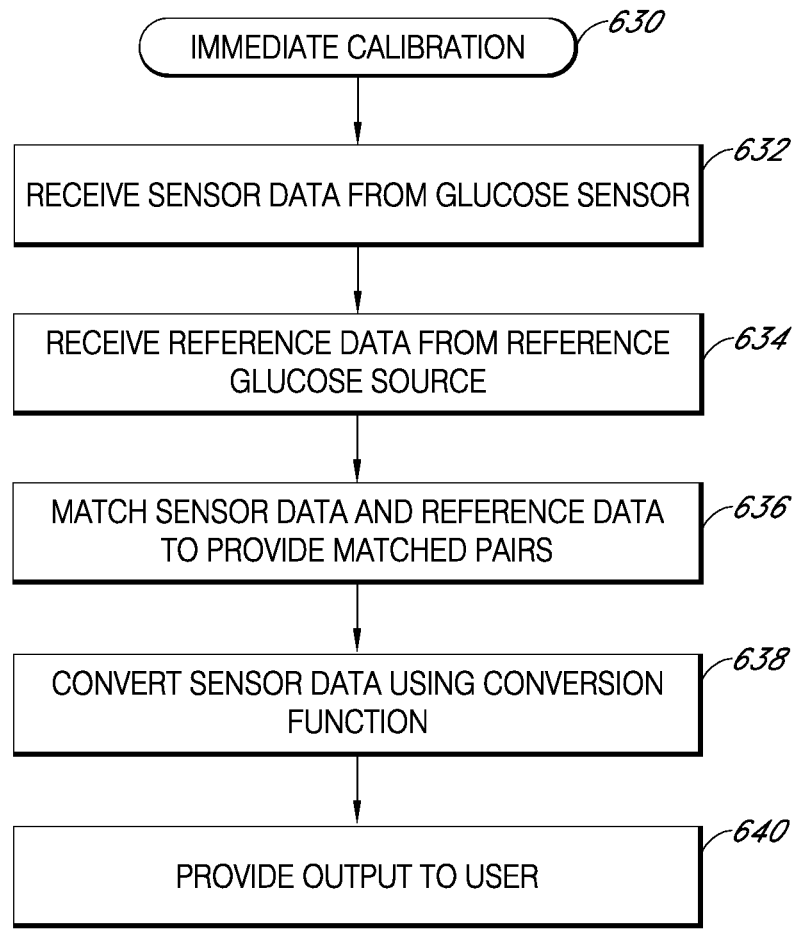
FIG. 6C is a flow chart that illustrates the process of immediate calibration of a continuous analyte sensor in one embodiment.

Reference is now made to FIG. 6C, which is a flow chart 630 that illustrates the process of immediate calibration of a continuous analyte sensor in one embodiment.

In conventional analyte sensors, during initial calibration, update calibration and/or recalibration of a sensor system, a user must wait a predetermined period of time (e.g., at least about 5, 10, 15, 20, 25 or more minutes after entry of a reference analyte value for the system to output (e.g., display) its first calibrated analyte measurement, resulting in an inconvenience to the user including a time delayed response of calibrated sensor data and/or whether or not the reference analyte value was accepted for calibration.

The preferred embodiments provide systems and methods to improve the responsiveness of a user interface (e.g., data output) to received reference analyte values (e.g., a reading from a blood glucose meter) for faster feedback to the user. Although calibration preferably compensates for a time lag between the reference analyte values (e.g., blood glucose meter readings) and glucose sensor readings (e.g., continuous glucose sensor readings subject to processing such as filtering), some circumstances exist wherein an immediate calibration does not compensate for a time lag (e.g., prior to receiving time-corresponding sensor data). In one example, a 5-minute time lag is induced in continuous sensor data by a filter or integrator of raw continuous sensor data (e.g., a signal)).

At block 632, a sensor data receiving module, also referred to as the sensor data module, or processor module, receives sensor data (e.g., a data stream), including one or more time-spaced sensor data points hereinafter referred to as "data stream," "sensor data," "sensor analyte data", or "glucose signal," from a sensor via the receiver, which can be in wired or wireless communication with the sensor. The sensor data can be raw or smoothed (filtered), or include both raw and smoothed data. In some embodiments, raw sensor data may include an integrated digital data value, e.g., a value averaged over a time period such as by a charge capacitor. Smoothed sensor data point(s) can be filtered in certain embodiments using a filter, for example, a finite impulse response (FIR) or infinite impulse response (IIR) filter. Some or all of the sensor data point(s) can be replaced by estimated signal values to address signal noise such as described in more detail elsewhere herein. It is noted that during the initialization of the sensor, prior to initial calibration, the receiver 300 (e.g., computer system) receives and stores the sensor data, however it may not display any data to the user until initial calibration and eventually stabilization of the sensor has been determined. In some embodiments, the data stream can be evaluated to determine sensor break-in (equilibrium of the sensor in vitro or in vivo).

At block 634, a reference data receiving module, also referred to as the reference input module, or the processor module, receives reference data from a reference glucose monitor, including one or more reference data points. In one embodiment, the reference glucose points can comprise results from a self-monitored blood 504 (e.g., from a finger stick test). In one such embodiment, the user can administer a self-monitored blood glucose test to obtain a glucose value (e.g., point) using any known glucose sensor, and enter the numeric glucose value into the computer system. In another such embodiment, a self-monitored blood glucose test comprises a wired or wireless connection to the receiver 300 (e.g. computer system) so that the user simply initiates a connection between the two devices, and the reference glucose data is passed or downloaded between the self-monitored blood glucose test and the receiver 300. In yet another such embodiment, the self-monitored glucose test is integral with the receiver 300 so that the user simply provides a blood sample to the receiver 300, and the receiver 300 runs the glucose test to determine a reference glucose value. Co-pending U.S. patent application Ser. No. 10/991, 966 filed on Nov. 17, 2004 and entitled "INTEGRATED RECEIVER FOR CONTINUOUS ANALYTE SENSOR" describes some systems and methods for integrating a reference analyte monitor into a receiver for a continuous analyte sensor.

In some alternative embodiments, the reference data is based on sensor data from another substantially continuous analyte sensor, e.g., a transcutaneous analyte sensor or another type of suitable continuous analyte sensor. In an embodiment employing a series of two or more transcutaneous (or other continuous) sensors, the sensors can be employed so that they provide sensor data in discrete or overlapping periods. In such embodiments, the sensor data from one continuous sensor can be used to calibrate another continuous sensor, or be used to confirm the validity of a subsequently employed continuous sensor.

At block 636, an data matching is performed by matching a reference analyte value to the closest sensor data point (e.g., prior, estimated and/or predicted sensor data point), also referred to as an "immediate match," such that calibration can be performed and immediate feedback given to the user. Preferably, immediate calibration enables display of the one or more estimated analyte values within about 10, 8, 6, 5, 4, 3, 2, or 1 minute(s) of receiving the reference analyte value. Preferably, immediate calibration is accomplished by matching data pairs immediately, for example, without compensating for a time lag between the reference glucose value and the sensor glucose value such that a time stamp of the reference glucose value is as close as possible to a time stamp of the sensor glucose value. In some further embodiments, the time stamp of the reference glucose value is within about 5 minutes, 2.5 minutes, 1 minute or less of the time stamp of the sensor glucose value in the matched data pair.

In another embodiment, an immediate calibration is performed by matching a reference analyte value to a projected sensor data point (e.g., using prediction described herein elsewhere) such that calibration can be performed and immediate feedback given to the user. The projected value will therefore be used to compensate for the time differential between obtaining the analyte sensor value and converting this value to one comparable to the reference analyte value. Preferably, this embodiment of immediate calibration enables display of the one or more estimated analyte values within about 10, 8, 6, 5, 4, 3, 2, or 1 minute of calculating the projected reference analyte value.

Subsequently, "standard calibration," is performed, also referred to as subsequent calibration, wherein the reference analyte value can be re-matched to a more optimal sensor data point, such as described in more detail elsewhere herein with reference to matching data pairs, for example, when additional sensor data points are obtained. In some embodiments, the subsequent calibration, also referred to as "standard calibration," is performed once additional sensor data is obtained and matched with the receiving reference analyte value as described in more detail elsewhere herein, for example with reference to the data matching module. In some embodiments, the standard calibration utilizes matched data pairs chosen to adjust for a time lag between a reference glucose value and a sensor glucose value. In one such example, a time lag is induced at least in part by a filter applied to raw glucose sensor data measured by the continuous glucose sensor. In some embodiments, for example, wherein optimal sensor data for matching with the reference analyte data is not available (e.g., due to sensor-receiver communication problems), the immediate calibration is utilized (e.g., calibrated data displayed using the immediate match) until one or more additional reference analyte values are available for calibration.

In some embodiments, immediate calibration provides a calibration line that determines, predicts or estimates the calibration state that will be found with the subsequent calibration (e.g., whether the sensor will be in-calibration or out-of-calibration responsive to the received reference analyte value). Preferably, the immediate calibration provides sufficient accuracy such that displayed sensor data during immediate calibration corresponds to and/or flows with the glucose values displayed after the standard calibration (e.g., substantially without non-physiological fluctuations in the displayed data). Accordingly, immediate calibration is preferably configured with other processing and fail-safes, as described in more detail elsewhere herein with reference to calibration (e.g., algorithms such as outlier detection, intelligent selection of other matched data pairs in the calibration set, and the like). In preferred embodiments, the conversion function provided by the immediate calibration (e.g., the immediate match calibration line) is similar to the conversion function provided by the standard calibration (e.g., the subsequent calibration line), for example within about +/−20%.

At block 638, a sensor data transformation module, also referred to as the processor module, uses a conversion function (described elsewhere herein) to transform sensor data into substantially real-time glucose value estimates, also referred to as calibrated data, or converted sensor data, as sensor data is continuously (or intermittently) received from the sensor. For example, the sensor data, which can be provided to the receiver in "counts," is translated in to estimate analyte value(s) in mg/dL as described in reference to FIG. 6A.

At block 640, an output module, also referred to as the processor module, provides output to the user via the user interface. The output is representative of the estimated glucose value, which is determined by converting the sensor data into a meaningful glucose value such as described in more detail with reference to block 612, above. User output can be in the form of a numeric estimated glucose value, an indication of directional trend of glucose concentration, and/or a graphical representation of the estimated glucose data over a period of time, for example. Other representations of the estimated glucose values are also possible, for example audio and tactile.

Figure 7:
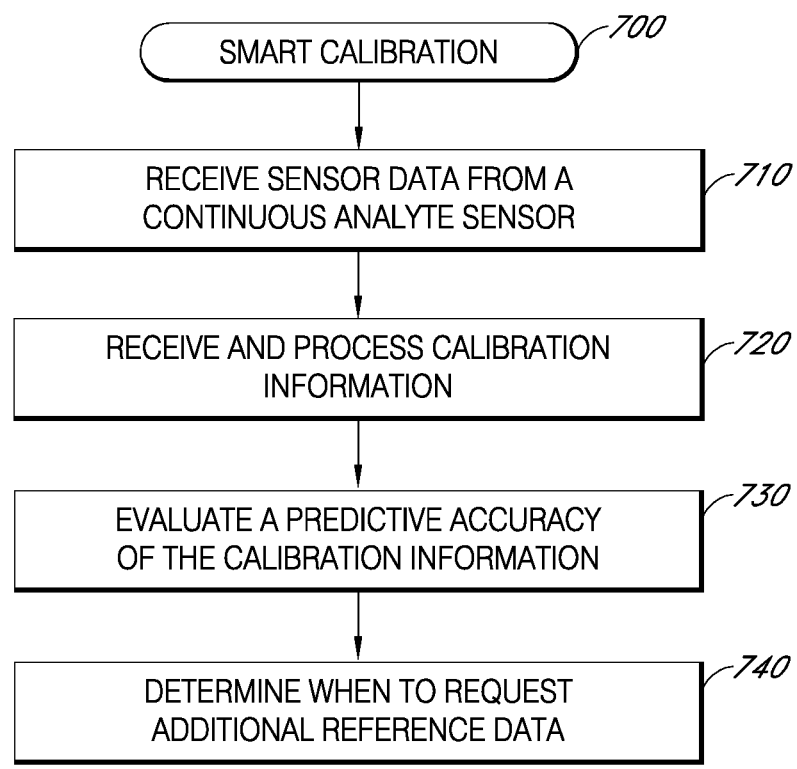
FIG. 7 is a flow chart that illustrates the process of smart or intelligent calibration of a continuous analyte sensor in one embodiment.

Reference is now made to FIG. 7, which is a flow chart 700 that illustrates the process of smart or intelligent calibration of a continuous analyte sensor in one embodiment. In general, conventional calibration of analyte sensors can have some inaccuracy, for example, caused by drift of the sensor signal, algorithmic-induced inaccuracies, reference analyte measurement error and signal disagreement (e.g., between the sensor signal and reference signal). As one example, a temporary signal disagreement, or a transient lack of correlation between interstitial analyte sensor data and blood analyte reference data, can be related to biology, such as differences in interstitial and blood glucose levels. Accordingly, conventional sensors can suffer from calibration inaccuracy as a result of temporary signal disagreement, and the like.

Some conventional continuous analyte sensors request reference data at predetermined time periods during sensor use (e.g., a sensor session), for example every 12 hours or at certain predetermined regular or irregular intervals. However, because of reasons described above, more or fewer reference data (analyte values) may be required to calibrate the sensor accurately, which can vary from sensor to sensor and/or host to host. For example, if a sensor signal exhibits a lot of drift, more reference data may be necessary. If a sensor signal exhibits very little drift, less reference data may be sufficient for good sensor calibration. Preferably, the smart calibration 700 as described herein associates sensor calibration with sensor performance. Accordingly, the embodiments described herein enable a sensor that avoids or overcomes calibration inaccuracies caused by signal drift, temporary signal disagreement, and the like.

In some preferred embodiments, systems and methods are provided for calibration of a continuous glucose sensor, wherein the system determines an amount of drift on the sensor signal over a time period and requests reference data when the amount of drift is greater than a threshold. Sensor drift can be determined by monitoring a change in signal strength (e.g., using a low pass filter) during a sensor session and/or monitoring a change in calibration information (e.g., matched data pairs, calibration set and/or calibration line) over a sensor session, for example.

In some preferred embodiments, systems and methods are provided for calibration of a continuous glucose sensor, wherein the system determines a predictive accuracy of calibration information and requests reference data based at least in part on the predictive accuracy of the calibration information.

At block 710, a sensor data receiving module, also referred to as the sensor data module, or processor module, receives sensor data (e.g., a data stream), including one or more time-spaced sensor data points hereinafter referred to as "data stream," "sensor data," "sensor analyte data", "signal," from a sensor via the receiver, which can be in wired or wireless communication with the sensor. The sensor data receiving module is described in more detail elsewhere herein, for example, with reference to FIG. 5.

At block 720, a calibration module, also referred to as the processor module, receives and processes calibration information. In some embodiments, the calibration module receives reference data from a reference analyte monitor (e.g., glucose monitor), including one or more reference data points, which is described in more detail with reference to the reference data receiving module, for example, with reference to FIG. 5. In general, reference data can be received at sensor start-up and/or periodically or intermittently throughout the sensor session. It is appreciated by one of ordinary skill in the art that reference data can be received before, during and/or after receiving sensor data.

In some embodiments, the calibration module, matches reference data (e.g., one or more reference glucose data points) with substantially time corresponding sensor data (e.g., one or more sensor data points) to provide one or more matched data pairs, which is described in more detail elsewhere herein, for example, with reference to the data matching module associated with FIG. 6A. In one embodiment, one reference data point is matched to one time corresponding sensor data point to form a matched data pair.

In some embodiments, the calibration module, forms a calibration set from a set of one or more matched data pairs, which are used to determine the relationship between the reference analyte (e.g., glucose) data and the sensor analyte (e.g., glucose data), such as described in more detail with reference to block 730, for example.

At block 730, an evaluation module, also referred to as the processor module, evaluates a predictive accuracy of the calibration information. The term "predictive accuracy" as used herein is a broad term and is to be given its ordinary and customary meaning to a person of ordinary skill in the art (and is not to be limited to a special or customized meaning), and furthermore refers without limitation to a measure of how accurate or indicative calibration information is to a true correlation between the analyte signal and the actual analyte concentration, for example, a measure of how well a matched data pair, a plurality of matched data pairs, a calibration set, and/or a calibration line will accurately predict (i.e., estimate/correlate) glucose concentration from a sensor signal across a physiologically relevant range of glucose concentrations (e.g., between about 30 mg/dL and 600 mg/dL of glucose concentration).

In general, the evaluation module evaluates the predictive accuracy by evaluating a correlation (or lack thereof), a discordance (or lack thereof), a goodness of fit (or lack thereof), a leverage (or lack thereof), and/or the like, of sensor performance and/or calibration information to determine a predictive accuracy of the calibration using a data association function, clinical acceptability, and/or the like.

In some embodiments, the evaluation module evaluates a predictive accuracy by determining a correlation of (or lack of correlation of) one or more matched pairs (e.g., a newly received matched data pair) with an existing calibration set. For example, the evaluation module can evaluate whether a newly received matched data pair(s) fits within the existing calibration set or the newly received matched data pair(s) changes the calibration set, such as by evaluating a change in a calibration line (e.g., regression line) formed with and without the newly received matched data pair(s) included therein.

In some embodiments, after receiving a new matched data pair, the processor module forms a new calibration set that includes the newly received matched data pair, and forms a new calibration line from the new calibration set; subsequently, the evaluation module evaluates a predictive accuracy by evaluating a correlation of the matched data pairs in the (existing) calibration set (e.g., the calibration set without the newly received matched data pair) with the new calibration line (e.g., formed from the new calibration set including the newly received matched data pair).

In some embodiments, after receiving a new matched data pair and forming a new calibration set including the newly received matched data pair, the evaluation module evaluates a predictive accuracy by evaluating a discordance of the new matched data pair and/or the matched data pairs in the new calibration set. In some embodiments, a new matched pair is compared against the distribution (e.g., "cloud") of matched data pairs in the calibration set, whereby a predictive accuracy is determined based on a correlation and/or deviation of the new matched data pair relative to the distribution of matched data pairs in the calibration set.

In some embodiments, the evaluation module evaluates a predictive accuracy by iteratively evaluating a plurality of combinations of matched data pairs in the calibration set to obtain a plurality of calibration lines; for example, if the calibration set includes 5 matched data pairs, the processor module can systematically remove each of the matched data pairs from the calibration set, one at a time, and evaluate the resulting 4-data pair calibration sets. One skilled in the art appreciates the variety of combinations of matched data pairs in a calibration set that can be evaluated, which is dependent upon the number of matched data pairs in the calibration set and the number of matched data pairs that are removed during each iteration, all of which is encompassed herein. In some embodiments, the processor module removes one or more of the matched data pairs from the calibration set in response to the iterative evaluation; for example, due to a lack of correlation of and/or a discordance of a calibration set and/or calibration line, resulting from one or more matched data pairs that do not fit well with other of the matched data pairs in the calibration set. Advantageously, this embodiment identifies matched data pairs to remove from the calibration set (e.g., due to inaccuracies and/or drift of the sensor signal).

In some embodiments, the evaluation module evaluates a predictive accuracy by evaluating a leverage of the reference data based at least in part on a glucose concentration associated with the reference data. The term "leverage" as used herein is a broad term and is to be given its ordinary and customary meaning to a person of ordinary skill in the art (and is not to be limited to a special or customized meaning), and furthermore refers without limitation to a measure of how much calibration information increases a predictive accuracy of the sensor calibration, for example, how much newly received reference data increases the accuracy of the calibration across a physiologically relevant range of glucose concentration (e.g., 30 to 600 mg/dL). In some embodiments, the evaluation module evaluates a glucose concentration of the reference data to determine its leverage in a calibration set, wherein a glucose concentration that significantly increases the spread of glucose concentrations represented in a calibration set provides leverage, and wherein a glucose concentration that does not significantly increase the spread of glucose concentration represented in the existing calibration provides more redundancy than leverage, for example.

In some embodiments, the evaluation module evaluates a predictive accuracy by evaluating a goodness of fit of a calibration set with a calibration line drawn from the calibration set. In some embodiments, a goodness of fit is measured to determine how well the data that form a regression line actually fit with the regression line, which can be calculated as an average error (distribution) from the line, and/or a confidence interval associated with the line drawn from a set of data, for example.

In some embodiments, the predictive accuracy is calculated in terms of a percentage change in baseline value in a dual electrode sensor, for example, using the percent deviation formula defined as $$[(BV_1-BV_0)/BV_0]*100\%,$$

where, $BV_1$ represents the baseline value at the end of the period and $BV_0$ represents the value of the baseline at the beginning of the period. For example, a certain percentage (e.g. 80%, 90% or 100%) of deviations (e.g., of the baseline value) are within a predefined deviation range (e.g., no more than 10, 15, 20, 25, 30, 35, 40, 50 or 60 mg/dL) and/or are not more than a predefined percent difference (e.g., 5%, 10%, 15%, 20%, 25%, 30%, 35%, or 40%). In some embodiments, predictive accuracy is calculated in terms of a certain deviation value within certain boundaries (e.g., clinical error grids and/or statistical thresholds).

Preferably, the evaluation module evaluates a predictive accuracy of the calibration information using known statistical and/or clinical accuracy measures. In some embodiments, the predictive accuracy is calculated in terms of a percentage, for example a certain percentage of points within predefined bounds, for example, 60%, 70%, 80%, 85%, 90%, 95%, 98% or 100% of data points with a predefined boundary, such as the A and B zones of a Clark Error Grid. In some embodiments, the predictive accuracy is calculated in terms of a difference between the sensor data and its corresponding reference data, for example, a certain percentage (e.g., 80%, 90% or 100%) of matched data pairs (e.g., in the calibration set) are within a predefined glucose concentration range (e.g., no more than 10, 15, 20, 25, 30, 35, 40, 50 or 60 mg/dL difference) and/or are not more than a predefined percent difference (e.g., 5%, 10%, 15%, 20%, 25%, 30%, 35%, or 40% percent difference) In some embodiments, a predictive accuracy is calculated in terms of an R or R-squared value, for example, when evaluating a correlation or goodness of fit. In some embodiments, predictive accuracy is calculated in terms of a certain number of points (or the last point) within certain boundaries (clinical error grids and/or statistical thresholds). In some embodiments, the predictive accuracy is calculated on converted sensor data (e.g., calibrated data such as glucose concentration in mg/dL). Alternatively, predictive accuracy is calculated on non-converted/non-calibrated sensor data.

At block 740, a determination module, also referred to as the processor module, determines when to request additional reference data. In general, the processor module can be programmed to intermittently request additional reference data at predetermined times during a sensor session and/or at times determined by the processor module during the sensor session to increase accuracy of sensor calibration with a minimum number of reference data requests (e.g., no more than about 2 per day, no more than about 1 per day, no more than about 7 per 7-day sensor session, no more than about 5 per 7-day sensor session, no more than about 3 per 7-day sensor session, no more than about 3 per 3-day sensor session, and no more than about 2 per-3 day sensor session).

In some embodiments, the processor module is configured to request additional reference data after a time period determined in response to the results of the evaluation described above; this time period can be any time period within the sensor session, for example, in a sensor configured for 7-days of in vivo use, the time period is between about 0 minutes and about 7 days. In one exemplary embodiment, after the evaluation process described with reference to block 730, the processor module 406 is programmed to request additional reference data after a time period determined by the determination module of from about 0-, 5-, 10-, 20-, 30-, 60-minutes, or 2-, 4-, 6-, 9-, 12-, 18-, or 24-hours to about 1½-, 2-, 3-, 4-, 5-, 6- or 7-days.

Accordingly, in some embodiments, the computer system (e.g., the processor module) is configured to request reference data at a time determined by the evaluation of the matched data pair and/or the calibration set. In one exemplary embodiment, the computer system is configured to display an amount of time before a next reference data will be requested.

In some embodiments, for example, when the evaluation module evaluates a correlation of the new matched data pair with the calibration set, the determination module determines when to request additional reference data based at least in part on the correlation of the new matched data pair and the calibration set.

In some embodiments, for example, when the evaluation module 730 evaluates a correlation of the matched data pairs in an (existing) calibration set (e.g., a calibration set without a newly received matched data pair) with a new calibration line (e.g., formed from a new calibration set including the newly received matched data pair), the determination module 740 determines when to request additional reference data based at least in part on the correlation of the matched pairs in the calibration set and the new calibration line.

In some embodiments, for example, when the evaluation module 730 evaluates a discordance of the new matched data pair and/or the matched data pairs in the new calibration set, the determination module determines when to request additional reference data based at least in part on the discordance of the new matched data pair and/or the matched data pairs in the new calibration set.

In some embodiments, for example, wherein the evaluation module 730 iteratively evaluates a plurality of combinations of matched data pairs in the calibration set to obtain a plurality of calibration lines, the determination module 740 determines when to request additional reference data based at least in part on the iterative evaluation.

In some embodiments, for example, wherein the evaluation module 730 evaluates an accuracy of the calibration set, the determination module 740 determines when to request additional reference data based at least in part on the accuracy of the calibration line and an estimated glucose concentration.

Accordingly, the predictive accuracy of the calibration information such as described above, can be quantified by the computer system (e.g., processor module) and a time to next reference value determined (e.g., in order to determine when the next reference value should be requested). In general, the results of the predictive accuracy are input into a model and a time to next reference data determined, wherein a greater predictive accuracy results in a longer time to next reference data request and a lesser predictive accuracy results in a shorter time to next reference data, which allows the number of reference data requests to be minimized while ensuring a level of predictive accuracy in the sensor calibration. In some embodiments, the model includes a look-up table, wherein the results of the predictive accuracy are compared against a table, and a time to next reference data request determined. In some embodiments, the results of the predictive accuracy are input into a formula, function or equation, and the time to next reference data request determined.

In some embodiments, the predictive accuracy is calculated and compared against one or more thresholds (e.g., 1, 2, 3, 4, 5, 6, 7 or more thresholds or criteria), from which an output is determined. In one exemplary embodiment, if the predictive accuracy is determined to be within a first range of accuracy (e.g., at least about 70%, 75%, 80%, 85%, 90%, 95%), then additional reference data is/are not requested by the processor module for (or is requested by the processor module after) a first request time period (e.g., 12, 24, 36, or 48 hours), wherein the first request time period is longer than other request time periods (described below). If the predictive accuracy is within a second range of accuracy (e.g., at least about 30%, 35%, 40%, 45%, 50%, 55%, 60%, or 65%, and/or no more than about 65%, 70%, 75%, 80%, 85%, or 90%), then additional reference data is/are not requested by the processor module for (or is requested by the processor module after) a second request time period (e.g., 3 hours, 6 hours, 9 hours, 12 hours, or 18 hours), wherein the second request time period is less than the first time period. If the predictive accuracy is within a third range of accuracy (e.g., no more than about 30%, 35%, 40%, 45%, 50%, 55%, 60%, or 65%), then additional reference data is/are not requested by the processor module for (or is requested by the processor module after) a third request time period (e.g., 0 minutes, 30 minutes, 1 hour, 2 hours, 3 hours, 6 hours, or 9 hours), wherein the third request time period is less than the second time period. Although one exemplary embodiment with three ranges of accuracy is described above, one, two, three, four, five or more ranges, thresholds, criteria, and the like, can be used to determine when to request additional reference data.

In some embodiments, wherein the evaluation module evaluates the glucose concentration(s) associated with the matched data pair(s) in the calibration set, the processor module is configured to request reference data based on present glucose concentration and glucose concentration associated with matched pairs in the cal set, for example, the determination module 740 is configured to request additional reference data when the host's glucose concentration is at a level that would increase the spread of the glucose concentrations associated with the matched data pairs in the calibration set. Advantageously, an increased spread of matched data pairs in a calibration set increases accuracy of the calibration line.

In some embodiments, one or more of the above embodiments are combined; for example, the determination module 740 can be configured to determine when to request additional reference data based on accuracy of the matched data pairs in the calibration set and a spread of glucose concentrations associated with matched data pairs in the calibration set.

In some embodiments, the dual electrode sensor (as described elsewhere herein) can be configured to provide information that can be used to evaluate a predictive accuracy. In an exemplary embodiment, the dual-electrode analyte sensor includes a non-enzyme or second working electrode that is configured to generate a signal associated with background noise. Certain fluctuations in the non-enzyme related signal can be indicators of drift and can be quantified to give a predictive accuracy, which can provide an indication of when calibration is needed, for example.

In an exemplary embodiment, a regression analysis is performed to calibrate information using the slope-intercept equation ($y=mx+b$), which defines a conversion function (described elsewhere herein), where the value of the baseline (b) is represented by the signal associated with the background noise. A predictive accuracy can be calculated using this equation by analyzing a deviation in the value of b over a period of time (e.g. 1 min, 5 min, 10 min, 1 hour, 12 hours, 24 hours, 36 hours, 48 hours, or more).

Additionally or alternatively to the determination module, the predictive accuracy determined by the evaluation module enables decision making of display, calibration, alarming, sensor health/diagnostics, insulin delivery, and the like. In some embodiments, the output module, or processor module, is configured to control an output based at least in part on the predictive accuracy. In some embodiments, the system is configured to control a display (e.g., a user interface 416) based at least in part on a predictive accuracy. In some embodiments, the system is configured to control the display of raw and/or filtered data (e.g., on a user interface or display) based at least in part on a predictive accuracy. In some embodiments, the system is configured to display rate of change information based at least in part on a predictive accuracy. In some embodiments, the system is configured to control alarms indicative of at least one of hypoglycemia, hyperglycemia, predicted hypoglycemia, and predicted hyperglycemia based at least in part on a predictive accuracy. In some embodiments, the system is configured to controlling insulin delivery and/or insulin therapy instructions based at least in part on a predictive accuracy, for example, when to fall back to a more conservative recommendation or when to open the loop (request user interaction) of a closed loop insulin delivery system. In some embodiments, the system is configured to diagnose a sensor condition based at least in part on a predictive accuracy. In some embodiments, the system is configured to suspend display of sensor data based at least in part on a predictive accuracy. In some embodiments, the system is configured to shut down a sensor session based at least in part on a predictive accuracy.

Additional methods for processing sensor glucose data are disclosed in U.S. Patent Publication No. US-2005-0027463-A1. In view of the above-described data processing, it is believed that improving the accuracy of the data stream will be advantageous for improving output of glucose sensor data. Accordingly, the following description is related to improving data output by decreasing signal artifacts on the raw data stream from the sensor. The data smoothing methods of preferred embodiments can be employed in conjunction with any sensor or monitor measuring levels of an analyte in vivo, wherein the level of the analyte fluctuates over time, including but not limited to such sensors as described in U.S. Pat. No. 6,001,067 to Shults et al.; U.S. Patent Publication No. US-2003-0023317-A1 U.S. Pat. No. 6,212,416 to Ward et al.; U.S. Pat. No. 6,119,028 to Schulman et al; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al; U.S. Pat. No. 6,514,718 to Heller et al; and U.S. Pat. No. 5,985,129 to Gough et al.

Signal

Generally, implantable sensors measure a signal related to an analyte of interest in a host. For example, an electrochemical sensor can measure glucose, creatinine, or urea in a host, such as an animal (e.g., a human). Generally, the signal is converted mathematically to a numeric value indicative of analyte status, such as analyte concentration, such as described in more detail, above. The signal detected by the sensor can be broken down into its component parts. For example, in an enzymatic electrochemical analyte sensor, preferably after sensor break-in is complete, the total signal can be divided into an "analyte component," which is representative of analyte (e.g., glucose) concentration, and a "noise component," which is caused by non-analyte-related species that have a redox potential that substantially overlaps with the redox potential of the analyte (or measured species, e.g., $H_2O_2$) at an applied voltage. The noise component can be further divided into its component parts, i.e., constant and non-constant noise. It is not unusual for a sensor to experience a certain level of noise. In general, "constant noise" (sometimes referred to as constant background or baseline) is caused by non-analyte-related factors that are relatively stable over time, including but not limited to electroactive species that arise from generally constant (e.g., daily) metabolic processes. Constant noise can vary widely between hosts. In contrast, "non-constant noise" (sometimes referred to as non-constant background, signal artifacts, signal artifact events (or episodes), transient noise, noise events, noise episodes, and the like) is caused by non-constant, non-analyte-related species (e.g., non-constant noise-causing electroactive species) that arise during transient events, such as during host metabolic processes (e.g., wound healing or in response to an illness), or due to ingestion of certain compounds (e.g., certain drugs). In some circumstances, noise can be caused by a variety of noise-causing electroactive species, which are discussed in detail elsewhere herein.

Figure 8A:
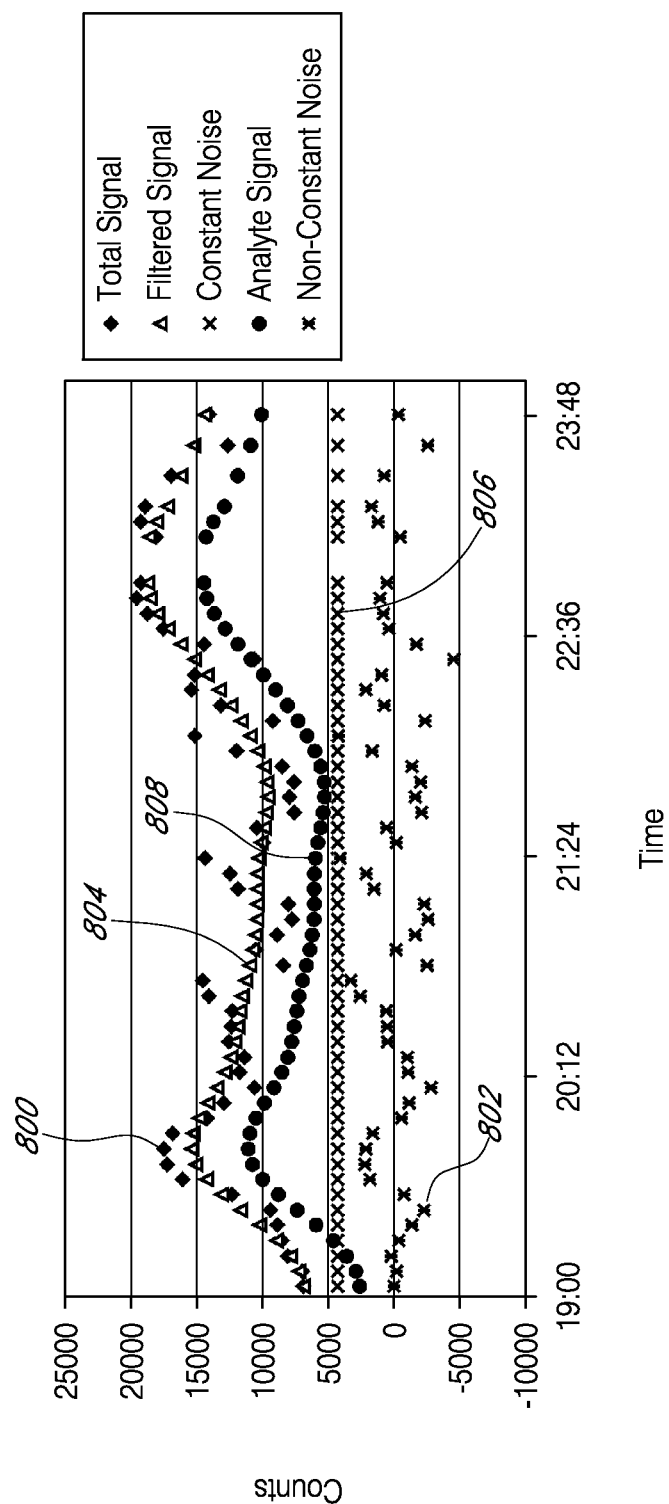
FIG. 8A is a graph illustrating the components of a signal measured by a transcutaneous glucose sensor (after sensor break-in was complete), implanted in a non-diabetic, human volunteer host.

FIG. 8A is a graph illustrating the components of a signal measured by a transcutaneous glucose sensor (after sensor break-in was complete), in a non-diabetic volunteer host. The Y-axis indicates the signal amplitude (in counts) detected by the sensor. The term "counts" as used herein is a broad term, and is to be given its ordinary and customary meaning to a person of ordinary skill in the art (and it is not to be limited to a special or customized meaning), and refers without limitation to a unit of measurement of a digital signal. In one example, a raw data stream measured in counts is directly related to a voltage (for example, converted by an A/D converter), which is directly related to current from a working electrode. The X-axis indicates time.

The total signal collected by the sensor is represented by line 800, which includes components related to glucose, constant noise, and non-constant noise, which are described in more detail elsewhere herein. In some embodiments, the total signal is a raw data stream, which can include a signal averaged or integrated by a charge-counting device, for example.

The non-constant noise component of the total signal is represented by line 802. The non-constant noise component 802 of the total signal 800 can be obtained by filtering the total signal 800 to obtain a filtered signal 804 using any of a variety of known filtering techniques, and then subtracting the filtered signal 804 from the total signal 800. In some embodiments, the total signal can be filtered using linear regression analysis of the n (e.g., 10) most recent sampled sensor values. In some embodiments, the total signal can be filtered using non-linear regression. In some embodiments, the total signal can be filtered using a trimmed regression, which is a linear regression of a trimmed mean (e.g., after rejecting wide excursions of any point from the regression line). In this embodiment, after the sensor records glucose measurements at a predetermined sampling rate (e.g., every 30 seconds), the sensor calculates a trimmed mean (e.g., removes highest and lowest measurements from a data set) and then regresses the remaining measurements to estimate the glucose value. In some embodiments, the total signal can be filtered using a non-recursive filter, such as a finite impulse response (FIR) filter. An FIR filter is a digital signal filter, in which every sample of output is the weighted sum of past and current samples of input, using only some finite number of past samples. In some embodiments, the total signal can be filtered using a recursive filter, such as an infinite impulse response (IIR) filter. An IIR filter is a type of digital signal filter, in which every sample of output is the weighted sum of past and current samples of input. In some embodiments, the total signal can be filtered using a maximum-average (max-average) filtering algorithm, which smoothes data based on the discovery that the substantial majority of signal artifacts observed after implantation of glucose sensors in humans, for example, is not distributed evenly above and below the actual blood glucose levels. It has been observed that many data sets are actually characterized by extended periods in which the noise appears to trend downwardly from maximum values with occasional high spikes. To overcome these downward trending signal artifacts, the max-average calculation tracks with the highest sensor values, and discards the bulk of the lower values. Additionally, the max-average method is designed to reduce the contamination of the data with unphysiologically high data from the high spikes. The max-average calculation smoothes data at a sampling interval (e.g., every 30 seconds) for transmission to the receiver at a less frequent transmission interval (e.g., every 5 minutes), to minimize the effects of low non-physiological data. First, the processor finds and stores a maximum sensor counts value in a first set of sampled data points (e.g., 5 consecutive, accepted, thirty-second data points). A frame shift time window finds a maximum sensor counts value for each set of sampled data (e.g., each 5-point cycle length) and stores each maximum value. The processor then computes a rolling average (e.g., 5-point average) of these maxima for each sampling interval (e.g., every 30 seconds) and stores these data. Periodically (e.g., every $10^{th}$ interval), the sensor outputs to the receiver the current maximum of the rolling average (e.g., over the last 10 thirty-second intervals as a smoothed value for that time period (e.g., 5 minutes)). In some embodiments, the total signal can be filtered using a "Cone of Possibility Replacement Method," which utilizes physiological information along with glucose signal values in order define a "cone" of physiologically feasible glucose signal values within a human. Particularly, physiological information depends upon the physiological parameters obtained from continuous studies in the literature as well as our own observations. A first physiological parameter uses a maximal sustained rate of change of glucose in humans (e.g., about 4 to 5 mg/di/min) and a maximum sustained acceleration of that rate of change (e.g., about 0.1 to 0.2 mg/min/min). A second physiological parameter uses the knowledge that rate of change of glucose is lowest at the maxima and minima, which are the areas of greatest risk in patient treatment. A third physiological parameter uses the fact that the best solution for the shape of the curve at any point along the curve over a certain time period (e.g., about 20-25 minutes) is a straight line. It is noted that the maximum rate of change can be narrowed in some instances. Therefore, additional physiological data can be used to modify the limits imposed upon the Cone of Possibility Replacement Method for sensor glucose values. For example, the maximum per minute rate change can be lower when the subject is lying down or sleeping; on the other hand, the maximum per minute rate change can be higher when the subject is exercising, for example. In some embodiments, the total signal can be filtered using reference changes in electrode potential to estimate glucose sensor data during positive detection of signal artifacts from an electrochemical glucose sensor, the method hereinafter referred to as reference drift replacement. In this embodiment, the electrochemical glucose sensor comprises working, counter, and reference electrodes. This method exploits the function of the reference electrode as it drifts to compensate for counter electrode limitations during oxygen deficits, pH changes, and/or temperature changes. In alternative implementations of the reference drift method, a variety of algorithms can therefore be implemented based on the changes measured in the reference electrode. Linear algorithms, and the like, are suitable for interpreting the direct relationship between reference electrode drift and the non-glucose rate limiting signal noise such that appropriate conversion to signal noise compensation can be derived. Additional description of signal filtering can be found in more detail elsewhere herein.

Referring again to FIG. 8A, the constant noise signal component 806 can be obtained by calibrating the sensor signal using reference data, such as one or more blood glucose values obtained from a hand-held blood glucose meter, from which the baseline "b" of a regression can be obtained, representing the constant noise signal component 806.

The analyte signal component 808 can be obtained by subtracting the constant noise signal component 806 from the filtered signal 804.

Noise

Noise is clinically important because it can induce error and can reduce sensor performance, such as by providing a signal that causes the analyte concentration to appear higher or lower than the actual analyte concentration. For example, upward or high noise (e.g., noise that causes the signal to increase) can cause the host's glucose concentration to appear higher than it truly is which can lead to improper treatment decisions. Similarly, downward or low noise (e.g., noise that causes the signal to decrease) can cause the host's glucose concentration to appear lower than it is which can also lead to improper treatment decisions.

Noise can be caused by a variety of factors, ranging from mechanical factors to biological factors. For example, it is known that macro- or micro-motion, ischemia, pH changes, temperature changes, pressure, stress, or even unknown mechanical, electrical, and/or biochemical sources can cause noise, in some embodiments. Interfering species, which are known to cause non-constant noise, can be compounds, such as drugs that have been administered to the host, or intermittently produced products of various host metabolic processes. Exemplary interferents include but are not limited to a variety of drugs (e.g., acetaminophen), $H_2O_2$ from exterior sources (e.g., produced outside the sensor membrane system), and reactive metabolic species (e.g., reactive oxygen and nitrogen species, some hormones, etc.). Some known interfering species for a glucose sensor include but are not limited to acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

In some experiments of implantable glucose sensors, it was observed that noise increased when some hosts were intermittently sedentary, such as during sleep or sitting for extended periods. When the host began moving again, the noise quickly dissipated. Noise that occurs during intermittent, sedentary periods (sometimes referred to as intermittent sedentary noise) can occur during relatively inactive periods, such as sleeping. Non-constant, non-analyte-related factors can cause intermittent sedentary noise, such as was observed in one exemplary study of non-diabetic individuals implanted with enzymatic-type glucose sensors built without enzyme. These sensors (without enzyme) could not react with or measure glucose and therefore provided a signal due to non-glucose effects only (e.g., constant and non-constant noise). During sedentary periods (e.g., during sleep), extensive, sustained signal was observed on the sensors. Then, when the host got up and moved around, the signal rapidly corrected. As a control, in vitro experiments were conducted to determine if a sensor component might have leached into the area surrounding the sensor and caused the noise, but none was detected. From these results, it is believed that a host-produced non-analyte related reactant was diffusing to the electrodes and producing the unexpected non-constant noise signal.

While not wishing to be bound by theory, it is believed that a concentration increase of noise-causing electroactive species, such as electroactive metabolites from cellular metabolism and wound healing, can interfere with sensor function and cause noise observed during host sedentary periods. For example, local lymph pooling, which can occur when a part of the body is compressed or when the body is inactive, can cause, in part, this local build up of interferants (e.g., electroactive metabolites). Similarly, a local accumulation of wound healing metabolic products (e.g., at the site of sensor insertion) likely causes noise on the sensor. Noise-causing electroactive species can include but are not limited to compounds with electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing, for example. For a more complete discussion of noise and its sources, see U.S. Patent Publication No. US-2007-0027370-A1.

Noise can be recognized and/or analyzed in a variety of ways. For example, in some circumstances, non-constant noise changes faster than the analyte signal and/or does not follow an expected analyte signal pattern; and lasts for a period of about 10 hours or more, 8 hours, 6 hours, 4 hours, 2 hours, 60 minutes, 30 minutes, or 10 minutes or less. In some embodiments, the sensor data stream can be monitored, signal artifacts detected, and data processing performed based at least in part on whether or not a signal artifact has been detected, such as described in more detail elsewhere herein.

In some conventional analyte sensors, non-constant noise can be a significant component of the total signal, for example, 30%, 40%, 50%, 60% or more of the total signal. Additionally, non-constant noise can occur for durations of minutes or hours, in some circumstances. In some circumstances, non-constant noise can be equivalent to a glucose concentration of about 400-mg/dl or more. Noise can induce error in the sensor reading, which can reduce sensor accuracy and clinically useful data. However, a high level of sensor accuracy is critical for successful patient care and desirable clinical outcomes.

In some embodiments, an electrochemical analyte detection system is provided, which includes a sensor configured for substantially continuous analyte detection, such as in an ambulatory host. The sensor includes at least one electrode and electronics configured to provide a signal measured at the electrode; wherein the measured signal can be broken down (e.g., after sensor break-in) into its component parts, a substantially analyte-related component, a substantially constant non-analyte-related component (i.e., constant noise) and a substantially non-constant non-analyte-related component (i.e., non-constant noise).

In some embodiments, a signal component's percentage of the total signal is determined using one or more of a variety of methods of quantifying an amplitude of signal components and total signal, from which each components percent contribution can be calculated, as is appreciated by one skilled in the art. In some embodiments, the signal component(s) can be quantified by comparing the peak-to-peak amplitudes of each signal component for a time period, whereby the peak-to-peak amplitudes of each component can be compared to the peak-to-peak amplitude of the total signal to determine its percentage of the total signal, as is appreciated by one skilled in the art. In some embodiments, the signal component(s) can be quantified by determining the Root Mean Square (RMS) of the signal component for a time period. In one exemplary of Root Mean Square analysis of signal components, the signal component(s) can be quantified using the formula:

$$RMS = \sqrt{\frac{\sum (x_1^2 + x_2^2 + x_3^2 + x_n^2)}{n}}$$

wherein there are a number (n) of data values (x) for a signal (e.g., analyte component, non-constant noise component, constant noise component, and/or total signal) during a predetermined time period (e.g., about 1 day, about 2 days, about 3 days, etc). Once the signal components and/or total signal are quantified, the signal components can be compared to the total signal to determine a percentage of each signal component within the total signal.

Signal Artifact Detection and Replacement

Typically, a glucose sensor produces a data stream that is indicative of the glucose concentration of a host, such as described in more detail above. However, it is well known that of the glucose sensors described above, there are only a few examples of glucose sensors that are able to provide a raw data output indicative of the concentration of glucose. Thus, it should be understood that the systems and methods described herein, including signal artifacts detection, signal artifacts replacement, and other data processing, can be applied to a data stream obtained from any glucose sensor.

Raw data streams typically have some amount of "system noise," caused by unwanted electronic or diffusion-related noise that degrades the quality of the signal and thus the data. Accordingly, conventional glucose sensors are known to smooth raw data using methods that filter out this system noise, and the like, in order to improve the signal to noise ratio, and thus data output. One example of a conventional data-smoothing algorithm includes a finite impulse response filter (FIR), which is particularly suited for reducing high-frequency noise (see Steil et al. U.S. Pat. No. 6,558,351).

Figure 8B:
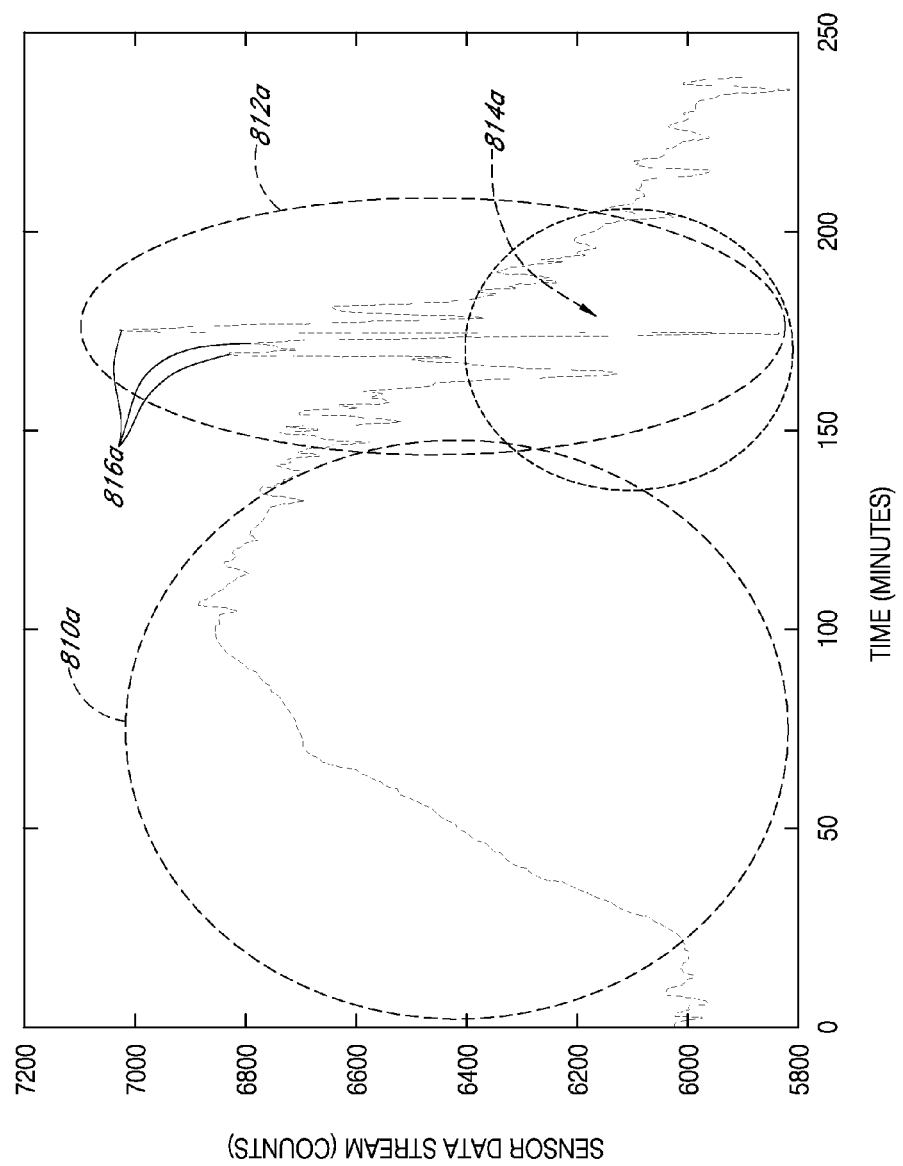
FIG. 8B is a graph that shows a raw data stream obtained from a glucose sensor over a 4 hour time span in one example.
Figure 8C:
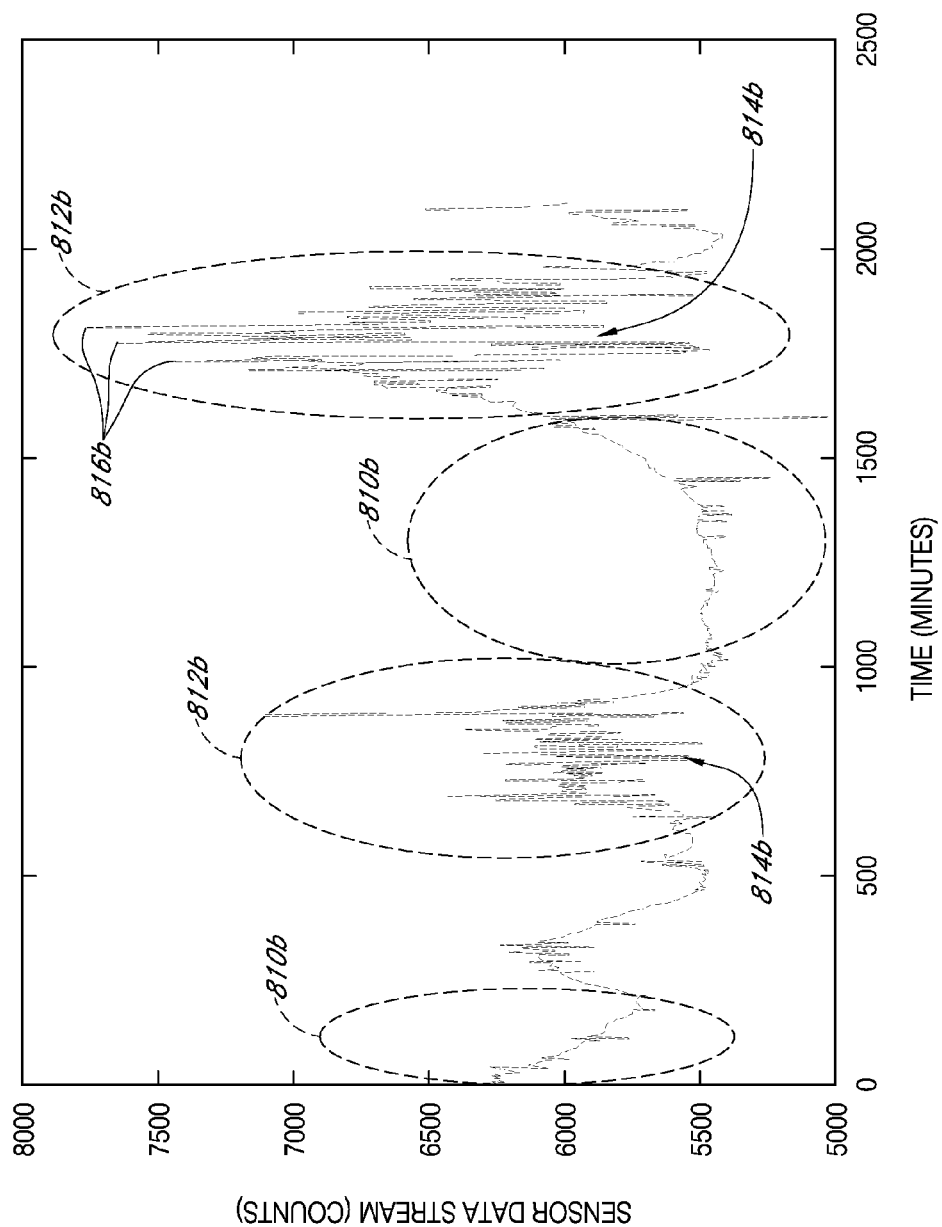
FIG. 8C is a graph that shows a raw data stream obtained from a glucose sensor over a 36 hour time span in another example.

FIGS. 8B and 8C are graphs of raw data streams from an implantable glucose sensor prior to data smoothing in one embodiment. FIG. 8B is a graph that shows a raw data stream obtained from a glucose sensor over an approximately 4 hour time span in one example. FIG. 8C is a graph that shows a raw data stream obtained from a glucose sensor over an approximately 36 hour time span in another example. The x-axis represents time in minutes. The y-axis represents sensor data in counts. In these examples, sensor output in counts is transmitted every 30-seconds.

The "system noise" such as shown in sections 810a, 810b of the data streams of FIGS. 8B and 8C, respectively, illustrate time periods during which system noise can be seen on the data stream. This system noise can be characterized as Gaussian, Brownian, and/or linear noise, and can be substantially normally distributed about the mean. The system noise is likely electronic and diffusion-related, and the like, and can be smoothed using techniques such as by using an FIR filter. As another example, the raw data can be represented by an integrated value, for example, by integrating the signal over a time period (e.g., 30 seconds or 5 minutes), and providing an averaged (e.g., integrated) data point there from. The system noise such as shown in the data of sections 810a, 810b is a fairly accurate representation of glucose concentration and can be confidently used to report glucose concentration to the user when appropriately calibrated.

The "signal artifacts," also referred to as "signal artifact events" or "noise episodes" for example, such as shown in sections 812a, 812b of the data stream of FIGS. 8B and 8C, respectively, illustrate time periods during which "signal artifacts" can be seen, which are significantly different from the previously described system noise (sections 810a, 810b). This noise, such as shown in section 812a and 812b, is referred to herein as "signal artifacts" and may be described as "transient non-glucose dependent signal artifacts that have higher amplitude than system noise." At times, signal artifacts comprise low noise, which generally refers to noise that substantially decreases signal amplitude 814a, 814b herein, which is best seen in the signal artifacts 812b of FIG. 8C. Occasional high spikes 816a, 816b, which generally correspond to noise that substantially increases signal amplitude, can also be seen in the signal artifacts, which generally occur after a period of low noise. These high spikes are generally observed after transient low noise and typically result after reaction rate-limiting phenomena occur. For example, in an embodiment where a glucose sensor requires an enzymatic reaction, local ischemia creates a reaction that is rate-limited by oxygen, which is responsible for low noise. In this situation, glucose would be expected to build up in the membrane because it would not be completely catabolized during the oxygen deficit. When oxygen is again in excess, there would also be excess glucose due to the transient oxygen deficit. The enzyme rate would speed up for a short period until the excess glucose is catabolized, resulting in high noise. Additionally, noise can be distributed both above and below the expected signal.

Analysis of signal artifacts such as shown sections 812a, 812b of FIGS. 8B and 8C, respectively, indicates that the observed low noise is caused by substantially non-glucose reaction dependent phenomena, such as ischemia that occurs within or around a glucose sensor in vivo, for example, which results in the reaction becoming oxygen dependent. As a first example, at high glucose levels, oxygen can become limiting to the enzymatic reaction, resulting in a non-glucose dependent downward trend in the data (best seen in FIG. 8C). As a second example, certain movements or postures taken by the patient can cause transient downward noise as blood is squeezed out of the capillaries resulting in local ischemia, and causing non-glucose dependent low noise. Because excess oxygen (relative to glucose)

is necessary for proper sensor function, transient ischemia can result in a loss of signal gain in the sensor data. In this second example oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue.

In another example of non-glucose reaction rate-limiting phenomena, skin temperature can vary dramatically, which can result in thermally related erosion of the signal (e.g., temperature changes between 32 and 39 degrees Celsius have been measured in humans). In yet another embodiment, wherein the glucose sensor is placed intravenously, increased impedance can result from the sensor resting against wall of the blood vessel, for example, producing this non-glucose reaction rate-limiting noise due to oxygen deficiency.

Figure 9:
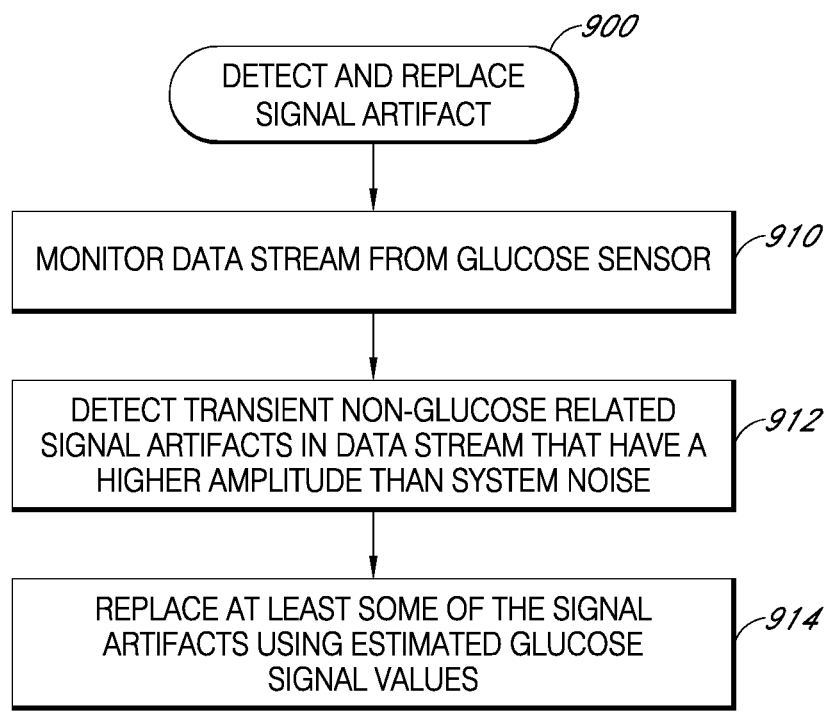
FIG. 9 is a flow chart that illustrates the process of detecting and replacing transient non-glucose related signal artifacts in a data stream in one embodiment.

FIG. 9 is a flow chart 900 that illustrates the process of detecting and replacing signal artifacts in certain embodiments. It is noted that "signal artifacts" particularly refers to the transient non-glucose related artifacts such as described in more detail elsewhere herein. Typically, signal artifacts are caused by non-glucose rate-limiting phenomenon such as described in more detail above.

At block 910, a sensor data receiving module, also referred to as the sensor data module 910, or processor module, receives sensor data (e.g., a data stream), including one or more time-spaced sensor data points. In some embodiments, the data stream is stored in the sensor for additional processing; in some alternative embodiments, the sensor periodically transmits the data stream to the receiver 300, which can be in wired or wireless communication with the sensor. In some embodiments, raw and/or filtered data is stored in the sensor and/or receiver.

At block 912, a signal artifacts detection module, also referred to as the signal artifacts detector 914 or signal reliability module, is programmed to detect transient non-glucose related signal artifacts in the data stream. The signal artifacts detector can comprise an oxygen detector, a pH detector, a temperature detector, and/or a pressure/stress detector, for example, the signal artifacts detector 228 in FIG. 2. In some embodiments, the signal artifacts detector at block 912 is located within the processor 214 in FIG. 2 and utilizes existing components of the glucose sensor to detect signal artifacts, for example by pulsed amperometric detection, counter electrode monitoring, reference electrode monitoring, and frequency content monitoring, which are described elsewhere herein. In yet other embodiments, the data stream can be sent from the sensor to the receiver which comprises programming in the processor 406 in FIG. 4A that performs algorithms to detect signal artifacts, for example such as described with reference to "Cone of Possibility Detection" method and/or by comparing raw data vs. filtered data, both of which are described in more detail below. Numerous embodiments for detecting signal artifacts are described in more detail in the section entitled, "Signal Artifacts Detection and Replacement," all of which are encompassed by the signal artifacts detection at block 912.

In certain embodiments, the processor module in either the sensor electronics and/or the receiver electronics can evaluate an intermittent or continuous signal-to-noise measurement to determine aberrancy of sensor data responsive to a signal-to-noise ratio above a set threshold. In certain embodiments, signal residuals (e.g., by comparing raw and filtered data) can be intermittently or continuously analyzed for noise above a set threshold. In certain embodiments, pattern recognition can be used to identify noise associated with physiological conditions, such as low oxygen, or other known signal aberrancies. Accordingly, in these embodiments, the system can be configured, in response to aberrancies in the data stream, to trigger signal estimation, adaptively filter the data stream according to the aberrancy, and the like, as described in more detail elsewhere herein.

At block 914, the signal artifacts replacement module, also referred to as the signal estimation module, replaces some or an entire data stream with estimated glucose signal values using signal estimation. Numerous embodiments for performing signal estimation are described in more detail in the section entitled "Signal Artifacts Detection and Replacement," all of which are encompassed by the signal artifacts replacement module, block 914. It is noted that in some embodiments, signal estimation/replacement is initiated in response to positive detection of signal artifacts on the data stream, and subsequently stopped in response to detection of negligible signal artifacts on the data stream. In some embodiments, the system waits a predetermined time period (e.g., between 30 seconds and 30 minutes) before switching the signal estimation on or off to ensure that a consistent detection has been ascertained. In some embodiments, however, signal estimation/replacement can continuously or continually run.

Some embodiments of signal estimation can additionally include discarding data that is considered sufficiently unreliable and/or erroneous such that the data should not be used in a signal estimation algorithm. In these embodiments, the system can be programmed to discard outlier data points, for example data points that are so extreme that they can skew the data even with the most comprehensive filtering or signal estimation, and optionally replace those points with a projected value based on historical data or present data (e.g., linear regression, recursive filtering, and the like). One example of discarding sensor data includes discarding sensor data that falls outside of a "Cone of Possibility" such as described in more detail elsewhere herein. Another example includes discarding sensor data when signal artifacts detection detects values outside of a predetermined threshold (e.g., oxygen concentration below a set threshold, temperature above a certain threshold, signal amplitude above a certain threshold, etc). Any of the signal estimation/replacement algorithms described herein can then be used to project data values for those data that were discarded.

Analysis of signals from glucose sensors indicates at least two types of noise, which are characterized herein as 1) system noise and 2) signal artifacts, such as described in more detail above. It is noted that system noise is easily smoothed using the algorithms provided herein; however, the systems and methods described herein particularly address signal artifacts, by replacing transient erroneous signal noise caused by rate-limiting phenomenon (e.g., non-glucose related signal) with estimated signal values, for example.

In certain embodiments of signal artifacts detection, oxygen monitoring is used to detect whether transient non-glucose dependent signal artifacts due to ischemia. Low oxygen concentrations in or near the glucose sensor can account for a large part of the transient non-glucose related signal artifacts as defined herein on a glucose sensor signal, particularly in subcutaneously implantable glucose sensors. Accordingly, detecting oxygen concentration, and determining if ischemia exists can discover ischemia-related signal artifacts. A variety of methods can be used to test for oxygen. For example, an oxygen-sensing electrode, or other oxygen sensor can be employed. The measurement of oxygen concentration can be sent to a processor, which determines if the oxygen concentration indicates ischemia.

Additional description of signal artifact detection and replacement can be found in U.S. Patent Publication Nos. 2005/0043598, 2007/0032706, 2007/0016381, and 2007/0066873, and U.S. patent application Ser. No. 11/762,638, filed on Jun. 13, 2007 and entitled "SYSTEMS AND METHODS FOR REPLACING SIGNAL ARTIFACTS IN A GLUCOSE SENSOR DATA STREAM," all of which are incorporated by reference herein in their entirety.

In one embodiment of signal artifacts detection that utilizes examination or evaluation of the signal information content, filtered (e.g., smoothed) data is compared to raw data (e.g., in sensor electronics or in receiver electronics). In one such embodiment, a signal residual is calculated as the difference between the filtered data and the raw data. For example, at one time point (or one time period that is represented by a single raw value and single filtered value), the filtered data can be measured at 50,000 counts and the raw data can be measured at 55,500 counts, which would result in a signal residual of 5,500 counts. In some embodiments, a threshold can be set (e.g., 5000 counts) that represents a first level of noise (e.g., signal artifact) in the data signal, when the residual exceeds that level. Similarly, a second threshold can be set (e.g., 8,000 counts) that represents a second level of noise in the data signal. Additional thresholds and/or noise classifications can be defined as is appreciated by one skilled in the art. Consequently, signal filtering, processing, and/or displaying decisions can be executed based on these conditions (e.g., the predetermined levels of noise).

Although the above-described example illustrates one method of determining a level of noise, or signal artifact(s), based on a comparison of raw vs. filtered data for a time point (or single values representative of a time period), a variety of alternative methods are contemplated. In an alternative exemplary embodiment for determining noise, signal artifacts are evaluated for noise episodes lasting a certain period of time. For example, the processor (in the sensor or receiver) can be configured to look for a certain number of signal residuals above a predetermined threshold (representing noise time points or noisy time periods) for a predetermined period of time (e.g., a few minutes to a few hours or more).

In one exemplary embodiment, a processor is configured to determine a signal residual by subtracting the filtered signal from the raw signal for a predetermined time period. It is noted that the filtered signal can be filtered by any known smoothing algorithm such as described herein, for example a 3-point moving average-type filter. It is further noted that the raw signal can include an average value, e.g., wherein the value is integrated over a predetermined time period (such as 5-minutes). Furthermore, it is noted that the predetermined time period can be a time point or representative data for a time period (e.g., 5 minutes). In some embodiments, wherein a noise episode for a predetermined time period is being evaluated, a differential (delta residual) can be obtained by comparing a signal residual with a previous signal residual (e.g., a residual at time (t)=0 as compared to a residual at (t)–5 minutes.) Similar to the thresholds described above with regard to the signal residual, one or more thresholds can be set for the differentials, whereby one or more differentials above the predetermined differential thresholds defines a particular noise level. It has been shown in certain circumstances that a differential measurement as compared to a residual measurement as described herein, amplifies noise and therefore may be more sensitive to noise episodes, without increasing false positives due to fast, but physiological, rates of change. Accordingly, a noise episode, or noise episode level, can be defined by one or more points (e.g., residuals or differentials) above a predetermined threshold, and in some embodiments, for a predetermined period of time. Similarly, a noise level determination can be reduced or altered when a different (e.g., reduced) number of points above the predetermined threshold are calculated in a predetermined period of time.

In some embodiments, the amplitude of total signal, which can also be described as power of the total signal, analyte signal (with or without baseline (e.g., non-constant noise)), and/or non-constant noise, is periodically or continuously obtained using methods such as are described in more detail elsewhere herein (e.g., RMS method), wherein the amplitude is a measure of the strength of the signal component. In some embodiments, signal artifact events are detected by analysis of amplitudes of various signal components, such as the amplitude of the non-constant noise component as compared to the amplitude of the analyte signal (with or without baseline).

In some embodiments, a start of a signal artifact event is determined when the amplitude (power) of a signal artifact meets a first predetermined condition. In one embodiment, the first predetermined condition includes a residual amplitude of at least about 2, 3, 4, 5, 6, 7, 8, 9, 10, 12, 14, 16, 18, 20 or 25% of the total signal or analyte signal amplitude (with or without baseline). In another embodiment, the first predetermined condition includes a differential amplitude (amplitude of a differential) of at least about 2, 3, 4, 5, 6, 7, 8, 9, 10, 12, 14, 16, 18, 20 or 25% of the total signal or analyte signal amplitude (with or without baseline). In some embodiments, the first predetermined condition includes a plurality of points (e.g., non-constant noise signal, residual, or differential) within a predetermined period (e.g., 5, 10, 30, or 60 minutes) above a predetermined threshold (e.g., an amplitude or a percentage amplitude), wherein the plurality of points includes 2, 3, 4, 5, 6, 7, 8 or more values.

In some embodiments, an end of a signal artifact event is determined when then the amplitude (power) of a signal artifact meets a second predetermined condition. In one embodiment, the second predetermined condition includes a residual amplitude of no more than about 2, 3, 4, 5, 6, 7, 8, 9, 10, 12, 14, 16, 18, 20 or 25% of the total signal or analyte signal amplitude (with or without baseline). In another embodiment, the second predetermined condition comprises a differential amplitude of no more than about 2, 3, 4, 5, 6, 7, 8, 9, 10, 12, 14, 16, 18, 20 or 25% of the total signal or analyte signal amplitude (with or without baseline). In some embodiments, the second predetermined condition includes a plurality of points (e.g., non-constant noise signal, residual, or differential) within a predetermined period (e.g., 5, 10, 30, or 60 minutes) below a predetermined threshold (e.g., an amplitude or a percentage amplitude), wherein the plurality of points includes 2, 3, 4, 5, 6, 7, 8 or more values.

Preferably, the system is configured to use hysteresis to process signals so that the output (start/end (on/off) of noise episodes) reacts slowly by taking recent history into account; this prevents rapid switching on and off as the glucose signal drifts around a threshold, for example. In some embodiments, the first predetermined condition is different from the second predetermined condition. In some embodiments, the second condition includes criteria such as waiting a time period (e.g., 20, 30, 40, 60, 90 minutes, or more) after the start of a noise episode before determining an end of the noise episode. In some embodiments, the second condition includes criteria such as waiting until the signal increases beyond a predetermined threshold before determining an end of the noise episode, wherein the predetermined threshold can be higher than another threshold within the second condition that triggers an end of the noise episode. In some embodiments, the first and second conditions have different amplitude (power) thresholds. In some embodiments, the first and second conditions have different window lengths over which the evaluation is done. While not wishing to be bound by theory, it is believed that condition(s) for determining a start of a noise episode can be different from condition(s) for determining an end of a noise episode. Accordingly, use of different start and end thresholds can reduce toggling between start/end (or on/off) modes of the noise episode too quickly. In one exemplary embodiment, the system is configured to determine a start of a noise episode when the non-constant noise is at least about 10% of the analyte signal and the system is configured to determine an end of a noise episode at least about one hour after the start of the noise episode and when the non-constant noise is no more than about 10% of the analyte signal.

One or a plurality of the above signal artifacts detection models can be used alone or in combination to detect signal artifacts such as described herein. Accordingly, the data stream associated with the signal artifacts can be discarded, replaced, or otherwise processed in order to reduce or eliminate these signal artifacts and thereby improve the value of the glucose measurements that can be provided to a user. Although much of the following description is drawn to replacing signal artifacts, circumstances exist wherein signal noise is too severe and/or too long in duration to replace. In some embodiments, the system is configured to determine whether a signal artifact and/or signal artifact episode has exceeded a predetermined threshold. If the threshold is exceeded, then data is not displayed (e.g., rather than replacing the signal as described in more detail, below). In some embodiments, a signal artifact and/or signal artifact episode threshold of (e.g., absolute threshold and/or relative threshold such as high signal amplitude threshold, high noise amplitude threshold, and/or percentage threshold) is used. In some embodiments, a signal artifact and/or signal artifact episode threshold of at least about 20, 30, 40, 60, 90, 120, 180 minutes or more duration is used.

Figure 10:
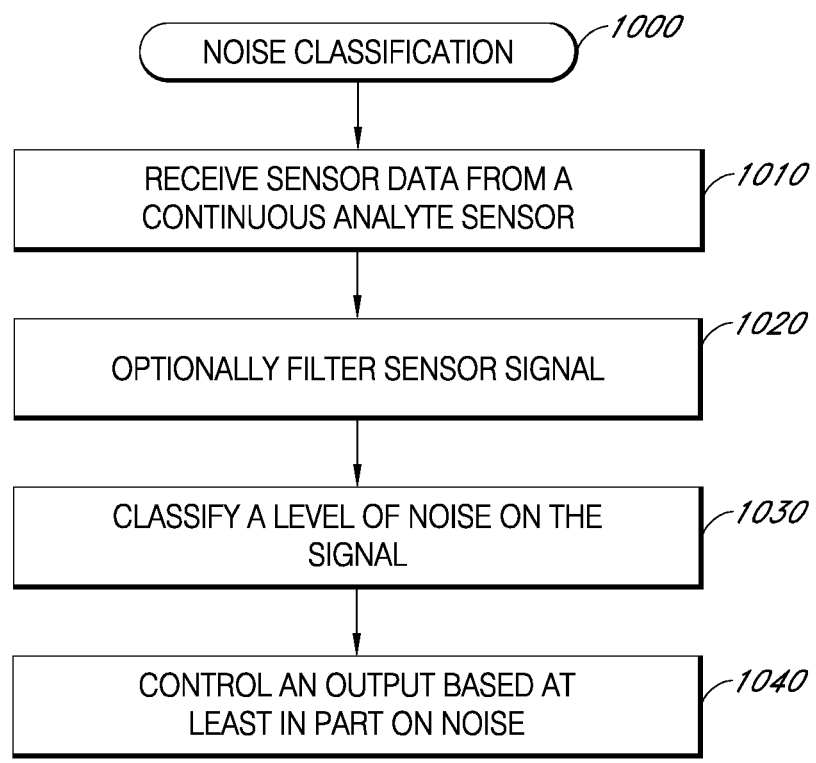
FIG. 10 is a graph that illustrates a method of classifying noise in a data stream from a glucose sensor in one embodiment.

Reference is now made to FIG. 10, which is a flow chart 1000 that illustrates the process of noise classification of the glucose sensor signal in one embodiment. Preferably, the system is configured to classify a level of noise in a signal obtained from a continuous analyte sensor, for example, numerically and/or into groups. Advantageously, classification of the noise level enables decision making of display, calibration, alarming, sensor health/diagnostics, insulin delivery, and the like.

At block 1010, a sensor data receiving module, also referred to as the sensor data module, or processor module, receives sensor data (e.g., a data stream), including one or more time-spaced sensor data points hereinafter referred to as "data stream," "sensor data," "sensor analyte data", "signal," from a sensor via the receiver, which can be in wired or wireless communication with the sensor. The sensor data receiving module is described in more detail elsewhere herein, for example, with reference to FIG. 5.

At block 1020, the processor module optionally filters the signal received from the continuous analyte sensor. Filtering can be accomplished by sensor electronics and/or the receiver electronics, which are both encompassed by the term "computer system."

At block 1030, a noise classification module, also referred to as the processor module, classifies a level of noise on the signal. In general, one or more noise classification thresholds and/or criteria are programmed within the computer system and/or adaptively determined by the computer system.

In some embodiments, the signal noise is classified numerically and/or by grouping. In one exemplary embodiment, the level of noise is classified as light, medium, and heavy. In another exemplary embodiment, the noise is classified as level1, level2, and level3, etc. However, any types or numbers of classifications associated with predetermined thresholds and/or criteria can be used. For example, in some embodiments, the noise thresholds are predetermined (e.g., programmed into the computer system (e.g., receiver)).

In some preferred embodiments, the noise thresholds are adaptively determined by the computer system (e.g., for each sensor and/or iteratively during a sensor session) based on a signal strength of the sensor signal, which enables the noise thresholds to be customized to the signal strength of the sensor and/or sensor in a particular host.

In one exemplary embodiment, the processor module applies a low pass filter to the signal (raw or filtered) to determine a signal strength thereof. Although a first order low pass filter may be preferred in some embodiments, other orders ($2^{nd}$, $3^{rd}$, etc) are also possible.

In some further embodiments, for example, wherein the processor module applies a low pass filter to the signal to determine a signal strength, the system is configured to define one or more noise thresholds for classification of the level of noise on the signal based at least in part on a percentage of the signal strength (e.g., NoiseThreshold1 corresponds to a first percentage of signal strength, NoiseThreshold2 corresponds to a second percentage of signal strength, Noise Threshold3 corresponds to a third percentage of signal strength).

Conventionally, filters are configured to filter the signal to provide an average of the signal. However, in some preferred embodiments, the system is configured to "track the noise envelope," (i.e., to track the outer amplitude of noise (e.g., without fluctuations) to obtain a worst case scenario of noise on the sensor signal). In some embodiments, low pass filters, RMS methods, and/or median filters applied to wide windows of data (e.g., greater than or equal to about 30 min.) are applied to the sensor signal. Advantageously, low pass filters track the slow varying DC component (i.e., signal strength) of the analyte signal and can be used to determine noise thresholds, which are described in more detail, below.

In some embodiments, the processor module is configured to apply one or more low pass filters to the noise signal to obtain one or more noise indicators and subsequently compare the noise indicators with one or more noise thresholds (either predefined noise thresholds or adaptively determined noise thresholds). In the exemplary embodiment wherein the system is configured to use a first order low pass filter to define noise thresholds for noise classification, the system is further configured to vary a coefficient of a low pass filter (e.g., the same or another low pass filter), for example, by using the noise thresholds defined as percentage of the signal strength, to detect noise of varying thresholds. Namely, the processor module is configured to apply one or more low pass filters to the noise signal to obtain one or more noise indicators and compare the noise indicators with one or more noise thresholds.

Additionally or alternatively, other methods of filtering, such as determining a median point within a window of data, detecting a maximum point within a window of data, and/or the like can be used to determined the signal strength and/or classify noise based on thresholds.

In some alternative embodiments, a root mean square (RMS) method can be used to determine signal strength.

In some alternative embodiments, spectral analysis can be used to determine a signal strength and classify noise.

In some embodiments, the noise signal is a signal residual obtained by comparing a raw signal to a filtered signal; however the differential of the residual (delta residual), absolute delta residual, and/or the like can also be used as the noise signal input to one or more of the filters.

In some embodiments, the processor module is configured to use hysteresis in classifying a level of noise in order to avoid waver between noise classifications. For example, by defining different criteria for returning back to a previous noise classification (e.g., a greater number of data points (or time) in a noise level to return to a previous level than to move to the level initially).

At block 1040, the output module, or processor module, is configured to control an output based at least in part on the noise classification determined at block 1030. In general, the system is configured to control the output based on a level of resolution of the signal, a level of confidence in the signal, and/or a level of reliability of the signal.

In some embodiments, the system is configured to control a display (e.g., a user interface 416) based at least in part on a noise classification. In some embodiments, the system is configured to control the display of raw and/or filtered data (e.g., on a user interface or display) based at least in part on a noise classification. In some embodiments, the system is configured to display rate of change information based at least in part on a noise classification. In some embodiments, the system is configured to control alarms indicative of at least one of hypoglycemia, hyperglycemia, predicted hypoglycemia, and predicted hyperglycemia based at least in part on a noise classification. In some embodiments, the system is configured to controlling medicament delivery (e.g., insulin delivery) and/or therapy instructions based at least in part on a noise classification, for example, when to fall back to a more conservative recommendation or when to open the loop (request user interaction) of a closed loop delivery system. In some embodiments, the system is configured to diagnose a sensor condition (e.g., sensor failure) based at least in part on a noise classification. In some embodiments, the system is configured to suspend display of sensor data based at least in part on a noise classification. In some embodiments, the system is configured to shut down a sensor session based at least in part on a noise classification.

In some embodiments, the system is configured to display the noise classification on the user interface 416. In some embodiments, the system is configured to display information indicative of a level of noise on the sensor signal (e.g., light/medium/heavy or level1/level2/level3). In some embodiments, the system is configured to display information indicative of an amount of time that the signal has been classified as having a level of noise (e.g., a time-elapsed counter).

Signal Artifacts Replacement

One or a plurality of the above signal artifacts detection models can be used alone or in combination to detect signal artifacts (e.g., a level/classification of noise on the signal) such as described herein. Accordingly, the data stream associated with the signal artifacts can be discarded, replaced, or otherwise processed in order to reduce or eliminate these signal artifacts and thereby improve the value of the glucose measurements that can be provided to a user.

In some embodiments, Signal Artifacts Replacement can use systems and methods that reduce or replace these signal artifacts that can be characterized by transience, high frequency, high amplitude, and/or substantially non-linear noise. Accordingly, a variety of filters, algorithms, and other data processing are provided that address the detected signal artifacts by replacing the data stream, or a portion of the data stream, with estimated glucose signal values. It is noted that "signal estimation" as used herein, is a broad term, which includes filtering, data smoothing, augmenting, projecting, and/or other algorithmic methods that estimate glucose signal values based on present and historical data.

It is noted that a glucose sensor can contain a processor, and/or the like, that processes periodically received raw sensor data (e.g., every 30 seconds). Although a data point can be available constantly, for example by use of an electrical integration system in a chemo-electric sensor, relatively frequent (e.g., every 30 seconds), or less frequent data point (e.g., every 5 minutes), can be more than sufficient for patient use. It is noted that according to the Nyquist Theory, a data point is required about every 10 minutes to accurately describe physiological change in glucose in humans. This represents the lowest useful frequency of sampling. However, it should be recognized that it can be desirable to sample more frequently than the Nyquist minimum, to provide for sufficient data in the event that one or more data points are lost, for example. Additionally, more frequently sampled data (e.g., 30-second) can be used to smooth the less frequent data (e.g., 5-minute) that are transmitted. It is noted that in this example, during the course of a 5-minute period, 10 determinations are made at 30-second intervals.

In some embodiments of Signal Artifacts Replacement, signal estimation can be implemented in the sensor and transmitted to a receiver for additional processing. In some embodiments of Signal Artifacts Replacement, raw data can be sent from the sensor to a receiver for signal estimation and additional processing therein. In some embodiments of Signal Artifacts Replacement, signal estimation is performed initially in the sensor, with additional signal estimation in the receiver.

In some embodiments of Signal Artifacts Replacement, wherein the sensor is an implantable glucose sensor, signal estimation can be performed in the sensor to ensure a continuous stream of data. In alternative embodiments, data can be transmitted from the sensor to the receiver, and the estimation performed at the receiver; It is noted however that there can be a risk of transmit-loss in the radio transmission from the sensor to the receiver when the transmission is wireless. For example, in embodiments wherein a sensor is implemented in vivo, the raw sensor signal can be more consistent within the sensor (in vivo) than the raw signal transmitted to a source (e.g., receiver) outside the body (e.g., if a patient were to take the receiver off to shower, communication between the sensor and receiver can be lost and data smoothing in the receiver would halt accordingly). Consequently, It is noted that a multiple point data loss in the filter can take for example, about 25 to about 40 minutes for the data to recover to near where it would have been had there been no data loss.

In some embodiments of Signal Artifacts Replacement, signal estimation is initiated only after signal artifacts are positively detected and stopped once signal artifacts are negligibly detected. In some alternative embodiments signal estimation is initiated after signal artifacts are positively detected and then stopped after a predetermined time period. In some alternative embodiments, signal estimation can be continuously or continually performed. In some alternative embodiments, one or more forms of signal estimation can be accomplished based on the severity of the signal artifacts, such as described in more detail with reference to U.S. Patent Publication Nos. 2005/0043598, 2007/0032706, 2007/0016381, and 2007/0066873, and co-pending U.S. patent application Ser. No. 11/762,638, filed on Jun. 13, 2007 and entitled "SYSTEMS AND METHODS FOR REPLACING SIGNAL ARTIFACTS IN A GLUCOSE SENSOR DATA STREAM," all of which are incorporated herein by reference in their entirety.

In some embodiments of Signal Artifacts Replacement, the processor module performs a linear regression. In one such implementation, the processor module performs a linear regression analysis of the n (e.g., 10) most recent sampled sensor values to smooth out the noise. A linear regression averages over a number of points in the time course and thus reduces the influence of wide excursions of any point from the regression line. Linear regression defines a slope and intercept, which is used to generate a "Projected Glucose Value," which can be used to replace sensor data. This regression can be continually performed on the data stream or continually performed only during the transient signal artifacts. In some alternative embodiments, signal estimation can include non-linear regression.

In another embodiment of Signal Artifacts Replacement, the processor module performs a trimmed regression, which is a linear regression of a trimmed mean (e.g., after rejecting wide excursions of any point from the regression line). In this embodiment, after the sensor records glucose measurements at a predetermined sampling rate (e.g., every 30 seconds), the sensor calculates a trimmed mean (e.g., removes highest and lowest measurements from a data set and then regresses the remaining measurements to estimate the glucose value.

In another embodiment of Signal Artifacts Replacement, the processor module runs a non-recursive filter, such as a finite impulse response (FIR) filter. A FIR filter is a digital signal filter, in which every sample of output is the weighted sum of past and current samples of input, using only some finite number of past samples.

In another embodiment of Signal Artifacts Replacement, the processor module runs a recursive filter, such as an infinite impulse response (IIR) filter. An IIR filter is a type of digital signal filter, in which every sample of output is the weighted sum of past and current samples of input. In one exemplary implementation of an IIR filter, the output is computed using 6 additions/subtractions and 7 multiplications as shown in the following equation:

$$y(n) = \frac{a_0 * x(n) + a_1 * x(n-1) + a_2 * x(n-2) + a_3 * x(n-3) - b_1 * y(n-1) - b_2 * y(n-2) - b_3 * y(n-3)}{b_0}$$

This polynomial equation includes coefficients that are dependent on sample rate and frequency behavior of the filter. Frequency behavior passes low frequencies up to cycle lengths of 40 minutes, and is based on a 30 second sample rate. In alternative implementations, the sample rate and cycle lengths can be more or less. See Lynn "Recursive Digital Filters for Biological Signals" Med. & Biol. Engineering, Vol. 9, pp. 37-43, which is incorporated herein by reference in its entirety.

In another embodiment of Signal Artifacts Replacement, the processor module runs a maximum-average (max-average) filtering algorithm. The max-average algorithm smoothes data based on the discovery that the substantial majority of signal artifacts observed after implantation of glucose sensors in humans, for example, is not distributed evenly above and below the actual blood glucose levels. It has been observed that many data sets are actually characterized by extended periods in which the noise appears to trend downwardly from maximum values with occasional high spikes such as described in more detail above with reference to FIG. 7C, section 74b, which is likely in response to limitations in the system that do not allow the glucose to fully react at the enzyme layer and/or proper reduction of $H_2O_2$ at the counter electrode, for example. To overcome these downward trending signal artifacts, the max-average calculation tracks with the highest sensor values, and discards the bulk of the lower values. Additionally, the max-average method is designed to reduce the contamination of the data with non-physiologically high data from the high spikes.

In another embodiment of Signal Artifacts Replacement, the processor module runs a "Cone of Possibility Replacement Method." It is noted that this method can be performed in the sensor and/or in the receiver. The Cone of Possibility Detection Method utilizes physiological information along with glucose signal values in order define a "cone" of physiologically feasible glucose signal values within a human. Particularly, physiological information depends upon the physiological parameters obtained from continuous studies in the literature as well as our own observations. A first physiological parameter uses a maximal sustained rate of change of glucose in humans (e.g., about 4 to 5 mg/di/min) and a maximum sustained acceleration of that rate of change (e.g., about 0.1 to 0.2 mg/min/min). A second physiological parameter uses the knowledge that rate of change of glucose is lowest at the maxima and minima, which are the area of greatest risk in patient treatment, such as described with reference to Cone of Possibility Detection, above. A third physiological parameter uses the fact that the best solution for the shape of the curve at any point along the curve over a certain time period (e.g., about 20-25 minutes) is a straight line. It is noted that the maximum rate of change can be narrowed in some instances. Therefore, additional physiological data can be used to modify the limits imposed upon the Cone of Possibility Replacement Method for sensor glucose values. For example, the maximum per minute rate change can be lower when the subject is lying down or sleeping; on the other hand, the maximum per minute rate change can be higher when the subject is exercising, for example.

The Cone of Possibility Replacement Method utilizes physiological information along with blood glucose data in order to improve the estimation of blood glucose values within a human in an embodiment of Signal Artifacts Replacement. The Cone of Possibility Replacement Method can be performed on raw data in the sensor, on raw data in the receiver, or on smoothed data (e.g., data that has been replaced/estimated in the sensor or receiver by one of the methods described above) in the receiver.

In other embodiments of Signal Artifacts Replacement, prediction algorithms, also referred to as projection algorithms, can be used to replace glucose data signals for data which does not exist because 1) it has been discarded, 2) it is missing due to signal transmission errors and the like, or 3) it represents a time period (e.g., future) for which a data stream has not yet been obtained based on historic and/or present data. Prediction/projection algorithms include any of the above described Signal Artifacts Replacement algorithms, and differ only in the fact that they are implemented to replace time points/periods during which no data is available (e.g., for the above-described reasons), rather than including that existing data, within the algorithmic computation.

In some embodiments, signal replacement/estimation algorithms are used to predict where the glucose signal should be, and if the actual data stream varies beyond a certain threshold of that projected value, then signal artifacts are detected. In alternative embodiments, other data processing can be applied alone, or in combination with the above-described methods, to replace data signals during system noise and/or signal artifacts.

Figure 11:
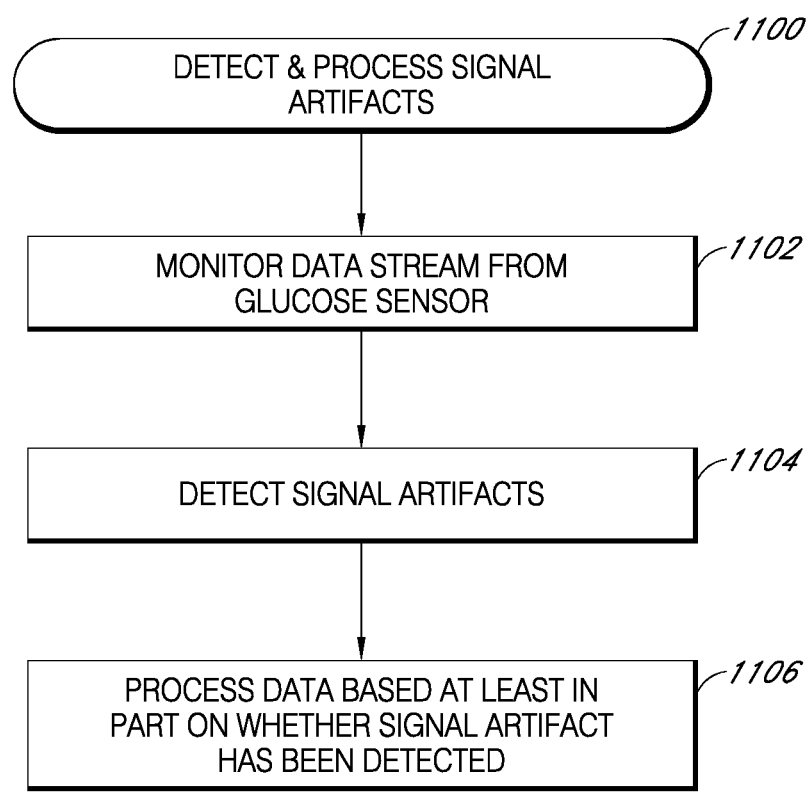
FIG. 11 is a flow chart that illustrates a method of detecting and processing signal artifacts in the data stream from a glucose sensor in one embodiment.

FIG. 11 is a flow chart 1100 that illustrates the process of detecting and processing signal artifacts in some embodiments.

At block 1102, a sensor data receiving module, also referred to as the sensor data module, or processor module, receives sensor data (e.g., a data stream), including one or more time-spaced sensor data points. In some embodiments, the data stream is stored in the sensor for additional processing; in some alternative embodiments, the sensor periodically transmits the data stream to the receiver, which can be in wired or wireless communication with the sensor. In some embodiments, raw and/or filtered data is stored in the sensor and/or transmitted and stored in the receiver, as described in more detail elsewhere herein.

At block 1104, a signal artifacts detection module, also referred to as the signal artifacts detector, or signal reliability module, is programmed to detect transient non-glucose related signal artifacts in the data stream. In some embodiments, the signal artifacts detector can comprise an oxygen detector, a pH detector, a temperature detector, and/or a pressure/stress detector, for example, the signal artifacts detector 228 in FIG. 2. In some embodiments, the signal artifacts detector is located within the processor 214 (FIG. 2) and utilizes existing components of the glucose sensor to detect signal artifacts, for example by pulsed amperometric detection, counter electrode monitoring, reference electrode monitoring, and frequency content monitoring, which are described elsewhere herein. In yet other embodiments, the data can be sent from the sensor to the receiver which comprises programming in the processor 406 (FIG. 4) that performs algorithms to detect signal artifacts, for example such as described with reference to "Cone of Possibility Detection" method and/or by comparing raw data vs. filtered data, both of which are described in more detail elsewhere herein.

In some exemplary embodiments, the processor module in either the sensor electronics and/or the receiver electronics evaluates an intermittent or continuous signal-to-noise measurement to determine aberrancy of sensor data responsive to a signal-to-noise ratio above a set threshold. In some exemplary embodiments, signal residuals (e.g., by comparing raw and filtered data) are intermittently or continuously analyzed for noise above a set threshold. In some exemplary embodiments, pattern recognition can be used to identify noise associated with physiological conditions, such as low oxygen, or other known signal aberrancies. Accordingly, in these embodiments, the system can be configured, in response to aberrancies in the data stream, to trigger signal estimation, adaptively filter the data stream according to the aberrancy, and the like, as described in more detail elsewhere herein.

In some embodiments, one or more signal residuals are obtained by comparing received data with filtered data, whereby a signal artifact can be determined. In some embodiments, a signal artifact event is determined to have occurred if the residual is greater than a threshold. In some exemplary embodiments, another signal artifact event is determined to have occurred if the residual is greater than a second threshold. In some exemplary embodiments, a signal artifact event is determined to have occurred if the residual is greater than a threshold for a period of time or an amount of data. In some exemplary embodiments, a signal artifact event is determined to have occurred if a predetermined number of signal residuals above a predetermined threshold occur within a predetermined time period (or an amount of data). In some exemplary embodiments, an average of a plurality of residuals is evaluated over a period of time or amount of data to determine whether a signal artifact has occurred. The use of residuals for noise detection can be preferred in circumstances where data gaps (non-continuous) data exists.

In some exemplary embodiments, a differential, also referred to as a derivative of the residual (delta residual), is determined by comparing a first residual (e.g., at a first time point) and a second residual (e.g., at a second time point), wherein a signal artifact event is determined to have occurred when the differential is above a predetermined threshold. In some exemplary embodiments, a signal artifact event is determined to have occurred if the differential is greater than a threshold for a period of time or amount of data. In some exemplary embodiments, an average of a plurality of differentials is calculated over a period of time or amount of data to determine whether a signal artifact has occurred.

Numerous embodiments for detecting signal artifacts are described in more detail in the section entitled, "Signal Artifacts Detection," all of which are encompassed by the signal artifacts detection at block 1104.

At block 1106, the processor module is configured to process the sensor data based at least in part on whether the signal artifact event has occurred.

In some embodiments, the sensor data is filtered in the receiver processor to generate filtered data if the signal artifact event is determined to have occurred; filtering can be performed either on the raw data, or can be performed to further filter received filtered data, or both.

In some embodiments, signal artifacts detection and processing is utilized in outlier detection, such as described in more detail elsewhere herein, wherein a disagreement between time corresponding reference data and sensor data can be analyzed, e.g., noise analysis data (e.g., signal artifacts detection and signal processing) can be used to determine which value is likely more reliable (e.g., whether the sensor data and/or reference data can be used for processing). In some exemplary embodiments wherein the processor module receives reference data from a reference analyte monitor, a reliability of the received data is determined based on signal artifacts detection (e.g., if a signal artifact event is determined to have occurred.) In some exemplary embodiments, a reliability of the sensor data is determined based on signal artifacts detection (e.g., if the signal artifact event is determined to have not occurred.) The term "reliability," as used herein, is a broad term and is used in its ordinary sense, including, without limitation, a level of confidence in the data (e.g., sensor or reference data), for example, a positive or negative reliance on the data (e.g., for calibration, display, and the like) and/or a rating (e.g., of at least 60%, 70%, 80%, 90% or 100% confidence thereon.)

In some embodiments wherein a matched data pair is formed by matching reference data to substantially time corresponding sensor data (e.g., for calibration and/or outlier detection) described in more detail elsewhere herein, matching of a data pair can be configured to occur based on signal artifacts detection (e.g., only if a signal artifact event is determined to have not occurred.) In some embodiments wherein the reference data is included in a calibration factor for use in calibration of the glucose sensor as described in more detail elsewhere herein, the reference data can be configured to be included based on signal artifacts detection (e.g., only if the signal artifact event is determined to have not occurred.) In general, results of noise analysis (e.g., signal artifact detection and/or signal processing) can be used to determine when to use or eliminate a matched pair for use in calibration (e.g., calibration set).

In some embodiments, a user is prompted for a reference glucose value based on signal artifacts detection (e.g., only if a signal artifact event is determined to have not occurred.) While not wishing to be bound by theory, it is believed certain more preferable times for calibration (e.g., not during noise episodes) can be detected and processed by prompting the user for calibration during those times.

In some embodiments, results of noise analysis (e.g., signal artifact detection and/or signal processing) can be used to determine how to process the sensor data. For example, different levels of signal processing and display (e.g., raw data, integrated data, filtered data utilizing a first filter, filtered data utilizing a second filter, which may be "more aggressive" than the first filter by filtering over a larger time period, and the like.) Accordingly, the different levels of signal processing and display can be selectively chosen responsive to a reliability measurement, a positive or negative determination of signal artifact, and/or signal artifacts above first and second predetermined thresholds.

In some embodiments, results of noise analysis (e.g., signal artifact detection and/or signal processing) can be used to determine when to utilize and/or display different representations of the sensor data (e.g., raw vs. filtered data), when to turn filters on and/or off (e.g., processing and/or display of certain smoothing algorithms), and/or when to further process the sensor data (e.g., filtering and/or displaying). In some embodiments, the display of the sensor data is dependent upon the determination of signal artifact(s). For example, when a certain predetermined threshold of signal artifacts have been detected (e.g., noisy sensor data), the system is configured to modify or turn off a particular display of the sensor data (e.g., display filtered data, display processed data, disable display of sensor data, display range of possible data values, display indication of direction of glucose trend data, replace sensor data with predicted/estimated sensor data, and/or display confidence interval representative of a level of confidence in the sensor data.) In some exemplary embodiments, a graphical representation of filtered sensor data is displayed if the signal artifact event is determined to have occurred. Alternatively, when a certain predetermined threshold of signal artifacts has not been detected (e.g., minimal, insignificant, or no noise in the data signal), the system is configured to modify or turn on a particular display of the sensor data (e.g., display unfiltered (e.g., raw or integrated) data, a single data value, an indication of direction of glucose trend data, predicted glucose data for a future time period and/or a confidence interval representative of a level of confidence in the sensor data.)

In some embodiments wherein a residual (or differential) is determined as described in more detail elsewhere herein, the residual (or differential) is used to modify the filtered data during signal artifact event(s). In one such exemplary embodiment, the residual is measured and then added back into the filtered signal. While not wishing to be bound by theory, it is believed that some smoothing algorithms may result in some loss of dynamic behavior representative of the glucose concentration, which disadvantage may be reduced or eliminated by the adding of the residual back into the filtered signal in some circumstances.

In some embodiments, the sensor data can be modified to compensate for a time lag, for example by predicting or estimating an actual glucose concentration for a time period considering a time lag associated with diffusion of the glucose through the membrane, digital signal processing, and/or algorithmically induced time lag, for example.

Figure 12:
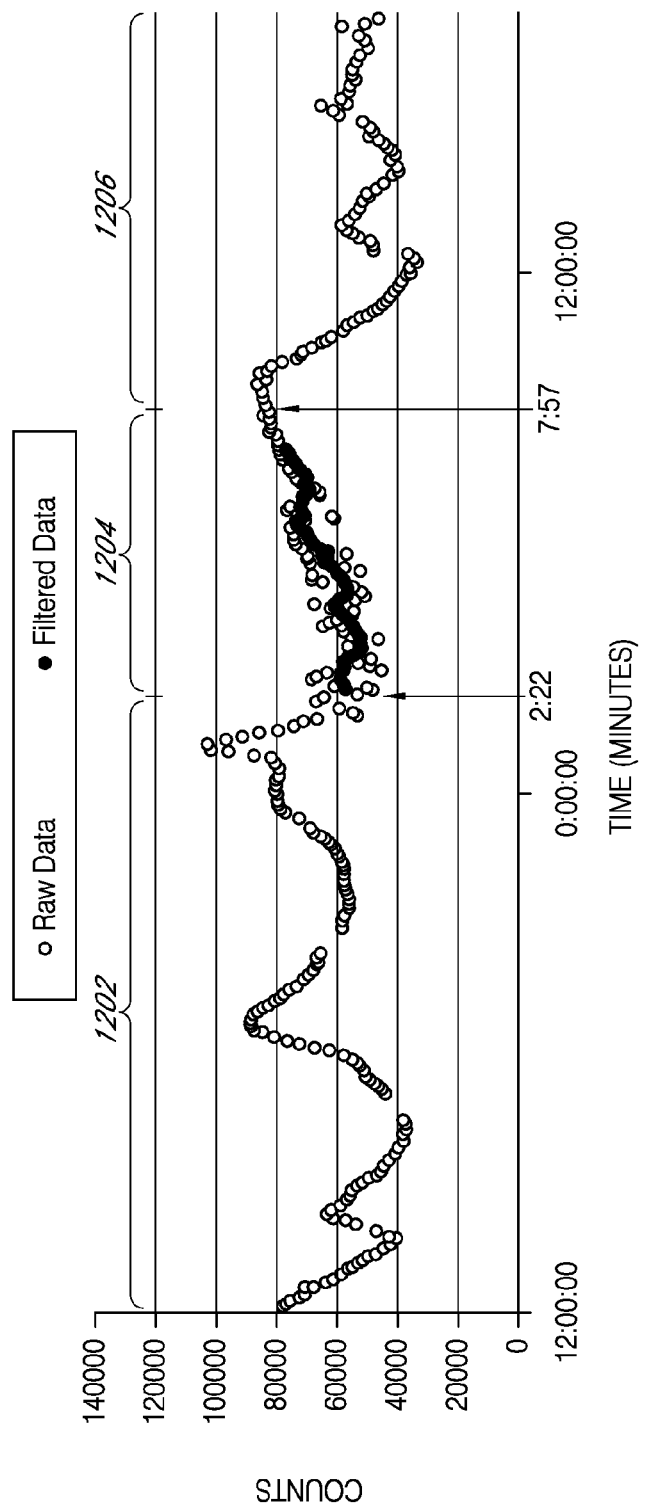
FIG. 12 is a graph that illustrates a raw data stream from a glucose sensor for approximately 24 hours with a filtered version of the same data stream superimposed on the same graph.

FIG. 12 is a graph that illustrates a raw data stream from a glucose sensor for approximately 24 hours with a filtered version of the same data stream superimposed on the same graph. Additionally, this graph illustrates a noise episode, the beginning and end of which was detected by a noise detection algorithm of the preferred embodiments, and during which a particular filter was applied to the data. The x-axis represents time in minutes; the y-axis represents the raw and filtered data values in counts. In this example, the raw data stream was obtained in 5 minute intervals from a transcutaneous glucose sensor such as described in more detail above, with reference to FIG. 1B and in U.S. Patent Publication No. US-2006-00201087-A1.

In section 1202 of the data, which encompasses an approximately 14 hour period up to time=2:22, the filtered data was obtained by applying a 3-point moving average window to the raw data. During that period, the noise detection algorithm was applied to detect a noise episode. In this example, the algorithm included the following: calculating a residual signal by subtracting the filtered data from the raw data (e.g., for each 5-minute point); calculating a differential by subtracting the residual for each 5-minute point from its previous 5-minute residual; determining if each differential exceeds a threshold of 5000 counts (and declaring a noisy point if so); and determining whether 6 out of 12 points in the past 1 hour exceed that threshold (and declaring a noise episode if so). Accordingly, a noise episode was declared at time=2:22 and a more aggressive filter was applied as described with reference to section 1204.

In section 1204 of the data, also referred to as a noise episode, which encompasses an approximately 5½ hour period up to time=7:57, the filtered data was obtained by applying a 7-point moving average window to the raw data. The 7-point moving average window was in this example was an effective filter in smoothing out the noise in the data signal as can be seen on the graph. During that period, an algorithm was applied to detect when the noise episode had ended. In this example, the algorithm included the following: calculating a residual signal by subtracting the filtered data (using the 3-point moving average filter described above) from the raw data (e.g., for each 5-minute point); calculating a differential of the residual by subtracting the residual for each 5-minute point from its previous 5-minute residual; determining if each differential exceeds a threshold of 5000 counts (and declaring a noisy point if so); and determining whether less than 2 noisy points had occurred in the past hour (and declaring the noise episode over if so). Accordingly, the noise episode was declared as over at time-7:57 and the less aggressive filter (e.g., 3-point moving average) was again applied with the noise detection algorithm as described with reference to section 1202, above.

In section 1206 of the data, which encompasses more than 4 hours of data, the filtered data was obtained by applying a 3-point moving average window to the raw data. During that period, the noise detection algorithm (described above) did not detect a noise episode. Accordingly, raw or minimally filtered data could be displayed to the patient during this time period.

It was shown that the above-described example provided smoother glucose information during noise episodes, by applying a more aggressive filter to smooth out the noise. It is believed that when displayed, the smoother data will avoid presenting potentially misleading or inaccurate information to the user. Additionally, it was shown in the above-described example that during non-noisy periods (when noise episodes are not detected), raw or less aggressively filtered data can be displayed to the user in order to provide more accurate data with minimal or no associated filter-induced time lag in the data. Furthermore, it is believed that proper detection of noise episodes aids in determining proper times for calibration, ensuring more accurate calibration than may otherwise be possible.

In the above-described example, the criteria for the onset & offset of noise episodes were different; for example, the onset criteria included 6 out of 12 points in the past 1 hour exceeding a threshold, while the offset criteria included less than 2 noisy points in the past 1 hour. In this example, these different criteria were found to create smoother transitions in the data between the raw and filtered data and avoided false detections of noise episodes.

Figure 13:
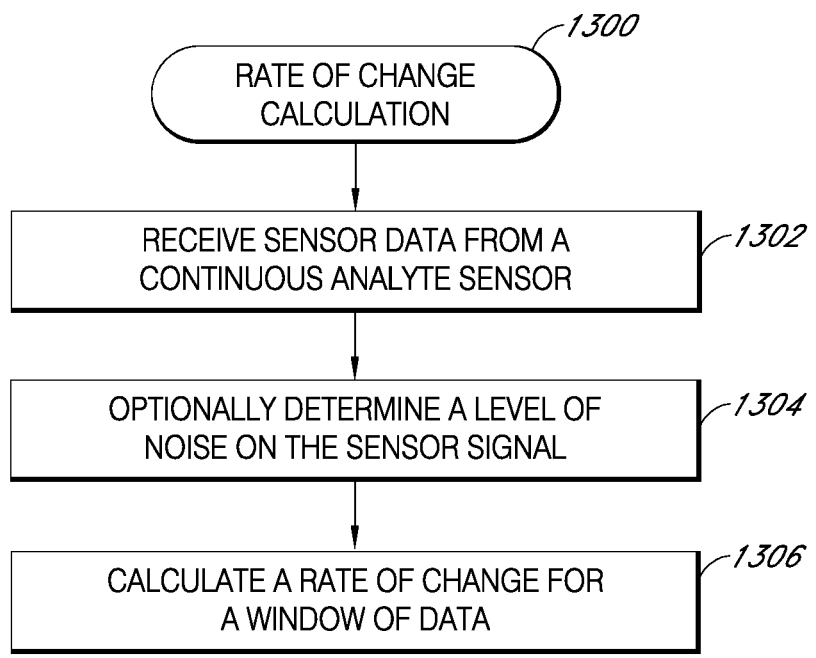
FIG. 13 is a flow chart that illustrates a method of calculating a rate of change of sensor data from a glucose sensor in one embodiment.

FIG. 13 is a flowchart 1300 that illustrates a process for determining a rate of change of a continuous analyte sensor signal, in one embodiment.

At block 1302, a sensor data receiving module, also referred to as the sensor data module, computer system, or processor module, receives sensor data (e.g., a data stream), including one or more time-spaced sensor data points hereinafter referred to as "data stream," "sensor data," "sensor analyte data", "signal," from a sensor via the receiver, which can be in wired or wireless communication with the sensor. The sensor data receiving module is described in more detail elsewhere herein, for example, with reference to FIG. 5.

At block 1304, optionally determining a level of noise on the sensor signal, which is described in more detail elsewhere herein.

At block 1306, the computer system (e.g., processor module) calculates a rate of change for a window of sensor data, wherein the window of sensor data includes two or more sensor data points. In some embodiments, the window of sensor data is a user selectable time period. In some embodiments, the window of sensor data is a programmable time period. In some embodiments, wherein the window of sensor data adaptively adjusts based at least in part on a level of noise in the sensor data. Accordingly, one or more windows of data can be user-selected (or adaptively-selected by the computer system) depending upon what type of trend data is to be displayed. As one example of a window of data, a "current trend" includes rate of change information from recent data (e.g., within about 5, 10, 15, 20, 25, 30, 35, 40 minutes). As another example of a window of data, a "sustained trend" includes rate of change information from a wider window of data than the current trend (e.g., within about 20, 30, 40, 50, 60 or more minutes).

In some embodiments, the computer system is configured to use either raw sensor data or filtered sensor data (including adaptive filtering) in the rate of change calculation depending at least in part upon the level of noise determined. In some embodiments, the rate of change calculation comprises calculating at least two rate of change calculations, and filtering the rate of change calculation to obtain a filtered rate of change value as described in more detail elsewhere herein. In some embodiments, the rate of change calculation comprises calculating at least two point-to-point rate of change calculations, and wherein the rate of change calculation further comprises adaptively selecting a filter to apply to the point-to-point rate of change calculation based at least in part on the level of noise determined.

In some embodiments, the rate of change calculation described herein is used to predict one or more analyte values, which is described in more detail with reference to FIG. 14, for example. In some embodiments, a trend arrow is displayed on the user interface based at least in part on the rate of change calculation described herein. In some embodiments, the rate of change calculation described herein is issued to determine a therapy instruction, for example, a medicament delivery type and/or amount of medicament for delivery via an open-loop, semi-open loop and/or closed loop system.

Figure 14:
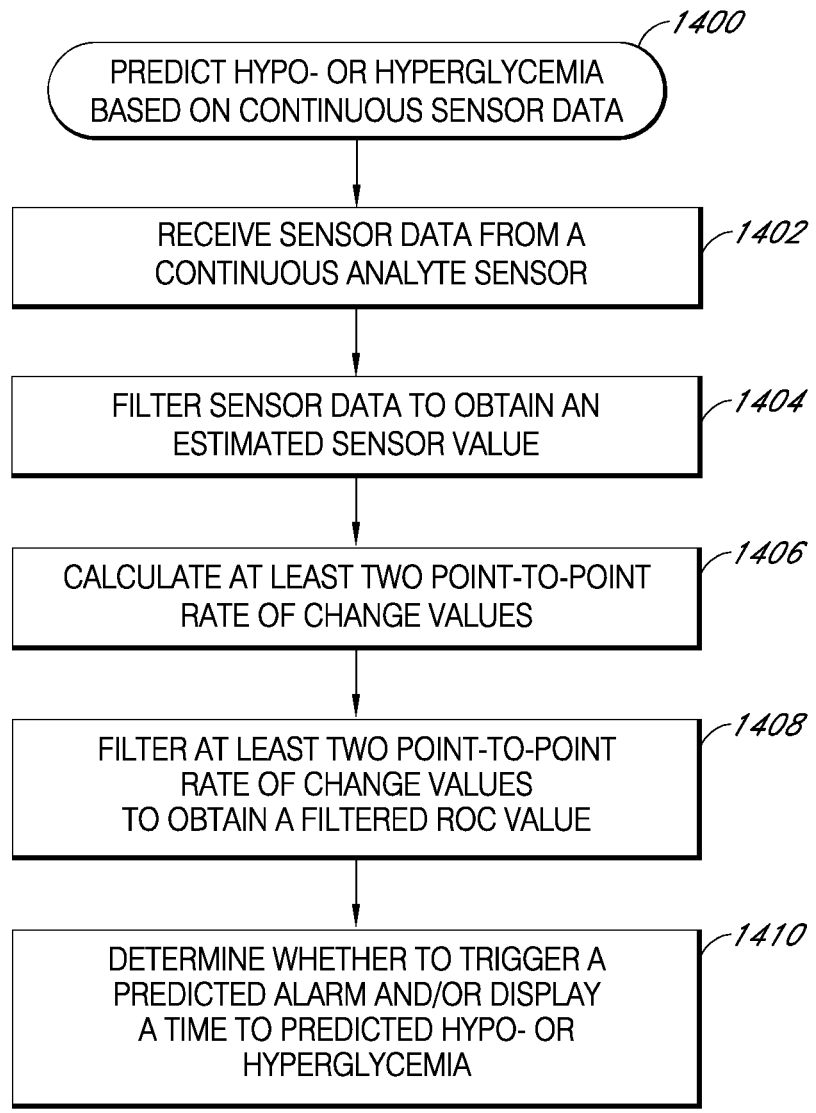
FIG. 14 is a flow chart that illustrates a method of predicting hypoglycemic and/or hyperglycemic episodes based on continuous glucose sensor data in one embodiment.

FIG. 14 is a flowchart 1400 that illustrates a process for prediction based on a continuous analyte sensor signal, in one embodiment, including determining whether to trigger a predicted hypoglycemia or predicted hyperglycemia alarm and/or to display a predicted time to predicted hypoglycemia or predicted hyperglycemia. In the embodiment described herein with reference to FIG. 13, a "free flow algorithm" is used for the predictive algorithm, which is in contrast to a conventional predictive algorithms that use model or curve-fitting type algorithms. Advantageously, the free flow algorithm described herein is robust to the non-stationary condition of signal.

At block 1402, a sensor data receiving module, also referred to as the sensor data module, computer system, or processor module, receives sensor data (e.g., a data stream), including one or more time-spaced sensor data points hereinafter referred to as "data stream," "sensor data," "sensor analyte data", "signal," from a sensor via the receiver, which can be in wired or wireless communication with the sensor. The sensor data receiving module is described in more detail elsewhere herein, for example, with reference to FIG. 5.

At block 1404, the computer system optionally filters the sensor data to obtain an estimated sensor value (e.g., calibrated glucose concentration based on sensor data). In some embodiments, the estimated sensor value is at a time t=0; for example, the computer system compensates for time lag associated with filtering and/or the sensor. However, the computer system can additionally and/or alternatively compensate for a time lag in other processing step or modules, such as block 1410.

At block 1406, the computer system calculates a rate of change based on a time series analysis of rate of change information, wherein the time series analysis includes at least two rate of change values. In some embodiments, the rate of change values can be obtained by gradient tracking, multiple rate of change calculations, point-to-point rate of change calculations, and/or the like. In one exemplary embodiment, the computer system calculates at least two point-to-point rate of change values, as described in more detail elsewhere herein.

At block 1408, the computer system filters the at least two rate of change values to obtain a filtered ROC value. In some embodiments, the computer system continuously filters the at least two point-to-point rate of change values to obtain a filtered ROC value.

At block 1410, the computer system determines whether to trigger a predicted hypoglycemia or predicted hyperglycemia alarm and/or display a predicted time to predicted hypoglycemia or predicted hyperglycemia. For example, in some embodiments, the computer system determines a predicted value for a future time period based on the estimated sensor value, the filtered ROC value and a time to the future time period, which can be programmed into the computer or user selectable (e.g., 5, 10, 15, 20 minutes or more). In some embodiments, the computer system compares the predicted value against a threshold (e.g., 50, 60, 70, 80, 90 or 100 mg/dL for predicted hypoglycemia and/or 160, 180, 200, 220 or 240 for predicted hyperglycemia), which can be programmed into the computer system or user selectable. In some embodiments, the computer system triggers an alarm when the predicted value passes the threshold.

In some embodiments, the computer system determines a predicted time to a threshold, wherein the predicted time is based at least in part on the estimated sensor value, the filtered ROC value and a threshold (e.g., 50, 60, 70, 80, 90 or 100 mg/dL for predicted hypoglycemia and/or 160, 180, 200, 220 or 240 for predicted hyperglycemia), which can be programmed into the computer system or user selectable. In some embodiments, the computer system is configured to display the predicted time to threshold on a user interface. In some embodiments, the computer system is configured to display the predicted time to threshold only when the predicted time is below a predetermined value.

In some embodiments, the computer system determines an insulin therapy based at least in part on the filtered ROC value. In some embodiments, the computer system displays a trend arrow on a user interface based at least in part on the filtered ROC value.

In some embodiments, a trend arrow is displayed on the user interface based at least in part on the filtered rate of change calculation described herein. In some embodiments, the filtered rate of change calculation described herein is issued to determine a therapy instruction, for example, a medicament delivery type and/or amount for delivery via an open-loop, semi-open loop and/or closed loop system.

Figure 15:
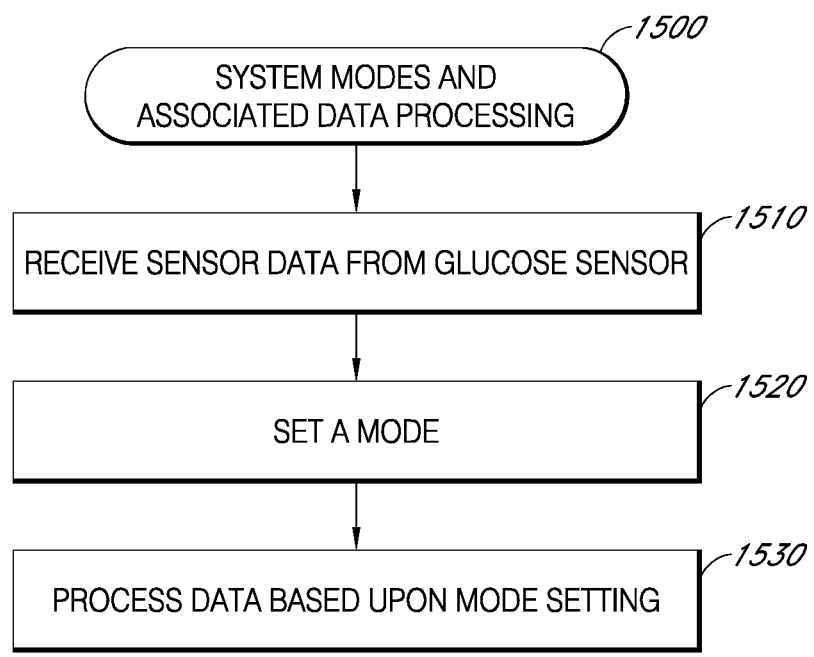
FIG. 15 is a flow chart that illustrates a method of setting a mode and further processing data based upon a mode setting in one embodiment.

Reference is now made to FIG. 15, which is a flow chart 1500 that illustrates the process of receiving sensor data, setting a mode and further processing data based upon the mode. In general, the modes of the preferred embodiments enable systems and methods associated with processing analyte data, alarms, medicament delivery, at the like, to be adapted to and/or customized for a user's mode (e.g., activity, physiological condition and/or preference). In one embodiment, having different modes allows the system to evaluate and/or process the analyte data, (e.g., concentration, trends, etc) using additional information regarding the user's activity and/or preference (or "mode"). For example, when a person is exercising, his/her glucose levels may increase or decrease in trends that would be abnormal under any other circumstances; by setting the appropriate mode, the system is configured to modify its processing associated with the user in a particular mode, e.g., "exercise mode" to provide alarms, analyte estimates, trend information, therapy recommendations, and the like, customized with one or more criteria associated with exercise.

In some preferred embodiments, systems and methods are provided to account for the various events that can occur in the life of the user and/or the preferences (e.g. the user simply not wanting to be disturbed) of the user to determine whether alarms and/or medicament delivery instructions are necessary in response to the user's glucose data. Depending upon the event that the user has scheduled or the user's preference, the user may or may not want to be alarmed of certain analyte values and/or trends in their glucose levels and therefore, by setting a mode, the user can control a sensitivity of the alarms (e.g., high, medium, low) to dictate how often the user is alarmed. For example, when a user is sleeping he/she may not want to be alarmed of levels and/or changes in glucose unless they are of urgent need (e.g. low sensitivity), accordingly, the systems is configured to alter alarm criteria to be less sensitive during "resting mode."

At block 1510, a sensor data receiving module, also referred to as the sensor data module, or processor module, receives sensor data (e.g., a data stream), including one or more time-spaced sensor data points hereinafter referred to as "data stream," "sensor data," "sensor analyte data", "signal," from a sensor via the receiver, which can be in wired or wireless communication with the sensor. The sensor data receiving module is described in more detail elsewhere herein, for example, with reference to FIG. 5.

At block 1520, a mode setting module, sets the mode of the system. In preferred embodiments, the mode is set based at least in part upon one or more inputs (e.g. buttons, menus) and/or data received from various devices (e.g. accelerometer, temperature sensor, timer, mode profile, scheduling software). In the preferred embodiment, the system, at least in part, uses the data received from inputs and/or devices to set a mode from a plurality of predetermined modes (e.g. resting mode, do not disturb mode, exercise mode, illness mode, menstruation mode, mealtime mode, snooze mode, day mode, night mode, hyperglycemia mode, hypoglycemia mode, clinical risk mode, noise mode, and the like). In general, each mode correlates to an activity, event, physiological condition, sensor condition, and/or preference of the user.

In some embodiments, the system is configured to set the mode at least in part responsive to receipt of a user input. In an exemplary embodiment, the system comprises one or more buttons, and wherein the processor module is configured to receive the user input by selection of one or more buttons (e.g., dedicated mode buttons or universal buttons that enable selection from a user interface). In another exemplary embodiment, the system comprises a screen configured to display one or more menus and receive the user input by selection of one or more items from the one or more menus. In some embodiments, the system is configured to operably connect (e.g. via wired connection, wireless connection) with another computer system (e.g. mobile phone, personal digital assistant, personal computer, and the like) such that data (e.g. modes, mode profiles) can be transmitted to the system of the preferred embodiments. In an exemplary embodiment, the system is operably connected using a wired connection (e.g. cat 5, USB). In yet another exemplary embodiment, the system is operably connected using a wireless connection. Advantageously, setting of modes as described in the preferred embodiments enables the user to switch preferences and/or criteria associated with alarms, therapy instruction, data processing, and/or the like, to correspond with the user's life quickly and easily.

In some embodiments, the system is configured to set a mode responsive to programming configured to schedule and organize events on a calendar (e.g. Microsoft Outlook, Eudora). In another embodiment, the system is further configured to set the mode at least in part responsive to a mode profile, wherein the system or the user can set the mode profile. For example, a "work week" mode profile would have defined modes that correspond to the user's usual schedule during a 5-day work week. Mode profiles can be default system profiles, customizable default system profiles, user definable profiles, and the like. Accordingly, the embodiments described herein allow the user to schedule a series of time-based modes that occur on a recurring basis.

In some embodiments, the system is configured to automatically set the mode at least in part responsive to a comparison of data with one or more criteria (e.g. accelerometer, temperature sensor and/or criteria associated with the adaptive mode learning module as described in more detail herein). In an exemplary embodiment, the system includes and/or is configured to receive data from an accelerometer. The term "accelerometer" as used herein is a broad term and is to be given its ordinary and customary meaning to a person of ordinary skill in the art (and is not limited to a special or customized meaning), and furthermore refers without limitation to a device that monitors movement. In another exemplary embodiment, the system includes and/or is configured to receive data from a temperature sensor.

In one exemplary embodiment, the system comprises programming configured to automatically set the mode at least in part responsive to an adaptive mode-learning module (e.g. within the processor module). Preferably, the adaptive mode-learning module is configured to process (historic) sensor data and time-corresponding modes over time and determine patterns or trends used to automatically set a mode when similar trends or patterns are detected on real-time sensor data. For example, the system is configured to adaptively switch in and out of modes without constant user interaction by comparing real time data with historic data.

In yet another exemplary embodiment, the system comprises a timer associated with one or more modes, wherein the timer is configured to set the mode for a predetermined amount of time (e.g. 20 minutes, 30 minutes, 1 hour, 4 hours, 8 hours, etc.). Either the user or the system can set the timer. In some embodiments, the timer is a default timer that allows a user to select a mode with a single click for a predetermined time period. In general, the system is configured to have any combination of automatic timers, default timers, user settable times, profile driven timers, and/or the like, for any combination of one or more modes.

In one embodiment, the system is configured to classify a level of noise in the continuous analyte sensor data, as described in more detail elsewhere herein. The level of noise can be an indicator of a level of accuracy of the sensor data and can be user to set a mode (e.g. automatically by the system) responsive at least in part to the level of noise.

At block 1530, continuous sensor data is received and processed based at least in part on the mode. In general, each mode is associated with one or more criteria and/or inputs (e.g. alarm criteria and/or types of alarms, parameters associated with calculating a therapy instruction, and/or processing instructions associated with estimating analyte values and/or outputting analyte sensor information). In general, modes provide customized processing of sensor data associated with an activity, event, physiological condition, sensor condition, and/or preference of a user, for example.

In some embodiments, the system is configured to determine a type or alarm to activate (e.g. audible sound, visual display, vibration, alphanumeric message, and/or wireless transmission) based at least in part on the mode. In some embodiments, the system is configured to alter the alarm criteria (e.g., threshold analyte values, rate of change, and/or acceleration).

In some embodiments, the system comprises a therapy module (e.g. processor module) configured to determine a therapy instruction (e.g. a quantified dosage of a medicament, an activity, a recommend caloric intake) based at least in part on the mode. In some embodiments, the system is operably connected with a medicament delivery device (e.g. a device used to deliver a dose of insulin to the user), wherein the medicament type and/or amount to be delivered is based at least in part on the mode. In some embodiments, the system is configured to require a validation of the medicament delivery instruction prior to delivery of the medicament (e.g. insulin) based at least in part on the mode. Advantageously, the therapy instructions of the preferred embodiment are customizable for an activity, event, physiological condition, sensor condition, and/or preference of a user.

In some embodiments, the estimation of analyte values is based at least in part on a mode. In one such exemplary embodiment, the system is configured to aggressively filter data during "night mode" because the trade off of a time delay associated with aggressively filtered data versus reduced false alarms caused by noise spikes in unfiltered data would be advantageous to a sleeping patient. In some embodiments, the user interface is controlled, at least in part based on the mode.

As one example, resting mode sets a reduced sensitivity of alarms (e.g., hypoglycemic alarms with analyte thresholds that are 5%, 10, %, 15%, 20% or more higher than default settings) and/or to turn off audible alarms sounds. As another example, do not disturb mode is activated by a button on the receiver's user interface, whereby a user can simply press the "do not disturb button" and all alarms and therapy calculations turn off and/or are not activated for a predetermined time period. As another example, exercise mode sets parameters to ensure the therapy module calculates appropriate caloric intake suitable during and after exercise. As another example, mealtime mode sets parameters to ensure the therapy module calculates appropriate medicament delivery suitable during and after a meal. As another example, day mode is associated with more sensitive alarm thresholds and more noticeable alarm types.

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; U.S. Pat. No. 6,862,465; U.S. Pat. No. 7,074,307; U.S. Pat. No. 7,081,195; U.S. Pat. No. 7,108,778; U.S. Pat. No. 7,110,803; U.S. Pat. No. 7,192,450; U.S. Pat. No. 7,226,978; U.S. Pat. No. 7,310,544; U.S. Pat. No. 7,364,592; U.S. Pat. No. 7,366,556; and U.S. Pat. No. 7,424,318.

Methods and devices that are suitable for use in conjunction with aspects of the preferred embodiments are disclosed in U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No.

US-2005-0090607-A1; U.S. Patent Publication No.
US-2005-0187720-A1; U.S. Patent Publication No.
US-2005-0161346-A1; U.S. Patent Publication No.
US-2006-0015020-A1; U.S. Patent Publication No.
US-2005-0043598-A1; U.S. Patent Publication No.
US-2005-0033132-A1; U.S. Patent Publication No.
US-2005-0031689-A1; U.S. Patent Publication No.
US-2004-0186362-A1; U.S. Patent Publication No.
US-2005-0027463-A1; U.S. Patent Publication No.
US-2005-0027181-A1; U.S. Patent Publication No.
US-2005-0027180-A1; U.S. Patent Publication No.
US-2006-0020187-A1; U.S. Patent Publication No.
US-2006-0036142-A1; U.S. Patent Publication No.
US-2006-0020192-A1; U.S. Patent Publication No.
US-2006-0036143-A1; U.S. Patent Publication No.
US-2006-0036140-A1; U.S. Patent Publication No.
US-2006-0019327-A1; U.S. Patent Publication No.
US-2006-0020186-A1; U.S. Patent Publication No.
US-2006-0036139-A1; U.S. Patent Publication No.
US-2006-0020191-A1; U.S. Patent Publication No.
US-2006-0020188-A1; U.S. Patent Publication No.
US-2006-0036141-A1; U.S. Patent Publication No.
US-2006-0020190-A1; U.S. Patent Publication No.
US-2006-0036145-A1; U.S. Patent Publication No.
US-2006-0036144-A1; U.S. Patent Publication No.
US-2006-0016700-A1; U.S. Patent Publication No.
US-2006-0142651-A1; U.S. Patent Publication No.
US-2006-0086624-A1; U.S. Patent Publication No.
US-2006-0068208-A1; U.S. Patent Publication No.
US-2006-0040402-A1; U.S. Patent Publication No.
US-2006-0036142-A1; U.S. Patent Publication No.
US-2006-0036141-A1; U.S. Patent Publication No.
US-2006-0036143-A1; U.S. Patent Publication No.
US-2006-0036140-A1; U.S. Patent Publication No.
US-2006-0036139-A1; U.S. Patent Publication No.
US-2006-0142651-A1; U.S. Patent Publication No.
US-2006-0036145-A1; U.S. Patent Publication No.
US-2006-0036144-A1; U.S. Patent Publication No.
US-2006-0200022-A1; U.S. Patent Publication No.
US-2006-0198864-A1; U.S. Patent Publication No.
US-2006-0200019-A1; U.S. Patent Publication No.
US-2006-0189856-A1; U.S. Patent Publication No.
US-2006-0200020-A1; U.S. Patent Publication No.
US-2006-0200970-A1; U.S. Patent Publication No.
US-2006-0183984-A1; U.S. Patent Publication No.
US-2006-0183985-A1; U.S. Patent Publication No.
US-2006-0195029-A1; U.S. Patent Publication No.
US-2006-0229512-A1; U.S. Patent Publication No.
US-2006-0222566-A1; U.S. Patent Publication No.
US-2007-0032706-A1; U.S. Patent Publication No.
US-2007-0016381-A1; U.S. Patent Publication No.
US-2007-0027370-A1; U.S. Patent Publication No.
US-2007-0027384-A1; U.S. Patent Publication No.
US-2007-0032718-A1; U.S. Patent Publication No.
US-2007-0059196-A1; U.S. Patent Publication No.
US-2007-0066873-A1; U.S. Patent Publication No.
US-2007-0197890-A1; U.S. Patent Publication No.
US-2007-0173710-A1; U.S. Patent Publication No.
US-2007-0163880-A1; U.S. Patent Publication No.
US-2007-0203966-A1; U.S. Patent Publication No.
US-2007-0213611-A1; U.S. Patent Publication No.
US-2007-0232879-A1; U.S. Patent Publication No.
US-2007-0235331-A1; U.S. Patent Publication No.
US-2008-0021666-A1; U.S. Patent Publication No.
US-2008-0033254-A1; U.S. Patent Publication No.
US-2008-0045824-A1; U.S. Patent Publication No.
US-2008-0071156-A1; U.S. Patent Publication No.
US-2008-0086042-A1; U.S. Patent Publication No.
US-2008-0086044-A1; U.S. Patent Publication No.
US-2008-0086273-A1; U.S. Patent Publication No.
US-2008-0083617-A1; U.S. Patent Publication No.
US-2008-0119703-A1; U.S. Patent Publication No.
US-2008-0119704-A1; U.S. Patent Publication No.
US-2008-0119706-A1 U.S. Patent Publication No.
US-2008-0194936-A1; U.S. Patent Publication No.
US-2008-0194937-A1; U.S. Patent Publication No.
US-2008-0195967-A1; U.S. Patent Publication No.
US-2008-0183061-A1; U.S. Patent Publication No.
US-2008-0183399-A1; U.S. Patent Publication No.
US-2008-0189051-A1; U.S. Patent Publication No.
US-2008-0214918-A1; U.S. Patent Publication No.
US-2008-0194938-A1; U.S. Patent Publication No.
US-2008-0214915-A1; U.S. Patent Publication No.
US-2008-0194935-A1; U.S. Patent Publication No.
US-2008-0188731-A1; U.S. Patent Publication No.
US-2008-0242961-A1; U.S. Patent Publication No.
US-2008-0208025-A1; U.S. Patent Publication No.
US-2008-0197024-A1; U.S. Patent Publication No.
US-2008-0200788-A1; U.S. Patent Publication No.
US-2008-0200789-A1; U.S. Patent Publication No.
US-2008-0200791-A1; U.S. Patent Publication No.
US-2008-0228054-A1; and U.S. Patent Publication No. US-2008-0228051-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 11/691,426 filed Mar. 26, 2007 and entitled "ANALYTE SENSOR"; U.S. patent application Ser. No. 12/103,594 filed Apr. 15, 2008 and entitled "BIOINTERFACE WITH MACRO- AND MICRO-ARCHITECTURE"; U.S. patent application Ser. No. 12/113,724 filed May 1, 2008 and entitled "LOW OXYGEN IN VIVO ANALYTE SENSOR"; U.S. patent application Ser. No. 12/055,098 filed Mar. 25, 2008 and entitled "ANALYTE SENSOR"; U.S. patent application Ser. No. 12/054,953 filed Mar. 25, 2008 and entitled "ANALYTE SENSOR"; U.S. patent application Ser. No. 12/055,114 filed Mar. 25, 2008 and entitled "ANALYTE SENSOR"; U.S. patent application Ser. No. 12/133,820 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/133,789 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/133,761 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/133,738 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/139,305 filed Jun. 13, 2008 and entitled "ELECTRODE SYSTEMS FOR ELECTROCHEMICAL SENSORS"; U.S. patent application Ser. No. 12/175,391 filed Jul. 17, 2008 and entitled "TRANSCUTANEOUS ANALYTE SENSOR"; U.S. patent application Ser. No. 12/182,008 filed Jul. 29, 2008 and entitled "INTEGRATED RECEIVER FOR CONTINUOUS ANALYTE SENSOR"; U.S. patent application Ser. No. 12/182,073 filed Jul. 29, 2008 and entitled "INTEGRATED RECEIVER FOR CONTINUOUS ANALYTE SENSOR"; U.S. patent application Ser. No. 12/182,083 filed Jul. 29, 2008 and entitled "INTEGRATED RECEIVER FOR CONTINUOUS ANALYTE SENSOR"; U.S. patent application Ser. No. 12/195,191 filed Aug. 20, 2008 and entitled "SYSTEM AND METHODS FOR PROCESSING ANALYTE SENSOR DATA"; U.S. patent application Ser. No. 12/195,773 filed Aug. 21, 2008 and entitled "SYSTEM AND METHODS FOR PROCESSING ANALYTE SENSOR DATA"; U.S. patent application Ser. No. 12/247,137 filed Oct. 7, 2008 and entitled "IMPLANTABLE ANALYTE SENSOR"; U.S. patent application Ser. No. 12/250,918 filed Oct. 14, 2008 and entitled "ANALYTE SENSOR"; U.S. patent application Ser. No. 12/253,125 filed Oct. 16, 2008 and entitled "SIGNAL PROCESSING FOR CONTINUOUS ANALYTE SENSOR"; U.S. patent application Ser. No. 12/253,120 filed Oct. 16, 2008 and entitled "SIGNAL PROCESSING FOR CONTINUOUS ANALYTE SENSOR"; U.S. patent application Ser. No. 12/253,064 filed Oct. 16, 2008 and entitled "SIGNAL PROCESSING FOR CONTINUOUS ANALYTE SENSOR"; U.S. patent application Ser. No. 12/252,996 filed Oct. 16, 2008 and entitled "SIGNAL PROCESSING FOR CONTINUOUS ANALYTE SENSOR"; U.S. patent application Ser. No. 12/252,967 filed Oct. 16, 2008 and entitled "SIGNAL PROCESSING FOR CONTINUOUS ANALYTE SENSOR"; and U.S. patent application Ser. No. 12/252,952 filed Oct. 16, 2008 and entitled "SIGNAL PROCESSING FOR CONTINUOUS ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for generating analyte measurements of a host, the method comprising:
    generating sensor data during a first time period using an analyte sensor coupled to a sensor electronics unit, wherein the sensor electronics unit is adhered to a body of a host;
    receiving, using a receiver in wireless communication with the sensor electronics unit, a reference analyte value generated by a reference analyte monitor;
    responsive to receiving the reference analyte value, determining a first estimated analyte concentration value to display using an immediate calibration algorithm that includes matching the reference analyte value to a sensor data point closest with respect to time, wherein the first estimated analyte concentration value is associated with the analyte concentration of the host at a point in time;
    determining a second estimated analyte concentration value to display using the reference analyte value and the sensor data for the first time period in a standard calibration algorithm that is different from the immediate calibration algorithm, wherein the standard calibration algorithm includes re-matching the reference analyte value to an optimal sensor data point or points, and wherein the second estimated analyte concentration value is associated with the analyte concentration of the host at the same point in time as the first estimated analyte concentration value; and
    displaying, on a display of the receiver, a numerical analyte value selected from the first estimated analyte value and the second estimated analyte value, wherein the first estimated analyte concentration value is selected as the displayed numerical value until the second estimated analyte concentration is available, and subsequently selecting the second estimated analyte concentration value to be the displayed numerical value.

2. The method of claim 1, wherein the sensor data for the first time period is not used to determine the first estimated analyte concentration value.

3. A method for generating analyte measurements of a host, the method comprising:
    generating sensor data during a first time period using an analyte sensor coupled to a sensor electronics unit, wherein the sensor electronics unit is adhered to a body of a host;
    receiving, using a receiver in wireless communication with the sensor electronics unit, a reference analyte value generated by a reference analyte monitor;
    responsive to receiving the reference analyte value, determining a first estimated analyte concentration value associated with a point in time to display using an immediate calibration algorithm that includes matching the reference analyte value to a sensor data point closest with respect to time;
    projecting an analyte concentration value, wherein using the immediate calibration algorithm comprises comparing the projected analyte concentration value to the reference data value;
    determining a second estimated analyte concentration value associated with the point in time to display using the reference analyte value and the sensor data for the first time period in a standard calibration algorithm that is different from the immediate calibration algorithm, wherein the standard calibration algorithm includes matching the reference analyte value to an optimal sensor data point or points; and displaying, on a display of the receiver, a numerical analyte value selected from the first estimated analyte value and the second estimated analyte value, wherein the first estimated analyte concentration value is selected as the displayed numerical value until the second estimated analyte concentration is available, and subsequently selecting the second estimated analyte concentration value to be the displayed numerical value.

4. The method of claim 3, wherein the projected analyte value is projected based on sensor data generated by the analyte sensor during a second time period that is prior to the first time period.

5. The method of claim 1, wherein determining the second estimated analyte concentration value to display is performed responsive to determining that both the sensor data for the first time period and the reference analyte value are available for calibration.

6. The method of claim 5, further comprising periodically establishing wireless communication between the sensor electronics unit and the receiver, wherein the receiver sends the reference analyte value to the sensor electronics unit during the periodically established wireless communication and wherein the sensor electronics unit sends the first estimated analyte value to the receiver during the periodically established wireless communication.

7. The method of claim 6, wherein the second estimated analyte concentration value is not available due to the communication between the sensor electronics and the receiver.

8. The method of claim 1, wherein the second estimated analyte concentration value is not available until both the reference analyte value and the sensor data generated during the first time period are available to be used in the standard calibration algorithm.

9. The method of claim 1, wherein the standard calibration algorithm is performed by the sensor electronics module.

10. The method of claim 1, wherein the immediate calibration algorithm is performed by the receiver.

11. The method of claim 1, wherein receiving the reference analyte value comprises receiving user input using a user interface of the receiver or wirelessly receiving the reference analyte value using the receiver from the reference analyte monitor.

12. The method of claim 1, wherein the reference analyte monitor is a single-point blood glucose monitor.

13. The method of claim 1, where the analyte is glucose and wherein the sensor is a continuous glucose sensor.

14. The method of claim 1, wherein the standard calibration algorithm comprises a conversion function, wherein the conversion function is based on a matching of the reference analyte value to sensor data.

15. The method of claim 1, wherein displaying the first estimated analyte value is performed within 1 minute of receiving the reference analyte value and displaying the second estimated analyte value is performed subsequent to the reference analyte value and the sensor data being available for matching.

16. The method of claim 1, further comprising displaying a graphical representation of estimated analyte data over a time period simultaneously with the numerical analyte value.

17. The method of claim 1, wherein the optimal sensor data point or points includes an average of a plurality of sensor data points in a timeframe associated with the reference analyte value.

* * * * *

UNITED STATES PATENT AND TRADEMARK OFFICE
CERTIFICATE OF CORRECTION

PATENT NO.        : 9,717,449 B2
APPLICATION NO.   : 13/742178
DATED             : August 1, 2017
INVENTOR(S)       : Apurv Ullas Kamath It is certified that error appears in the above-identified patent and that said Letters Patent is hereby corrected as shown below:

On the Title Page

In Column 2 (page 9, item (56)) at Line 2, Under Other Publications, change "hypoglycaemic" to --hypoglycemic--.

In Column 2 (page 9, item (56)) at Line 25, Under Other Publications, change "Thechnol." to --Technol.--.

In Column 2 (page 9, item (56)) at Line 28, Under Other Publications, change "Senso" to --Sensor--.

In Column 2 (page 9, item (56)) at Line 42, Under Other Publications, change "glycisylated" to --glycosylated--.

In Column 1 (page 10, item (56)) at Line 18, Under Other Publications, change "basedon" to --based on--.

In Column 1 (page 10, item (56)) at Line 34, Under Other Publications, change "14:641/646." to --17:647/654.--.

In Column 1 (page 10, item (56)) at Line 43, Under Other Publications, change "/impintable," to --/implantable,--.

In Column 1 (page 10, item (56)) at Line 46, Under Other Publications, change "reliablity" to --reliability--.

In Column 1 (page 10, item (56)) at Line 47, Under Other Publications, change "Biollogy" to --Biology--.

In Column 1 (page 10, item (56)) at Line 55, Under Other Publications, change "Enzymlology," to --Enzymology,--.

Signed and Sealed this
Fourteenth Day of November, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,717,449 B2

In Column 2 (page 10, item (56)) at Line 2, Under Other Publications, change "your and your" to --you and your--.

In Column 2 (page 10, item (56)) at Line 16, Under Other Publications, change "dynamcs" to --dynamics--.

In Column 2 (page 10, item (56)) at Line 26, Under Other Publications, change "Hypoglycaemia/" to --Hypoglycemia/--.

In Column 2 (page 10, item (56)) at Line 67, Under Other Publications, change "patents" to --patients--.

In Column 1 (page 11, item (56)) at Line 28, Under Other Publications, change "Annu Annu" to --Annu--.

In Column 1 (page 11, item (56)) at Line 45, Under Other Publications, change "Aniodic" to --Anodic--.

In Column 2 (page 11, item (56)) at Line 34, Under Other Publications, change "Norm" to --Horm.--.

In Column 1 (page 12, item (56)) at Line 23, Under Other Publications, change "Electronanalysis" to --Electroanalysis--.

In Column 1 (page 12, item (56)) at Line 59, Under Other Publications, change "amperometeric" to --amperometric--.

In Column 1 (page 12, item (56)) at Line 66, Under Other Publications, change "Thechnol." to --Technol.--.

In Column 2 (page 12, item (56)) at Line 41, Under Other Publications, change "Apllied" to --Applied--.

In Column 1 (page 13, item (56)) at Line 64, Under Other Publications, change "Subcutaenous" to --Subcutaneous--.

In Column 2 (page 13, item (56)) at Line 2, Under Other Publications, change "assitance" to --assistance--.

In Column 2 (page 13, item (56)) at Line 3, Under Other Publications, change "Thechnol." to --Technol.--.

In Column 2 (page 13, item (56)) at Line 12, Under Other Publications, change "Membran," to --Membrane,--.

In Column 1 (page 14, item (56)) at Line 29, Under Other Publications, change "Norm." to --Horm.--.

CERTIFICATE OF CORRECTION (continued)

In Column 1 (page 14, item (56)) at Line 69, Under Other Publications, change "impleated" to --implanted--.

In Column 2 (page 14, item (56)) at Line 6, Under Other Publications, change "impleated" to --implanted--.

In Column 1 (page 15, item (56)) at Line 32, Under Other Publications, change "Videoganes:" to --Videogames:--.

In Column 1 (page 15, item (56)) at Line 44, Under Other Publications, change "Polythylene Specidications" to --Polyethylene Specifications--.

In Column 1 (page 15, item (56)) at Line 45, Under Other Publications, change ".com/poly.sub.--p.htm" to --.com/polye_p.htm--.

In Column 1 (page 15, item (56)) at Line 54, Under Other Publications, change "implntable," to --implantable,--.

In Column 1 (page 15, item (56)) at Line 54, Under Other Publications, change "glucode" to --glucose--.

In Column 1 (page 15, item (56)) at Line 68, Under Other Publications, change "Technolgoy" to --Technology--.

In Column 2 (page 15, item (56)) at Line 1, Under Other Publications, change "Method" to --Methods--.

In Column 2 (page 15, item (56)) at Line 4, Under Other Publications, change "Educations" to --Educational--.

In Column 2 (page 15, item (56)) at Line 10, Under Other Publications, change "case" to --care--.

In Column 2 (page 15, item (56)) at Line 12, Under Other Publications, change "for" to --of--.

In Column 2 (page 15, item (56)) at Line 18, Under Other Publications, change "Busainess" to --Business--.

In Column 2 (page 15, item (56)) at Line 21, Under Other Publications, after "Optical" insert --coherence--.

In Column 2 (page 15, item (56)) at Line 23, Under Other Publications, change "343:181-191." to --343:188-191.--.

In Column 2 (page 15, item (56)) at Line 26, Under Other Publications, change "Technlogy" to --Technology--.

In Column 2 (page 15, item (56)) at Line 30, Under Other Publications, change "inactiviation" to --inactivation--.

In Column 2 (page 15, item (56)) at Line 51, Under Other Publications, change "activitiy," to --activity,--.

In Column 2 (page 15, item (56)) at Line 56, Under Other Publications, change "glocuse" to --glucose--.

In Column 2 (page 15, item (56)) at Line 61, Under Other Publications, change "valication" to --validation--.

In Column 2 (page 15, item (56)) at Lines 61-62, Under Other Publications, change "iunsulin interaaction in tyhpe 1" to --insulin interaction in type 1--.

In Column 2 (page 15, item (56)) at Line 69, Under Other Publications, change "Meidca" to --Medica--.

In Column 1 (page 16, item (56)) at Line 13, Under Other Publications, change "enzymoes" to --enzymes--.

In Column 1 (page 16, item (56)) at Line 13, Under Other Publications, change "termistor" to --thermistor--.

In Column 1 (page 16, item (56)) at Line 19, Under Other Publications, change "Analyticak" to --Analytical--.

In Column 2 (page 16, item (56)) at Line 5, Under Other Publications, change "Electrocheical" to --Electrochemical--.

In Column 2 (page 16, item (56)) at Line 8, Under Other Publications, change "mixture" to --mixtures--.

In Column 2 (page 16, item (56)) at Line 10, Under Other Publications, change "Chemica" to --Chemical--.

In Column 2 (page 16, item (56)) at Line 12, Under Other Publications, change "cholesteral" to --cholesterol--.

In Column 2 (page 16, item (56)) at Line 14, Under Other Publications, change "Filder" to --Filter--.

In Column 2 (page 16, item (56)) at Line 25, Under Other Publications, change "Chemistr4y" to --Chemistry--.

In Column 2 (page 16, item (56)) at Line 40, Under Other Publications, change "C," to --Series C,--.

CERTIFICATE OF CORRECTION (continued)
U.S. Pat. No. 9,717,449 B2

In Column 2 (page 16, item (56)) at Line 41, Under Other Publications, change "electodes." to --electrodes.--.

In Column 2 (page 16, item (56)) at Line 52, Under Other Publications, change "Engineenng" to --Engineering--.

In the Specification

In Column 4 at Line 41, After "data" insert --.--.

In Column 7 at Line 36, After "value" insert --.--.

In Column 8 at Line 10 (approx.), After "threshold" insert --.--.

In Column 16 at Line 53, Change "andrenostenedione;" to --androstenedione;--.

In Column 17 at Line 2, Change "diptheria/tetanus" to --diphtheria/tetanus--.

In Column 17 at Line 9, Change "perioxidase;" to --peroxidase;--.

In Column 17 at Line 18, Change "perioxidase;" to --peroxidase;--.

In Column 17 at Line 22, Change "perioxidase;" to --peroxidase;--.

In Column 17 at Line 30, Change "Trepenoma pallidium," to --Treponema pallidum,--.

In Column 17 at Line 31, Change "stomatis" to --stomatitis--.

In Column 17 at Lines 51-52, Change "(barbituates," to --(barbiturates,--.

In Column 17 at Line 67, Change "(FHIAA)." to --(HIAA).--.

In Column 22 at Line 24, Change "the a" to --the--.

In Column 28 at Line 44, Change "(2 e-)," to --(2e-),--.

In Column 29 at Line 8, Change "can by" to --can be--.

In Column 29 at Line 28, Change "(2 e-)" to --(2e-)--.

In Column 29 at Line 49, Change "Bellafonte," to --Bellefonte,--.

In Column 31 at Line 9, Change "(2 e-)" to --(2e-)--.

In Column 32 at Line 30, After "configurations" insert --.--.

CERTIFICATE OF CORRECTION (continued)
U.S. Pat. No. 9,717,449 B2

In Column 48 at Line 28, Change "minute" to --15 minute--.

In Column 53 at Line 64, Change "signal))." to --signal).--.

In Column 59 at Line 18 (approx.), After "as" insert --:--.

In Column 64 at Line 59, Change "mg/di/min)" to --mg/dl/min)--.

In Column 74 at Line 36, Change "Noise Threshold3" to --NoiseThreshold3--.

In Column 78 at Line 36-37, Change "mg/di/min)" to --mg/dl/min)--.

In Column 90 at Line 7, After "A1" insert --;--.